(12) United States Patent
Shah

(10) Patent No.: US 12,227,481 B2
(45) Date of Patent: Feb. 18, 2025

(54) CRYSTALLINE SOLID FORMS OF SALTS OF N-{4-[(6,7-DIMETHOXYQUINOLIN-4-YL)OXY]PHENYL}-N'-(4-FLUOROPHENYL) CYCLOPROPANE-1,1-DICARBOXAMIDE, PROCESSES FOR MAKING, AND METHODS OF USE

(71) Applicant: Exelixis, Inc., Alameda, CA (US)

(72) Inventor: Khalid Shah, Half Moon Bay, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 18/344,267

(22) Filed: Jun. 29, 2023

(65) Prior Publication Data

US 2024/0010621 A1 Jan. 11, 2024

Related U.S. Application Data

(63) Continuation of application No. 17/668,098, filed on Feb. 9, 2022, now Pat. No. 11,731,941, which is a continuation of application No. 16/617,352, filed as application No. PCT/US2018/034784 on May 26, 2018, now Pat. No. 11,279,675.

(60) Provisional application No. 62/511,714, filed on May 26, 2017.

(51) Int. Cl.
*C07D 215/22* (2006.01)

(52) U.S. Cl.
CPC ........ *C07D 215/22* (2013.01); *C07B 2200/13* (2013.01)

(58) Field of Classification Search
CPC ............................ C07D 215/22; C07B 2200/13
See application file for complete search history.

(56) References Cited

U.S. PATENT DOCUMENTS

| | | | | |
|---|---|---|---|---|
| 10,501,418 B2 * | 12/2019 | Aftab | ............... | C07D 215/233 |
| 10,851,061 B2 * | 12/2020 | Aftab | ............... | A61P 35/00 |
| 10,980,792 B2 | 4/2021 | Sun | | |
| 11,261,160 B2 | 3/2022 | Srinivasan et al. | | |
| 11,279,675 B2 * | 3/2022 | Shah | ............... | C07D 215/22 |
| 11,298,349 B2 * | 4/2022 | Wilson | ............... | A61P 35/00 |
| 11,724,986 B2 * | 8/2023 | Aftab | ............... | A61P 35/00 514/312 |
| 11,731,941 B2 * | 8/2023 | Shah | ............... | C07D 215/22 514/312 |
| 11,760,726 B2 * | 9/2023 | Aftab | ............... | A61P 35/00 514/312 |
| 2021/0198205 A1 | 7/2021 | Aftab et al. | | |

FOREIGN PATENT DOCUMENTS

| | | |
|---|---|---|
| CN | 104649969 A | 5/2015 |
| CN | 104961680 A | 10/2015 |
| CN | 104961681 A | 10/2015 |
| WO | 2005030140 A2 | 4/2005 |
| WO | 2010083414 A1 | 7/2010 |
| WO | 2011017639 | 2/2011 |
| WO | 2015177758 A1 | 11/2015 |
| WO | 2016150963 A1 | 9/2016 |
| WO | 2016150966 A1 | 9/2016 |

OTHER PUBLICATIONS

Berge et al., "Pharmaceutical salts," J Pharm. Sci., 66 (1): 1-19 (Jan. 1977).
International Search Report for PCT/US2018/034784, mailed Aug. 14, 2018.
Assessment report of Cometriq (International non-proprietary name: cabozantinib) by the Committee for Medicinal Products for Human Uses (CHMP) under the European Medicines Agency (EMA), published on Dec. 19, 2013.
Assessment report of CABOMETYX (International non-proprietary name: cabozantinib) by the Committee for Medicinal Products for Human Uses (CHMP) under the European Medicines Agency (EMA), published on Jul. 21, 2016.
Stahl, P. Heinrich and Camille G. Wermuth, Handbook of Pharmaceutical Salts Properties, Selection and Use, Publisher: Wiley-VCH. (p. 329-350). 2002.
Morissette, et al; "High-throughput crystallization: polymorphs, salts, co-crystals and solvates of pharmaceutical solids", ScienceDirect, Advanced Drug Delivery Reviews, 56, (2004) 275-300.
Qiu, Y., et al., Developing Solid Oral Dosage Forms: Pharmaceutical Theory and Practice 2009, pp. 75-86 (chapter 4).
Roy, et al., "A Novel Multiple Tyrosine-kinase Targeted Agent to Explore the Future Perspectives of Anti-Angiogenic Therapy for the Treatment of Multiple Solid Tumors: Cabozantinib", Anti-Cancer Agents in Medicinal Chemistry, 2015, 15, 37-47.
Serajuddin, Abu; "Salt formation to improve drug solubility", ScienceDirect, Advanced Drug Delivery Reviews, 59, (2007) 603-616.
Bastin, Richard J., et al., "Salt Selection and Optimisation Procedures for Pharmaceutical New Chemical Entities", Organic Process Research & Development, 2000, vol. 4, pp. 427-435.
Aitipamula, S and Nangia, A, 'Polymorphism: Fundamentals and Applications', Supramolecular Chemistry: From Molecules to Nanomaterials. Mar. 15, 2012.

\* cited by examiner

*Primary Examiner* — D Margaret M Seaman
(74) *Attorney, Agent, or Firm* — Honigman LLP; Heidi M. Berven; Li Gao

(57) ABSTRACT

The invention relates to novel crystalline solid forms of salts of the chemical compound N-{4-[(6,7-dimethoxyquinolin-4-yl)oxy]phenyl}-N'-(4-fluorophenyl) cyclopropane-1,1-dicarboxamide, and solvates thereof, including hydrates, that are useful for the treatment of cancer. Also disclosed are pharmaceutical compositions comprising the crystalline solid forms and processes for making the crystalline solid forms, as well as methods of using them for the treatment of cancer, particularly renal cell carcinoma (RCC) and medullary thyroid cancer (MTC).

9 Claims, 67 Drawing Sheets

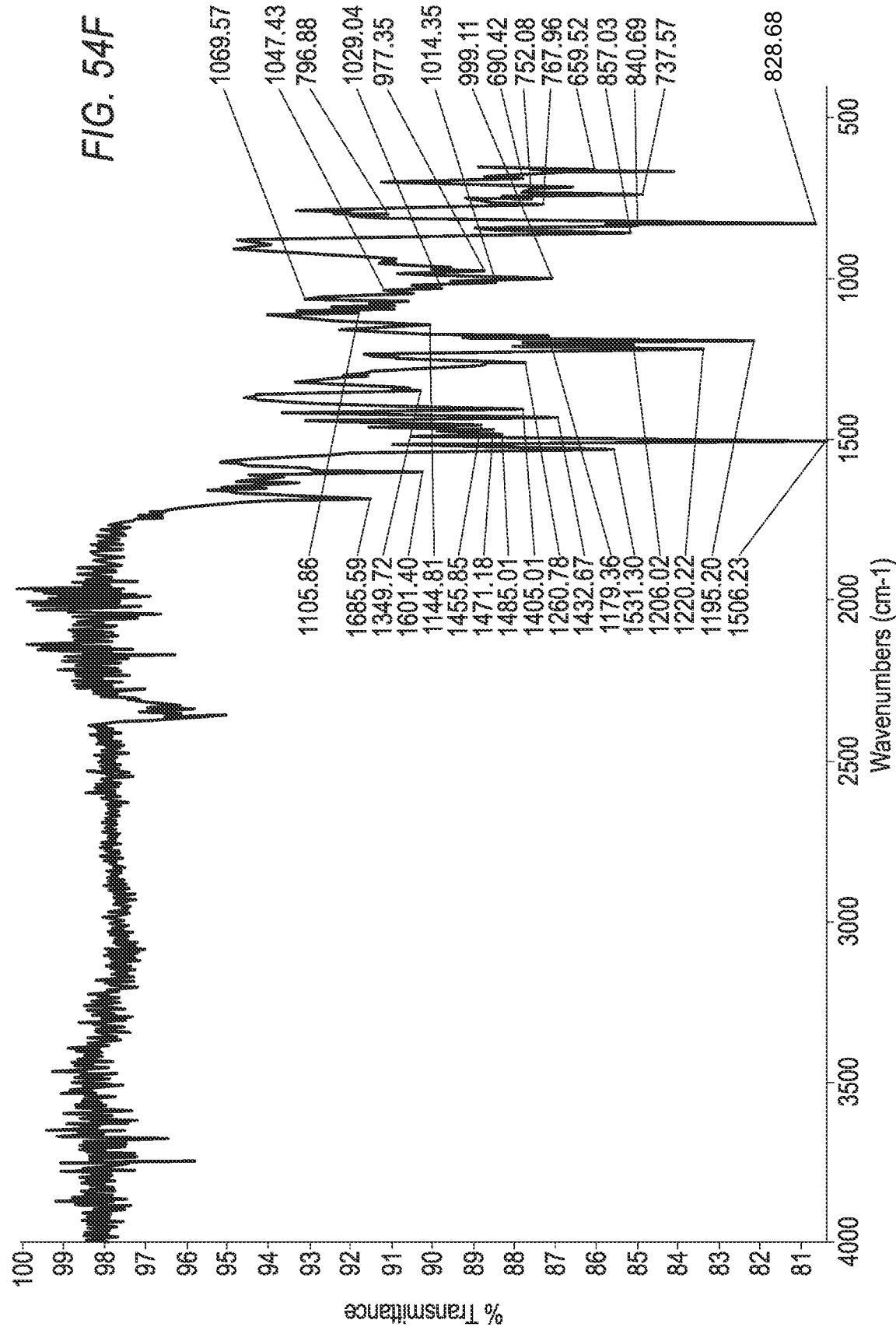

CRYSTALLINE SOLID FORMS OF SALTS OF N-{4-[(6,7-DIMETHOXYQUINOLIN-4-YL)OXY]PHENYL}-N'-(4-FLUOROPHENYL) CYCLOPROPANE-1,1-DICARBOXAMIDE, PROCESSES FOR MAKING, AND METHODS OF USE

RELATED APPLICATION

This application is a continuation application of U.S. Ser. No. 17/668,098, filed Feb. 9, 2022, which is a continuation application of U.S. Ser. No. 16/617,352, filed Nov. 26, 2019, which is a United States National Phase filing of PCT/US2018/034784, filed May 26, 2018, which claims the benefit of priority to U.S. Provisional Application No. 62/511,714, filed May 26, 2017, the entire contents of which are incorporated herein by reference.

TECHNICAL FIELD OF THE INVENTION

The invention relates to novel crystalline solid forms of salts of the chemical compound N-{4-[(6,7-dimethoxyquinolin-4-yl)oxy]phenyl}-N'-(4-fluorophenyl) cyclopropane-1,1-dicarboxamide, and solvates thereof, including hydrates, that are useful for the treatment of cancer. Also disclosed are pharmaceutical compositions comprising the crystalline solid forms and processes for making the crystalline solid forms, as well as methods of using them for the treatment of cancer, particularly renal cell carcinoma (RCC) and medullary thyroid cancer (MTC).

BACKGROUND OF THE INVENTION

Commonly assigned PCT Patent Publication No. WO 2005/030140, incorporated by reference herein in its entirety, discloses novel inhibitors of multiple receptor tyrosine kinases (RTKs) implicated in tumor growth and angiogenesis, pathologic bone remodeling, and metastatic progression of cancer. In particular, the compound N-{4-[(6,7-dimethoxyquinolin-4-yl)oxy]phenyl}-N'-(4-fluorophenyl) cyclopropane-1,1-dicarboxamide is specifically described in WO 2005/030140 as an RTK inhibitor. N-{4-[(6,7-dimethoxyquinolin-4-yl)oxy]phenyl}-N'-(4-fluorophenyl) cyclopropane-1,1-dicarboxamide is also known in the art as cabozantinib. The chemical structure of N-{4-[(6,7-dimethoxyquinolin-4-yl)oxy]phenyl}-N'-(4-fluorophenyl) cyclopropane-1,1-dicarboxamide (cabozantinib) is represented by Compound 1.

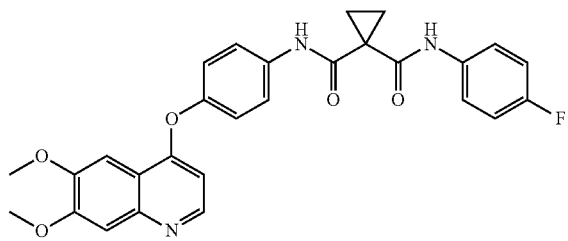

Compound 1

Compound 1 was found to have an enzyme Ret $IC_{50}$ value of about 5.2 nM (dihydrate) and an enzyme c-Met $IC_{50}$ value of about 1.3 nM (dihydrate). The assay that was used to measure this c-Met activity is described in paragraph [0458] in WO2005/030140.

During initial development experiments, Compound 1 (a free base) was found to be a BCS class II compound having low solubility and high permeability. Because Compound 1 was observed to have low solubility in water, it was initially considered unsuitable for solid oral dosage development, and hence the pharmaceutical development focused on finding a salt with suitable hygroscopicity, thermal stability, chemical stability, physical stability, and solubility.

The malate salt of Compound 1, as described in WO 2010/083414, the entire contents of which is incorporated by reference, was subsequently identified as providing an acceptable combination of crystallinity, solubility, and stability as compared to Compound 1 free base. On Nov. 29, 2012, the S-malate salt of N-{4-[(6,7-dimethoxyquinolin-4-yl)oxy]phenyl}-N'-(4-fluorophenyl) cyclopropane-1,1-dicarboxamide (also known as cabozantinib or COMETRIQ®) was approved by the United States Food and Drug Administration for the treatment of progressive, metastatic medullary thyroid cancer (MTC). In December 2013, the European Committee for Medicinal Products for Human Use (CHMP), issued a positive opinion on the Marketing Authorization Application (MAA), submitted to the European Medicines Agency, or EMA, for COMETRIQ® for the proposed indication of progressive, unresectable, locally advanced, or metastatic MTC. More recently, in 2015, cabozantinib as the S-malate salt was approved as CABOMETYX® for the treatment of advance renal cell carcinoma.

Besides therapeutic efficacy, the Applicant continues to endeavor to provide suitable form(s) of Compound 1 that have favorable properties related to processing, manufacturing, storage stability, and/or usefulness as a drug. Accordingly, the discovery of new crystalline solid forms of Compound 1 that possesses some or all of these desired properties remains vital to drug development. Thus, disclosed herein are novel crystalline solid forms of Compound 1 that may be used in pharmaceutical compositions for the treatment of proliferative diseases such as cancer.

SUMMARY OF THE INVENTION

These and other needs are met by the present invention, which is directed to novel crystalline solid forms of salts of Compound 1, as well as pharmaceutical compositions containing, methods for using, and processes for making such crystalline solid forms. The crystalline solid forms include solvated solid forms, including hydrates. Among other uses, crystalline solid forms of Compound 1 are useful for preparing pharmaceutical compositions expected to have utility in treating cancer. Accordingly, one aspect of the invention pertains to a pharmaceutical composition comprising a pharmaceutically acceptable carrier and a therapeutically effective amount of a solid form of Compound 1.

As indicated previously, Compound 1 inhibits multiple receptor tyrosine kinases (RTKs) implicated in tumor growth and angiogenesis, pathologic bone remodeling, and metastatic progression of cancer. Accordingly, crystalline solid forms of the Compound 1 are useful for treating cancer. Thus, another aspect of the invention pertains to a method for treating cancer comprising administering to a subject a therapeutically effective amount of a solid form of Compound 1 as disclosed herein. The invention is also directed to processes for preparing crystalline solid forms of Compound 1.

The solid forms are summarized in Table 1.

TABLE 1

Novel crystalline solid forms of salts of N-{4-[(6,7-dimethoxyquinolin-4-yl)oxy]phenyl}-N'-(4-fluorophenyl) cyclopropane-1,1-dicarboxamide

| Form | Comment |
|---|---|
| 1 | Compound 1•citrate, monohydrate, 1:1 |
| 2 | Compound 1•malonate, 3.6 mol eq water, 1:1 |
| 3 | Compound 1•oxalate, anhydrous, 1:1 |
| 4 | Compound 1•ethane disulfonate, deliquescent, 1:1 |
| 5 | Compound 1•sulphate, 3.7 mol eq water, 1:1 |
| 6 | Compound 1•besylate, anhydrous, 1:1 |
| 7 | Compound 1•esylate, anhydrous, 1:1 |
| 8 | Novel form related to Compound 1 free base |
| 9 | Compound 1•mesylate, anhydrous, 1:1 |
| 10 | Compound 1•tosylate, anhydrous, 1:1 |
| 11 | Compound 1•sulfate, 2.4 mol eq water, 1:1 |
| 12 | Compound 1•ethane disulfonate, anhydrous, 2:1 API:acid |
| 13 | Compound 1•oxalate, anhydrous, 1:1 |
| 14 | Compound 1•pyruvate, anhydrous, 1:1 |
| 15 | Compound 1•besylate, 1.4 mol. eq. THF, 1:1 |
| 16 | Compound 1•mesylate, dihydrate, 1:1 |
| 17 | Compound 1•succinate, 0.4 mol eq acetonitrile and 0.86 mol eq water, 1:0.7 API:acid |
| 18 | Compound 1•esylate, 0.4 mol eq acetonitrile, 1:1 |
| 19 | Compound 1•isethionate, monohydrate, 1:1 |
| 20 | Compound 1•glutarate, 0.59 mol eq water, 1:1 |
| 21 | Compound 1•sulfate, monohydrate, 1:1 |
| 22 | Compound 1•tosylate, 0.8 mol eq water, 1:1 |
| 23 | Compound 1•succinate, TGA weight loss equates to ~0.8 mol eq of water |
| 24 | Compound 1•malonate, anhydrous, 1:1 |
| 25 | Compound 1•mesylate, 0.3 mol eq acetonitrile, 1:1 |
| 26 | Compound 1•gluconate, 2.6 moles water, 1:1 |
| 27 | Compound 1•isethionate, monohydrate, 1:1 |

A total of 27 forms were observed during the screen. One of the patterns (Form 8) was free base related. The remaining 26 solids were assessed according to their crystallinity, solvation state, stoichiometry, ease of manufacture, deliquescence, stability to desolvation, molecular weight, and acceptability/toleration with respect to oral dosing. Aqueous solubility and optical microscopy were also determined.

In a particular aspect, the invention is directed to crystalline solid salts of N-{4-[(6,7-dimethoxyquinolin-4-yl)oxy]phenyl}-N'-(4-fluorophenyl) cyclopropane-1,1-dicarboxamide (Compound 1), wherein the salts are selected from the group consisting of: N-{4-[(6,7-dimethoxyquinolin-4-yl)oxy]phenyl}-N'-(4-fluorophenyl) cyclopropane-1,1-dicarboxamide (Compound 1)•pyruvate; N-{4-[(6,7-dimethoxyquinolin-4-yl)oxy]phenyl}-N'-(4-fluorophenyl) cyclopropane-1,1-dicarboxamide (Compound 1)•glutarate; and N-{4-[(6,7-dimethoxyquinolin-4-yl)oxy]phenyl}-N'-(4-fluorophenyl) cyclopropane-1,1-dicarboxamide (Compound 1)•isethionate monohydrate.

Forms 14, 19, and 20 (pyruvate, glutarate, and isethionate) were prepared on a 250-1000 mg scale and confirmed as the same forms that were observed in the initial screen. The three salts were also fully characterized by XRPD, DSC, TG/DTA, DVS, and $^1$H NMR microscopy. An investigation into their crystal habit was also performed. Compound 1 pyruvate and glutarate were irregular particles with low aspect ratio, whereas Compound 1 isethionate showed a crystal habit of needle morphology.

The salt forms described herein possess a number of advantageous properties. Examples of such advantageous properties include a lower molecular weight giving a higher activity per weight ratio, higher solubility, improved filterability and flow properties due to particle morphology/aspect ratio, and lower hygroscopicity. Further, many of the salts described herein are natural human metabolites and are therefore well-tolerated in vivo.

BRIEF DESCRIPTION OF THE DRAWINGS

FIG. 54F is the infrared (IR) spectrum of Form 20, Compound 1 glutarate.

DETAILED DESCRIPTION

Definitions

Figure 1:
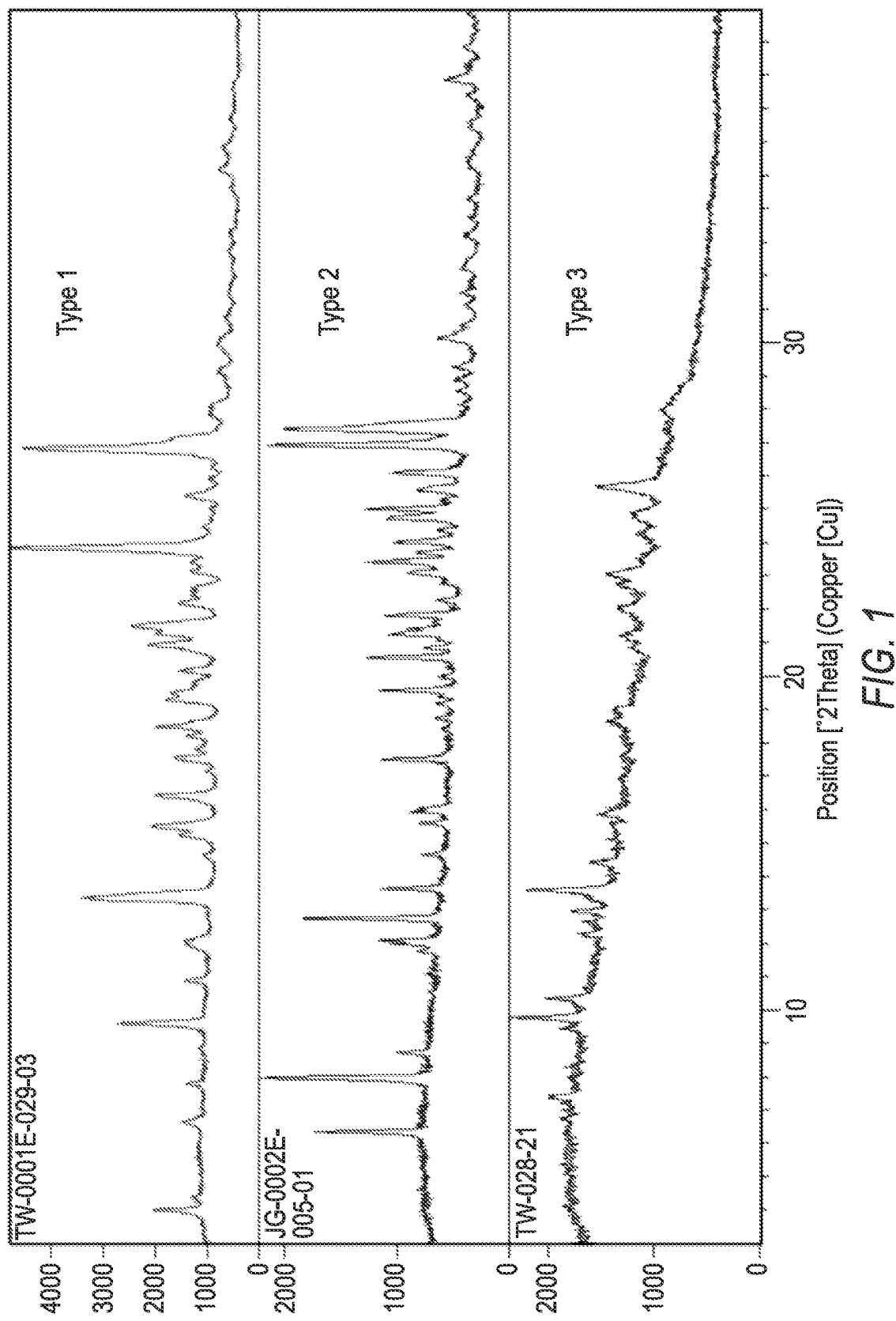
FIG. 1 is a chart showing the XRPD spectra of Forms 1, 2, and 3.

Processes described herein can be used to prepare the compositions of this invention. The amounts and the features of the components used in the processes would be as described herein.

When describing the compounds, compositions, methods, and processes of the invention, the following terms have the following meanings unless otherwise indicated.

The term "solvate" means a complex or aggregate formed by one or more molecules of a solute, i.e., a crystalline Compound 1, and one or more molecules of a solvent. Such solvates typically have a substantially fixed molar ratio of solute and solvent. This term also includes clathrates, including clathrates with water. Representative solvents include, for example, water, methanol, ethanol, isopropanol, acetic acid, and the like. When the solvent is water, the solvate formed is a hydrate.

"Therapeutically effective amount" means an amount sufficient to effect treatment when administered to a subject in need of treatment. "The amount of a compound of the invention which constitutes a "therapeutically effective amount" will vary depending on the compound, the disease state and its severity, the age of the subject to be treated, and the like. The therapeutically effective amount can be determined routinely by one of ordinary skill in the art, taking into consideration his own knowledge and this disclosure. Thus, a "therapeutically effective amount" of Compound 1 refers to an amount sufficient to treat a subject suffering from any of a variety of cancers associated with abnormal cell proliferation and angiogenesis. A therapeutically effective amount according to this disclosure is an amount therapeutically useful for the treatment or prevention of the disease states and disorders discussed herein. Compound 1 (including the solid state forms disclosed herein) possess therapeutic activity to inhibit, regulate, and/or modulate the signal transduction of kinases such as described in WO2005/030140.

"Treating" or "treatment" as used herein means the treatment of a disease-state in a human, which disease-state is characterized by abnormal cellular proliferation and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state.

The term "pharmaceutically acceptable" refers to a material that is not biologically or otherwise undesirable. For example, the term "pharmaceutically acceptable carrier" refers to a material that can be incorporated into a composition and administered to a subject without causing undesirable biological effects or interacting in a deleterious manner with other components of the composition. Such pharmaceutically acceptable materials typically have met the required standards of toxicological and manufacturing testing and include those materials identified as suitable inactive ingredients by the U.S. Food and Drug Administration.

The term "dosage form" refers to a physically discrete unit suitable for dosing a subject, i.e., each unit containing a predetermined quantity of a compound of the invention calculated to produce the desired therapeutic effect either alone or in combination with one or more additional units. For example, such unit dosage forms may be capsules, tablets, pills, and the like.

As used herein, "amorphous" refers to a solid form of a molecule and/or ion that is not crystalline. An amorphous solid does not display a definitive X-ray diffraction pattern with sharp maxima.

As used herein, the term "substantially pure" means the solid form of Compound 1 referred to contains at least about 90 weight percent based on the weight of such solid form. The term "at least about 90 weight percent," while not intending to limit the applicability of the doctrine of equivalents to the scope of the claims, includes, but is not limited to, for example, about 90, about 91, about 92, about 93, about 94, about 95, about 96, about 97, about 98, about 99, and about 100 weight percent, based on the weight of the solid form referred to. The remainder of the solid form of Compound 1 may comprise other solid form(s) of Compound 1 and/or reaction impurities and/or processing impurities that arise, for example, when the crystalline form is prepared. The presence of reaction impurities and/or processing impurities may be determined by analytical techniques known in the art, such as, for example, chromatography, nuclear magnetic resonance spectroscopy, mass spectroscopy, and/or infrared spectroscopy.

As used herein "crystalline solids" refers to Compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

As used herein "the European Pharmacopoeia classification" is a system whereby a chemical Compound 1 as classified based on hygroscopicity. The classification is determined according to Table 2:

TABLE 2

European Pharmacopoeia classification

| Classification | Weight increase at 80% RH (25° C.) |
| --- | --- |
| Non hygroscopic | <0.2% |
| Slightly hygroscopic | ≥0.2% and <2% |
| Hygroscopic | ≥2% and <15% |
| Very hygroscopic | ≥15% |
| Deliquescent | sufficient water is absorbed to form a liquid |

Hygroscopicity of a chemical compound can be determined by procedures know to those skilled in the art, such as, but not limited to, Dynamic Vapor Sorption (DVS).

Additionally, unless otherwise stated, structures depicted herein are also meant to include Compounds that differ only in the presence of one or more isotopically enriched atoms. For example, Compound 1, wherein one or more hydrogen atoms are replaced deuterium or tritium, or one or more carbon atoms are replaced by a $^{13}C$- or $^{14}C$-enriched carbon, are within the scope of this invention. Such Compounds are useful, for example, as analytical tools, probes in biological assays, or Compounds with improved therapeutic profile.

EMBODIMENTS

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•citrate monohydrate, characterized as Form 1, wherein the crystalline solid comprises Compound 1 and citrate in a 1:1 molar ratio. In one embodiment, Form 1 is characterized by one or more peaks on a 2-theta scale in an XRPD pattern selected from the group consisting of 4.02, 9.61, 13.35, 13.50, 15.52, 16.45, 18.49, 20.94, 21.29, 21.50, 21.59, 23.85, 26.83, and 27.12 degrees. In another embodiment, Form 1 is characterized by one or more peaks on a 2-theta scale in an XRPD pattern selected from the group consisting of 9.61, 13.35, 13.50, 21.50, 23.85, 26.83, and 27.12 degrees. In a further embodiment, Form 1 is characterized by peaks at 9.61, 13.35, 13.50, 21.50, 23.85, 26.83, and 27.12 degrees on a 2-theta scale in an XRPD pattern. In still a further embodiment, Form 1 is characterized by an XRPD pattern according to FIG. 1. In another further embodiment, Form 1 is characterized by an XRPD pattern having peak values according to Table 3.

TABLE 3

Form 1

| 2θ | Relative Intensity (%) |
| --- | --- |
| 4.02 | 24.46 |
| 9.61 | 42.36 |
| 13.35 | 62.09 |
| 13.50 | 38.77 |

TABLE 3-continued

Form 1

| 2θ | Relative Intensity (%) |
| --- | --- |
| 15.52 | 30.28 |
| 16.45 | 29.05 |
| 18.49 | 27.79 |
| 20.94 | 32.01 |
| 21.29 | 29.25 |
| 21.50 | 40.49 |
| 21.59 | 32.63 |
| 23.85 | 100.00 |
| 26.83 | 95.31 |
| 27.12 | 24.41 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•malonate (3.6 molar equivalents of water), characterized as Form 2, wherein the crystalline solid comprises Compound 1 and malonate in a 1:1 molar ratio. In one embodiment, Form 2 is characterized by one or more peaks on a 2-theta scale in an XRPD pattern selected from the group consisting of 6.36, 7.97, 11.99, 12.09, 12.75, 13.64, 17.52, 19.58, 20.57, 21.82, 23.43, 24.73, 24.79, 25.01, 26.09, 26.93, 27.36, 27.42, and 27.61 degrees. In another embodiment, Form 2 is characterized by one or more peaks on a 2-theta scale in an XRPD pattern selected from the group consisting of 6.36, 7.97, 12.75, 19.58, 20.57, 23.43, 25.01, 26.93, 27.36, and 27.42 degrees. In a further embodiment, Form 2 is characterized by peaks at 6.36, 7.97, 12.75, 19.58, 20.57, 23.43, 25.01, 26.93, 27.36, and 27.42 degrees on a 2-theta scale in an XRPD pattern. In still a further embodiment, Form 2 is characterized by an XRPD pattern according to FIG. 1. In another further embodiment, Form 2 is characterized by an XRPD pattern having peak values according to Table 4.

TABLE 4

Form 2

| 2θ | Relative Intensity (%) |
| --- | --- |
| 6.36 | 56.89 |
| 7.97 | 83.93 |
| 11.99 | 24.88 |
| 12.09 | 28.91 |
| 12.75 | 70.21 |
| 13.64 | 30.76 |
| 17.52 | 34.12 |
| 19.58 | 38.24 |
| 20.57 | 44.66 |
| 21.82 | 36.96 |
| 23.43 | 44.73 |
| 24.73 | 34.38 |
| 24.79 | 33.11 |
| 25.01 | 43.93 |
| 26.09 | 36.33 |
| 26.93 | 100.00 |
| 27.36 | 81.02 |
| 27.42 | 92.63 |
| 27.61 | 35.74 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•oxalate (anhydrous), characterized as Form 3, wherein the crystalline solid comprises Compound 1 and oxalate in a 1:1 molar ratio. In one embodiment, Form 3 is characterized by one or more peaks on a 2-theta scale in an XRPD pattern selected from the group consisting of 7.40, 9.44, 9.78, 10.36, 12.67, 12.97, 13.60, 14.42, 15.87, 18.65, 19.06, 21.21, 22.05, 22.76, 23.07, 24.89, and 25.69 degrees. In another embodiment, Form 3 is characterized by one or more peaks on a 2-theta scale in an XRPD pattern selected from the group consisting of 9.78, 10.36, 12.97, 13.60, 23.07, and 25.69 degrees. In a further embodiment, Form 3 is characterized by peaks at 9.78, 10.36, 12.97, 13.60, 23.07, and 25.69 degrees on a 2-theta scale in an XRPD pattern. In still a further embodiment, Form 3 is characterized by an XRPD pattern according to FIG. 1. In another further embodiment, Form 3 is characterized by an XRPD pattern having peak values according to Table 5.

TABLE 5

| Form 3 | |
|---|---|
| 2θ | Relative Intensity (%) |
| 7.40 | 35.52 |
| 9.44 | 29.34 |
| 9.78 | 85.32 |
| 10.36 | 53.05 |
| 12.67 | 27.37 |
| 12.97 | 43.74 |
| 13.60 | 100.00 |
| 14.42 | 29.48 |
| 15.87 | 28.88 |
| 18.65 | 29.21 |
| 19.06 | 28.47 |
| 21.21 | 27.88 |
| 22.05 | 31.42 |
| 22.76 | 34.96 |
| 23.07 | 48.76 |
| 24.89 | 29.47 |
| 25.69 | 73.85 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•ethane disulfonate (deliquescent), characterized as Form 4, wherein the crystalline solid comprises Compound 1 and ethane disulfonate in a 1:1 molar ratio. In one embodiment, Form 4 is characterized by one or more peaks on a 2-theta scale in an XRPD pattern selected from the group consisting of 6.83, 8.37, 11.67, 13.10, 13.65, 22.09, 22.48, 22.70, 24.66, and 27.19 degrees. In another embodiment, Form 4 is characterized by one or more peaks on a 2-theta scale in an XRPD pattern selected from the group consisting of 8.37, 11.67, 13.10, 22.48, 22.70, 24.66, and 27.19 degrees. In a further embodiment, Form 4 is characterized by peaks at 8.37, 11.67, 13.10, 22.48, 22.70, 24.66, and 27.19 degrees on a 2-theta scale in an XRPD pattern. In still a further embodiment, Form 4 is characterized by an XRPD pattern according to FIG. 2. In another further embodiment, Form 4 is characterized by an XRPD pattern having peak values according to Table 6.

TABLE 6

| Form 4 | |
|---|---|
| 2θ | Relative Intensity (%) |
| 6.83 | 24.03 |
| 8.37 | 36.97 |
| 11.67 | 47.17 |
| 13.10 | 65.30 |
| 13.65 | 27.64 |
| 22.09 | 30.92 |
| 22.48 | 51.17 |

TABLE 6-continued

| Form 4 | |
|---|---|
| 2θ | Relative Intensity (%) |
| 22.70 | 38.88 |
| 24.66 | 100.00 |
| 27.19 | 56.32 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•sulfate (3.7 molar equivalents of water), characterized as Form 5, wherein the crystalline solid comprises Compound 1 and sulfate in a 1:1 molar ratio. In one embodiment, Form 5 is characterized by one or more peaks on a 2-theta scale in an XRPD pattern selected from the group consisting of 9.56, 10.08, 13.29, 13.86, 14.17, 22.27, 22.60, 22.93, 25.16, and 27.70 degrees. In another embodiment, Form 5 is characterized by one or more peaks on a 2-theta scale in an XRPD pattern selected from the group consisting of 9.56, 10.08, 13.29, 13.86, 22.60, and 25.16 degrees. In a further embodiment, Form 5 is characterized by peaks at 9.56, 10.08, 13.29, 13.86, 22.60, and 25.16 degrees on a 2-theta scale in an XRPD pattern. In still a further embodiment, Form 5 is characterized by an XRPD pattern according to FIG. 2. In another further embodiment, Form 5 is characterized by an XRPD pattern having peak values according to Table 7.

TABLE 7

| Form 5 | |
|---|---|
| 2θ | Relative Intensity (%) |
| 9.56 | 31.55 |
| 10.08 | 54.68 |
| 13.29 | 100.00 |
| 13.86 | 29.19 |
| 14.17 | 25.67 |
| 22.27 | 29.42 |
| 22.60 | 32.23 |
| 22.93 | 22.45 |
| 25.16 | 42.68 |
| 27.70 | 22.46 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•besylate (anhydrous), characterized as Form 6, wherein the crystalline solid comprises Compound 1 and besylate in a 1:1 molar ratio. In one embodiment, Form 6 is characterized by one or more peaks on a 2-theta scale in an XRPD pattern selected from the group consisting of 9.77, 10.52, 13.26, 14.34, 15.90, 15.98, 17.93, 18.69, 19.54, 22.83, 26.78, and 26.85 degrees. In another embodiment, Form 6 is characterized by one or more peaks on a 2-theta scale in an XRPD pattern selected from the group consisting of 9.77, 10.52, 13.26, 14.34, 15.90, 18.69, 19.54, 22.83, 26.78, and 26.85 degrees. In a further embodiment, Form 6 is characterized by peaks at 9.77, 10.52, 13.26, 14.34, 15.90, 18.69, 19.54, 22.83, 26.78, and 26.85 degrees on a 2-theta scale in an XRPD pattern. In still a further embodiment, Form 6 is characterized by an XRPD pattern according to FIG. 2. In another further embodiment, Form 6 is characterized by an XRPD pattern having peak values according to Table 8.

TABLE 8

Form 6

| 2θ | Relative Intensity (%) |
|---|---|
| 9.77 | 49.49 |
| 10.52 | 50.51 |
| 13.26 | 43.13 |
| 14.34 | 60.99 |
| 15.90 | 63.28 |
| 15.98 | 39.22 |
| 17.93 | 28.79 |
| 18.69 | 95.51 |
| 19.54 | 98.11 |
| 22.83 | 44.56 |
| 26.78 | 100.00 |
| 26.85 | 49.18 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•esylate (anhydrous), characterized as Form 7, wherein the crystalline solid comprises Compound 1 and esylate in a 1:1 molar ratio. In one embodiment, Form 7 is characterized by one or more peaks on a 2-theta scale in an XRPD pattern selected from the group consisting of 5.18, 11.63, 14.09, 14.79, 16.89, 19.92, 21.05, and 26.46 degrees. In another embodiment, Form 7 is characterized by one or more peaks on a 2-theta scale in an XRPD pattern selected from the group consisting of 14.79 and 19.92 degrees. In a further embodiment, Form 7 is characterized by peaks at 14.79 and 19.92 degrees on a 2-theta scale in an XRPD pattern. In still a further embodiment, Form 7 is characterized by an XRPD pattern according to FIG. 3. In another further embodiment, Form 7 is characterized by an XRPD pattern having peak values according to Table 9.

TABLE 9

Form 7

| 2θ | Relative Intensity (%) |
|---|---|
| 5.18 | 13.98 |
| 11.63 | 21.79 |
| 14.09 | 13.92 |
| 14.79 | 34.44 |
| 16.89 | 26.58 |
| 19.92 | 100.00 |
| 21.05 | 14.72 |
| 26.46 | 21.78 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1), characterized as Form 8 (free base). In one embodiment, Form 8 is characterized by one or more peaks on a 2-theta scale in an XRPD pattern selected from the group consisting of 6.76, 12.35, 12.85, 18.88, 21.01, 22.83, 23.59, 25.10, 26.30, 27.96, and 28.02 degrees. In another embodiment, Form 8 is characterized by one or more peaks on a 2-theta scale in an XRPD pattern selected from the group consisting of 12.35, 12.85, 18.88, 21.01, 22.83, 23.59, 25.10, and 26.30 degrees. In a further embodiment, Form 8 is characterized by peaks at 12.35, 12.85, 18.88, 21.01, 22.83, 23.59, 25.10, and 26.30 degrees on a 2-theta scale in an XRPD pattern. In still a further embodiment, Form 8 is characterized by an XRPD pattern according to FIG. 3. In another further embodiment, Form 8 is characterized by an XRPD pattern having peak values according to Table 10.

TABLE 10

Form 8

| 2θ | Relative Intensity (%) |
|---|---|
| 6.76 | 36.60 |
| 12.35 | 83.87 |
| 12.85 | 93.30 |
| 18.88 | 41.62 |
| 21.01 | 57.43 |
| 22.83 | 59.91 |
| 23.59 | 100.00 |
| 25.10 | 86.37 |
| 26.30 | 46.74 |
| 27.96 | 30.77 |
| 28.02 | 34.16 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•mesylate (anhydrous), characterized as Form 9, wherein the crystalline solid comprises Compound 1 and mesylate in a 1:1 molar ratio. In one embodiment, Form 9 is characterized by one or more peaks on a 2-theta scale in an XRPD pattern selected from the group consisting of 5.75, 11.33, 15.57, 16.19, 16.34, 16.76, 17.36, 17.90, 20.87, 22.69, and 23.08 degrees. In another embodiment, Form 9 is characterized by one or more peaks on a 2-theta scale in an XRPD pattern selected from the group consisting of 5.75, 15.57, 16.19, 17.90, 20.87, 22.69, and 23.08 degrees. In a further embodiment, Form 9 is characterized by peaks at 5.75, 15.57, 16.19, 17.90, 20.87, 22.69, and 23.08 degrees on a 2-theta scale in an XRPD pattern. In still a further embodiment, Form 9 is characterized by an XRPD pattern according to FIG. 3. In another further embodiment, Form 9 is characterized by an XRPD pattern having peak values according to Table 11.

TABLE 11

Form 9

| 2θ | Relative Intensity (%) |
|---|---|
| 5.75 | 77.52 |
| 11.33 | 23.45 |
| 15.57 | 48.39 |
| 16.19 | 52.53 |
| 16.34 | 34.44 |
| 16.76 | 37.72 |
| 17.36 | 39.23 |
| 17.90 | 89.49 |
| 20.87 | 100.00 |
| 22.69 | 45.69 |
| 23.08 | 46.44 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•tosylate (anhydrous), characterized as Form 10, wherein the crystalline solid comprises Compound 1 and tosylate in a 1:1 molar ratio. In one embodiment, Form 10 is characterized by one or more peaks on a 2-theta scale in an XRPD pattern selected from the group consisting of 4.77, 9.58, 14.17, 14.26, 15.55, 15.61, 18.20, 18.29, 19.30, 20.12, 26.13, 26.20, 27.11, and 28.99 degrees. In another embodiment, Form 10 is characterized by one or more peaks on a 2-theta scale in an XRPD pattern selected from the group consisting of 15.55, 18.29, 19.30, 20.12, 26.13, and 26.20 degrees. In a further embodiment, Form 10 is characterized by peaks at 15.55, 18.29, 19.30, 20.12, 26.13, and 26.20 degrees on a 2-theta scale in an XRPD pattern. In still a further embodiment, Form 10 is characterized by an XRPD pattern according to FIG. 4. In another further embodiment, Form 10 is characterized by an XRPD pattern having peak values according to Table 12.

TABLE 12

| 2θ | Relative Intensity (%) |
|---|---|
| Form 10 | |
| 4.77 | 11.91 |
| 9.58 | 30.05 |
| 14.17 | 26.31 |
| 14.26 | 20.29 |
| 15.55 | 34.55 |
| 15.61 | 29.75 |
| 18.20 | 33.26 |
| 18.29 | 55.08 |
| 19.30 | 68.74 |
| 20.12 | 37.56 |
| 26.13 | 100.00 |
| 26.20 | 63.10 |
| 27.11 | 20.63 |
| 28.99 | 15.17 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•sulfate (2.4 molar equivalents of water), characterized as Form 11, wherein the crystalline solid comprises Compound 1 and sulfate in a 1:1 molar ratio. In one embodiment, Form 11 is characterized by one or more peaks on a 2-theta scale in an XRPD pattern selected from the group consisting of 6.75, 9.64, 11.06, 12.70, 13.70, 13.92, 14.76, 21.13, 23.58, 24.46, 24.52, 26.66, 27.62, and 29.81 degrees. In another embodiment, Form 11 is characterized by one or more peaks on a 2-theta scale in an XRPD pattern selected from the group consisting of 12.70, 13.92, 23.58, 24.46, 24.52, and 26.66 degrees. In a further embodiment, Form 11 is characterized by peaks at 12.70, 13.92, 23.58, 24.46, 24.52, and 26.66 degrees on a 2-theta scale in an XRPD pattern. In still a further embodiment, Form 11 is characterized by an XRPD pattern according to FIG. 4. In another further embodiment, Form 11 is characterized by an XRPD pattern having peak values according to Table 13.

TABLE 13

| 2θ | Relative Intensity (%) |
|---|---|
| Form 11 | |
| 6.75 | 24.55 |
| 9.64 | 22.13 |
| 11.06 | 22.35 |
| 12.70 | 86.90 |
| 13.70 | 30.12 |
| 13.92 | 100.00 |
| 14.76 | 33.17 |
| 21.13 | 31.01 |
| 23.58 | 55.23 |
| 24.46 | 43.65 |
| 24.52 | 42.57 |
| 26.66 | 73.75 |
| 27.62 | 36.17 |
| 29.81 | 27.23 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•ethane disulfonate (anhydrous), characterized as Form 12, wherein the crystalline solid comprises Compound 1 and ethane disulfonate in a 2:1 molar ratio (Compound 1 to disulfonate). In one embodiment, Form 12 is characterized by one or more peaks on a 2-theta scale in an XRPD pattern selected from the group consisting of 13.20, 13.75, 14.56, 16.45, 16.74, 18.07, 18.23, 20.18, 22.28, 23.46, 24.98, 25.69, 27.62, and 31.26 degrees. In another embodiment, Form 12 is characterized by one or more peaks on a 2-theta scale in an XRPD pattern selected from the group consisting of 13.20, 13.75, 14.56, 20.18, 22.28, 24.98, and 25.69 degrees. In a further embodiment, Form 12 is characterized by peaks at 13.20, 13.75, 14.56, 20.18, 22.28, 24.98, and 25.69 degrees on a 2-theta scale in an XRPD pattern. In another further embodiment, Form 12 is characterized by peaks at 13.20, 14.56, 20.18, 22.28, 24.98, and 25.69 degrees on a 2-theta scale in an XRPD pattern. In still a further embodiment, Form 12 is characterized by an XRPD pattern according to FIG. 4. In another further embodiment, Form 12 is characterized by an XRPD pattern having peak values according to Table 14.

TABLE 14

| 2θ | Relative Intensity (%) |
|---|---|
| Form 12 | |
| 13.20 | 56.12 |
| 13.75 | 30.38 |
| 14.56 | 59.77 |
| 16.45 | 31.95 |
| 16.74 | 32.59 |
| 18.07 | 25.49 |
| 18.23 | 36.19 |
| 20.18 | 96.92 |
| 22.28 | 100.00 |
| 23.46 | 29.93 |
| 24.98 | 52.41 |
| 25.69 | 43.16 |
| 27.62 | 27.04 |
| 31.26 | 23.92 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•oxalate (anhydrous), characterized as Form 13, wherein the crystalline solid comprises Compound 1 and oxalate in a 1:1 molar ratio. In one embodiment, Form 13 is characterized by one or more peaks on a 2-theta scale in an XRPD pattern selected from the group consisting of 12.67, 12.86, 13.63, 20.83, 21.28, 22.65, 23.59, 25.89, 26.55, and 26.60 degrees. In another embodiment, Form 13 is characterized by one or more peaks on a 2-theta scale in an XRPD pattern selected from the group consisting of 12.67, 13.63, 20.83, 22.65, 23.59, and 26.55 degrees. In a further embodiment, Form 13 is characterized by peaks at 12.67, 13.63, 20.83, 22.65, 23.59, and 26.55 degrees on a 2-theta scale in an XRPD pattern. In another further embodiment, Form 13 is characterized by peaks at 12.67, 13.63, 22.65, 23.59, and 26.55 degrees on a 2-theta scale in an XRPD pattern. In still a further embodiment, Form 13 is characterized by an XRPD pattern according to FIG. 5. In another further embodiment, Form 13 is characterized by an XRPD pattern having peak values according to Table 15.

TABLE 15

| Form 13 | |
|---|---|
| 2θ | Relative Intensity (%) |
| 12.67 | 49.07 |
| 12.86 | 28.41 |
| 13.63 | 65.97 |
| 20.83 | 37.19 |
| 21.28 | 27.03 |
| 22.65 | 100.00 |
| 23.59 | 45.84 |
| 25.89 | 29.45 |
| 26.55 | 39.75 |
| 26.60 | 35.81 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•pyruvate (anhydrous), characterized as Form 14, wherein the crystalline solid comprises Compound 1 and pyruvate in a 1:1 molar ratio. In one embodiment, Form 14 is characterized by one or more peaks on a 2-theta scale in an XRPD pattern selected from the group consisting of 7.84, 8.81, 11.58, 15.67, 16.30, 16.55, 17.67, 17.92, 18.00, 18.20, 18.62, 19.66, 20.54, 20.75, 23.84, 26.35, and 26.42 degrees. In another embodiment, Form 14 is characterized by one or more peaks on a 2-theta scale in an XRPD pattern selected from the group consisting of 8.81, 17.67, 23.84, and 26.42 degrees. In a further embodiment, Form 14 is characterized by peaks at 8.81, 17.67, 23.84, and 26.42 degrees on a 2-theta scale in an XRPD pattern. In another further embodiment, Form 14 is characterized by peaks at 8.81, 11.58, 17.67, 18.00, 23.84, and 26.35 degrees on a 2-theta scale in an XRPD pattern. In still a further embodiment, Form 14 is characterized by an XRPD pattern according to FIG. 5. In another further embodiment, Form 14 is characterized by an XRPD pattern having peak values according to Table 16.

TABLE 16

| Form 14 | |
|---|---|
| 2θ | Relative Intensity (%) |
| 7.84 | 19.94 |
| 8.81 | 29.73 |
| 11.58 | 28.31 |
| 15.67 | 22.49 |
| 16.30 | 22.56 |
| 16.55 | 19.61 |
| 17.67 | 33.68 |
| 17.92 | 21.55 |
| 18.00 | 24.02 |
| 18.20 | 18.83 |
| 18.62 | 19.80 |
| 19.66 | 16.87 |
| 20.54 | 16.54 |
| 20.75 | 21.33 |
| 23.84 | 100.00 |
| 26.35 | 34.88 |
| 26.42 | 22.64 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•besylate (1.4 molar equivalents of tetrahydrofuran), characterized as Form 15, wherein the crystalline solid comprises Compound 1 and besylate in a 1:1 molar ratio. In one embodiment, Form 15 is characterized by one or more peaks on a 2-theta scale in an XRPD pattern selected from the group consisting of 5.75, 10.42, 13.04, 15.59, 16.47, 17.95, 18.17, 18.85, 19.41, 20.90, 22.50, 23.24, and 24.36 degrees. In another embodiment, Form 15 is characterized by one or more peaks on a 2-theta scale in an XRPD pattern selected from the group consisting of 5.75, 10.42, 15.59, 16.47, and 24.36 degrees. In a further embodiment, Form 15 is characterized by peaks at 5.75, 10.42, 15.59, 16.47, and 24.36 degrees on a 2-theta scale in an XRPD pattern. In another further embodiment, Form 15 is characterized by peaks at 5.75, 10.42, 15.59, 16.47, 17.95, 18.17, and 24.36 degrees on a 2-theta scale in an XRPD pattern. In still a further embodiment, Form 15 is characterized by an XRPD pattern according to FIG. 5. In another further embodiment, Form 15 is characterized by an XRPD pattern having peak values according to Table 17.

TABLE 17

| Form 15 | |
|---|---|
| 2θ | Relative Intensity (%) |
| 5.75 | 100.00 |
| 10.42 | 52.58 |
| 13.04 | 18.12 |
| 15.59 | 34.24 |
| 16.47 | 39.17 |
| 17.95 | 30.64 |
| 18.17 | 34.46 |
| 18.85 | 25.65 |
| 19.41 | 20.77 |
| 20.90 | 24.88 |
| 22.50 | 30.47 |
| 23.24 | 29.38 |
| 24.36 | 40.92 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•mesylate dihydrate, characterized as Form 16, wherein the crystalline solid comprises Compound 1 and mesylate in a 1:1 molar ratio. In one embodiment, Form 16 is characterized by one or more peaks on a 2-theta scale in an XRPD pattern selected from the group consisting of 6.71, 9.70, 10.76, 13.35, 13.47, 15.67, 16.20, 18.65, 19.09, 19.33, 21.77, 21.87, 23.00, 23.98, 25.25, 26.86, and 27.19 degrees. In another embodiment, Form 16 is characterized by one or more peaks on a 2-theta scale in an XRPD pattern selected from the group consisting of 9.70, 13.47, 21.77, 21.87, 23.98, and 26.86 degrees. In a further embodiment, Form 16 is characterized by peaks at 9.70, 13.47, 21.77, 21.87, 23.98, and 26.86 degrees on a 2-theta scale in an XRPD pattern. In another further embodiment, Form 16 is characterized by peaks at 9.70, 13.35, 13.47, 19.33, 21.77, 21.87, 23.98, and 26.86 degrees on a 2-theta scale in an XRPD pattern. In still a further embodiment, Form 16 is characterized by an XRPD pattern according to FIG. 6. In another further embodiment, Form 16 is characterized by an XRPD pattern having peak values according to Table 18.

TABLE 18

| Form 16 | |
|---|---|
| 2θ | Relative Intensity (%) |
| 6.71 | 18.17 |
| 9.70 | 59.63 |
| 10.76 | 25.96 |
| 13.35 | 44.84 |
| 13.47 | 100.00 |
| 15.67 | 35.43 |

TABLE 18-continued

| Form 16 | |
|---|---|
| 2θ | Relative Intensity (%) |
| 16.20 | 25.26 |
| 18.65 | 25.03 |
| 19.09 | 25.70 |
| 19.33 | 37.30 |
| 21.77 | 48.80 |
| 21.87 | 49.48 |
| 23.00 | 25.44 |
| 23.98 | 91.31 |
| 25.25 | 29.44 |
| 26.86 | 50.21 |
| 27.19 | 35.69 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•succinate (0.4 molar equivalents of acetonitrile and 0.86 molar equivalents of water), characterized as Form 17, wherein the crystalline solid comprises Compound 1 and succinate in a 1:0.7 molar ratio (Compound 1 to succinate). In one embodiment, Form 17 is characterized by one or more peaks on a 2-theta scale in an XRPD pattern selected from the group consisting of 5.96, 6.74, 11.88, 12.15, 13.69, 13.74, 16.47, 20.43, 20.70, 22.85, 24.69, 24.76, and 26.59 degrees. In another embodiment, Form 17 is characterized by one or more peaks on a 2-theta scale in an XRPD pattern selected from the group consisting of 5.96, 6.74, 11.88, 13.74, 20.70, and 24.76 degrees. In a further embodiment, Form 17 is characterized by peaks at 5.96, 6.74, 11.88, 13.74, 20.70, and 24.76 degrees on a 2-theta scale in an XRPD pattern. In another further embodiment, Form 17 is characterized by peaks at 6.74, 11.88, 20.70, 24.69, 24.76, and 26.59 degrees on a 2-theta scale in an XRPD pattern. In still a further embodiment, Form 17 is characterized by an XRPD pattern according to FIG. 6. In another further embodiment, Form 17 is characterized by an XRPD pattern having peak values according to Table 19.

TABLE 19

| Form 17 | |
|---|---|
| 2θ | Relative Intensity (%) |
| 5.96 | 34.77 |
| 6.74 | 82.57 |
| 11.88 | 100.00 |
| 12.15 | 36.46 |
| 13.69 | 33.30 |
| 13.74 | 36.80 |
| 16.47 | 35.44 |
| 20.43 | 37.25 |
| 20.70 | 57.89 |
| 22.85 | 30.96 |
| 24.69 | 61.62 |
| 24.76 | 59.65 |
| 26.59 | 43.91 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•esylate (0.4 molar equivalents of acetonitrile), characterized as Form 18, wherein the crystalline solid comprises Compound 1 and esylate in a 1:1 molar ratio. In one embodiment, Form 18 is characterized by one or more peaks on a 2-theta scale in an XRPD pattern selected from the group consisting of 9.45, 9.86, 15.31, 16.85, 20.83, 21.72, 22.82, and 24.60 degrees. In another embodiment, Form 18 is characterized by one or more peaks on a 2-theta scale in an XRPD pattern selected from the group consisting of 9.45, 9.86, 20.83, and 21.72 degrees. In a further embodiment, Form 18 is characterized by peaks at 9.45, 9.86, 20.83, and 21.72 degrees on a 2-theta scale in an XRPD pattern. In another further embodiment, Form 18 is characterized by peaks at 9.45, 9.86, 20.83, 21.72, and 24.60 degrees on a 2-theta scale in an XRPD pattern. In still a further embodiment, Form 18 is characterized by an XRPD pattern according to FIG. 6. In another further embodiment, Form 18 is characterized by an XRPD pattern having peak values according to Table 20.

TABLE 20

| Form 18 | |
|---|---|
| 2θ | Relative Intensity (%) |
| 9.45 | 50.39 |
| 9.86 | 54.92 |
| 15.31 | 25.33 |
| 16.85 | 25.19 |
| 20.83 | 100.00 |
| 21.72 | 67.97 |
| 22.82 | 25.97 |
| 24.60 | 42.96 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•isethionate monohydrate, characterized as Form 19, wherein the crystalline solid comprises Compound 1 and isethionate in a 1:1 molar ratio. In one embodiment, Form 19 is characterized by one or more peaks on a 2-theta scale in an XRPD pattern selected from the group consisting of 8.54, 11.10, 12.22, 12.67, 14.12, 17.19, 18.73, 22.19, and 24.33 degrees. In another embodiment, Form 19 is characterized by one or more peaks on a 2-theta scale in an XRPD pattern selected from the group consisting of 8.54, 12.67, 22.19, and 24.33 degrees. In a further embodiment, Form 19 is characterized by peaks at 8.54, 12.67, 22.19, and 24.33 degrees on a 2-theta scale in an XRPD pattern. In a further embodiment, Form 19 is characterized by peaks at 8.54, 11.10, 12.67, 14.12, 22.19, and 24.33 degrees on a 2-theta scale in an XRPD pattern. In still a further embodiment, Form 19 is characterized by an XRPD pattern according to FIG. 7. In another further embodiment, Form 19 is characterized by an XRPD pattern having peak values according to Table 21.

TABLE 21

| Form 19 | |
|---|---|
| 2θ | Relative Intensity (%) |
| 8.54 | 100.00 |
| 11.10 | 40.77 |
| 12.22 | 38.21 |
| 12.67 | 72.83 |
| 14.12 | 41.22 |
| 17.19 | 37.21 |
| 18.73 | 38.42 |
| 22.19 | 49.83 |
| 24.33 | 44.13 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•glutarate (0.59 molar equivalents of water), characterized as Form 20, wherein the crystalline solid comprises Compound 1 and glutarate in a 1:1 molar ratio. In one embodiment, Form 20 is characterized by one or more peaks on a 2-theta scale in an XRPD pattern selected from the group consisting of 8.06, 11.77, 19.97, 20.21, 22.27, 23.11, 23.17, 25.81, 25.87, 26.00, and 26.06 degrees. In another embodiment, Form 20 is characterized by one or more peaks on a 2-theta scale in an XRPD pattern selected from the group consisting of 8.06, 11.77, 20.21, 22.27, and 26.06 degrees. In a further embodiment, Form 20 is characterized by peaks at 8.06, 11.77, 20.21, 22.27, and 26.06 degrees on a 2-theta scale in an XRPD pattern. In a further embodiment, Form 20 is characterized by peaks at 8.06, 11.77, 20.21, 22.27, 23.11, 25.81, 25.87, and 26.00 degrees on a 2-theta scale in an XRPD pattern. In still a further embodiment, Form 20 is characterized by an XRPD pattern according to FIG. 7. In another further embodiment, Form 20 is characterized by an XRPD pattern having peak values according to Table 22.

TABLE 22

| Form 20 | |
| --- | --- |
| 2θ | Relative Intensity (%) |
| 8.06 | 47.38 |
| 11.77 | 46.03 |
| 19.97 | 41.28 |
| 20.21 | 55.57 |
| 22.27 | 100.00 |
| 23.11 | 71.55 |
| 23.17 | 39.02 |
| 25.81 | 78.71 |
| 25.87 | 51.94 |
| 26.00 | 49.11 |
| 26.06 | 36.46 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•sulfate monohydrate, characterized as Form 21, wherein the crystalline solid comprises Compound 1 and sulfate in a 1:1 molar ratio. In one embodiment, Form 21 is characterized by one or more peaks on a 2-theta scale in an XRPD pattern selected from the group consisting of 6.61, 13.26, 13.60, 14.67, 16.40, 17.66, 19.96, 20.37, 20.76, 21.09, 21.25, and 23.30 degrees. In another embodiment, Form 21 is characterized by one or more peaks on a 2-theta scale in an XRPD pattern selected from the group consisting of 6.61, 13.60, 20.37, 20.76, 21.09, and 23.30 degrees. In a further embodiment, Form 21 is characterized by peaks at 6.61, 13.60, 20.37, 20.76, 21.09, and 23.30 degrees on a 2-theta scale in an XRPD pattern. In another further embodiment, Form 21 is characterized by peaks at 13.60, 20.37, 20.76, 21.09, and 23.30 degrees on a 2-theta scale in an XRPD pattern. In still a further embodiment, Form 21 is characterized by an XRPD pattern according to FIG. 7. In another further embodiment, Form 21 is characterized by an XRPD pattern having peak values according to Table 23.

TABLE 23

| Form 21 | |
| --- | --- |
| 2θ | Relative Intensity (%) |
| 6.61 | 48.77 |
| 13.26 | 40.99 |
| 13.60 | 91.27 |
| 14.67 | 42.40 |

TABLE 23-continued

| Form 21 | |
| --- | --- |
| 2θ | Relative Intensity (%) |
| 16.40 | 37.43 |
| 17.66 | 42.58 |
| 19.96 | 34.17 |
| 20.37 | 58.18 |
| 20.76 | 66.31 |
| 21.09 | 52.18 |
| 21.25 | 40.45 |
| 23.30 | 100.00 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•tosylate (0.8 molar equivalents of water), characterized as Form 22, wherein the crystalline solid comprises Compound 1 and tosylate in a 1:1 molar ratio. In one embodiment, Form 22 is characterized by one or more peaks on a 2-theta scale in an XRPD pattern selected from the group consisting of 13.75, 14.20, 14.77, 18.05, 19.28, 19.88, 20.51, 22.63, 25.41, 25.48, and 27.29 degrees. In another embodiment, Form 22 is characterized by one or more peaks on a 2-theta scale in an XRPD pattern selected from the group consisting of 13.75, 14.77, 18.05, 19.88, 22.63, and 25.41 degrees. In a further embodiment, Form 22 is characterized by peaks at 13.75, 14.77, 18.05, 19.88, 22.63, and 25.41 degrees on a 2-theta scale in an XRPD pattern. In still a further embodiment, Form 22 is characterized by an XRPD pattern according to FIG. 8. In another further embodiment, Form 22 is characterized by an XRPD pattern having peak values according to Table 24.

TABLE 24

| Form 22 | |
| --- | --- |
| 2θ | Relative Intensity (%) |
| 13.75 | 64.13 |
| 14.20 | 37.16 |
| 14.77 | 66.83 |
| 18.05 | 100.00 |
| 19.28 | 35.53 |
| 19.88 | 55.33 |
| 20.51 | 42.49 |
| 22.63 | 64.15 |
| 25.41 | 89.50 |
| 25.48 | 52.94 |
| 27.29 | 38.14 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•succinate (0.8 molar equivalents of water), characterized as Form 23, wherein the crystalline solid comprises Compound 1 and succinate in a 1:0.6 molar ratio. In one embodiment, Form 23 is characterized by one or more peaks on a 2-theta scale in an XRPD pattern selected from the group consisting of 6.35, 11.82, 12.20, 12.47, 13.76, 17.86, 18.04, 20.96, 21.96, 22.96, 23.79, 24.10, 24.96, and 25.59 degrees. In another embodiment, Form 23 is characterized by one or more peaks on a 2-theta scale in an XRPD pattern selected from the group consisting of 11.82, 12.47, 22.96, and 24.96 degrees. In a further embodiment, Form 23 is characterized by peaks at 11.82, 12.47, 22.96, and 24.96 degrees on a 2-theta scale in an XRPD pattern. In another further embodiment, Form 23 is characterized by peaks at 11.82, 12.47, 17.86, 22.96, 23.79, and 24.96 degrees on a 2-theta scale in an XRPD pattern. In still a further embodiment, Form 23 is characterized by an XRPD pattern according to FIG. 8. In another further embodiment, Form 23 is characterized by an XRPD pattern having peak values according to Table 25.

TABLE 25

Form 23

| 2θ | Relative Intensity (%) |
|---|---|
| 6.35 | 37.04 |
| 11.82 | 85.55 |
| 12.20 | 45.18 |
| 12.47 | 100.00 |
| 13.76 | 35.31 |
| 17.86 | 64.71 |
| 18.04 | 40.96 |
| 20.96 | 36.92 |
| 21.96 | 49.64 |
| 22.96 | 76.81 |
| 23.79 | 61.31 |
| 24.10 | 50.29 |
| 24.96 | 80.63 |
| 25.59 | 48.68 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•malonate (anhydrous), characterized as Form 24, wherein the crystalline solid comprises Compound 1 and malonate in a 1:1 molar ratio. In one embodiment, Form 24 is characterized by one or more peaks on a 2-theta scale in an XRPD pattern selected from the group consisting of 6.77, 12.36, 12.86, 21.02, 22.85, 23.61, 25.12, 26.31, 28.01, and 30.36 degrees. In another embodiment, Form 24 is characterized by one or more peaks on a 2-theta scale in an XRPD pattern selected from the group consisting of 12.36, 12.86, 21.02, 22.85, 23.61, and 25.12 degrees. In a further embodiment, Form 24 is characterized by peaks at 12.36, 12.86, 21.02, 22.85, 23.61, and 25.12 degrees on a 2-theta scale in an XRPD pattern. In still a further embodiment, Form 24 is characterized by an XRPD pattern according to FIG. 8. In another further embodiment, Form 24 is characterized by an XRPD pattern having peak values according to Table 26.

TABLE 26

Form 24

| 2θ | Relative Intensity (%) |
|---|---|
| 6.77 | 35.81 |
| 12.36 | 80.89 |
| 12.86 | 83.28 |
| 21.02 | 54.92 |
| 22.85 | 62.92 |
| 23.61 | 80.96 |
| 25.12 | 100.00 |
| 26.31 | 38.90 |
| 28.01 | 37.61 |
| 30.36 | 20.24 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•mesylate (0.3 molar equivalents of acetonitrile), characterized as Form 25, wherein the crystalline solid comprises Compound 1 and mesylate in a 1:1 molar ratio. In one embodiment, Form 25 is characterized by one or more peaks on a 2-theta scale in an XRPD pattern selected from the group consisting of 9.42, 9.75, 10.72, 11.98, 15.52, 17.71, 19.51, 19.66, 21.65, 21.96, 22.54, 23.35, 24.55, and 25.92 degrees. In another embodiment, Form 25 is characterized by one or more peaks on a 2-theta scale in an XRPD pattern selected from the group consisting of 9.42, 9.75, 19.66, 21.65, 22.54, 23.35, and 24.55 degrees. In a further embodiment, Form 25 is characterized by peaks at 9.42, 9.75, 19.66, 21.65, 22.54, 23.35, and 24.55 degrees on a 2-theta scale in an XRPD pattern. In still a further embodiment, Form 25 is characterized by an XRPD pattern according to FIG. 9. In another further embodiment, Form 25 is characterized by an XRPD pattern having peak values according to Table 27.

TABLE 27

Form 25

| 2θ | Relative Intensity (%) |
|---|---|
| 9.42 | 36.69 |
| 9.75 | 100.00 |
| 10.72 | 17.26 |
| 11.98 | 29.71 |
| 15.52 | 26.67 |
| 17.71 | 19.68 |
| 19.51 | 20.00 |
| 19.66 | 38.10 |
| 21.65 | 84.01 |
| 21.96 | 17.63 |
| 22.54 | 73.54 |
| 23.35 | 56.68 |
| 24.55 | 37.86 |
| 25.92 | 33.51 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•gluconate (2.6 molar equivalents of water), characterized as Form 26, wherein the crystalline solid comprises Compound 1 and gluconate in a 1:1 molar ratio. In one embodiment, Form 26 is characterized by one or more peaks on a 2-theta scale in an XRPD pattern selected from the group consisting of 10.50, 10.59, 13.58, 13.98, 14.05, 18.71, 21.01, 22.59, 23.24, 24.35, 25.38, 25.46, 26.73, 26.88, 27.40, and 27.96 degrees. In another embodiment, Form 26 is characterized by one or more peaks on a 2-theta scale in an XRPD pattern selected from the group consisting of 13.58, 13.98, 22.59, and 25.46 degrees. In a further embodiment, Form 26 is characterized by peaks at 13.58, 13.98, 22.59, and 25.46 degrees on a 2-theta scale in an XRPD pattern. In another further embodiment, Form 26 is characterized by peaks at 13.58, 13.98, 14.05, 22.59, 25.35, and 25.46 degrees on a 2-theta scale in an XRPD pattern. In still a further embodiment, Form 26 is characterized by an XRPD pattern according to FIG. 9. In another further embodiment, Form 26 is characterized by an XRPD pattern having peak values according to Table 28.

TABLE 28

Form 26

| 2θ | Relative Intensity (%) |
|---|---|
| 10.50 | 26.15 |
| 10.59 | 28.32 |
| 13.58 | 100.00 |
| 13.98 | 47.54 |
| 14.05 | 37.72 |
| 18.71 | 27.02 |
| 21.01 | 30.19 |
| 22.59 | 45.50 |

TABLE 28-continued

Form 26

| 2θ | Relative Intensity (%) |
|---|---|
| 23.24 | 27.89 |
| 24.35 | 31.45 |
| 25.38 | 44.19 |
| 25.46 | 48.12 |
| 26.73 | 21.49 |
| 26.88 | 19.13 |
| 27.40 | 21.45 |
| 27.96 | 16.13 |

In one aspect, the invention includes Crystalline solid N-{4-[(6,7-dimethoxyquinolin-4-yl)oxy]phenyl}-N'-(4-fluorophenyl) cyclopropane-1,1-dicarboxamide (Compound 1)•isethionate monohydrate, characterized as Form 27, wherein the crystalline solid comprises Compound 1 and isethionate in a 1:1 molar ratio. In one embodiment, Form 27 is characterized by one or more peaks on a 2-theta scale in an XRPD pattern selected from the group consisting of 6.56, 12.39, 12.59, 13.14, 16.57, 17.55, 21.68, 23.66, 24.33, 26.09, 26.53, 26.69, and 27.40 degrees. In another embodiment, Form 27 is characterized by one or more peaks on a 2-theta scale in an XRPD pattern selected from the group consisting of 12.39, 12.59, 17.55, 21.68, 23.66, and 26.09 degrees. In a further embodiment, Form 27 is characterized by peaks at 12.39, 12.59, 17.55, 21.68, 23.66, and 26.09 degrees on a 2-theta scale in an XRPD pattern. In a further embodiment, Form 27 is characterized by peaks at 12.39, 12.59, 17.55, 21.68, 23.66, 24.33, and 26.09 degrees on a 2-theta scale in an XRPD pattern. In still a further embodiment, Form 27 is characterized by an XRPD pattern according to FIG. 9. In another further embodiment, Form 27 is characterized by an XRPD pattern having peak values according to Table 29.

TABLE 29

Form 27

| 2θ | Relative Intensity (%) |
|---|---|
| 6.56 | 42.00 |
| 12.39 | 100.00 |
| 12.59 | 93.66 |
| 13.14 | 25.50 |
| 16.57 | 49.22 |
| 17.55 | 90.99 |
| 21.68 | 57.20 |
| 23.66 | 84.95 |
| 24.33 | 61.05 |
| 26.09 | 65.46 |
| 26.53 | 42.97 |
| 26.69 | 35.13 |
| 27.40 | 29.37 |

In another aspect, the invention includes a pharmaceutical composition comprising a therapeutically effective amount of a substantially pure crystalline solid form of a salt of Compound 1 as described herein, and a pharmaceutically acceptable carrier.

In still another aspect, the invention includes a pharmaceutical composition comprising a therapeutically effective amount of a mixture of crystalline solid forms of a salt of Compound 1 as described herein, and a pharmaceutically acceptable carrier.

In another aspect, the invention includes a method of treating cancer comprising administering to a subject a therapeutically effective amount of a crystalline solid form of a salt of Compound 1 as described herein.

In still another aspect, the invention includes a method of treating cancer comprising administering to a subject a pharmaceutical composition as described herein.

In one embodiment of this aspect, the cancer is selected from thyroid cancer, stomach cancer, esophageal carcinoma, kidney cancer, liver cancer, ovarian carcinoma, cervical carcinoma, large bowel cancer, small bowel cancer, brain cancer, lung cancer, bone cancer, prostate carcinoma, pancreatic carcinoma, skin cancer, bone cancer, lymphoma, solid tumors, Hodgkin's disease, or non-Hodgkin's lymphoma.

In a further embodiment, the thyroid cancer is medullary thyroid cancer.

In another further embodiment, the kidney cancer is renal cell carcinoma.

In another embodiment, the liver cancer is hepatocellular carcinoma.

In another embodiment, the brain cancer is an astrocytic tumor.

In a further embodiment, the astrocytic tumor is selected from a glioblastoma, a giant cell glioblastoma, and a gliosarcoma.

In still a further embodiment, the glioblastoma possesses oligodendroglial components.

In one embodiment, the lung cancer is non-small cell lung cancer.

In another embodiment, the prostate carcinoma is castration resistant prostate cancer.

In another aspect, the invention includes a method of treating diseases or disorders associated with uncontrolled, abnormal, and/or unwanted cellular activities due to cMET or RET overexpression, comprising administering to a subject in need of such treatment a therapeutically effective amount of at least one solid form of Compound 1 as disclosed herein.

In still another aspect, the invention includes a method of treating diseases or disorders associated with uncontrolled, abnormal, and/or unwanted cellular activities due to cMET or RET overexpression, comprising administering to a subject in need of such treatment a therapeutically effective amount of a pharmaceutical composition as disclosed herein.

Pharmaceutical Compositions and Methods of Treatment

Another aspect of this disclosure relates to a pharmaceutical composition comprising at least one crystalline solid form of Compound 1 as described herein in any of the aspects and/or embodiments, or combinations thereof, and a pharmaceutically acceptable excipient. Pharmaceutical compositions of Compound 1 have been disclosed in, for example, commonly assigned PCT Patent Publication Nos. WO 2005/030140, WO 2012/009722, and WO 2012/109510, each of which is incorporated by reference herein in its entirety.

The amount of the crystalline Compound 1 solid form or combinations thereof in the pharmaceutical composition can be a therapeutically effective amount. The crystalline solid forms of Compound 1 may individually be present in the pharmaceutical composition or as combinations. The crystalline solid forms as disclosed herein include Forms 1-27. Accordingly, another aspect of this disclosure relates to a solid or dispersion pharmaceutical composition comprising at least one of a therapeutically effective amount of a solid form of Compound 1, as described herein in any of the aspects and/or embodiments, or combinations thereof, and a pharmaceutically acceptable excipient.

A pharmaceutical composition such as disclosed herein may be any pharmaceutical form which contains an active crystalline Compound 1 solid form. The pharmaceutical composition may be, for example, a tablet, capsule, liquid suspension, injectable, topical, or transdermal. The pharmaceutical compositions generally contain about 1% to about 99% by weight of the active compound(s), or a solid form of the active compound(s), and 99% to 1% by weight of a suitable pharmaceutical excipient. In one example, the composition will be between about 5% and about 75% by weight of active compound, with the rest being suitable pharmaceutical excipients or other adjuvants, as discussed below.

The actual amount required for treatment of any particular subject will depend upon a variety of factors, including the disease state being treated and its severity; the specific pharmaceutical composition employed; the age, body weight, general health, sex, and diet of the subject; the mode of administration; the time of administration; the route of administration; and the rate of excretion of the active compound(s), or a solid form of the active compound(s), according to this disclosure; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173, 2001, which is incorporated herein by reference. The active compound(s), or a solid form of active compound(s), according to this disclosure and pharmaceutical compositions comprising them, may be used in combination with anticancer or other agents that are generally administered to a subject being treated for cancer. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends partly upon the desired method of administration to be used. For a pharmaceutical composition of this disclosure, that is, one of the active compound(s), or a solid form of the active compound(s), of this disclosure, a carrier should be chosen so as to substantially maintain the particular form of the active compound(s), whether it would be solid or not. In other words, the carrier should not substantially alter the form of the active compound(s). Nor should the carrier be otherwise incompatible with the form of the active compound(s), such as by producing any undesirable biological effect or otherwise interacting in a deleterious manner with any other component(s) of the pharmaceutical composition.

Filler

As indicated above, the pharmaceutical composition containing Compound 1 comprises a filler. Fillers are inert ingredients added to adjust the bulk in order to produce a size practical for compression. Examples of fillers include sodium starch glycolate, corn starch, talc, sucrose, dextrose, glucose, lactose, xylitol, fructose, sorbitol, calcium phosphate, calcium sulfate, calcium carbonate, and the like, or mixtures thereof. Microcrystalline cellulose may also be used as a filler and may be any suitable form of microcrystalline cellulose as is known and used in the tabletting art. Preferably, a mixture of lactose and microcrystalline cellulose is used as the filler. In one embodiment, the lactose is anhydrous lactose sold as Lactose 60M, which is readily commercially available from a number of suppliers. In one embodiment, the microcrystalline cellulose is Avicel PH-102, which is also commercially available.

Preferably, filler(s) are present in an amount of from about 50 to about 70 percent, and more preferably from about 57 to about 67 percent, by weight on a solids basis of the directly compressible formulation. Preferably, lactose is present in an amount of from about 18 to 22 percent by weight. Preferably, the microcrystalline cellulose is present in an amount of from about 38 to 40 percent by weight.

Binder

The pharmaceutical composition containing Compound 1 also comprises a binder. Binders are added to powders to impart cohesive qualities to the powder, which allows the compressed tablet to retain its integrity. The binder can be any pharmaceutically acceptable binder available in the tabletting art, such as acacia, alginic acid, carbomer, carboxymethylcellulose sodium, dextrin, ethylcellulose, gelatin, guar gum, hydrogenated vegetable oil (type I), hydroxyethyl cellulose, hydroxypropyl cellulose, hydroxypropyl methylcellulose, liquid glucose, magnesium aluminum silicate, maltodextrin, methylcellulose, polymethacrylates, povidone, pregelatinized starch, sodium alginate, starch, zein, and the like, or mixtures thereof.

The preferred binder is hydroxypropyl cellulose preferably in an amount of from about 2 to about 4 percent by weight on a solid basis of the directly compressible formulation. In one embodiment, the hydroxypropyl cellulose is commercially available Klucel EXF.

Disintegrant

The pharmaceutical composition containing Compound 1 also comprises a disintegrant. A disintegrant is a substance or a mixture of substances added to facilitate breakup or disintegrate after administration. The disintegrant may be any pharmaceutically acceptable disintegrant available in the tabletting art, including alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium alginate, starch, and the like, or mixtures thereof.

The preferred disintegrant is croscarmellose sodium, in an amount of from about 4 to about 8 percent by weight, on a solid basis of the directly compressible formulation. In one embodiment, the croscarmellose sodium is commercially available Ac-Di-Sol.

Glidant

The pharmaceutical composition containing Compound 1 also comprises a glidant. The glidant may be any pharmaceutically acceptable glidant which contributes to the compressibility, flowability, and homogeneity of the formulation and which minimizes segregation and does not significantly interfere with the release mechanism of the binders as set forth above. Preferably, the glidant is selected to improve the flow of the formulation. Silicon dioxide, particularly colloidal silicon dioxide, is preferred as a glidant.

The glidant is used in an amount of from about 0.2 to about 0.6 percent by weight on a solid basis of the directly compressible formulation. More particularly, silicon dioxide, particularly colloidal silicon dioxide, is used in an amount of from about 0.2 to about 0.6 percent by weight on a solid basis of the directly compressible formulation.

Lubricant

The pharmaceutical composition containing Compound 1 also comprises a lubricant. Lubricants are employed to prevent adhesion of the tablet material to the surface of dyes and punches. The lubricant may be any pharmaceutically acceptable lubricant which substantially prevents segregation of the powder by contributing to homogeneity of the formulation and which exhibits good flowability. Preferably, the lubricant functions to facilitate compression of the tablets and ejection of the tablets from the die cavity. Such lubricants may be hydrophilic or hydrophobic, and examples include magnesium stearate, Lubritab®, stearic acid, talc, and other lubricants known in the art or to be developed which exhibit acceptable or comparable properties, or mixtures thereof. Examples of lubricants include calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, zinc stearate, and the like, or mixtures thereof.

The lubricant should be selected to aid in the flow of the powder in the hopper and into the die. Magnesium stearate exhibits excellent properties in combination with the other preferred excipients of the formulation. Magnesium stearate contributes to reducing friction between the die wall and tablet formulation during compression, as well as to the easy ejection of the Compound 1 tablets. It also resists adhesion to punches and dies.

Preferably, the lubricant is magnesium stearate (non-bovine) used in an amount of from about 0.5 to about 1.0 percent by weight on a solid basis of the directly compressible formulation.

Film Coating

The pharmaceutical composition containing Compound 1 also comprises an optional film coating. The film coat concentration can be about 1 to about 10 percent by weight on a solid basis of the directly compressible formulation. Film coating suspensions may include combinations of the following components: hypromellose, carboxymethylcellulose sodium, carnauba wax, cellulose acetate phthalate, cetyl alcohol, confectioner's sugar, ethyl cellulose, gelatin, hydroxyethyl cellulose, hydroxypropyl cellulose, hydroxypropyl methylcellulose, liquid glucose, maltodextrin, methyl cellulose, microcrystalline wax, Opadry and Opadry II, polymethacrylates, polyvinyl alcohol, shellac, sucrose, talc, titanium dioxide, and zein.

Other Adjuvants

Other pharmaceutically acceptable adjuvants known in the pharmaceutical formulation art may also be used in the pharmaceutical compositions of this disclosure. These include, but are not limited to, preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. If desired, a pharmaceutical composition of this disclosure may also contain minor amounts of auxiliary substances such as wetting or emulsifying agents, pH buffering agents, and antioxidants, such as, for example, citric acid, sorbitan monolaurate, triethanolamine oleate, and butylated hydroxytoluene.

The pharmaceutical compositions of this disclosure may be prepared by methods know in the pharmaceutical formulation art, for example, see Remington's Pharmaceutical Sciences, 18$^{th}$ Ed., (Mack Publishing Company, Easton, Pa., 1990). In solid dosage forms, any one of Forms 1-27, or combinations thereof, is admixed with at least one pharmaceutically acceptable excipient such as sodium citrate or dicalcium phosphate or (a) fillers or extenders, as for example, starches, lactose, sucrose, glucose, mannitol, and silicic acid, (b) binders, as for example, cellulose derivatives, starch, alginates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

In some instances, the pharmaceutical dosage form may be a solid dispersion. The term "solid dispersion" refers to a system in a solid state comprising at least two components, wherein one component is dispersed throughout the other component or components. For example, the solid dispersion can be an amorphous solid dispersion. The tem "amorphous solid dispersion," as used herein, refers to stable solid dispersions comprising amorphous drug substance (Compound 1) and a stabilizing polymer. By "amorphous drug substance," it is meant that the amorphous solid dispersion contains a drug substance in a substantially amorphous solid form—that is at least 80% of the drug substance in the dispersion is in an amorphous form. More preferably, at least 90%, and most preferably at least 95%, of the drug substance in the dispersion is in amorphous form. The term "stabilizing polymer" means any polymer known to the skilled practitioner that is used to stabilize an amorphous drug substance in a solid dispersion, such as those described, for instance, in Remington's Pharmaceutical Sciences, 18$^{th}$ Ed., (Mack Publishing Company, Easton, Pa., 1990).

Processes for making such solid dispersions are also available to the skilled practitioner and include, for instance, spray drying, melt extrusion, freeze drying, rotary evaporation, drum drying, or other solvent removal processes. In the spray drying process, the amorphous dispersion is formed by dispersing or dissolving the drug substance and the stabilizing polymer in a suitable solvent to form a feed solution, pumping the feed solution through an atomizer into a drying chamber, and removing the solvent to form the amorphous solid dispersion powder in the drying chamber. A drying chamber uses hot gases, such as forced air, nitrogen, nitrogen-enriched air, or argon to dry particles. The feed solution can be atomized by conventional means well known in the art, such as a two-fluid sonicating nozzle and a two-fluid non-sonicating nozzle.

Solid dosage forms as described above can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the active compound(s), or a solid form of the active compound(s), with, for example, suitable non-irritating excipients or carriers such as cocoa butter, polyethyleneglycol, or a suppository wax, which are solid at ordinary temperatures but liquid at body temperature and therefore melt while in a suitable body cavity and release the active component therein.

Solid dosage forms are preferred for the pharmaceutical composition of this disclosure. Solid dosage forms for oral administration, which includes capsules, tablets, pills, powders, and granules, are particularly preferred. In such solid dosage forms, the active compound(s) mixed with at least one inert, pharmaceutically acceptable excipient (also known as a pharmaceutically acceptable carrier). Administration of the active compound(s), or a solid form of the active compound(s), in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, and aerosols, and the like, preferably in unit dosage forms suitable for simple administration of precise dosages. One preferable route of administration is oral administration, using a convenient dosage regimen that can be adjusted according to the degree of severity of the disease-state to be treated. For example, the dosage regimen can be as a capsule or tablet for oral administration.

The skilled artisan will recognize that a greater amount of Compound 1 as one of the salt forms described herein is present to provide a certain amount of Compound 1. For example, the molecular weight of Compound 1 is 501.51, and the molecular weight of Compound 1, pyruvate salt is 589.56. Thus, 117.56 mg of Compound 1, pyruvate salt is required is required to provide 100 mg of Compound 1. The "free base equivalent" (fbe) of a tablet containing 117.56 mg of Compound 1, pyruvate is 100 mg Compound 1. Proportionally smaller or larger amounts of Compound 1 L-malate salt are required for tablet compositions containing less or more of Compound 1.

In another aspect, the disclosure relates to a pharmaceutical composition comprising a Compound 1 in at least one of forms disclosed herein and a pharmaceutically acceptable carrier containing less than 100 ppm of 6,7-dimethoxy-quinoline-4-ol. 6,7-dimethoxy-quinoline-4-ol, the structure of which is

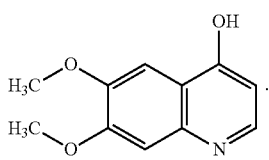

Minimizing the concentration of degradation products, contaminants, or byproducts such as 6,7-dimethoxy-quinoline-4-ol in pharmaceutical compositions destined for human administration is desirable. In one embodiment, a pharmaceutical composition comprising a Compound 1 in at least one of forms disclosed herein and a pharmaceutically acceptable carrier containing less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 2.5 ppm of 6,7-dimethoxy-quinoline-4-ol. 6,7-dimethoxy-quinoline-4-ol, the structure of which is

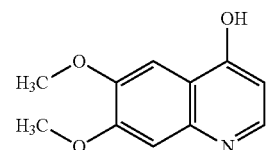

In another aspect, a pharmaceutical composition comprising a Compound 1 in at least one of forms disclosed herein and a pharmaceutically acceptable carrier containing 1 to 100 ppm, 1 to 80 ppm, 1 to 60 ppm, 1 to 40 ppm, 1 to 20 ppm, 1 to 10 ppm, 1 to 5 ppm, or 1 to 2.5 ppm of 6,7-dimethoxy-quinoline-4-ol. 6,7-dimethoxy-quinoline-4-ol, the structure of which is

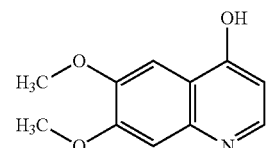

In another aspect, a pharmaceutical composition comprising a Compound 1 in at least one of forms disclosed herein and a pharmaceutically acceptable carrier containing 0.1 to 100 ppm, 0.1 to 80 ppm, 0.1 to 60 ppm, 0.1 to 40 ppm, 0.1 to 20 ppm, 0.1 to 10 ppm, 0.1 to 5 ppm, 0.1 to 2.5 ppm, or 0.1 to 1 ppm of 6,7-dimethoxy-quinoline-4-ol. 6,7-dimethoxy-quinoline-4-ol, the structure of which is

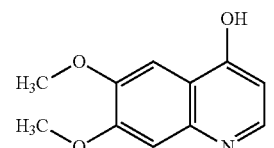

Capsule Formulation

In one embodiment, the dosage regimen is as a capsule formulation for oral administration.

In one embodiment, the capsule formulation comprises:
  5-60 percent by weight of Compound 1 in at least one of the forms disclosed herein;
  30-80 percent by weight of one or more fillers;
  1-15 percent by weight of one or more disintegrants;
  0.1 to 1.0 percent by weight of a glidant; and
  0.1 to 4.0 percent by weight of a lubricant.

In another embodiment, the capsule formulation comprises:
  5-60 percent by weight of Compound 1 in at least one of the forms disclosed herein;
  30-80 percent by weight of one or more fillers;
  2-12 percent by weight of one or more disintegrants;
  0.1 to 0.6 percent by weight of a glidant; and
  0.1 to 3.0 percent by weight of a lubricant.

In another embodiment, the capsule formulation comprises:
- 5-15 percent by weight of Compound 1 in at least one of the forms disclosed herein;
- 70-80 percent by weight of one or more fillers;
- 8-12 percent by weight of one or more disintegrants;
- 0.1 to 0.4 percent by weight of a glidant; and
- 0.1 to 2.0 percent by weight of a lubricant.

In another embodiment, the capsule formulation comprises:
- 5-15 percent by weight of Compound 1 in at least one of the forms disclosed herein;
- 70-80 percent by weight of one or more fillers;
- 9-11 percent by weight of one or more disintegrants;
- 0.2 to 0.4 percent by weight of a glidant; and
- 0.5 to 1.5 percent by weight of a lubricant.

In another embodiment, the capsule formulation comprises:
- 40-60 percent by weight of Compound 1 in at least one of the forms disclosed herein;
- 30-50 percent by weight of one or more fillers;
- 2-12 percent by weight of one or more disintegrants;
- 0.1 to 0.6 percent by weight of a glidant; and
- 0.1 to 3.0 percent by weight of a lubricant.

In another embodiment, the capsule formulation comprises:
- 45-55 percent by weight of Compound 1 in at least one of the forms disclosed herein;
- 35-40 percent by weight of one or more fillers;
- 8-12 percent by weight of one or more disintegrants;
- 0.2 to 0.5 percent by weight of a glidant; and
- 0.5 to 2.5 percent by weight of a lubricant.

In another embodiment, the capsule formulation comprises:
- 5-60 percent by weight of Compound 1 in at least one of the forms disclosed herein;
- 30-80 percent by weight of microcrystalline cellulose;
- 2-7 percent by weight of croscarmellose sodium;
- 2-7 percent by weight of sodium starch glycolate;
- 0.1 to 1.0 percent by weight of a fumed silica; and
- 0.1 to 4.0 percent by weight of stearic acid.

In another embodiment, the capsule formulation comprises:
- 5-60 percent by weight of Compound 1 in at least one of the forms disclosed herein;
- 30-80 percent by weight of microcrystalline cellulose;
- 3-6 percent by weight of croscarmellose sodium;
- 3-6 percent by weight of sodium starch glycolate;
- 0.1 to 0.6 percent by weight of fumed silica; and
- 0.1 to 3.0 percent by weight of stearic acid.

In another embodiment, the capsule formulation comprises:
- 5-15 percent by weight of Compound 1 in at least one of the forms disclosed herein;
- 70-80 percent by weight of microcrystalline cellulose;
- 4-6 percent by weight of croscarmellose sodium;
- 4-6 percent by weight of sodium starch glycolate;
- 0.1 to 0.4 percent by weight of fumed silica; and
- 0.1 to 2.0 percent by weight of stearic acid.

In another embodiment, the capsule formulation comprises:
- 5-15 percent by weight of Compound 1 in at least one of the forms disclosed herein;
- 70-80 percent by weight of microcrystalline cellulose;
- 4.5-5.5 percent by weight of croscarmellose sodium;
- 4.5-5.5 percent by weight of sodium starch glycolate;
- 0.2 to 0.4 percent by weight of fumed silica; and
- 0.5 to 1.5 percent by weight of stearic acid.

In another embodiment, the capsule formulation comprises:
- 40-60 percent by weight of Compound 1 in at least one of the forms disclosed herein;
- 30-50 percent by weight of microcrystalline cellulose;
- 2-7 percent by weight of croscarmellose sodium;
- 2-7 percent by weight of sodium starch glycolate;
- 0.1 to 0.6 percent by weight of fumed silica; and
- 0.1 to 3.0 percent by weight of stearic acid.

In another embodiment, the capsule formulation comprises:
- 45-55 percent by weight of Compound 1 in at least one of the forms disclosed herein;
- 35-40 percent by weight of microcrystalline cellulose;
- 3-6 percent by weight of croscarmellose sodium;
- 3-6 percent by weight of sodium starch glycolate;
- 0.2 to 0.5 percent by weight of fumed silica; and
- 0.5 to 2.5 percent by weight of stearic acid.

In one embodiment, the capsule compositions of this disclosure contain from 5 to about 200 mg of Compound 1 in at least one of the forms described herein. In another embodiment, the capsule compositions of this disclosure contain 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of Compound 1. In another embodiment, the capsule compositions of this disclosure contain from 105 to 200 mg of Compound 1. In another embodiment, the capsule compositions of this disclosure contain 105, 110, 115, 120, 125, 130, 135, 140, 145, 150, 155, 160, 165, 170, 175, 180, 185, 190, 195, or 200 mg of Compound 1. In another embodiment, the capsule compositions of this disclosure contain from 20 to 100 mg of Compound 1. In another embodiment, the capsule compositions of this disclosure contain 5, 10, 15, 20, 25, 30, 35, 40, 45, 50, 55, 60, 65, 70, 75, 80, 85, 90, 95, or 100 mg of Compound 1. In another embodiment, the capsule compositions of this disclosure contain from 20 to 60 mg of Compound 1. In another embodiment, the capsule compositions of this disclosure contain 5, 10, 15, 20, 25, 30, 35, 40, 45, 50, 55, or 60 mg of Compound 1. In another embodiment, the capsule compositions contain 20, 25, 40, 50, 60, 75, 80, or 100 mg of Compound 1. In another embodiment, the capsule compositions of this disclosure contain 20 mg of Compound 1. In another embodiment, the capsule compositions of this disclosure contain 40 mg of Compound 1. In another embodiment, the capsule compositions of this disclosure contain 60 mg of Compound 1. In another embodiment, the capsule compositions of this disclosure contain 80 mg of Compound 1.

In another aspect, the disclosure provides a pharmaceutical capsule composition according to Table 30.

TABLE 30

| Ingredient | mg/unit dose |
|---|---|
| Compound 1 (As one or more of Forms 1-27 (based on free base)) | 25 |
| Silicified Microcrystalline Cellulose | 196.75 |
| Croscarmellose sodium | 12.5 |
| Sodium starch glycolate | 12.5 |

TABLE 30-continued

| Ingredient | mg/unit dose |
| --- | --- |
| Fumed Silica | 0.75 |
| Stearic acid | 2.5 |
| Total Fill Weight | 250 |

In another aspect, the disclosure provides a pharmaceutical capsule composition according to Table 31.

TABLE 31

| Ingredient | mg/unit dose |
| --- | --- |
| Compound 1 (As one or more of Forms 1-27 (based on free base)) | 100 |
| Silicified Microcrystalline Cellulose | 75.40 |
| Croscarmellose sodium | 10.00 |
| Sodium Starch Glycolate | 10.00 |
| Fumed silica | 0.6 |
| Stearic Acid | 4.0 |
| Total Fill Weight | 200 |

The capsule formulations can be prepared according to methods available to the skilled person, by combining and mixing the components of the formulation and filling two-piece hard gelatin capsules. The capsule shell ingredients include gelatin and optionally colorant.

Tablet Formulation

In one embodiment, the dosage regimen is as a tablet formulation for oral administration.

In one embodiment, the tablet formulation comprises:
25-40 percent by weight of Compound 1 in at least one of the forms disclosed herein;
45-75 percent by weight of one or more diluents;
1-5 percent by weight of a binder;
2-10 percent by weight a disintegrant; and
0.05-1.0 percent by weight of a glidant;
and 0.5-1 percent by weight of a lubricant.

In another embodiment, the tablet composition comprises
28-38 percent by weight of Compound 1 in at least one of the forms disclosed herein;
48-68 percent by weight of one or more diluents;
1.5-4.5 percent by weight of a binder;
3-9 percent by weight a disintegrant; and
0.1-0.8 percent by weight of a glidant;
and 0.5-1 percent by weight of a lubricant.

In another embodiment, the tablet composition comprises
28-38 percent by weight of Compound 1 in at least one of the forms disclosed herein;
48-68 percent by weight of one or more diluents;
1.5-4.5 percent by weight of a binder;
3-9 percent by weight a disintegrant; and
0.1-0.8 percent by weight of a glidant;
and 0.5-1 percent by weight of a lubricant.

In another embodiment, the tablet composition comprises:
30-32 percent by weight of Compound 1 in at least one of the forms disclosed herein;
50-70 percent by weight of one or more diluents;
2-4 percent by weight of a binder;
4-8 percent by weight a disintegrant; and
0.2-0.6 percent by weight of a glidant;
and 0.5-1 percent by weight of a lubricant; wherein the composition is coated.

In another embodiment, the tablet formulation comprises:
25-40 percent by weight of Compound 1 in at least one of the forms disclosed herein;
35-45 percent by weight or microcrystalline cellulose;
15 to 25 percent by weight of lactose anhydrous;
1-5 percent by weight of hydroxypropyl cellulose;
2-10 percent by weight croscarmellose sodium;
0.05-1.0 percent by weight of a colloidal silicon dioxide; and
0.5-1 percent by weight magnesium stearate.

In another embodiment, the tablet composition comprises
28-38 percent by weight of Compound 1 in at least one of the forms disclosed herein;
36-42 percent by weight or microcrystalline cellulose;
18 to 22 percent by weight of lactose anhydrous;
1.5-4.5 percent by weight of a hydroxypropyl cellulose;
3-9 percent by weight a croscarmellose sodium; and
0.1-0.8 percent by weight of a colloidal silicon disoxide; and
0.5-1 percent by weight of a magnesium stearate.

In another embodiment, the tablet composition comprises
28-38 percent by weight of Compound 1 in at least one of the forms disclosed herein;
37-39 percent by weight or microcrystalline cellulose;
18 to 20 percent by weight of lactose anhydrous;
1.5-4.5 percent by weight of hydroxypropyl cellulose;
3-9 percent by weight a croscarmellose sodium; and
0.1-0.8 percent by weight of colloidal silicon dioxide; and
0.5-1 percent by weight of magnesium stearate.

In another embodiment, the tablet composition comprises:
30-32 percent by weight of Compound 1 in at least one of the forms disclosed herein;
38-39 percent by weight or microcrystalline cellulose;
19 to 20 percent by weight of lactose anhydrous;
2-4 percent by weight of hydroxypropyl cellulose;
4-8 percent by weight a croscarmellose sodium; and
0.2-0.6 percent by weight of colloidal silicon dioxide; and
0.5-1 percent by weight of a magnesium stearate.

The tablet formulations of these and other embodiments can be coated. Many coatings are known to the skilled person. An example of a coating is OPADRY Yellow, which contains hypromellose, titanium dioxide, triacetin, and iron oxide yellow.

In one embodiment, the tablet compositions of this disclosure contain from 5 to about 200 mg of Compound 1 in at least one of the forms described herein. In another embodiment, the tablet compositions of this disclosure contain 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of Compound 1. In another embodiment, the tablet compositions of this disclosure contain from 105 to 200 mg of Compound 1. In another embodiment, the tablet compositions of this disclosure contain 105, 110, 115, 120, 125, 130, 135, 140, 145, 150, 155, 160, 165, 170, 175, 180, 185, 190, 195, or 200 mg of Compound 1. In another embodiment, the tablet compositions of this disclosure contain from 20 to 100 mg of Compound 1. In another embodiment, the tablet compositions of this disclosure contain 5, 10, 15, 20, 25, 30, 35, 40, 45, 50, 55, 60, 65, 70, 75, 80, 85, 90, 95, or 100 mg of Compound 1. In another embodiment, the tablet compositions of this disclosure contain from 20 to 60 mg of Compound 1. In another embodiment, the tablet compositions of this disclosure contain 5, 10, 15, 20, 25, 30, 35, 40, 45, 50, 55, or 60 mg of Compound 1. In another embodiment, the tablet compositions contain 20, 25, 40, 50, 60, 75, 80, or 100 mg of Compound 1. In another embodiment, the tablet compositions of this disclosure contain 20 mg of Compound 1. In another embodiment, the tablet compositions of this disclosure contain 40 mg of Compound 1. In another embodiment, the tablet compositions of this disclosure contain 60 mg of Compound 1.

In another embodiment, the once-daily tablet comprises:

| Ingredient | (% w/w) |
|---|---|
| Compound 1 (As one or more of Forms 1-27 (based on free base)) | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmello se Sodium | 3.00 |
| Magnesium Stearate | 0.75 |
| Total | 100.00 |

In another embodiment, the once-daily tablet formulation comprises:

| Ingredient | (% w/w) |
|---|---|
| Compound 1 (As one or more of Forms 1-27 (based on free base)) | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, the once-daily tablet or capsule formulation comprises:

| Ingredient | Theoretical Quantity (mg/unit dose) |
|---|---|
| Compound 1 (As one or more of Forms 1-27 (based on free base)) | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In another embodiment, the once-daily tablet or capsule formulation comprises:

| Ingredient | % w/w |
|---|---|
| Compound 1 (As one or more of Forms 1-27 (based on free base)) | 31.7 |
| Microcrystalline Cellulose (Avicel PH-102) | 38.9 |
| Lactose Anhydrous (60M) | 19.4 |
| Hydroxypropyl Cellulose (EXF) | 3.0 |
| Croscarmellose Sodium (Ac-Di-Sol) | 6.0 |
| Colloidal Silicon Dioxide | 0.3 |
| Magnesium Stearate | 0.75 |
| Opadry Yellow Film Coating which includes: HPMC 2910/Hypromellose 6 cp Titanium dioxide Triacetin Iron Oxide Yellow | 4.00 |

This disclosure is also directed to a process for making the tablet pharmaceutical formulations comprising Compound 1 as one of the salts disclosed herein.

In an embodiment, the process for making the tablet formulation comprises mixing Compound 1 with one or more of the pharmaceutical excipients. The mixture is then taken up in an aqueous solution containing a binder to form a binder solution. The binder solution is granulated using a granulation technique known in the art. For example, the granulation method may comprise wet high shear granulation using a wet high shear granulator. The resulting wet granules are then screened and dried using fluid bed drying or the like. The dried granules are then milled. The resulting dry milled granules are then mixed with a glidant and a disintegrant to form an extra-granular blend. A lubricant is then blended into the extraganular blend to form the final blend. The final blend is subsequently compressed to form the compressed tablet, which may be film coated.

More particularly, the process for making the tablet formulation comprises delumping Compound 1 as needed prior to mixing with the excipients. Delumping ensures that the Compound 1 mixes homogeneously with the other excipients during the formulation process. Delumped Compound 1 is then mixed with microcrystalline cellulose, such as Avicel PH102, lactose (anhydrous, 60M), and croscarmellose sodium. This mixture is then combined with EXF grade hydroxypropyl cellulose in water to form a binder solution, which is then wet high shear granulated. The resulting wet granules are wet screened and then fluid bed dried according to methods available to the skilled artisan. The resulting dried granules are milled and combined with colloidal silicon dioxide and croscarmellose sodium. Magnesium stearate is added to the mixture. This final blend is then ready for tablet compression. The resulting uncoated core tablets are subsequently film coated. The film coating comprises Opadry Yellow, which contains hypromellose, titanium dioxide, triacetin, and iron oxide yellow.

More particularly, the formulation process comprises:

a) Delumping unmilled Compound 1;

b) Premixing the delumped Compound 1 with Avicel PH102, lactose anhydrous 60M, and croscarmellose sodium to form a binder solution;

c) Wet high shear granulation of the binder solution to produce wet granules;

d) Wet screening of the wet granules to produce wet screened granules;

e) Fluid bed drying of the wet screened granules to produce dried granules;

f) Dry milling of the dried granules to produce dried milled granules;

g) Blending the dried milled granules with colloidal silicon and croscarmellose to produce an extragranular blend;

h) Lubricant blending of the extragranular blend and magnesium stearate to produce a final blend;
i) Tablet compression of the final blend to form an uncoated core tablet; and
j) Film coating of the uncoated core tablet.

Treatment Methods

Another aspect of this disclosure relates to a method of treating cancer comprising administering to a subject in need thereof at least one of solid form of Compound 1 as described herein in any of the aspects and/or embodiments, or combinations thereof. Methods of treatment comprising administering Compound 1 have been disclosed in, for example, commonly assigned PCT Patent Publication Nos. WO 2005/030140, WO 2011/017639, WO 2012/044572, WO 2012/044577, WO 2012/151326, WO 2013/043840, WO 2013/070890, WO 2013/070903, and WO2013/066296, and US Patent Application Publication Nos. US 2012/0070368 and US 2012/0252840, each of which is incorporated by reference herein in its entirety. The amount of the Compound 1 solid form or combinations thereof administered can be a therapeutically effective amount.

Another aspect of this disclosure relates to a method of treating diseases or disorders associated with uncontrolled, abnormal, and/or unwanted cellular activities associated with RTK overexpression, particularly cMET of RET overexpression, comprising administering to a subject in need of such treatment a therapeutically effective amount of at least one solid form of Compound 1 as described herein in any of the aspects and/or embodiments, or combinations thereof, such as discussed above.

Another aspect of this disclosure relates to a use of solid Compound 1 according to any of the above embodiments for the manufacture of a medicament for the treatment of a disease or disorder discussed above. When dissolved, a solid or amorphous form according to this disclosure loses its solid state structure, and is therefore referred to as a solution of, for example, Compound 1. At least one solid form disclosed herein may be used to prepare at least one liquid formulation in which at least one solid form according to the disclosure is dissolved and/or suspended.

In another aspect, the invention is directed to a method of treating cancer, comprising: administering a pharmaceutical dosage form comprising one or more of Forms 1-27 or a pharmaceutical composition comprising one or more of Forms 1-27 and a pharmaceutically acceptable carrier.

In one embodiment of this aspect, the invention is directed to a method of treating cancer, comprising administering to a patient in need of such treatment a pharmaceutical dosage form comprising Compound 1 as one or more Forms 1-27 as a pharmaceutical dosage from described herein. In some embodiments, the dosage form is administered orally with fasting orally once daily as a tablet or capsule. In some embodiments, one or more of Forms 1-27 or a pharmaceutical composition comprising one or more of Forms 1-27 is administered as a tablet. In other embodiments, one or more of Forms 1-27 or a pharmaceutical composition comprising one or more of Forms 1-27 is administered as a capsule.

Any of the tablet or capsule formulations provided above can be adjusted according to the dose of Compound 1 desired. Thus, the amount of each of the formulation ingredients can be proportionally adjusted to provide a table formulation containing various amounts of Compound 1 as provided in the previous paragraphs. In another embodiment, the formulations can contain 20, 40, 60, or 80 mg free base equivalent of one or more of Forms 1-27.

In this method, the desired dosage of Compound 1 os one or more of Forms 1-27 as described herein can be achieved using a combination of tablets or capsules as needed. For example, to achieve a target dose of 20 mg would require administration of one 20 mg free base equivalent tablet or capsule. To achieve a target dose of 100 mg free base equivalent would require administration of one 80 mg free base equivalent tablet or capsule and one 20 mg free base equivalent tablet or capsule. To achieve a target dose of 80 mg free base equivalent would require administration of one 80 mg free base equivalent tablet or capsule. To achieve a target dose of 60 mg free base equivalent would require administration of three 20 mg free base equivalent tablets or capsules.

In another embodiment of this method, 60 mg free base equivalent of Compound 1 is administered once daily to a patient with cancer in need of treatment. To achieve a dose of 60 mg free base equivalent of Compound 1, a patient is administered three 20 mg free base equivalent tablets. The three 20 mg free base equivalent tablets can be taken at the same time or sequentially. In a further embodiment, Compound 1 is orally administered with fasting (that is, without eating) for approximately two hours before and 1 hour after administration. Compound 1 is preferably administered with a glass of water (approximately 8 ounces/240 mL).

In another embodiment of this method, 40 mg free base equivalent of Compound 1 is administered once daily to a patient with cancer in need of treatment. To achieve a dose of 40 mg free base equivalent of Compound 1, a patient is administered two 20 free base equivalent mg tablets. The two 20 mg free base equivalent tablets can be taken at the same time or sequentially. In a further embodiment, Compound 1 as one of the crystalline solid forms disclosed herein (that is, one or more of Forms 1-27) is orally administered with fasting (that is, without eating) for approximately two hours before and 1 hour after administration. Compound 1 is preferably administered with a glass of water (approximately 8 ounces/240 mL).

In another embodiment of this method, 20 mg free base equivalent of Compound 1 is administered once daily to a patient with cancer in need of treatment. To achieve a dose of 20 mg free base equivalent of Compound 1, a patient is administered one 20 mg free base equivalent tablet. In a further embodiment, Compound 1 is orally administered with fasting (that is, without eating) for approximately two hours before and 1 hour after administration. Compound 1 is preferably administered with a glass of water (approximately 8 ounces/240 mL).

In another embodiment, the method comprises administering one or more of Forms 1-27 orally once daily as a tablet or capsule.

In another embodiment, the method comprises administering one or more of Forms 1-27 orally once daily as a capsule as provided in the following table:

In another embodiment, the method comprises administering one or more of Forms 1-27 orally once daily as a tablet as provided in the following table:

| Ingredient | (% w/w) |
| --- | --- |
| Compound 1 (As one or more of Forms 1-27 (based on free base)) | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |

-continued

| Ingredient | (% w/w) |
|---|---|
| Silicon dioxide, Colloidal | 0.30 |
| Croscarmellose Sodium | 3.00 |
| Magnesium Stearate | 0.75 |
| Total | 100.00 |

In another embodiment, the method comprises administering one or more of Forms 1-27 orally once daily as a tablet as provided in the following table:

| Ingredient | (% w/w) |
|---|---|
| Compound 1 (As one or more of Forms 1-27 (based on free base)) | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, the method comprises administering one or more of Forms 1-27 orally once daily as a tablet as provided in the following table:

| Ingredient | Theoretical Quantity (mg/unit dose) |
|---|---|
| Compound 1 (As one or more of Forms 1-27 (based on free base)) | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In another embodiment, the method comprises administering one or more of Forms 1-27 orally once daily as a tablet as provided in the following table:

| Ingredient | % w/w |
|---|---|
| Compound 1 (As one or more of Forms 1-27 (based on free base)) | 31.7 |
| Microcrystalline Cellulose (Avicel PH-102) | 38.9 |
| Lactose Anhydrous (60M) | 19.4 |
| Hydroxypropyl Cellulose (EXF) | 3.0 |
| Croscarmellose Sodium (Ac-Di-Sol) | 6.0 |
| Colloidal Silicon Dioxide | 0.3 |
| Magnesium Stearate | 0.75 |
| Opadry Yellow Film Coating which includes: HPMC 2910/Hypromellose 6 cp Titanium dioxide Triacetin Iron Oxide Yellow | 4.00 |

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

In one embodiment, the cancer being treated is selected from stomach cancer, esophageal carcinoma, kidney cancer, liver cancer, bladder cancer, ovarian carcinoma, cervical carcinoma, large bowel cancer, small bowel cancer, brain cancer (including astrocytic tumor, which includes glioblastoma, giant cell glioblastoma, gliosarcoma, and glioblastoma with oligodendroglial components), lung cancer (including non-small cell lung cancer), bone cancer, prostate carcinoma, pancreatic carcinoma, skin cancer, bone cancer, lymphoma, solid tumors, Hodgkin's disease, non-Hodgkin's lymphoma, or thyroid cancer (including medullary thyroid cancer). More particularly, the cancer is pancreatic cancer, hepatocellular carcinoma (HCC), renal cell carcinoma, castration-resistant prostate cancer (CRPC), gastric or gastroesophageal junction cancer, melanoma, small cell lung cancer (SCLC), ovarian cancer, primary peritoneal or fallopian tube carcinoma, estrogen receptor positive breast cancer, estrogen receptor/progesterone receptor/HER2-negative (triple-negative) breast cancer, inflammatory (regardless of receptor status) breast cancer, non-small cell lung cancer (NSCLC), or medullary thyroid cancer.

Another aspect of this disclosure relates to a method of treating an astrocytic tumor (which includes glioblastoma, giant cell glioblastoma, gliosarcoma, and glioblastoma with oligodendroglial components) comprising administering to the subject in need of the treatment a therapeutically effective amount of Compound 1 in at least one of the forms described herein, pharmaceutically formulated as described herein.

Another aspect of this disclosure relates to a method of treating thyroid cancer (including medullary thyroid cancer) comprising administering to the subject in need of the treatment a therapeutically effective amount of Compound 1 in at least one of the forms described herein, pharmaceutically formulated as described herein.

Another aspect of this disclosure relates to a method of treating hepatocellular carcinoma comprising administering to the subject in need of the treatment a therapeutically effective amount of Compound 1 in at least one of the forms described herein, pharmaceutically formulated as described herein.

Another aspect of this disclosure relates to a method of treating renal cell carcinoma comprising administering to the subject in need of the treatment a therapeutically effective amount of Compound 1 in at least one of the forms described herein, pharmaceutically formulated as described herein.

Another aspect of this disclosure relates to a method of treating castration resistant prostate cancer comprising administering to the subject in need of the treatment a therapeutically effective amount of Compound 1 in at least one of the forms described herein, pharmaceutically formulated as described herein. The amount administered can be a therapeutically effective amount.

Another aspect of this disclosure relates to a method of breast cancer comprising administering to the subject in need of the treatment a therapeutically effective amount of Compound 1 in at least one of the forms described herein, pharmaceutically formulated as described herein.

Another aspect of this disclosure relates to a method of treating ovarian cancer comprising administering to the subject in need of the treatment a therapeutically effective amount of Compound 1 in at least one of the forms described herein, pharmaceutically formulated as described herein.

Another aspect of this disclosure relates to a method of treating bladder cancer comprising administering to the subject in need of the treatment a therapeutically effective amount of Compound 1 in at least one of the forms described herein, pharmaceutically formulated as described herein.

Another aspect of this disclosure relates to a method of treating diseases or disorders associated with uncontrolled, abnormal, and/or unwanted cellular activities. The method comprises administering to the subject in need of the treatment a therapeutically effective amount of Compound 1 in at least one of the forms described herein, pharmaceutically formulated as described herein.

In one embodiment, the cancer is thyroid cancer.
More particularly, the thyroid cancer is medullary thyroid cancer.
In one embodiment, the cancer in liver cancer.
More particularly, the liver cancer is hepatocellular carcinoma, cholangiocarcinoma, hepatoblastoma, angiosarcoma, hepatocellular adenoma, or hemagioma.
In one embodiment, the cancer is gastrointestinal cancer.
More particularly, the gastrointestinal cancer is cancer of the esophagus which is squamous cell carcinoma, adenocarcinoma, or leiomyosarcoma; cancer of the stomach which is carcinoma, or lymphoma; cancer of the pancreas, which is ductal adenocarcinoma, insulinoma, gucagonoma, gastrinoma, carcinoid tumors, or vipoma; cancer of the small bowel, which is adenocarcinoma, lymphoma, carcinoid tumors, Karposi's sarcoma, leiomyoma, hemagioma, lipoma; or cancer of the large bowel, which is adenocarcinoma, tubular adenoma, villous adenoma, hamartoma, or leiomyoma.
In one embodiment, the cancer is cancer of the pancreas.
More particularly, the cancer of the pancreas is ductal adenocarcinoma, insulinoma, gucagonoma, gastrinoma, carcinoid tumors, or vipoma.
In another embodiment, the cancer is bladder cancer. In a further embodiment, the bladder cancer is squamous cell carcinoma, transitional cell carcinoma, or adenocarcinoma.
In one embodiment, the cancer is bone cancer.
More particularly, the bone cancer is osteosarcoma, fibrosarcoma, malignant fibrous histiocytoma, chondrosarcoma, Ewing's sarcoma, malignant reticulum cell sarcoma, malignant giant cell tumor chordoma, osteocartiliginous exostoses, chondroblastoma, chondromyofibroma, or osteoid osteoma.
In one embodiment, the cancer is hematologic cancer.
More particularly, the hematologic cancer is myeloid leukemia, acute lymphoblastic leukemia, chronic lymphocytic leukemia, myeloproliferative diseases, multiple myeloma, or myelodysplastic syndrome.
In one embodiment, the cancer is skin cancer.
More particularly, the skin cancer is malignant melanoma, basal cell carcinoma, squamous cell carcinoma, or Karposi's sarcoma.
In one embodiment, the cancer is renal cancer.
More particularly, the renal cancer is a renal tumor.
In one embodiment, the cancer is breast cancer.
More particularly, the breast cancer is a breast tumor.
In one embodiment, the cancer is colon cancer.
More particularly, the colon cancer is a colon cancer tumor.
In one embodiment, the cancer is fallopian tube cancer.
More particularly, the fallopian tube cancer is fallopian tube carcinoma.
In one embodiment, the cancer is ovarian cancer.
More particularly, the ovarian cancer is ovarian carcinoma [serous cystadenocarcinoma, mucinous cystadenocarcinoma, unclassified carcinoma], granulosa-thecal cell tumors, Sertoli Leydig cell tumors, dysgerminoma, malignant teratoma), vulva (squamous cell carcinoma, intraepithelial carcinoma, adenocarcinoma, fibrosarcoma, or melanoma.
In another embodiment, the cancer is prostate cancer.
More particularly, the prostate cancer is adenocarcinoma or sarcoma.
In another embodiment, the prostate cancer is castration resistant prostate cancer (CRPC).
In another embodiment, the cancer is lung cancer.

More particularly, the lung cancer is bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, or inesothelioma.

Another aspect of this disclosure relates to a method of treating cancer comprising administering to the subject in need of the treatment a therapeutically effective amount of Compound 1 in at least one of the forms described herein, pharmaceutically formulated as described herein, optionally in combination with another agent. The method of treatment may be practiced by administering a tablet formulation of at Compound 1 in at least one of the forms described herein, pharmaceutically formulated as described herein.

The antitumor effect of the dosage form of the compound as a pharmaceutically acceptable salt is measured using serological and/or radiographic methods available to the skilled practitioner. For serological methods, the relative concentration of a cancer biomarker is measured before and after administration of one or more of Forms 1-27. A positive response means that there is a lower serological concentration of the biomarker after treatment as compared to the concentration before treatment.

Complete Serological Response: Marker level less than 0.2 ng/mL measured for 2 consecutive measurements at least 4 weeks apart.

Serological Partial Response (PR): Decline of marker value, referenced to the pre-study level, by greater than or equal to 50% for 2 consecutive measurements at least 2 weeks apart.

Stable Disease: Patients who do not meet the criteria for response (CR or PR) or serological progression.

Serological Progression (PD): Serological progression is observed when the marker level demonstrates an increase that is more than 50% of nadir, taking as reference the lowest recorded marker level since starting therapy. Two consecutive increases must be documented with each measurement obtained at least 2 weeks apart. On occasions, there may be an intermediate fluctuant value. In accordance with the Recommendations of Cancer Clinical Trials Working Group, this will not restart the evaluation period so long as the intermediate value was not below the previous nadir. These serological response levels can be modified as needed based on the biomarker at issue.

In one embodiment, a complete serological response is observed in patients being treated with the dosage form. In another embodiment, a serological partial response is observed in patients being treated with the dosage form. In a further embodiment, stable disease is observed in patients being treated with the dosage form.

With respect to radiographic methods, radiographic disease progression is defined by RECIST 1.1 for soft tissue disease, or the appearance of two or more new bone lesions on bone scan. Progression in the absence of clear symptomatic worsening at the first scheduled reassessment after commencement of treatment requires a confirmatory scan at later point in time. Standard imaging procedures available to the skilled practitioner, including technetium bone scans and CT scans, can be used to measure radiographic effect. Other radiographic methods such as NaF and FDG-PET may also be used to measure radiographic effect.

As indicated previously, the amount of one or more of Forms 1-27 that is administered as free base equivalent can be adjusted to avoid adverse events. For example, in one embodiment, a pharmaceutical dosage comprising 60 mg free base equivalent of one or more of Forms 1-27 is administered to a patient that had one or more adverse events at a dosage greater than 60 mg.

In another embodiments, 60 mg free base equivalent of one or more of Forms 1-27 is administered to a patient that had one or more adverse events at a pharmaceutical dosage between 80 mg and 160 mg.

In another embodiment, 60 mg free base equivalent of one or more of Forms 1-27 is administered to a patient that had one or more adverse events at a dosage of 70 mg.

In another embodiment, 60 mg free base equivalent of one or more of Forms 1-27 is administered to a patient that had one or more adverse events at a dosage of 80 mg.

In another embodiment, 60 mg free base equivalent of one or more of Forms 1-27 is administered to a patient that had one or more adverse event at a dosage of 90 mg.

In another embodiment, 60 mg free base equivalent of one or more of Forms 1-27 is administered to a patient that had one or more adverse events at a dosage of 100 mg.

In another embodiment, 60 mg free base equivalent of one or more of Forms 1-27 is administered to a patient that had one or more adverse events at a dosage of 110 mg.

In another embodiment, 60 mg free base equivalent of one or more of Forms 1-27 is administered to a patient that had one or more adverse events at a dosage of 120 mg.

In another embodiment, 60 mg free base equivalent of one or more of Forms 1-27 is administered to a patient that had one or more adverse events at a dosage of 130 mg.

In another embodiment, 60 mg free base equivalent of one or more of Forms 1-27 is administered to a patient that had one or more adverse events at a dosage of 140 mg.

In another embodiment, 60 mg free base equivalent of one or more of Forms 1-27 is administered to a patient that had one or more adverse events at a dosage of 150 mg.

In another embodiment, 60 mg free base equivalent of one or more of Forms 1-27 is administered to a patient that had one or more adverse events at a dosage of 160 mg.

In other embodiments, 60 mg free base equivalent of one or more of Forms 1-27 is administered to a patient that had one or more adverse events at a pharmaceutical dosage of 140 mg or 100 mg free base equivalent.

In another embodiment, the pharmaceutical dosage comprising 40 mg free base equivalent of one or more of Forms 1-27 is administered to a patient that had one or more adverse events at a dosage greater than 40 mg.

In another, 40 mg free base equivalent of one or more of Forms 1-27 is administered to a patient that had one or more adverse events at a pharmaceutical dosage between 60 mg and 160 mg.

In another embodiment, 40 mg free base equivalent of one or more of Forms 1-27 is administered to a patient that had one or more adverse events at a dosage of 50 mg.

In another embodiment, 40 mg free base equivalent of one or more of Forms 1-27 is administered to a patient that had one or more adverse events at a dosage of 60 mg.

In another embodiment, 40 mg free base equivalent of one or more of Forms 1-27 is administered to a patient that had one or more adverse events at a dosage of 70 mg.

In another embodiment, 40 mg free base equivalent of one or more of Forms 1-27 is administered to a patient that had one or more adverse events at a dosage of 80 mg.

In another embodiment, 40 mg free base equivalent of one or more of Forms 1-27 is administered to a patient that had one or more adverse events at a dosage of 90 mg.

In another embodiment, 40 mg free base equivalent of one or more of Forms 1-27 is administered to a patient that had one or more adverse events at a dosage of 100 mg.

In another embodiment, 40 mg free base equivalent of one or more of Forms 1-27 is administered to a patient that had one or more adverse events at a dosage of 110 mg of Compound 1.

In another embodiment, 40 mg free base equivalent of one or more of Forms 1-27 is administered to a patient that had one or more adverse events at a dosage of 120 mg of Compound 1.

In another embodiment, 40 mg free base equivalent of one or more of Forms 1-27 is administered to a patient that had one or more adverse events at a dosage of 130 mg.

In another embodiment, 40 mg free base equivalent of one or more of Forms 1-27 is administered to a patient that had one or more adverse events at a dosage of 140 mg.

In another embodiment, 40 mg free base equivalent of one or more of Forms 1-27 is administered to a patient that had one or more adverse events at a dosage of 150 mg.

In another embodiment, 40 mg free base equivalent of one or more of Forms 1-27 is administered to a patient that had one or more adverse events at a dosage of 160 mg.

In another embodiment, 40 mg free base equivalent of one or more of Forms 1-27 is administered to a patient that had one or more adverse events at a pharmaceutical dosage of 140 mg, 100 mg, or 60 mg.

In another embodiment, the pharmaceutical dosage comprising 20 mg free base equivalent of one or more of Forms 1-27 is administered to a patient that had one or more adverse events at a dosage greater than 60 mg.

In another embodiment, 20 mg free base equivalent of one or more of Forms 1-27 is administered to a patient that had one or more adverse events at a pharmaceutical dosage between 40 mg and 160 mg.

In another embodiment, 20 mg free base equivalent of one or more of Forms 1-27 is administered to a patient that had one or more adverse events at a dosage of 30 mg.

In another embodiment, 20 mg free base equivalent of one or more of Forms 1-27 is administered to a patient that had one or more adverse events at a dosage of 40 mg.

In another embodiment, 20 mg free base equivalent of one or more of Forms 1-27 is administered to a patient that had one or more adverse events at a dosage of 50 mg.

In another embodiment, 20 mg free base equivalent of one or more of Forms 1-27 is administered to a patient that had one or more adverse events at a dosage of 60 mg.

In another embodiment, 20 mg free base equivalent of one or more of Forms 1-27 is administered to a patient that had one or more adverse events at a dosage of 70 mg.

In another embodiment, 20 mg free base equivalent of one or more of Forms 1-27 is administered to a patient that had one or more adverse events at a dosage of 80 mg.

In another embodiment, 20 mg free base equivalent of one or more of Forms 1-27 is administered to a patient that had one or more adverse events at a dosage of 90 mg.

In another embodiment, 20 mg free base equivalent of one or more of Forms 1-27 is administered to a patient that had one or more adverse events at a dosage of 100 mg.

In another embodiment, 20 mg free base equivalent of one or more of Forms 1-27 is administered to a patient that had one or more adverse events at a dosage of 110 mg.

In another embodiment, 20 mg free base equivalent of one or more of Forms 1-27 is administered to a patient that had one or more adverse events at a dosage of 120 mg.

In another embodiment, 20 mg free base equivalent of one or more of Forms 1-27 is administered to a patient that had one or more adverse events at a dosage of 130 mg.

In another embodiment, 20 mg free base equivalent of one or more of Forms 1-27 is administered to a patient that had one or more adverse events at a dosage of 140 mg.

In another embodiment, 20 mg free base equivalent of one or more of Forms 1-27 is administered to a patient that had one or more adverse events at a dosage of 150 mg.

In another embodiment, 20 mg free base equivalent of one or more of Forms 1-27 is administered to a patient that had one or more adverse events at a dosage of 160 mg.

In other embodiments, 20 mg free base equivalent of one or more of Forms 1-27 is administered to a patient that had one or more adverse events at a pharmaceutical dosage of 140 mg, 100 mg, 60 mg, or 40 mg.

In some embodiments, the adverse event is one or more of diarrhea, stomatitis, palmar-plantar erythrodysesthesia syndrome (PPES), decreased weight, decreased appetite, nausea, fatigue, oral pain, hair color changes, dysgeusia, hypertension, abdominal pain, constipation, increased AST, increased ALT, lymphopenia, increased alkaline phosphatase, hypocalcemia, neutropenia, thrombocytopenia, hypophosphatemia, hyperbilirubinemia, perforations, fistulas, hemorrhage, thromboembolic events, wound complications, osteonecrosis of the jaw, proteinuria, reversible posterior leukoencephalopathy syndrome (RPLS), and embryo-fetal toxicity.

In some embodiments, the adverse event is Grade 1. In some embodiments, the adverse event is Grade 2. In some embodiments, the adverse event is Grade 3. In some embodiments, the adverse event is Grade 4. In some embodiments, the adverse event is Grade 5.

In one embodiment, treatment is temporarily suspended for a patient who had a Grade 4 adverse event. In another embodiment, upon resolution or improvement of the Grade 4 adverse event, the dose of Compound 1 is resumed at the same or a reduced dosage. In some embodiments, resolution or improvement of the Grade 4 adverse event means returning to baseline. In other embodiments, resolution or improvement of the Grade 4 adverse event means resolution to a Grade 1 adverse event.

In one embodiment, treatment is temporarily suspended for a patient who had a Grade 3 adverse event. In another embodiment, upon resolution or improvement of the Grade 3 adverse event, the dose of Compound 1 is resumed at the same or a reduced dosage. In some embodiments, resolution or improvement of the Grade 3 adverse event means returning to baseline. In other embodiments, resolution or improvement of the Grade 4 adverse event means resolution to a Grade 1 adverse event.

In one embodiment, treatment is temporarily suspended for a patient who had a Grade 2 adverse event. In another embodiment, upon resolution or improvement of the Grade 2 adverse event, the dose of Compound 1 is resumed at the same or a reduced dosage. In some embodiments, resolution or improvement of the Grade 2 adverse event means returning to baseline. In other embodiments, resolution or improvement of the Grade 2 adverse event means resolution to a Grade 1 adverse event.

In one embodiment, treatment is temporarily suspended for a patient who had a Grade 1 adverse event. In another embodiment, upon resolution or improvement of the Grade 1 adverse event, the dose of Compound 1 is resumed at the same or a reduced dosage. In some embodiments, resolution or improvement of the Grade 1 adverse event means returning to baseline.

In some embodiments, the dose is further reduced one or more times following the first reduction as a result of one or more adverse events. In one embodiment, the dose is reduced a first time. In another embodiment, the dose is reduced a first and second time. In another embodiment, the dose is reduced a first, second, and third time.

General Preparation Methods to Prepare Crystalline Solid Forms 1-27

Crystalline solid forms may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline solid forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; and adding antisolvents (countersolvents) to the solvent mixture. High throughput crystallization techniques may be employed to prepare crystalline solid forms including polymorphs.

Crystals of drugs, including polymorphs, methods of preparation, and characterization of drug crystals, are discussed in *Solid-State Chemistry of Drugs*, S. R. Byrn, R. R. Pfeiffer, and J. G. Stowell, $2^{nd}$ Edition, SSCI, West Lafayette, Indiana (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the Compound 1 in the solution and precipitate the formation of crystals. An antisolvent is a solvent in which a compound has low solubility.

In one method that can be used in preparing crystals, Compound 1 can be suspended and/or stirred in a suitable solvent to afford a slurry, which may be heated to promote dissolution. The term "slurry," as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the solid product. Accordingly, calculation of the amount of seeds needed depends on the size of the seed available and the desired size of an average product particle as described, for example, in "Programmed Cooling Batch Crystallizers," J. W. Mullin and J. Nyvlt, Chemical Engineering Science, 1971, 26, 3690377. In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired solid form (i.e., changing to an amorphous or other polymorphic form).

A cooled crystallization mixture may be filtered under vacuum and the isolated solid product washed with a suitable solvent, such as, for example, cold recrystallization solvent. After being washed, the product may be dried under a nitrogen purge to afford the desired solid form. The product may be analyzed by a suitable spectroscopic or analytical technique including, but not limited to, for example, differential scanning calorimetry (DSC); x-ray powder diffraction (XRPD); and thermogravimetric analysis (TGA) to assure the solid form of the compound has been formed. The resulting solid form may be produced in an amount greater than about 70 weight percent isolated yield, based on the weight of the compound originally employed in the crystallization procedure, and preferably greater than about 90 weight percent isolated yield. Optionally, the product may be delumped by being comilled or passed through mesh screen.

The features and advantages of this disclosure may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of this disclosure that are, for brevity reasons, described in the context of a single embodiment, may also be combined so as to form sub-combinations thereof. The disclosure is further illustrated by the following examples, which are not to be construed as limiting the disclosure in scope or spirit to the specific procedures described in them.

EXAMPLES

Experimental Techniques:

X-Ray Powder Diffraction (XRPD)

XRPD analyses were performed using a Panalytical Xpert Pro diffractometer equipped with a Cu X-ray tube and a Pixel detector system. The isothermal samples were analyzed in transmission mode and held between low density polyethylene films. The Almac default XRPD program was used (range 3-40° 2 θ, step size 0.013°, counting time 99 seconds, about 22 minute run time). XRPD patterns were sorted and manipulated using HighScore Plus 2.2c software.

Differential Scanning Calorimetry (DSC)

DSC analyses were carried out on a Perkin Elmer Jade Differential Scanning Calorimeter. Accurately weighed samples were placed in crimped aluminum pans. Each sample was heated under nitrogen at a rate of 10° C./minute to a maximum of 300° C. Indium metal was used as the calibration standard. Temperatures were reported at the transition onset to the nearest 0.01 degree. Note that DSC traces within this report may contain automated peak integrations which calculate DH of fusion. Where multiple thermal events are observed at similar temperatures, these DH values are prone to significant error.

Thermogravimetric Differential Thermal Analysis (TG/DTA)

Thermogravimetric analyses were carried out on a Mettler Toledo TG/DTA/DSC1 STARe. The calibration standards were indium and tin. Samples were placed in an aluminum sample pan, inserted into the TG furnace, and accurately weighed. The heat flow signal was stabilized for one minute at 30° C., prior to heating to 300° C. in a stream of nitrogen at a rate of 10° C./minute.

Dynamic Vapor Sorption (DVS)

Dynamic Vapor Sorption (DVS) was performed using a Hiden Analytical Instruments IGAsorp Vapor Sorption Balance. Approximately 30 mg of sample was placed into a wire mesh vapor sorption balance pan, loaded into the IGAsorp vapor sorption balance, and held at 25° C.±0.1° C. The sample was subjected to a step profile from 0 to 90% RH at 10% increments, followed by desorption from 80% RH to 0% RH at 10% increments. The equilibrium criterion was set to 99.0% step completion within a minimum of 60 minutes and a maximum of 5 hours for each increment. The weight change during the sorption cycle was monitored, allowing for the hygroscopic nature of the sample to be determined. The data collection interval was in seconds.

$^1$H Nuclear Magnetic Resonance spectroscopy (NMR)

NMR analysis was carried out on a Bruker 400 MHz or 500 MHz instrument in d-DMSO or $CDCl_3$. Instrumental parameters are listed on the relevant spectrum plots.

Polarized Light Microscopy

Microscopy analyses were carried out on an Olympus BX51 instrument. Photomicrographs of Compound 1 were obtained at objective lens magnifications ×10 using a polarized light source.

HPLC

The HPLC method used to determine aqueous equilibrium solubility is outlined in Table 32. The retention time of Compound 1 was typically 19.1±0.2 min and no new peaks were detected during the analysis of experimental samples.

TABLE 32

HPLC method for equilibrium solubility analysis of Compound 1.

| Parameter | Conditions |
| --- | --- |
| HPLC System | Waters Alliance 2695 |
| Column | Phenomenex Gemini C18, 3 μm, 4.6 × 150 mm |
| Oven Temperature | 25° C. |
| Injector Temperature | 25° C. |
| Flow Rate | 1.2 mL/min |
| Injection Volume | 5 mL |
| Sample Diluent | DMSO:MeOH:$H_2O$, 50:40:10, v/v/v |
| Mobile Phase | Mobile Phase A: $H_2O$:$CH_3CN$ 95:5, v/v containing 20 mM $NH_4OAc$ pH 8.0 ± 0.3 Mobile Phase B: $CH_3CN$ 100% |

| | Time (minutes) | % A | % B |
| --- | --- | --- | --- |
| Gradient | 0 | 95 | 5 |
| | 12 | 55 | 45 |
| | 22.5 | 45 | 55 |
| | 30 | 0 | 100 |
| | 31.5 | 0 | 100 |
| | 34.5 | 95 | 5 |
| | 42 | 95 | 5 |

| Run Time | 42 minutes |
| --- | --- |
| Detector Wavelength | 240 nm |

FT-IR Spectroscopy

FT-IR spectroscopy was carried out on a Thermonicolet Avatar 370 FT-IR spectrometer equipped with a Golden Gate ATR. Spectra were processed using GRAMS AI v8.0 software.

Materials and Reagents:

The acids and cocrystal formers used in the salt/cocrystal screen include mineral, sulfonic, and carboxylic acids. Isethionic acid was supplied as the sodium salt, and the free acid form was subsequently liberated by ion exchange chromatography.

EXPERIMENTAL EXAMPLES

The synthesis of Compound 1, and various polymorphic forms thereof, are disclosed in U.S. patent application Ser. No. 15/118,738, the entire contents of which is incorporated herein by reference.

Example 1: Preparation of Isethionic Acid from the Corresponding Sodium Salt

Isethionic acid was prepared from its sodium salt by ion exchange chromatography. Isethionic acid sodium salt (105.5 mg) in water (5 mL) was added to the washed resin (2.5 g), and the mixture was stirred at ambient temperature for 4 days. The mixture was filtered, and the resin was washed with water (about 4 mL). The filtrate was added to a 10 mL volumetric flask and filled to the mark with water affording about 0.07M isethionic acid solution.

Example 2: Screening Methods

Screening experiments were carried out at a scale of about 40 mg with 1:1 stoichiometry and 0.5:1 stoichiometry (API: acid). A range of methods for salt formation were carried out including precipitations, slurries, sonications, and evaporations.

Example 3: Preparation of Stock Solutions

Compound 1 (1.28 g) was added to a 50 mL volumetric flask, and TH/water (80:20) was added to the mark to form a 0.052M solution. This was sonicated in the water bath to ensure complete dissolution. Separately, Compound 1 (1.5 g) was added to a 150 mL volumetric flask, and acetone was added to the mark to form a 0.02M solution.

The acid solutions were prepared as described in Table 33. Solutions of sulfonic acids were added directly due to concern over the sulfonic acid reacting with MeOH (Table 34).

TABLE 33

Preparation of acid solutions

| Acid | Mol. Wt. | Amount of acid (mg) | Solvent | Molarity (M) | Volume (mL) |
| --- | --- | --- | --- | --- | --- |
| ascorbic | 176.12 | 176.70 | MeOH | 0.100 | 10 |
| lactic (L) | 90.08 | 266.5 | MeOH | 0.148 | 20 |
| glycolic (hydroxyacetic) | 76.05 | 69.0 | MeOH | 0.091 | 10 |
| citric (monohydrate) | 192.13 | 382.4 | MeOH | 0.100 | 20 |
| malic (L) | 134.09 | 139.8 | MeOH | 0.104 | 10 |
| succinic (butanedioic) | 118.09 | 266.3 | MeOH | 0.113 | 20 |
| ketoglutaric | 146.1 | 284.7 | MeOH | 0.097 | 20 |
| maleic | 116.08 | 232.8 | MeOH | 0.100 | 20 |
| malonic | 104.06 | 98.7 | MeOH | 0.095 | 10 |
| AcOH | 60.05 | 61.3 | MeOH | 0.102 | 10 |
| pyroglutamic (L) | 129.11 | 248.1 | MeOH | 0.096 | 20 |
| aceturic acid (N-acetylglycine) | 117.1 | 245.7 | MeOH | 0.105 | 20 |
| gluconic (D) | 196.16 | 61.3 | MeOH | 0.031 | 10 |
| glucuronic (D) | 194.14 | 377.7 | MeOH | 0.097 | 20 |
| glutaric (pentanedioic) | 132.12 | 132.1 | MeOH | 0.100 | 10 |
| α-ketoglutaric (oxoglutaric) | 146.1 | 284.7 | MeOH | 0.097 | 20 |
| oxalic | 90.04 | 89.9 | MeOH | 0.100 | 10 |
| pyruvic (2-oxopropanoic) | 88.06 | 61.3 | MeOH | 0.070 | 10 |
| erythritol | 122.12 | 121.3 | MeOH | 0.099 | 10 |
| lysine (L) monohydrate | 146.19 | 298.7 | MeOH | 0.102 | 20 |
| nicotinamide | 122.12 | 61.3 | MeOH | 0.050 | 10 |
| tromethamine (TRIS) | 121.14 | 126.7 | MeOH | 0.105 | 10 |
| urea | 60.06 | 63.4 | MeOH | 0.106 | 10 |
| xylitol | 152.15 | 159.9 | MeOH | 0.105 | 10 |

TABLE 34

Amount of sulfonic acids used in screening experiments

| Acid | Mol. Wt. | Amount (mg, 1.05 eq) |
|---|---|---|
| benzene sulfonic | 158.18 | 12.62 |
| ethane sulfonic | 110.13 | 8.78 |
| methane sulfonic | 96.11 | 7.67 |
| p-toluene sulfonic acid monohydrate | 190.22 | 15.17 |
| ethane-1,2-disulfonic (edisilic) | 190.2 | 15.17 |
| isethionic (2-hydroxy-ethane sulfonic) | 126.13 | 10.06 |

Example 4: Precipitation Experiments in THF/Water (80:20)

Acid solution (1.05 eq) was added to each HPLC vial and allowed to evaporate to dryness. In the case of sulfonic acids and liquid co-formers, these were added directly to the vial. Compound 1 in THF/water (1.6 mL, 1 eq) was added to each vial, and the solutions were stirred at ambient for 16 hours. Any solids which precipitated were isolated by centrifugation, the solvent was decanted, and the solids were dried with filter paper prior to XRPD analysis. Samples which remained as solutions were uncapped and evaporated, and the solids were analyzed by XRPD.

Solids that generated disordered XRPD patterns were slurried in THF (50° C.), EtOH (60° C.), or a mixture of THF/EtOH (50° C.) (see Table 35). The slurries were initially carried out at high temperature (1 hour), then slowly cooled to ambient temperature and slurried at ambient temperature for 16 hours.

Example 5: Precipitation Experiments in Acetone/THF (97:3)

Acid/co-former (1.05 eq), THF (100 µL), and Compound 1 (1 eq) in acetone (0.02M, 4 mL) were added to each HPLC vial, and the mixtures were stirred and heated at 50° C. for about 1 hour. These were allowed to cool and stirred at ambient temperature for 16-18 hours. If a precipitate had formed, the solids were isolated by centrifugation, the solvent was decanted, and the solids were dried with filter paper prior to analysis by XRPD. Reactions which formed solutions were uncapped and evaporated to about 1.5 mL. The solids were isolated as above (see Table 36). Any samples which remained as solutions were uncapped and evaporated, and any solids were analyzed by XRPD.

Example 6: Precipitation Experiments in Acetone/THF (97:3)

Acid/co-former (1.05 eq), THF (100 µL), and Compound 1 (1 eq) in acetone (0.02M, 4 mL) were added to each HPLC vial, and the mixtures were stirred and heated at 50° C. for about 1 hour. These were allowed to cool and stirred at ambient temperature for 16-18 hrs. If a precipitate formed, the solids were isolated by centrifugation, the solvent was decanted, and the solids were dried with filter paper prior to analysis by XRPD. Reactions which formed solutions were uncapped and evaporated to about 1.5 mL. The solids were isolated as above (see Table 36). Any samples which remained as solutions were uncapped and evaporated, and any solids were analyzed by XRPD.

Example 7: Slurry Experiments Using 0.5 Eq of Acid

Acid (0.5 eq) was charged to a vial, and 100 µL of THF added. A Compound 1 suspension in acetone (4 mL, 10 mg/mL) was added, and the suspensions were stirred. The vials were left open to allow the solvent to evaporate to about half volume to increase product yield. The suspensions were stirred at ambient temperature for 5 days, then they were centrifuged and the solvents were decanted. The solids were dried with strips of filter paper and analyzed by XRPD.

Example 8: Experiments Carried Out Using Liquid Acids

Compound 1 (about 40 mg) was charged to an HPLC vial and acid (1 mol. eq.), acetonitrile (100-200 µL) was added, and the slurries were stirred at ambient temperature for 16 hours. The slurries were sampled, and the solids were analyzed by XRPD.

Example 9: Sonication of Pastes

Acid solution (1 eq) was added to a vial and evaporated to dryness. Sulfonic acids, liquid co-formers, and 4-hydroxybenzoic acid, these were added directly to the vial. Compound 1 (about 40 mg, 1 eq) and 200 µL of solvent (acetonitrile or acetonitrile/H2O (87:13)) were added, and the mixture was sonicated at 30% intensity using a Cole-Parmer 130 W ultrasonic processor (3×30 sec). All solids recovered from these experiments were analyzed by XRPD.

Example 10: Humidity Stress Experiments

Compound 1 salts were accurately weighed into individual vials. The vials were placed unsealed into a vial containing a saturated solution of sodium chloride at 40° C. (75% relative humidity). The salts were stored for 5-7 days prior to visual inspection for deliquescence. The vials were re-weighed to assess % weight gain/loss, and the solids were analyzed by XRPD.

Example 11: Desolvation Experiments

The experiments were carried out by heating the material to just above the desolvation temperature on the TG/DTA and holding the material at that temperature for 15 minutes until desolvation was complete. The samples were analyzed by XRPD.

Example 12: HPLC solubility determination about 5 mg of each salt was added to a vial with distilled water (1 mL). These were stirred at ambient temperature (about 25° C.) for 24 hours. The solution was isolated by filtration through a 0.2 µm PTFE filter and was analyzed by HPLC for concentration. The pH of the solutions was checked with pH paper.

Example 13: Preparation of Compound 1 Pyruvate (Form 14)

Seeded:
Compound 1 (1000 mg) and acetone (80 mL) were added to a flask and stirred at 35° C. to form a pale white suspension (almost all the Compound 1 was dissolved). A solution of pyruvic acid (184 mg, 1.05 eq) in THF (10 mL) was added. This was washed with a further 5 mL of THF. A clear solution formed, which was stirred at ambient temperature. This was seeded with Form 14 material and allowed to stir for 18 hours. The resulting suspension was evaporated to about 40 mL and allowed to stir for a further 18 hours to maximize the yield. The solids were collected by filtration and dried on the sinter for about 30 minutes to yield the product as a white solid (671 mg, 57% yield).

Unseeded:

Compound 1 (100 mg), acetone/THF (97:3, 2 mL), and pyruvic acid (23.4 µL) were stirred at ambient temperature for about 96 hours. The solids were collected by centrifuge filtration and analyzed by XRPD.

Figure 53A:
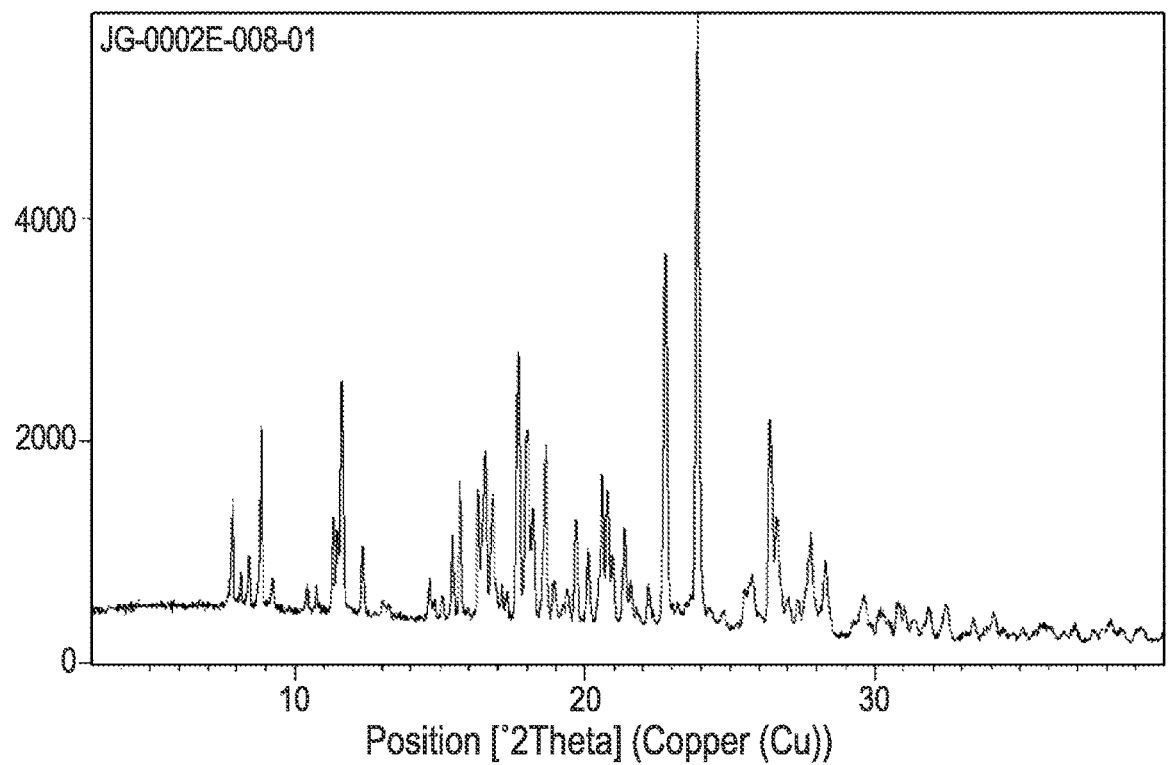
FIG. 53A is the XRPD spectrum of Form 14, Compound 1 pyruvate.

XRPD analysis indicated that the salt was crystalline (FIG. 53A). Polarised light microscopy confirmed crystallinity with some aggregation or agglomeration.

Figure 53B:
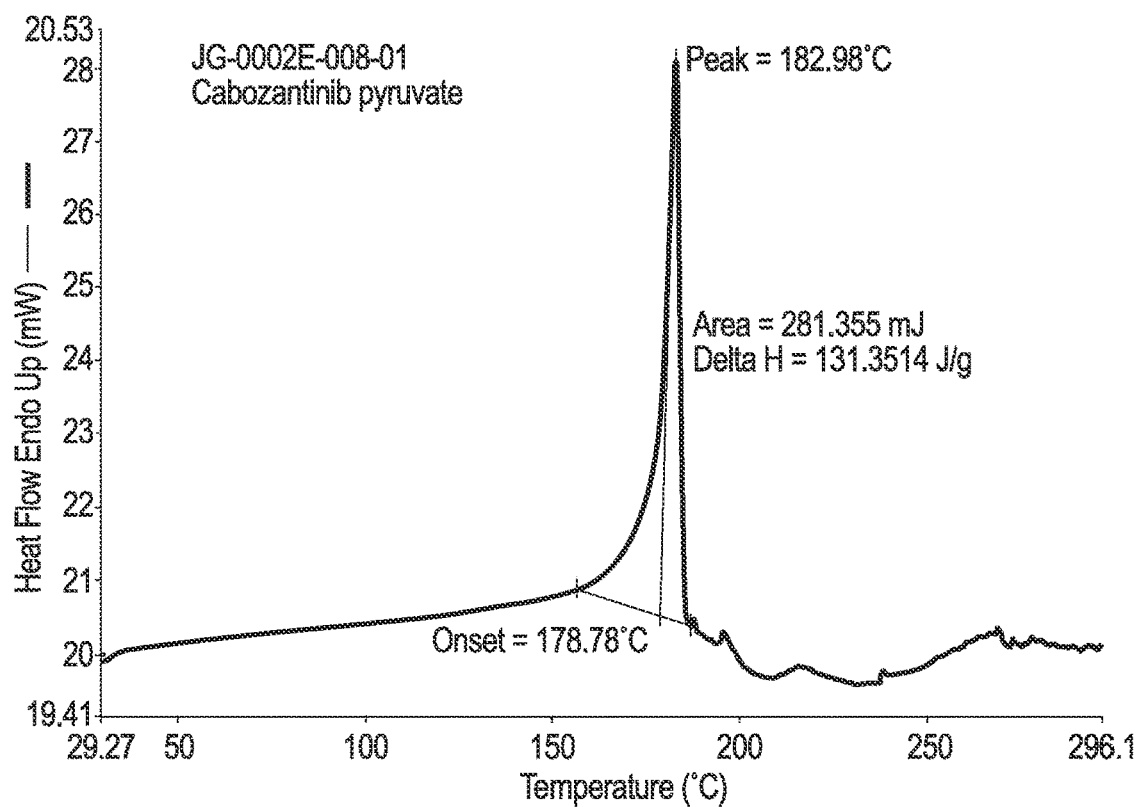
FIG. 53B is the DSC trace of Form 14, Compound 1 pyruvate.
Figure 53C:
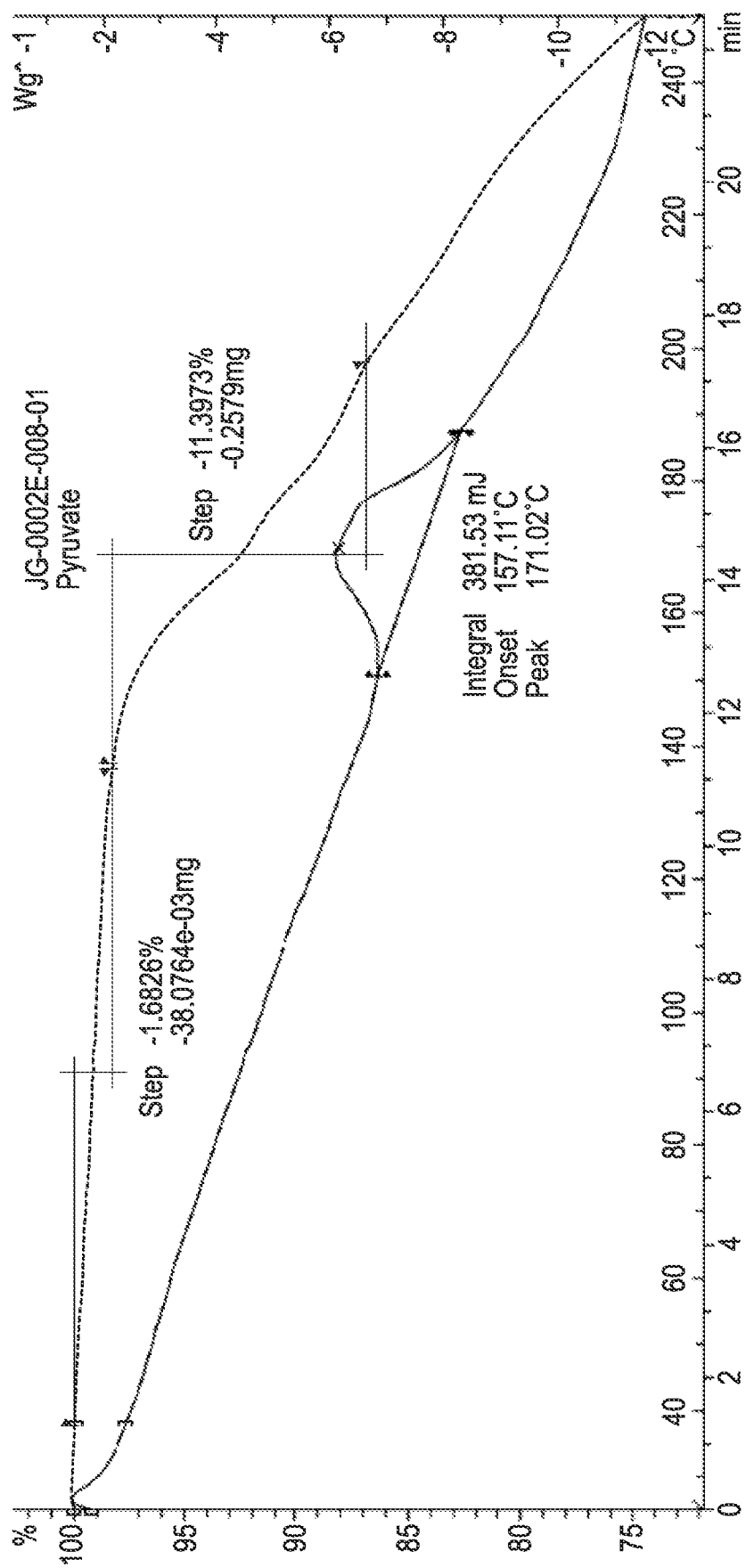
FIG. 53C is the TG/DTA thermogram of Form 14, Compound 1 pyruvate.

A DSC thermogram of Compound 1 pyruvate was recorded at 10° C./minute. A thermal event, with peak temperature at 183° C., is most likely to be due to the melt of the salt (FIG. 53B). The material appeared to decompose immediately after the melt. Thermal analysis (TG/DTA) (FIG. 53C) showed a small weight loss of about 1.7% between 30-140° C., probably due to residual moisture/solvent, which suggests that Compound 1 pyruvate is an anhydrous form. A broad endotherm was observed at onset 157° C. with an associated weight loss of about 11.4%, which corresponds to about 0.85 moles of pyruvic acid. It is suspected that as the material melts, pyruvic acid is lost, and the material decomposes.

Figure 53D:
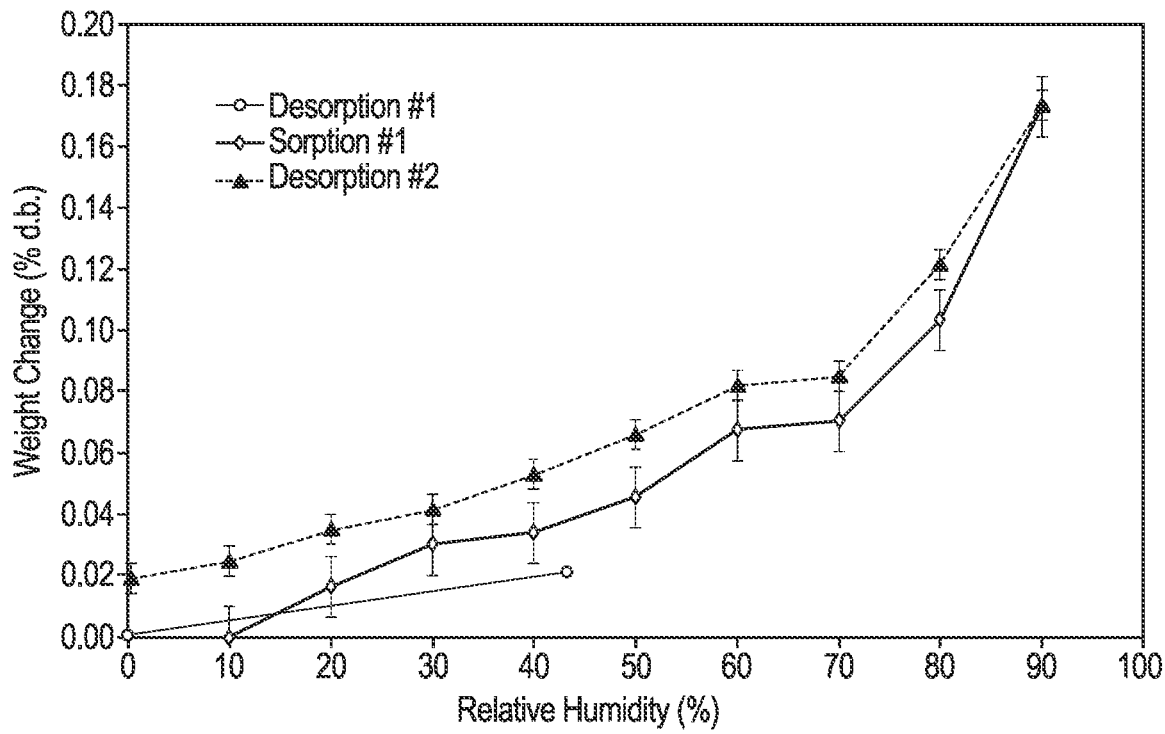
FIG. 53D is the DVS isotherm of Form 14, Compound 1 pyruvate.
Figure 53E:
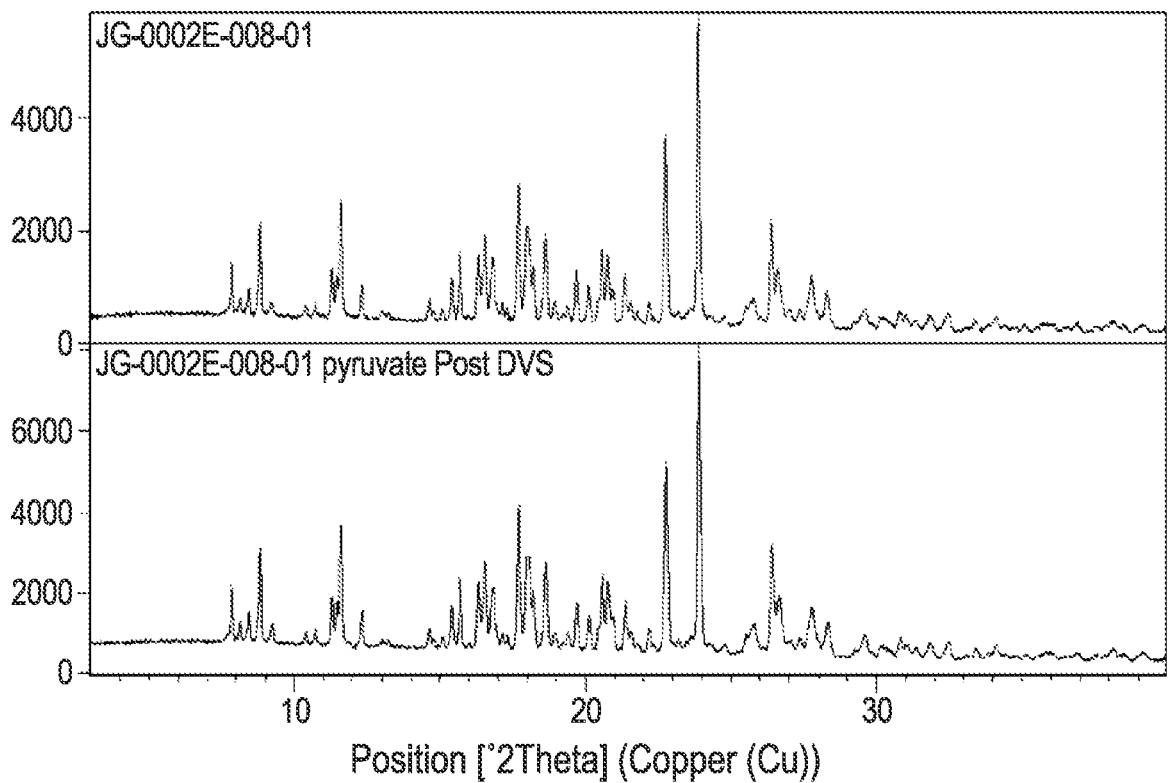
FIG. 53E is the XRPD spectrum of Form 14, Compound 1 pyruvate, pre DVS (top) and post DVS (bottom).

The hygroscopicity and the sorption properties of Compound 1 pyruvate were determined using Dynamic Vapor Sorption (DVS). The sample was dried at 0% RH prior to performing the sorption and desorption cycle. The isotherm (FIG. 53D) showed the total weight gain observed between 0% RH and 80% RH was 0.10% w/w, which indicates that the sample is non-hygroscopic according to the European Pharmacopoeia classification and less hygroscopic than both forms of Compound 1 (S)-malate (about 0.4% w/w). No significant hysteresis was observed between the sorption and desorption curves. XRPD analysis (FIG. 53E) of the post DVS sample showed the material remained unchanged.

Figure 53F:
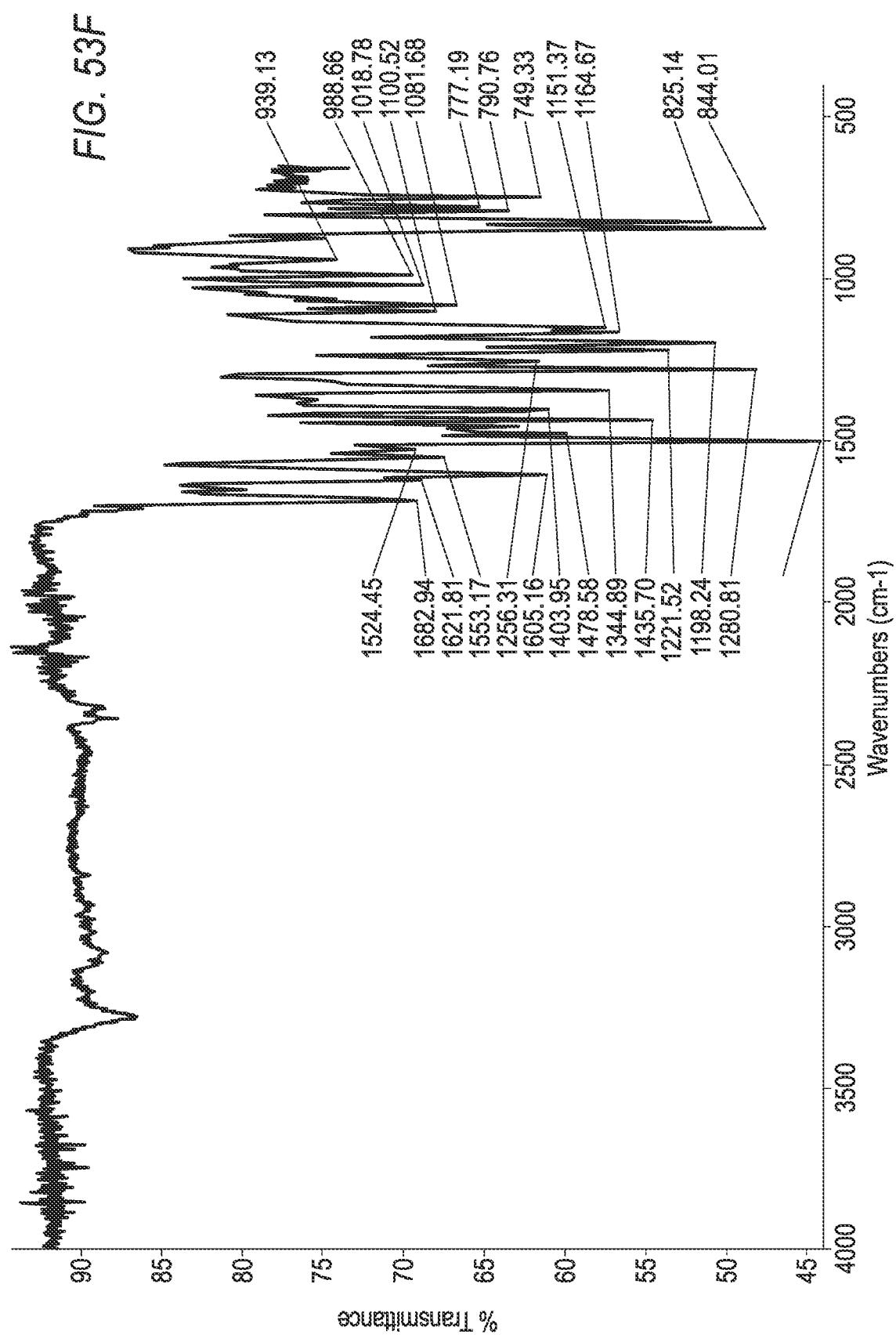
FIG. 53F is the FT-IR spectrum of Form 14, Compound 1 pyruvate.
Figure 53G:
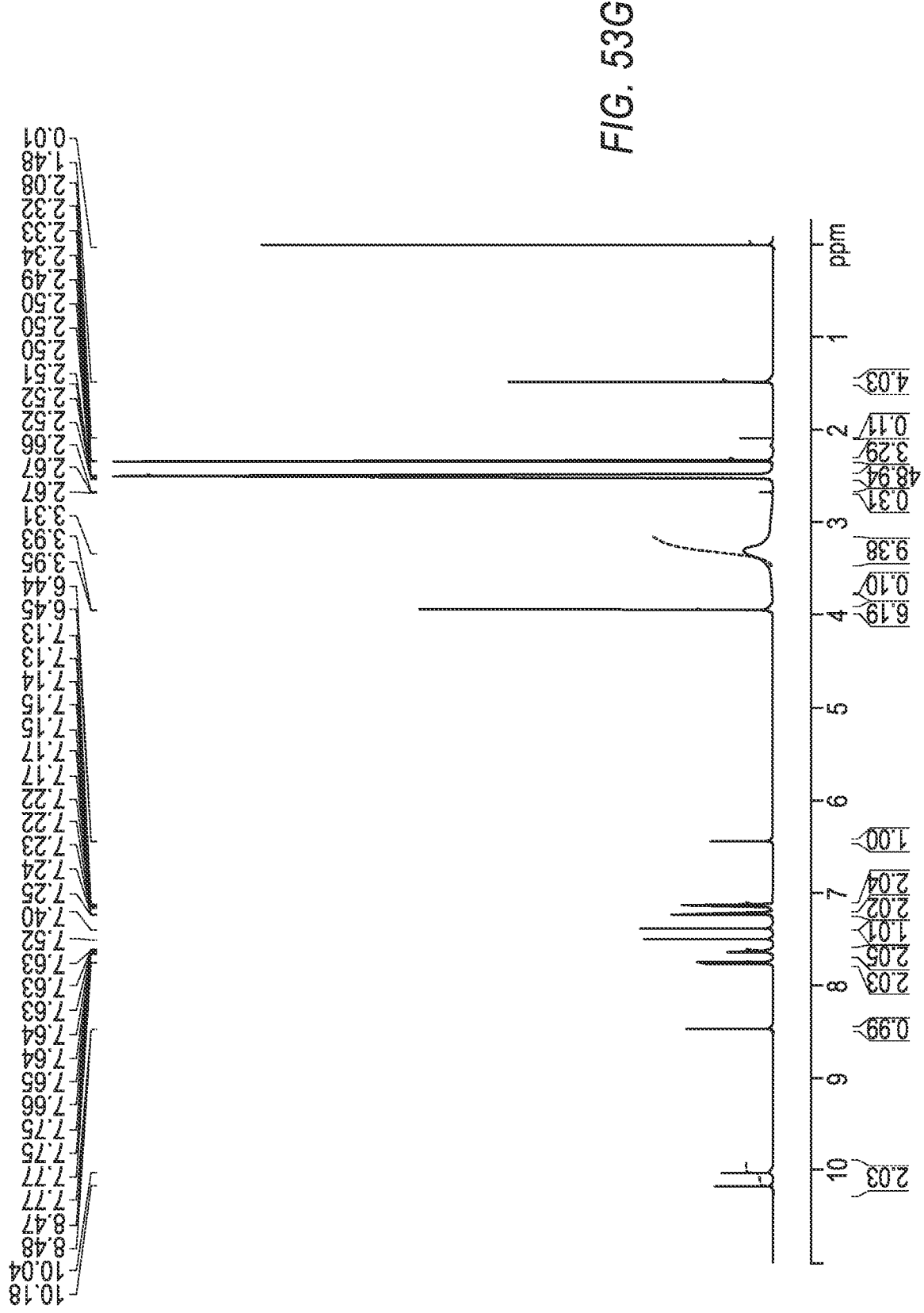
FIG. 53G is the $^1$H NMR (DMSO-$d^6$) of Form 14, Compound 1 pyruvate.

The FT-IR spectrum obtained for the material is shown in FIG. 53F and was shown to conform to the material structure with all expected functional groups present. The $^1$H NMR spectrum of Compound 1 pyruvate conformed to structure and confirmed the ratio of API peaks and acid peaks to be 1:1 (FIG. 53G).

The 1:1 Compound 1 pyruvate salt was a highly crystalline, non-hygroscopic, anhydrous material with a melting peak temperature at 183° C. and an aqueous solubility of about 0.133 mg/mL (pH about 3). Compared to the malate salt of Compound 1, the Compound 1 pyruvate salt has a lower molecular weight (which may result in higher drug loading compared to the malate salt of Compound 1), higher solubility, lower aspect ratio, and only one physical form observed to date. The improved particle morphology/aspect ratio may lead to improvements in filterability and flow properties compared to the malate salt of Compound 1. Pyruvate is well tolerated in vivo as it is a natural human metabolite.

Example 14: Preparation of Compound 1 Glutarate (Form 20)

Seeded:

Compound 1 (1000 mg), acetonitrile (10 mL), and glutaric acid (275 mg, 1.05 eq) were added to a glass vial and heated to 50° C. The mixture was seeded with Compound 1 glutarate and stirred for 30 minutes at 50° C. The mixture was very viscous, therefore a further 3 mL of acetonitrile was added, stirred for 3 hours, cooled to ambient temperature, and stirred for a further 16-20 hours. A sample was removed from the mixture, and the solids were isolated by centrifuge filtration to check for reaction completion. The solids were analyzed by XRPD analysis.

The remainder of the material was isolated by filtration and washed with acetonitrile (1 mL). The solids were air dried in the filter funnel. (Yield=1.145 g, 91%) Unseeded:

Compound 1 (100 mg), acetonitrile (1.5 mL), and glutaric acid (27.62 mg) were charged to a vial and heated to 50° C. for 1 hour. The mixture was cooled to ambient temperature and stirred for 96 hours. The experiment remained as a suspension throughout. The solids were collected by centrifuge filtration and analyzed by XRPD.

Figure 54A:
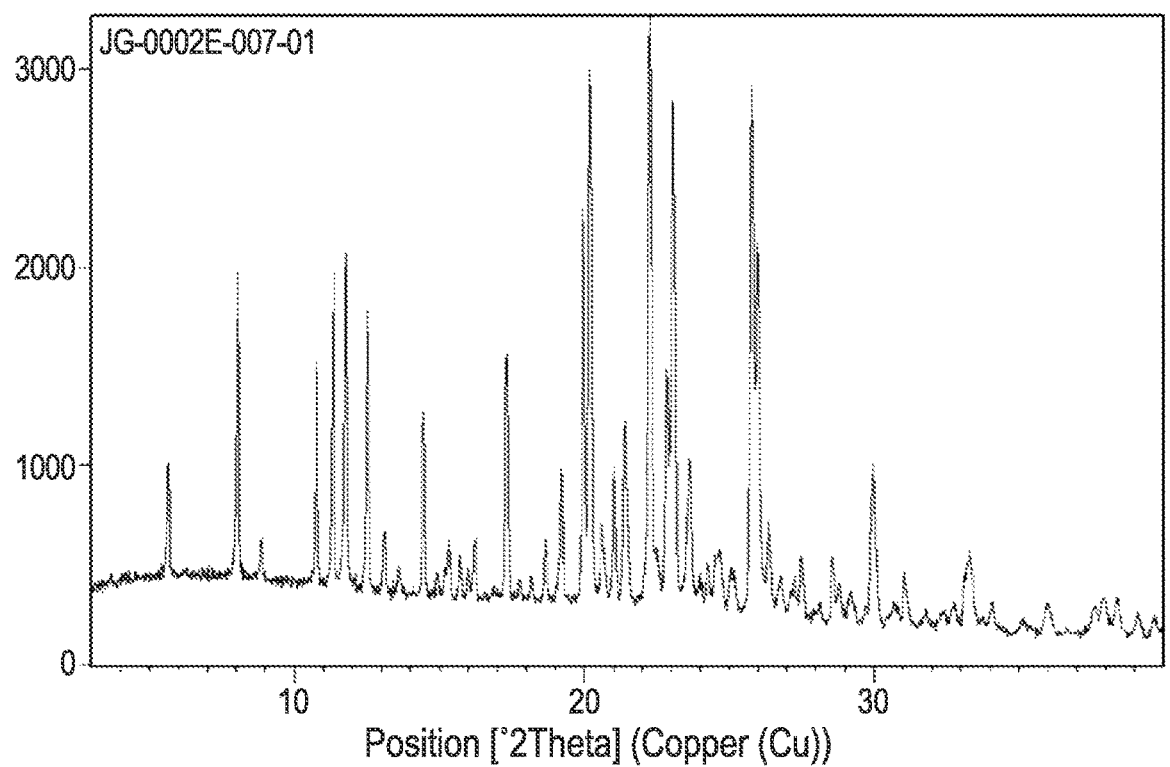
FIG. 54A is the XRPD spectrum of Form 20, Compound 1 glutarate.

XRPD analysis (FIG. 54A) indicated that the salt was highly crystalline. Optical microscopy confirmed the salts crystallinity showing birefringent irregularly shaped particles.

Figure 54B:
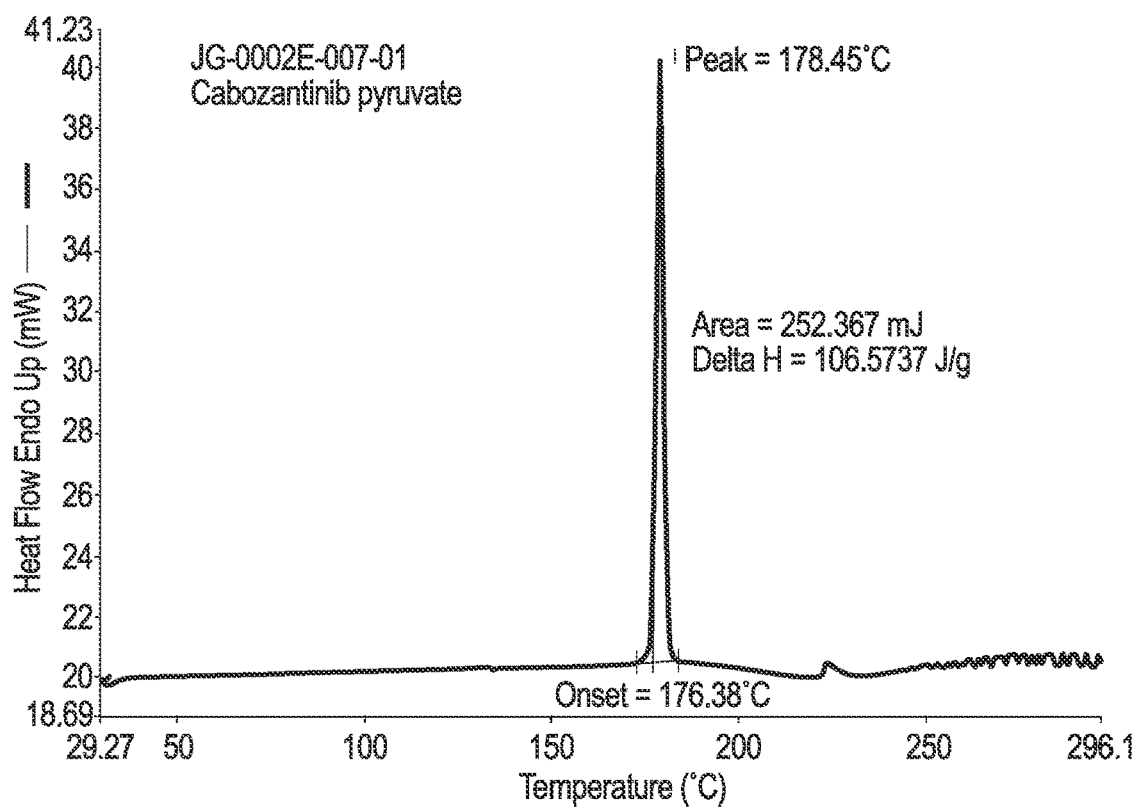
FIG. 54B is the DSC trace of Form 20, Compound 1 glutarate.
Figure 54C:
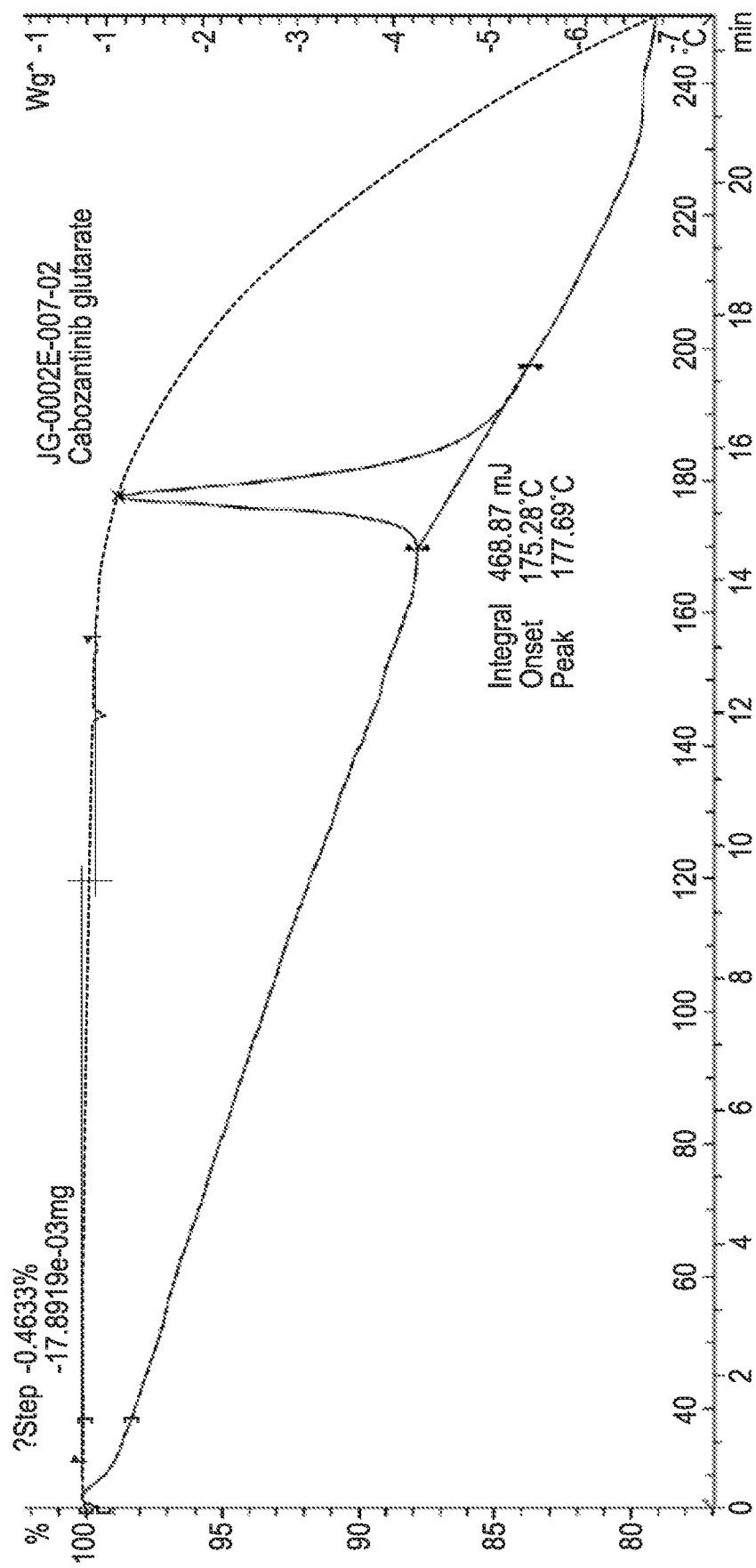
FIG. 54C is the TG/DTA thermogram of Form 20, Compound 1 glutarate.

The DSC thermogram obtained for Compound 1 glutarate is shown in FIG. 54B. The thermogram showed one endotherm at onset about 176° C., which was attributed to the melt. Thermal analysis by TG/DTA (FIG. 54C) showed a small amount of weight loss (0.5%) between 30-160° C., which may be due to residual moisture/solvent, suggesting Compound 1 glutarate is an anhydrous form. An endotherm was observed at an onset temperature of 175° C., with an associated weight loss of 0.5%.

Figure 54D:
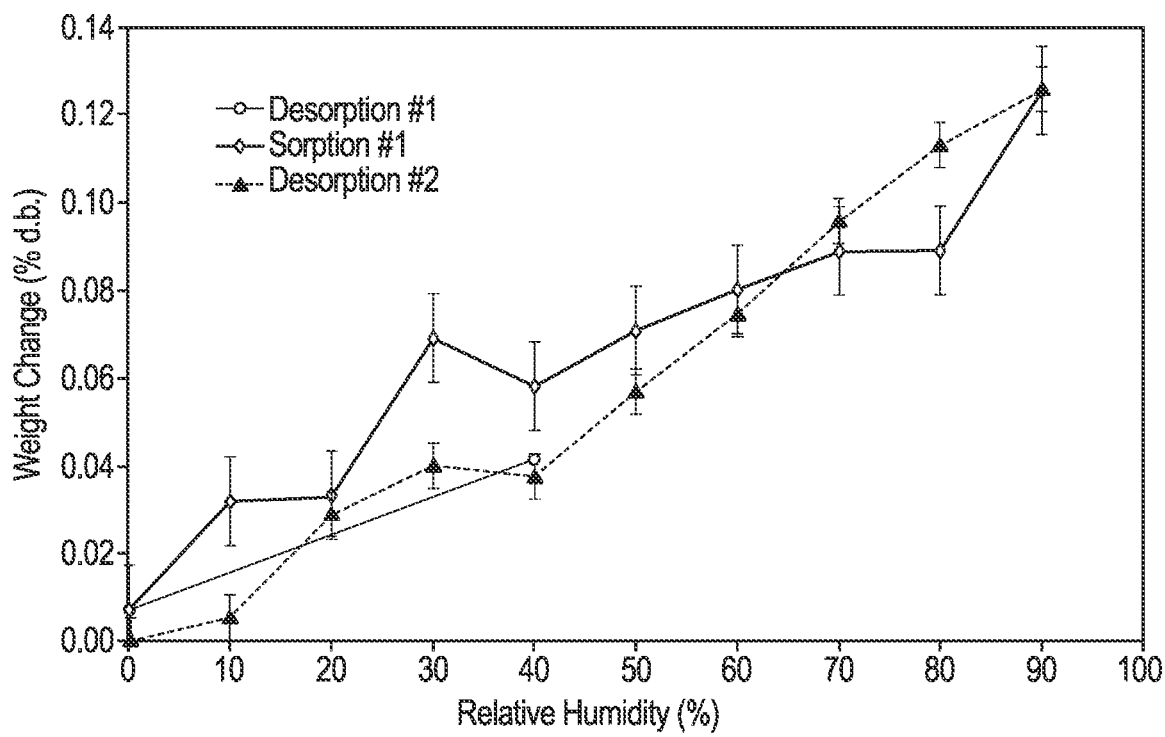
FIG. 54D is the DVS isotherm of Form 20, Compound 1 glutarate.
Figure 54E:
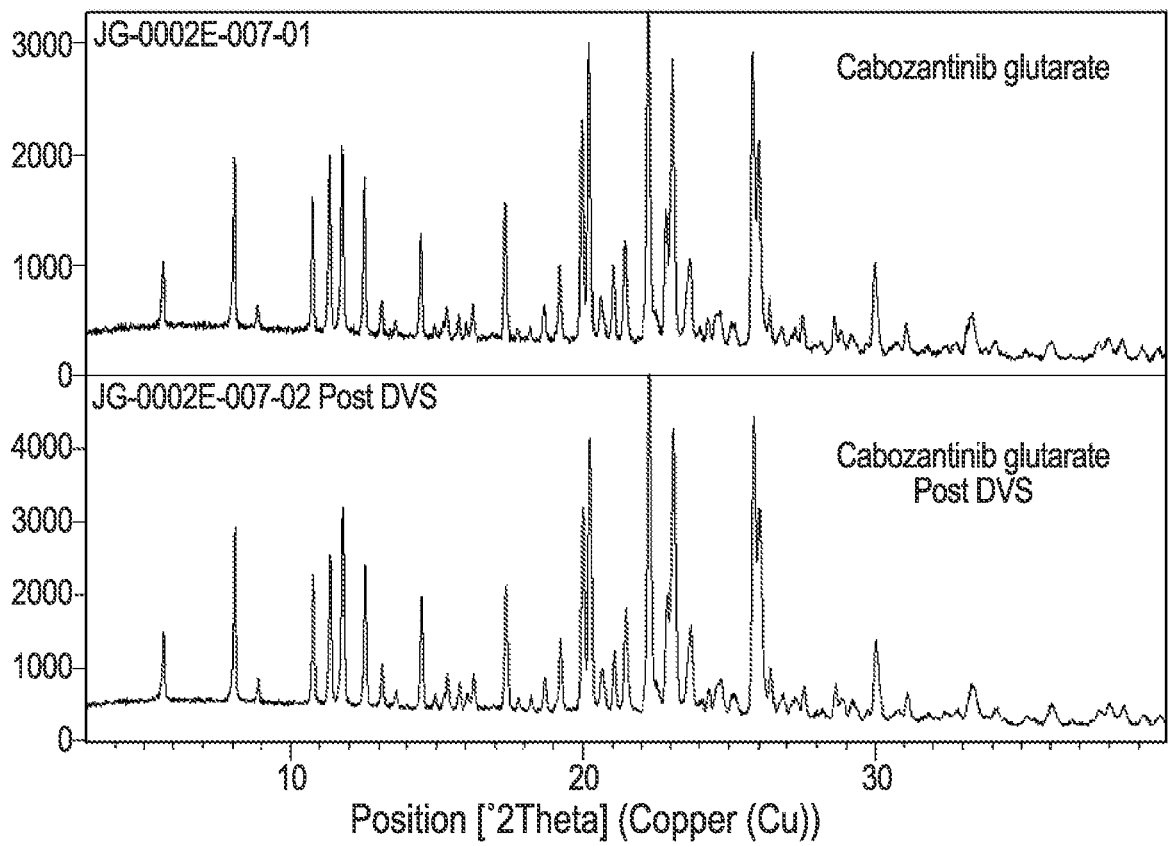
FIG. 54E is the XRPD spectrum of Form 20, Compound 1 glutarate, pre DVS (top) and post DVS (bottom).

The hygroscopicity and the sorption properties of Compound 1 glutarate were determined using Dynamic Vapor Sorption (DVS). The sample was dried at 0% RH prior to performing the sorption and desorption cycle. The isotherm (FIG. 54D) showed the total weight gain observed between 0% RH and 80% RH was 0.08% w/w, which indicates that the sample is non-hygroscopic according to the European Pharmacopoeia classification and less hygroscopic than both forms of Compound 1 (S)-malate (about 0.4% w/w). The low weight gain was reflected in the slightly noisy data. No significant hysteresis was observed between the sorption and desorption curves. XRPD analysis (FIG. 54E) of the post DVS sample showed the material remained unchanged.

Figure 54G:
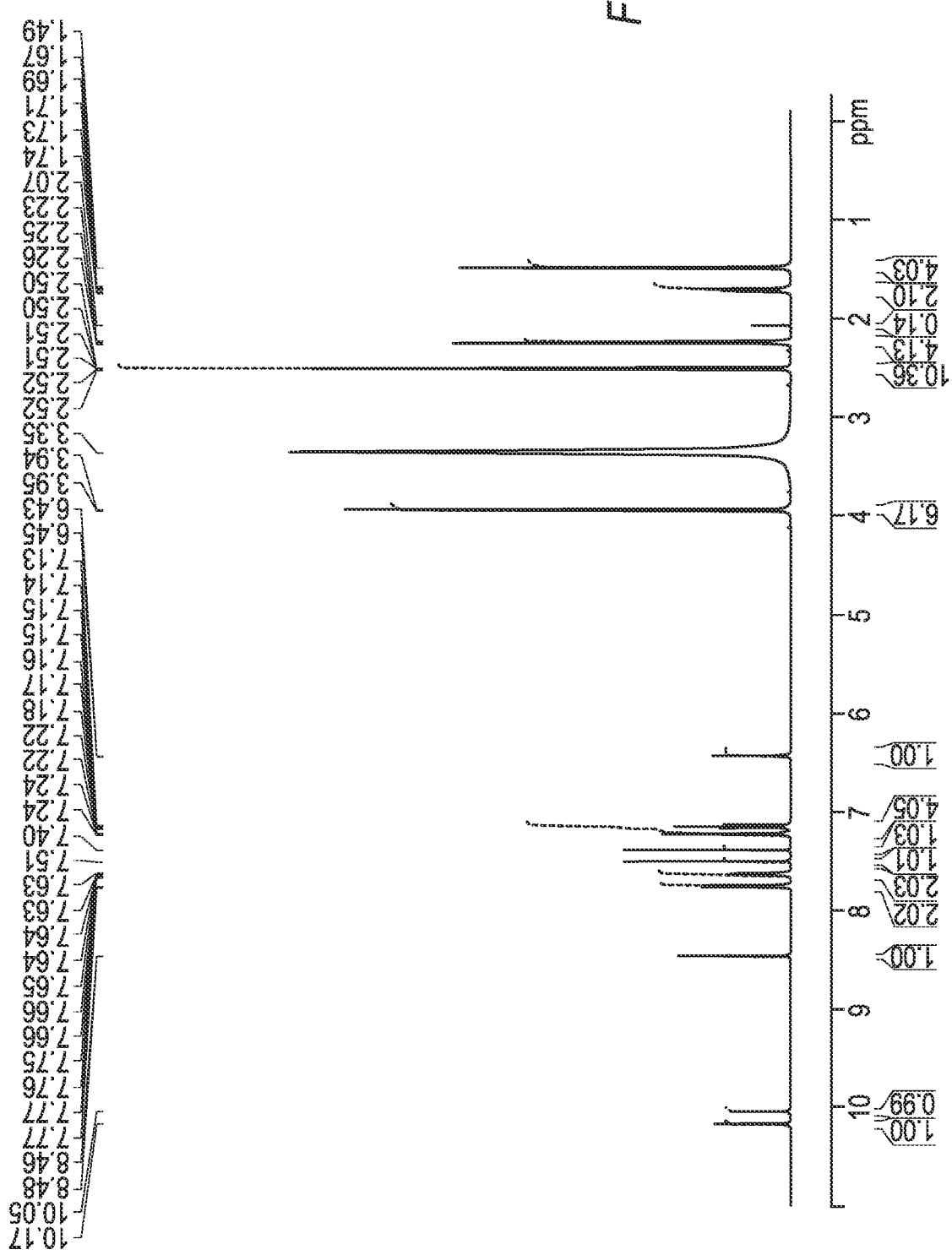
FIG. 54G is the $^1$H NMR (DMSO-$d^6$) of Form 20, Compound 1 glutarate.

The FT-IR spectrum obtained for the material (FIG. 54F) was shown to conform to the material structure with all expected functional groups present. $^1$H NMR spectroscopy (FIG. 54G) showed the material conformed to structure (API:acid, 1:1).

The 1:1 Compound 1 glutarate salt was a highly crystalline, non-hygroscopic, anhydrous material with a melting peak temperature at 178° C. It had an aqueous solubility of 0.016 mg/mL (pH about 3). Compared to malate salt of Compound 1, the Compound 1 glutarate salt has a lower hygroscopicity lower aspect ratio, and only one physical form observed to date. The improved particle morphology/ aspect ratio may lead to improvements in filterability and flow properties compared to the malate salt of Compound 1. Glutarate is well tolerated in vivo as it is a natural human metabolite.

Example 15: Preparation of Compound 1 Isethionate Monohydrate (Form 27)

0.07 M Isethionic acid solution in water (8.5 mL, 1.2 mol eq) was added to a glass vial, and the water was evaporated under a flow of $N_2$. Compound 1 (250 mg) and 2.5 mL of acetone/THF (97:3) were added. The suspension was heated at 50° C. for about 30 minutes. The experiment was slowly cooled to ambient temperature and stirred for about 96 hours. A sample was removed from the mixture, and the solids were isolated by centrifuge filtration and analyzed by XRPD analysis. XRPD analysis confirmed pure Form 27 material. The remainder of the material was isolated by filtration and washed with acetone/THF (97:3) (about 1 mL), and the solids air dried in the filter funnel for 30 minutes (approx. yield 215 mg, 68%).

Figure 55A:
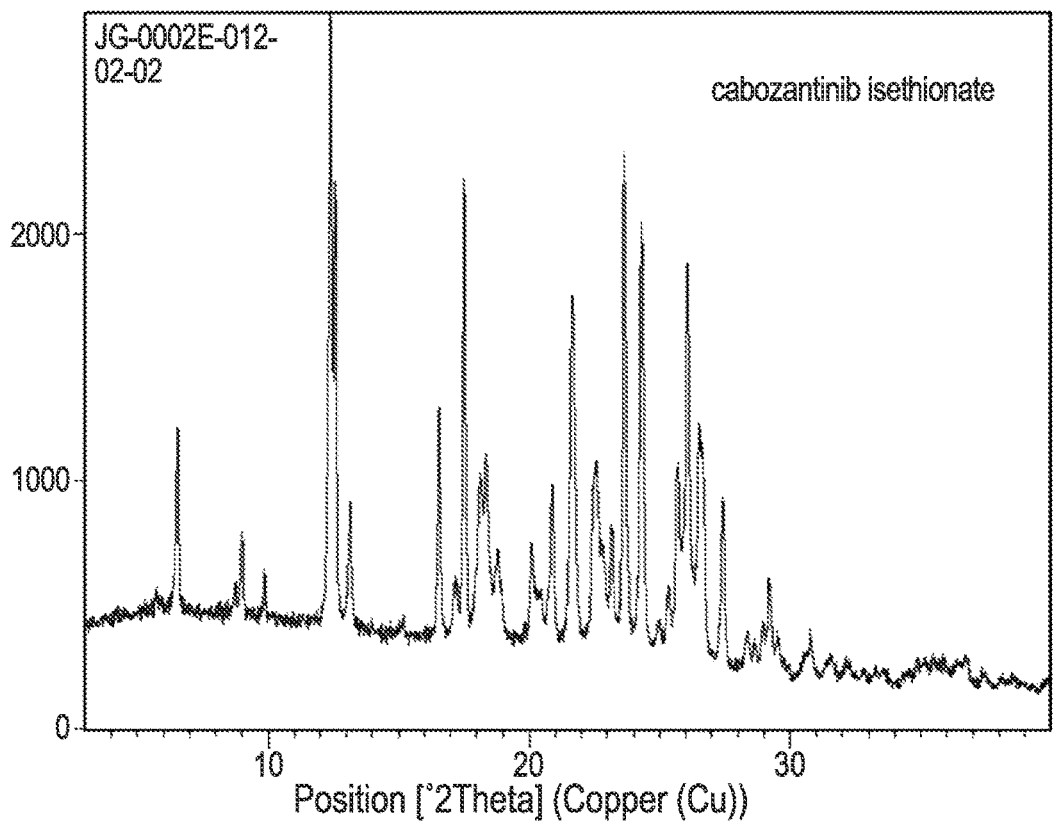
FIG. 55A is the XRPD spectrum of Form 27, Compound 1 isethionate, monohydrate.

XRPD analysis (FIG. 55A) indicated that the salt was crystalline. Optical microscopy confirmed the salts crystallinity showing birefringent needle shaped particles that readily aggregate.

Figure 55B:
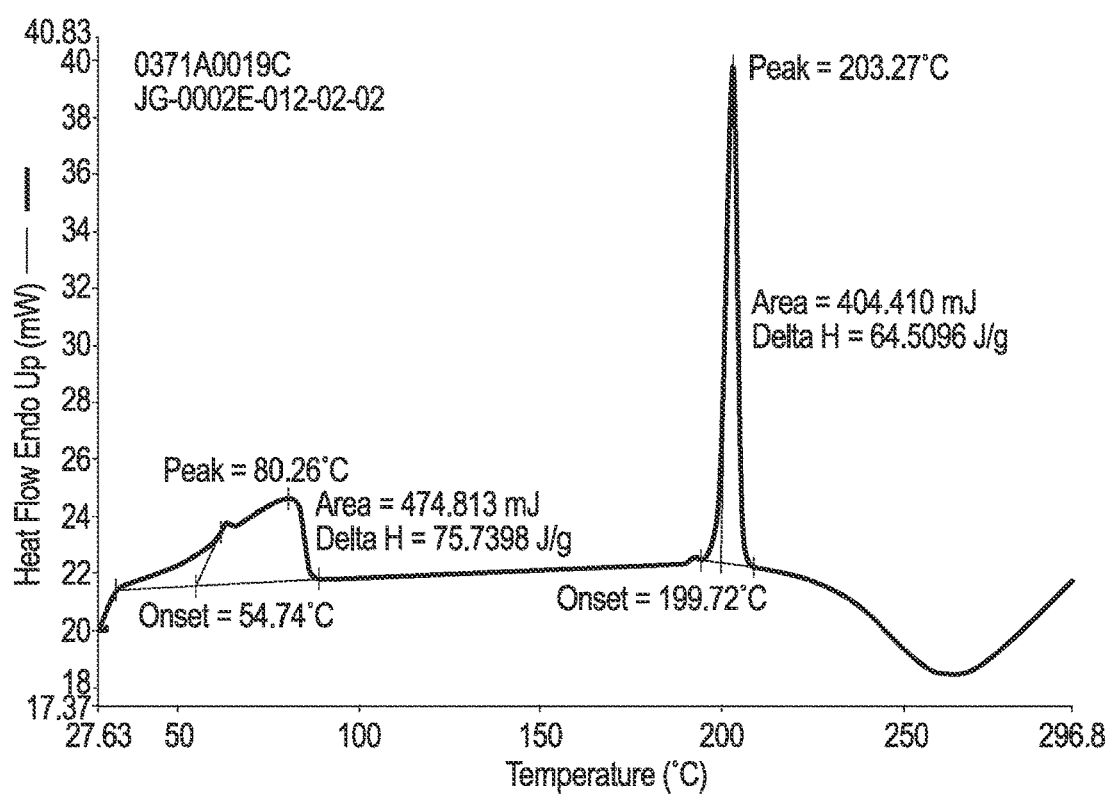
FIG. 55B is the DSC trace of Form 27, Compound 1 isethionate, monohydrate.
Figure 55C:
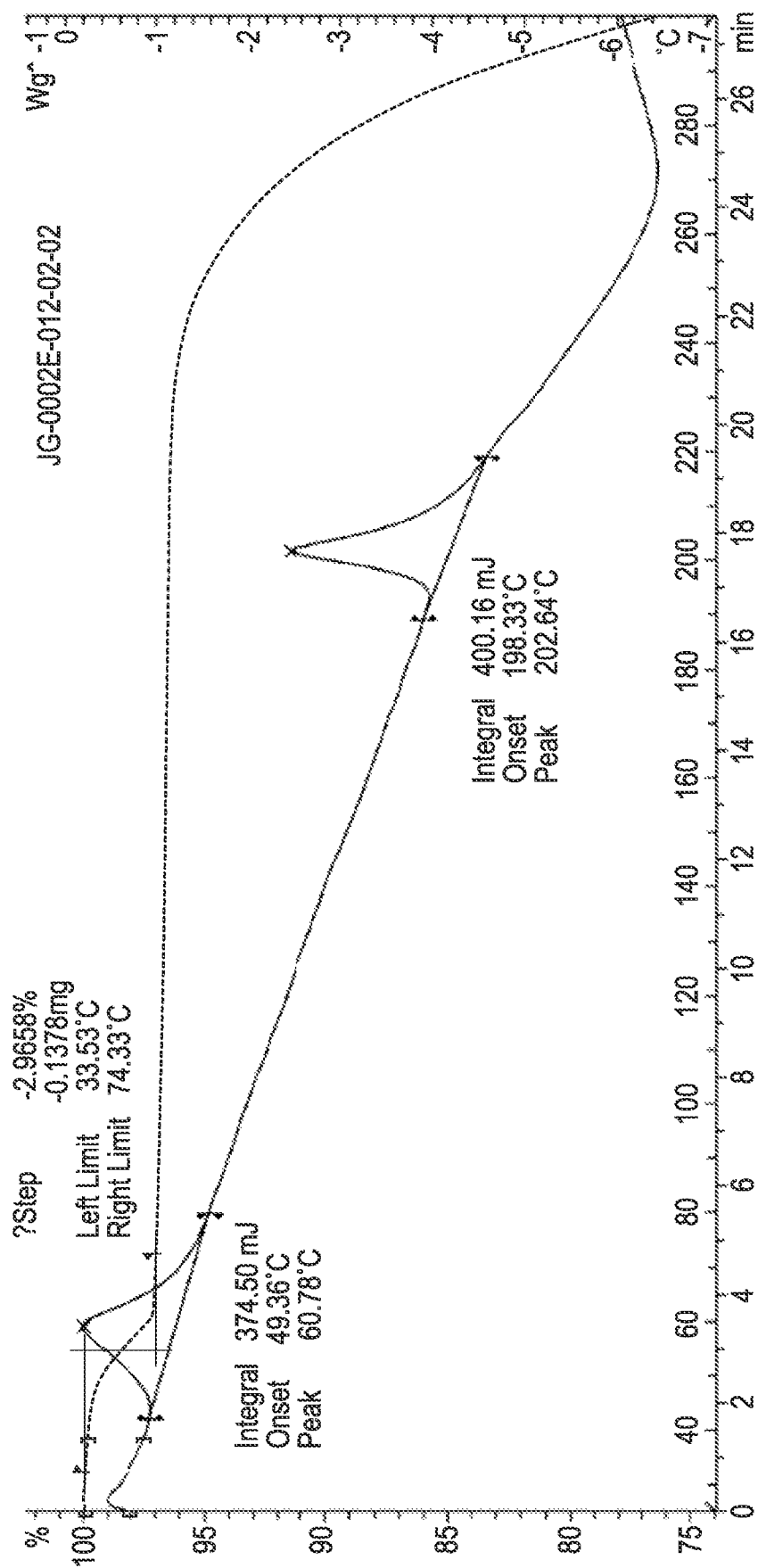
FIG. 55C is the TG/DTA thermogram of Form 27, Compound 1 isethionate, monohydrate.

The DSC thermogram obtained for Compound 1 isethionate is shown in FIG. 55B and shows two endothermic events consisting of a first thermal event with a peak temperature at about 80° C. and a second thermal event with a peak temperature at about 203° C. The TG/DTA trace (FIG. 55C) also shows two endotherms, the first endotherm occurs at onset about 49° C. and has an associated weight loss of 3% which corresponds to 1 molar equivalent of water. The second endothermic event at onset about 199° C. is due to the material melting.

Figure 55D:
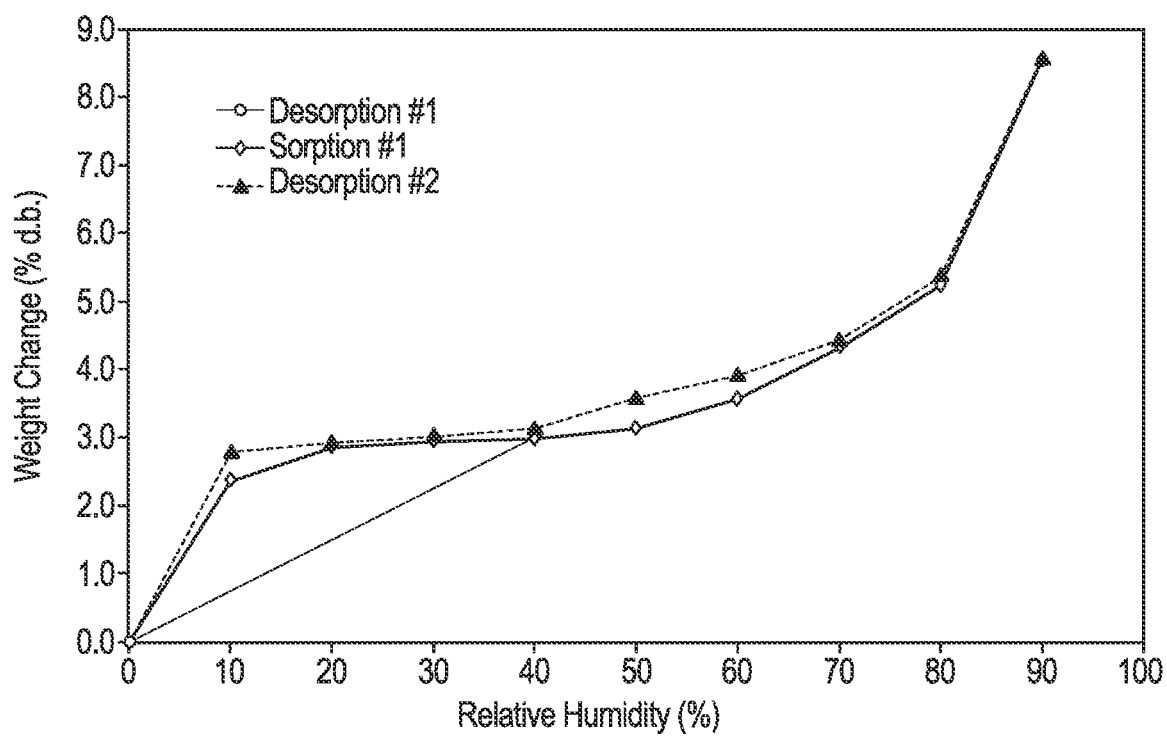
FIG. 55D is the DVS isotherm of Form 27, Compound 1 isethionate, monohydrate.
Figure 55E:
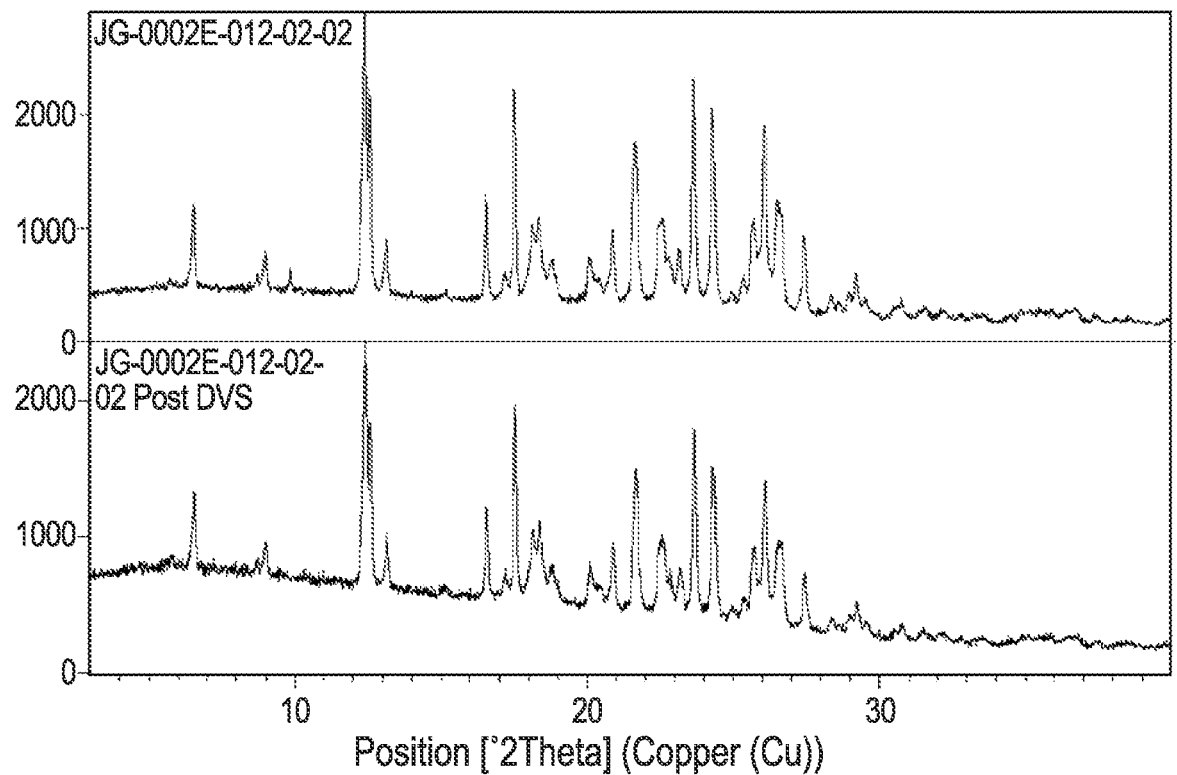
FIG. 55E is the XRPD spectrum of Form 27, Compound 1 isethionate, monohydrate, pre DVS (top) and post DVS (bottom).

The hygroscopicity and the sorption properties of Compound 1 isethionate monohydrate were determined using Dynamic Vapor Sorption (DVS). The sample was dried at 0% RH prior to performing the sorption and desorption cycle. The isotherm (FIG. 55D) showed a plateau of water content between 10-50% RH at about 3.0±0.1% w/w (1 mol. eq.). Above 50% RH, an increase in hygroscopicity was observed. The total weight gain observed between 20% RH and 80% RH was about 2.4% w/w, which implies that the hydrated form is hygroscopic. No significant hysteresis was observed between the sorption and desorption curves. XRPD analysis (FIG. 55E) of the post DVS sample showed the material remained unchanged.

Figure 55F:
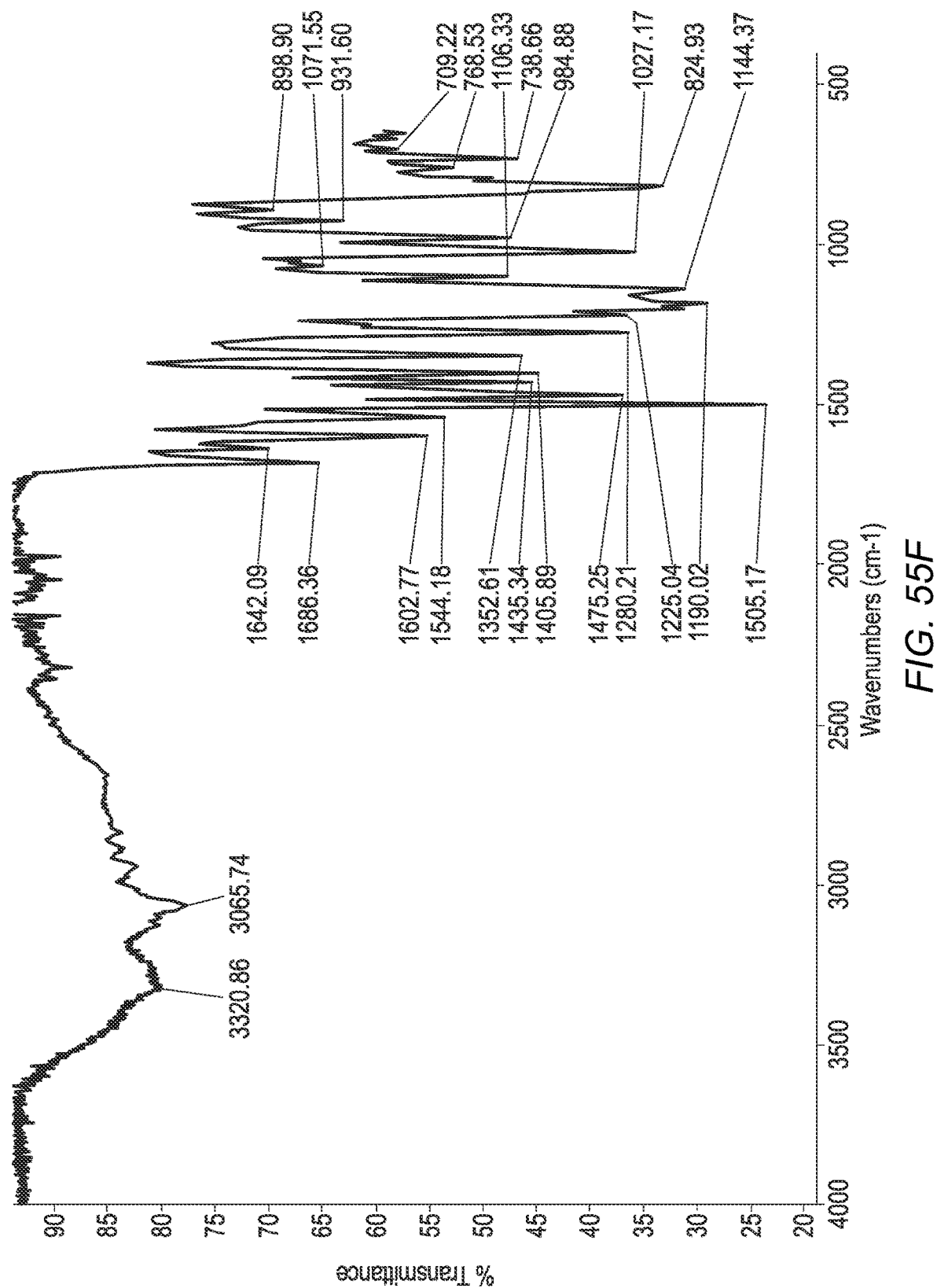
FIG. 55F is the infrared (IR) spectrum of Form 27, Compound 1 isethionate, monohydrate.
Figure 55G:
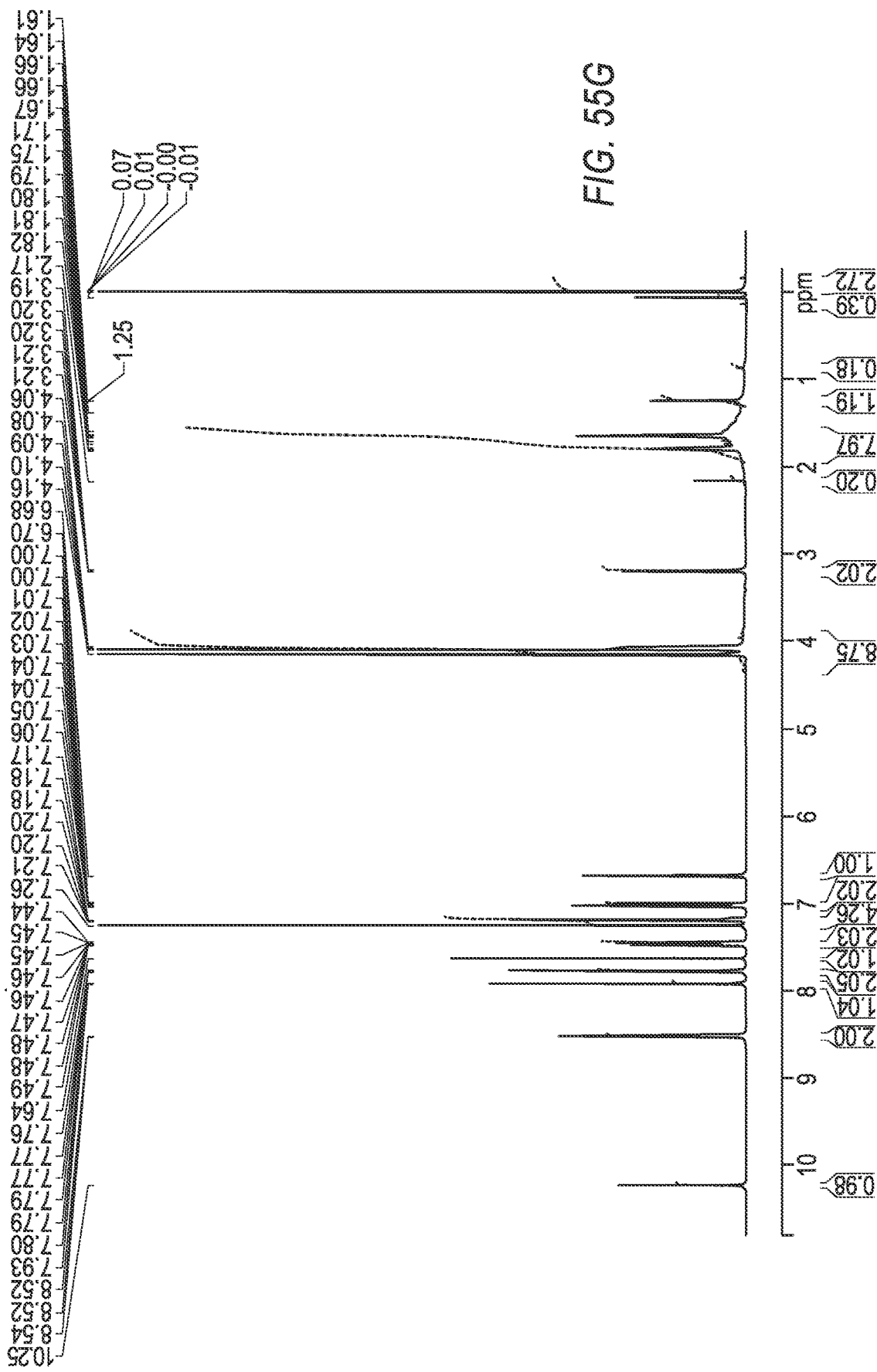
FIG. 55G is the $^1$H NMR (DMSO-$d^6$) of Form 27, Compound 1 isethionate, monohydrate.

The FT-IR spectrum obtained for the material is shown in FIG. 55F and was shown to conform to the material structure with all expected functional groups present. The $^1$H NMR spectrum of Compound 1 isethionate conformed to structure and confirmed the ratio of API peaks and acid peaks to be 1:1 (FIG. 55G).

The 1:1 Compound 1 isethionate monohydrate was a crystalline material with a melting peak temperature of the anhydrous form at 203° C. It had an aqueous solubility of 0.195 mg/mL (pH about 2). Compared to malate salt of Compound 1, the Compound 1 isethionate monohydrate salt has a much higher solubility.

Example 16: (Crystal Habit Experiment) Temperature Cycling in Acetone/Water (97:3, v/v)

Compound 1 salt (about 30 mg) was weighed into an HPLC vial, and 1 mL of acetone/water (97:3, v/v) added. The suspension was stirred at 400 rpm and subjected to 15 cycles of the following: 1) Heat from 23° C. to 53° C. at 0.5° C./minute, and 2) Cool from 53° C. to 23° C. at 0.2° C./minute. The samples were centrifuged, the solvents were decanted, and the solids were dried with strips of filter paper prior to XRPD analysis and optical microscopy.

Example 17: (Crystal Habit Experiment) Vapor Diffusion

Acetone/THF (50:50) was added in 100 μL aliquots to the Compound 1 salt until dissolution was almost reached. The suspension was filtered through a 0.2 μm filter into an HPLC vial, and this was placed inside a glass vial containing heptane. In the case of Compound 1 glutarate, seeds of glutarate salt were added to the solution. The solutions were left to stand at ambient temperature until sufficient solids were observed (3-6 days). The samples were centrifuged, the solvents were decanted, and the solids were dried with strips of filter paper prior to XRPD analysis and optical microscopy. Compound 1 salt (about 20 mg) was added to an HPLC vial, and the solid was dissolved in 200 μL of THF/H2O (80:20). The vial was placed uncapped into a glass vial containing acetone. Solids were collected by decanting solvent and drying the solids with strips of filter paper. XRPD analysis and optical microscopy were carried out on the solids.

Example 18: (Crystal Habit Experiment) Slow Evaporation from Acetone/THF

Compound 1 salt (about 20 mg) was dissolved in 1 mL of acetone/THF (50:50). The vial was covered with perforated aluminium foil and left to evaporate at ambient temperature. The solids were analyzed by XRPD and optical microscopy.

Example 19: (Crystal Habit Experiment) Slurry in Chloroform

Compound 1 pyruvate or glutarate (about 20 mg) was slurried in CDCl$_3$ (200-500 μL) at 50° C. for 24 hours. For isethionate, no solids were present, and the solution was cooled to ambient temperature and stirred for 6 days. Solids were collected by centrifugation and decantation of solvent, and the solids were dried with strips of filter paper. XRPD analysis and optical microscopy were carried out on the solids.

Example 20: (Crystal Habit Experiment) Slurry in EtOH

Compound 1 pyruvate or isethionate (about 20 mg) was slurried in EtOH (500 μL) at 50° C. for 24 hours, and the solids were collected by centrifugation and decantation of solvent. The solids were dried with strips of filter paper. XRPD analysis and optical microscopy were carried out on the solids. Compound 1 glutarate (about 20 mg) and EtOH (1 mL) were added to a vial. Dissolution was observed. The vial was covered with perforated aluminium foil, and the solvent evaporated. XRPD analysis and optical microscopy were carried out on the solids.

Example 21: Salt/Cocrystal Screening

Part A: Solvent Based Screening Techniques

Solvent based experiments were performed on approximately 40 mg scale in glass vials. The methods employed are described in detail herein. Evaporation, precipitation, sonication, and slurry (at ambient and elevated temperatures) are good methods for salt formation and were used in this screen.

Part B: Precipitation/Slurry Experiments

Precipitation experiments were carried out by mixing API and acid in THF/H$_2$O (80:20) or THF/acetone (97:3) and isolating any precipitated solids. Any experiments which remained as solutions were evaporated, and any solids generated were analyzed by XRPD. Solids which exhibited new XRPD patterns were further analyzed by $^1$H NMR spectroscopy and TG/DTA analysis to confirm stoichiometry and solvent content. Table 35 shows the results from the precipitation/slurry experiments carried out in THF/H$_2$ (80:20). Five of the experiments from THF/H$_2$O (80:20) gave precipitates with unique crystalline XRPD patterns (Forms 1-5). The remaining experiments were evaporated, and any solids isolated were analyzed by XRPD. In an attempt to generate more crystalline material, the solids were re-slurried in THF, THF/EtOH, or EtOH as described herein, yielding Forms 15 and 16.

TABLE 35

Results of precipitation experiments in THF/H$_2$O (80:20)

| Acid/Co-former | Ppt formed | Evap | XRPD (solids formed) | Slurry | XRPD after slurry |
|---|---|---|---|---|---|
| ascorbic | no | yes | disordered Form I | — | — |
| benzene sulfonic | no | yes | disordered | THF at 50° C. | Form 15 |
| citric | yes | no | Form 1 | — | — |
| ethane sulfonic | no | yes | disordered | THF at 50° C. | solution |
| glycolic | no | yes | disordered Form I | — | — |
| lactic (L) | no | yes | Form I | — | — |
| malonic | yes | yes | Form 2 | — | — |
| methane sulfonic | no | yes | very disordered | THF at 50° C. | Form 16 |
| p-toluene sulfonic | no | yes | disordered | THF at 50° C. | disordered |
| pyroglutamic (L) | no | yes | disordered | THF at 50° C. | solution |
| succinic | no | yes | disordered | solution | — |
| sulfuric | yes | no | Form 5 | — | — |
| 4-hydroxybenzoic | yes | no | Form I + amorphous | — | — |
| n-acetylglycine | no | yes | disordered Form II | — | — |
| ethane 1,2-disulfonic | yes | no | Form 4 | — | — |
| gluconic (D) | no | yes | disordered | THF at 50° C. | Form 26 |
| glucuronic (D) | no | yes | disordered | EtOH/THF at 50° C. | solution |
| glutaric | no | yes | disordered | THF at 50° C. | Form III |
| isethionic | no | yes | Form I | — | — |
| 2-ketoglutaric | no | yes | disordered | EtOH/THF at 50° C. | solution |
| oxalic | yes | no | Form 3 | — | — |
| pyruvic | no | yes | disordered | THF at 50° C. | solution |
| erythritol | no | yes | Form I + erythritol | — | — |
| lysine (L) | no | yes | Form I and Form II | — | — |
| nicotinamide | no | yes | Form I | — | — |
| tromethamine | no | yes | Form I, II and tromethamine | EtOH at 60° C. | solution |
| urea | no | yes | Form I | — | — |
| xylitol | no | yes | Form I + extra peaks | EtOH at 60° C. | Form III |

Table 36 shows the results from the precipitation/slurry experiments carried out in THF/acetone (97:3). Solids were recovered by centrifugation, decantation of the solvents, and drying with filter paper prior to analysis by XRPD. Experiments which did not contain solid after 16 hours were evaporated, and the solids were analyzed by XRPD. Forms 1, 6-14, and 27 were isolated from these experiments.

TABLE 36 results of precipitation experiments in THF/acetone (97:3)

| Acid/co-former | Heated to 50° C. | Dissolved | Solids 16 hrs? | Evap | XRPD | Reaction type |
|---|---|---|---|---|---|---|
| ascorbic | yes | yes | No | yes | — | evap |
| benzene sulfonic | yes | no | Yes | — | Form 6 | slurry |
| citric | no | yes | No | yes | Form 1 | evap |
| ethane sulfonic | yes | no | Yes | — | Form 8 | slurry |
| glycolic | yes | yes | No | yes | Form III | evap |
| lactic (L) (1M) | yes | yes | No | yes | Form III | evap |
| malonic | yes | no | Yes | — | Form 8 | slurry |
| methane sulfonic | yes | no | Yes | — | Form 9 | slurry |
| p-toluene sulfonic | yes | no | Yes | — | Form 10 | slurry |
| pyroglutamic (L) | yes | yes | No | yes | disordered Form III | evap |
| succinic | yes | yes | No | yes | disordered Form III | evap |
| sulfuric (1M) | yes | no | Yes | — | Form 11 | slurry |
| 4-hydroxybenzoic | no | no | Yes | — | Form III | slurry |
| n-acetylglycine | yes | yes | slight ppt | — | Form III + N-acetylglycine | pptn. |
| ethane 1,2-disulfonic | yes | no | Yes | — | Form 12 | slurry |
| gluconic (D) | yes | almost | slight ppt | — | Disordered Form III | slurry |
| glucuronic (D) | yes | almost | Yes | — | Form III + Dglucuronic | slurry |
| glutaric | yes | yes | No | yes | Form III | evap |
| isethionic | yes | no | Yes | — | Form 27 | slurry |
| 2-ketoglutaric | no | yes | No | yes | disordered | evap |
| oxalic | yes | no | Yes | — | Form 13 | slurry |
| pyruvic | yes | yes | No | yes | Form 14 | evap |
| erythritol | yes | yes | slight ppt | — | Form III + erythritol | pptn. |
| lysine (L) | yes | almost | Yes | — | Form III + disordered | slurry |
| nicotinamide | yes | yes | No | yes | Form III | evap |
| tromethamine | yes | yes | slight ppt | — | Form III | pptn. |

TABLE 36-continued results of precipitation experiments in THF/acetone (97:3)

| Acid/co-former | Heated to 50° C. | Dissolved | Solids 16 hrs? | Evap | XRPD | Reaction type |
|---|---|---|---|---|---|---|
| urea | yes | yes | No | yes | Form III | evap |
| xylitol | yes | yes | slight ppt | — | Form III | pptn. |

Part C: Salt Formations Using 0.5 Molar Equivalents of Co-Former

Salt formations were carried out as detailed herein using 2:1 equivalents of API:acid/co-former. Forms 11 and 12 were isolated from these experiments. $^1$H NMR spectroscopy of Forms 11 and 12 confirmed 2:1 ratio of API to acid.

TABLE 37

Screening results from 2:1 (API:acid) stoichiometry experiments in THF/acetone (97:3)

| Acid | Observations | XRPD |
|---|---|---|
| citric | suspension throughout | Form III + Type 1 |
| sulfuric (0.5M) | dissolved and precipitated | Form 11 |
| ethane 1,2-disulfonic | suspension throughout | Form 12 |
| 2-ketoglutaric | suspension throughout | Form III + extra peaks |
| oxalic | suspension throughout | Form III + Form 13 |
| pyruvic | suspension throughout | Form III + extra peaks |

Part D: Salt Formation with Liquid Acid and Compound 1

The reactions of Compound 1 in liquid acid in the absence of solvent did not yield any salts. Therefore, acetonitrile was added, and the mixtures were slurried for a further 16 hours. Forms 5, 25, and 26 (sulfate, mesylate, and gluconate) were isolated from these reactions.

TABLE 38

Screening results from salt formations with liquid acids

| Acid | Solvent | Result | XRPD |
|---|---|---|---|
| ethane sulfonic | none | solid | Form III |
| lactic (L) (1M) | none | solid | Form III + amorphous |
| methane sulfonic | none | solid | Form III + Type 9 |
| sulfuric (0.5M) | none | solid | amorphous + disordered |
| gluconic (D) | none | solid | Form III |
| pyruvic | none | solid | Form III + amorphous |
| ethane sulfonic | acetonitrile | solid | Type 18 |
| lactic (L) (1M) | acetonitrile | solid | Form I (PS) |
| methane sulfonic | acetonitrile | solid | Form 25 |
| sulfuric (0.5M) | acetonitrile | solid | Form 5 |
| gluconic (D) | acetonitrile | solid | Form 26 |
| pyruvic | acetonitrile | solid | Form 14(PS) + extra peaks |

Part E: Sonication

Table 39 shows the results of salt formation by sonication. Forms 6, 9, 10, 12, 14, 17, 18, 19, 20, 21, 22, and 26 were all isolated from these experiments.

TABLE 39

Screening results from sonication experiments

| Acid | Solvent | XRPD |
|---|---|---|
| ascorbic | CH$_3$CN | Form III + ascorbic acid |
|  | CH$_3$CN/H$_2$O (87:13) | Form III + amorphous |
| benzene sulfonic | CH$_3$CN | Form 6 |
|  | CH$_3$CN/H$_2$O (87:13) | Form 6 + extra peaks |

TABLE 39-continued

Screening results from sonication experiments

| Acid | Solvent | XRPD |
|---|---|---|
| citric | CH$_3$CN | Disordered Form III + Form 1 (small amt) |
|  | CH$_3$CN/H$_2$O (87:13) | Form 1 disordered |
| ethane sulfonic | CH$_3$CN | Form 18 |
|  | CH$_3$CN/H$_2$O (87:13) | highly disordered |
| glycolic | CH$_3$CN | Form III |
|  | CH$_3$CN/H$_2$O (87:13) | Form III |
| lactic (L) (1M) | CH$_3$CN | Form III |
|  | CH$_3$CN/H$_2$O (87:13) | Form III |
| malonic | CH$_3$CN | Form III (PS) + new peaks |
|  | CH$_3$CN/H$_2$O (87:13) | Form III (weak) |
| methane sulfonic | CH$_3$CN | Form 9 |
|  | CH$_3$CN/H$_2$O (87:13) | weak |
| p-toluene sulfonic | CH$_3$CN | Form 10 |
|  | CH$_3$CN/H$_2$O (87:13) | Form 22 |
| pyroglutamic (L) | CH$_3$CN | Form III |
|  | CH$_3$CN/H$_2$O (87:13) | Form III (weak) |
| succinic | CH$_3$CN | Form 17 |
|  | CH$_3$CN/H$_2$O (87:13) | Form III |
| sulfuric (0.5M) | CH$_3$CN | Form 21 |
|  | CH$_3$CN/H$_2$O (87:13) | disordered |
| 4-hydroxybenzoic | CH$_3$CN | Form III + extra peaks |
|  | CH$_3$CN/H$_2$O (87:13) | Form III + extra peaks |
| n-acetylglycine | CH$_3$CN | Form III + N-acetylglycine |
|  | CH$_3$CN/H$_2$O (87:13) | Form III |
| ethane 1,2-disulfonic | CH$_3$CN | Form 12 |
|  | CH$_3$CN/H$_2$O (87:13) | Form 12 |
| gluconic (D) | CH$_3$CN | Form 26 |
|  | CH$_3$CN/H$_2$O (87:13) | amorphous |
| glucuronic (D) | CH$_3$CN | Form III + gluconic |
|  | CH$_3$CN/H$_2$O (87:13) | disordered |
| glutaric | CH$_3$CN | Form 20 + Form III |
|  | CH$_3$CN/H$_2$O (87:13) | Form 20 + Form III |
| isethionic | CH$_3$CN | Form 19 |
|  | CH$_3$CN/H$_2$O (87:13) | disordered |
| 2-ketoglutaric | CH$_3$CN | Form III |
|  | CH$_3$CN/H$_2$O (87:13) | Form III |
| oxalic | CH$_3$CN | Form III |
|  | CH$_3$CN/H$_2$O (87:13) | Form III |
| pyruvic | CH$_3$CN | Form 14 |
|  | CH$_3$CN/H$_2$O (87:13) | disordered |
| erythritol | CH$_3$CN | Form III + erythritol |
|  | CH$_3$CN/H$_2$O (87:13) | Form III |
| lysine (L) | CH$_3$CN | Form III |
|  | CH$_3$CN/H$_2$O (87:13) | Form III |
| nicotinamide | CH$_3$CN | Form III + nicotinamide |
|  | CH$_3$CN/H$_2$O (87:13) | Form III + nicotinamide |
| tromethamine | CH$_3$CN | Form III + tromethamine |
|  | CH$_3$CN/H$_2$O (87:13) | Form III |
| urea | CH$_3$CN | Form III |
|  | CH$_3$CN/H$_2$O (87:13) | Form III |
| xylitol | CH$_3$CN | Form III |
|  | CH$_3$CN/H$_2$O (87:13) | Form III |

Example 22: Humidity Stress Experiments

Compound 1 salts were stressed at 40 CC/75% relative humidity for about 7 days and analyzed by XRPD to determine the physical stability at increased relative humidity. The weight change was also recorded (see Table 40). Forms 1, 2, 6, 9-14, 16, 19, 21, 22, 24, and 27 showed small weight changes and no change of form by XRPD analysis, indicating that these salts are relatively stable to high relative humidity. Forms 5, 7, 15, 17, 18, 25, and 26 showed larger weight changes and/or a change in physical form after humidity stressing. Compound 1 oxalate (Form 3) had a weight loss of 43.17% but no form change by XRPD analysis, suggesting that the salt contained a large amount of surface solvent and/or water.

TABLE 40 results from humidity stressing experiments

| Form | Acid | % Weight Change | XRPD |
|---|---|---|---|
| 1 | citric | −0.94 | Form 1 |
| 2 | malonic | +1.02 | Form 2 |
| 3 | oxalic | −43.17 | Form 3 |
| 5 | sulfuric (0.5M) | −51.79 | disordered |
| 6 | benzene sulfonic | −1.37 | Form 6 |
| 7 | ethane sulfonic | −0.90 | Form 4 |
| 9 | methane sulfonic | −0.82 | Form 9 |
| 10 | p-toluene sulfonic | −0.09 | Form 10 |
| 11 | sulfuric (0.5M) | −1.54 | Form 11 |
| 12 | ethane 1,2-disulfonic | +0.74 | Form 12 |
| 13 | oxalic | −0.41 | Form 13 + PS |
| 14 | pyruvic | −0.98 | Form 14 |
| 15 | benzene sulfonic | −22.01 | highly disordered |
| 16 | methane sulfonic | +0.85 | Form 16 |
| 17 | succinic | −46.46 | Form 23 |
| 18 | ethane sulfonic | +10.35 | highly disordered |
| 19 | isethionic | +2.02 | Form 19 |
| 20 | glutaric | +0.06 | Form 20 + Form III |
| 21 | sulfuric (0.5M) | +0.02 | Form 21 |
| 22 | p-toluene sulfonic | −0.25 | Form 22 |
| 24 | malonic | +0.22 | Form 24 |
| 25 | methane sulfonic | +6.71 | highly disordered |
| 26 | gluconic (D) | +2.52 | highly disordered |
| 27 | isethionic | −1.70 | Form 27 |

Example 23: Crystal Habit Investigation of Selected Compound 1 Salts

Investigation into crystal habit was carried out on each of the selected salts using a variety of experiments including temperature cycling, vapor diffusion, slow evaporation, and slurry experiments.

Part A: Crystal Habit Experiments on Compound 1 Pyruvate (Form 14)

Compound 1 pyruvate (Form 14) generated from a precipitation of Compound 1 and pyruvic acid in THF/acetone, consisted of small irregularly shaped particles. Attempts to increase the particle size were made by temperature cycling, vapor diffusion, slurries and slow evaporation. The solids were analyzed by XRPD analysis upon recovery. Slurrying in ethanol afforded Compound 1 (Form III), and vapor diffusion in acetone/THF with heptane yielded solids with a weak/amorphous XRPD diffractogram. Temperature cycling in acetone/water increased the particle size. Vapor diffusion using THF/water (80:20) as the solvent and acetone as the anti-solvent yielded very large crystals. Slurrying in chloroform and slow evaporation from acetone/THF caused no significant change in crystal habit.

Part B: Crystal Habit Experiments on Compound 1 Glutarate (Form 20)

Compound 1 glutarate (Form 20) formed from a slurry of Compound 1 and glutaric acid in acetonitrile consisted of small irregularly shaped particles. Attempts to increase the particle size were made by temperature cycling, vapor diffusion, slurries and slow evaporation. The solids remained as Form 20 except the solids isolated from slurrying in ethanol, which yielded Form III material. Temperature cycling in acetone/water (97:3% v/v) greatly increased particle size and large block-like particles (30-50 µm) were observed. Vapor diffusion using acetone/THF (50:50) as the solvent and heptane as the anti-solvent afforded larger elliptical shaped particles, which may improve filterability. Slurrying in chloroform, slow evaporation from acetone/THF, and vapor diffusion using THF/H$_2$O (80:20) as the solvent and acetone as the anti-solvent showed no significant change in crystal habit.

Part C: Crystal Habit Experiments on Compound 1 Isethionate Monohydrate (Form 27)

Compound 1 isethionate (Form 27) isolated from a slurry of Compound 1 and isethionic acid in acetone/THF consisted of needle like particles. Attempts to increase the particle size were made by temperature cycling, vapor diffusion, slurries and slow evaporation. The solids were analyzed by XRPD analysis upon recovery. Form 27 material was only recovered from two experiments: temperature cycling in acetone/water and vapor diffusion in THF/water with acetone. Temperature cycling slightly increased needle size and also gave some large block-like particles. Vapor diffusion from THF/water (80:20) solvent using acetone as the anti-solvent yielded longer acicular particles which may cause difficulties in filtration. A new pattern was observed from slurrying in EtOH, and $^1$H NMR suggests it is an ethanol solvate of the salt. Vapor diffusion using acetone/THF (50:50) as the solvent and heptane as the anti-solvent generated solids with a new XRPD pattern. $^1$H NMR spectroscopy showed the material to be free base related. Slow evaporation from acetone/THF (50:50) afforded Form III solids.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. Crystalline solid salts of N-{4-[(6,7-dimethoxyquinolin-4-yl)oxy]phenyl}-N'-(4-fluorophenyl) cyclopropane-1,1-dicarboxamide (Compound 1), wherein the crystalline solid salts are selected from the group consisting of:

N-{4-[(6,7-dimethoxyquinolin-4-yl)oxy]phenyl}-N'-(4-fluorophenyl) cyclopropane-1,1-dicarboxamide (Compound 1) citrate monohydrate Form 1;

N-{4-[(6,7-dimethoxyquinolin-4-yl)oxy]phenyl}-N'-(4-fluorophenyl) cyclopropane-1,1-dicarboxamide (Compound 1) malonate Form 2;

N-{4-[(6,7-dimethoxyquinolin-4-yl)oxy]phenyl}-N'-(4-fluorophenyl) cyclopropane-1,1-dicarboxamide (Compound 1) oxalate Form 3;

N-{4-[(6,7-dimethoxyquinolin-4-yl)oxy]phenyl}-N'-(4-fluorophenyl) cyclopropane-1,1-dicarboxamide (Compound 1) sulfate Form 5;

N-{4-[(6,7-dimethoxyquinolin-4-yl)oxy]phenyl}-N'-(4-fluorophenyl) cyclopropane-1,1-dicarboxamide (Compound 1) esylate Form 7;

N-{4-[(6,7-dimethoxyquinolin-4-yl)oxy]phenyl}-N'-(4-fluorophenyl) cyclopropane-1,1-dicarboxamide (Compound 1) mesylate Form 9;

N-{4-[(6,7-dimethoxyquinolin-4-yl)oxy]phenyl}-N'-(4-fluorophenyl) cyclopropane-1,1-dicarboxamide (Compound 1) tosylate Form 10;

N-{4-[(6,7-dimethoxyquinolin-4-yl)oxy]phenyl}-N'-(4-fluorophenyl) cyclopropane-1,1-dicarboxamide (Compound 1) sulfate Form 11;

N-{4-[(6,7-dimethoxyquinolin-4-yl)oxy]phenyl}-N'-(4-fluorophenyl) cyclopropane-1,1-dicarboxamide (Compound 1) oxalate Form 13;

N-{4-[(6,7-dimethoxyquinolin-4-yl)oxy]phenyl}-N'-(4-fluorophenyl) cyclopropane-1,1-dicarboxamide (Compound 1) besylate Form 15;

N-{4-[(6,7-dimethoxyquinolin-4-yl)oxy]phenyl}-N'-(4-fluorophenyl) cyclopropane-1,1-dicarboxamide (Compound 1) mesylate dihydrate Form 16;

N-{4-[(6,7-dimethoxyquinolin-4-yl)oxy]phenyl}-N'-(4-fluorophenyl) cyclopropane-1,1-dicarboxamide (Compound 1) succinate Form 17;

N-{4-[(6,7-dimethoxyquinolin-4-yl)oxy]phenyl}-N'-(4-fluorophenyl) cyclopropane-1,1-dicarboxamide (Compound 1) esylate Form 18;

N-{4-[(6,7-dimethoxyquinolin-4-yl)oxy]phenyl}-N'-(4-fluorophenyl) cyclopropane-1,1-dicarboxamide (Compound 1) sulfate monohydrate Form 21;

N-{4-[(6,7-dimethoxyquinolin-4-yl)oxy]phenyl}-N'-(4-fluorophenyl) cyclopropane-1,1-dicarboxamide (Compound 1) tosylate Form 22;

N-{4-[(6,7-dimethoxyquinolin-4-yl)oxy]phenyl}-N'-(4-fluorophenyl) cyclopropane-1,1-dicarboxamide (Compound 1) succinate Form 23;

N-{4-[(6,7-dimethoxyquinolin-4-yl)oxy]phenyl}-N'-(4-fluorophenyl) cyclopropane-1,1-dicarboxamide (Compound 1) malonate Form 24; and N-{4-[(6,7-dimethoxyquinolin-4-yl)oxy]phenyl}-N'-(4-fluorophenyl) cyclopropane-1,1-dicarboxamide (Compound 1) mesylate Form 25.

2. The crystalline solid salts of claim 1, wherein

Compound 1 •citrate monohydrate Form 1 comprises Compound 1 and citrate in a 1:1 molar ratio;

Compound 1 •malonate Form 2 comprises Compound 1 and malonate in a 1:1 molar ratio;

Compound 1 •oxalate Form 3 comprises Compound 1 and oxalate in a 1:1 molar ratio;

Compound 1 •sulfate Form 5 comprises Compound 1 and sulfate in a 1:1 molar ratio;

Compound 1 •esylate Form 7 comprises Compound 1 and esylate in a 1:1 molar ratio;

Compound 1 •mesylate Form 9 comprises Compound 1 and mesylate in a 1:1 molar ratio;

Compound 1 •tosylate Form 10 comprises Compound 1 and tosylate in a 1:1 molar ratio;

Compound 1 •sulfate Form 11 comprises Compound 1 and sulfate in a 1:1molar ratio;

Compound 1 •oxalate Form 13 comprises Compound 1 and oxalate in a 1:1 molar ratio;

Compound 1 •besylate Form 15 comprises Compound 1 and besylate in a 1:1 molar ratio;

Compound 1 •mesylate dihydrate Form 16 comprises Compound 1 and mesylate in a 1:1 molar ratio;

Compound 1 •succinate Form 17 comprises Compound 1 and succinate in a 1:0.7 molar ratio;

Compound 1 •esylate Form 18 comprises Compound 1 and esylate in a 1:1 molar ratio;

Compound 1 •sulfate monohydrate Form 21 comprises Compound 1 and sulfate in a 1:1 molar ratio;

Compound 1 •tosylate Form 22 comprises Compound 1 and tosylate in a 1:1 molar ratio;

Compound 1 •succinate Form 23 comprises Compound 1 and succinate in a 1:0.6 molar ratio;

Compound 1 •malonate Form 24 comprises Compound 1 and malonate in a 1:0.6 molar ratio; and Compound 1 •mesylate Form 25 comprises Compound 1 and mesylate in a 1:1 molar ratio.

3. The crystalline solid salts of claim 1, wherein

Compound 1 •citrate monohydrate Form 1 is characterized by an XRPD pattern comprising one or more peaks selected from 4.02, 9.61, 13.35, 13.50, 15.52, 16.45, 18.49, 20.94, 21.29, 21.50, 21.59, 23.85, 26.83, and 27.12 degrees 2θ;

Compound 1 •malonate Form 2 is characterized by an XRPD pattern comprising one or more peaks selected from 6.36, 7.97, 11.99, 12.09, 12.75, 13.64, 17.52, 19.58, 20.57, 21.82, 23.43, 24.73, 24.79, 25.01, 26.09, 26.93, 27.36, 27.42, and 27.61 degrees 2θ;

Compound 1 •oxalate Form 3 is characterized by an XRPD pattern comprising one or more peaks selected from 7.40, 9.44, 9.78, 10.36, 12.67, 12.97, 13.60, 14.42, 15.87, 18.65, 19.06, 21.21, 22.05, 22.76, 23.07, 24.89, and 25.69 degrees 2θ;

Compound 1 •sulfate Form 5 is characterized by an XRPD pattern comprising one or more peaks selected from 9.56, 10.08, 13.29, 13.86, 14.17, 22.27, 22.60, 22.93, 25.16, and 27.70 degrees 2θ;

Compound 1 •esylate Form 7 is characterized by an XRPD pattern comprising one or more peaks selected from 5.18, 11.63, 14.09, 14.79, 16.89, 19.92, 21.05, and 26.46 degrees 2θ;

Compound 1 •mesylate Form 9 is characterized by an XRPD pattern comprising one or more peaks selected from 5.75, 11.33, 15.57, 16.19, 16.34, 16.76, 17.36, 17.90, 20.87, 22.69, and 23.08 degrees 2θ;

Compound 1 •tosylate Form 10 is characterized by an XRPD pattern comprising one or more peaks selected from 4.77, 9.58, 14.17, 14.26, 15.55, 15.61, 18.20, 18.29, 19.30, 20.12, 26.13, 26.20, 27.11, and 28.99 degrees 2θ;

Compound 1 •sulfate Form 11 is characterized by an XRPD pattern comprising one or more peaks selected from 6.75, 9.64, 11.06, 12.70, 13.70, 13.92, 14.76, 21.13, 23.58, 24.46, 24.52, 26.66, 27.62, and 29.81 degrees 2θ;

Compound 1 •oxalate Form 13 is characterized by an XRPD pattern comprising one or more peaks selected from 12.67, 12.86, 13.63, 20.83, 21.28, 22.65, 23.59, 25.89, 26.55, and 26.60degrees 2θ;

Compound 1 •besylate Form 15 is characterized by an XRPD pattern comprising one or more peaks selected from 5.75, 10.42, 13.04, 15.59, 16.47, 17.95, 18.17, 18.85, 19.41, 20.90, 22.50, 23.24, and 24.36 degrees 2θ;

Compound 1 •mesylate dihydrate Form 16 is characterized by an XRPD pattern comprising one or more peaks selected from 6.71, 9.70, 10.76, 13.35, 13.47, 15.67, 16.20, 18.65, 19.09, 19.33, 21.77, 21.87, 23.00, 23.98, 25.25, 26.86, and 27.19 degrees 2θ;

Compound 1 •succinate Form 17 is characterized by an XRPD pattern comprising one or more peaks selected from 5.96, 6.74, 11.88, 12.15, 13.69, 13.74, 16.47, 20.43, 20.70, 22.85, 24.69, 24.76, and 26.59 degrees 2θ;

Compound 1 •esylate Form 18 is characterized by an XRPD pattern comprising one or more peaks selected from 9.45, 9.86, 15.31, 16.85, 20.83, 21.72, 22.82, and 24.60 degrees 2θ;

Compound 1 •sulfate monohydrate Form 21 is characterized by an XRPD pattern comprising one or more peaks selected from 6.61, 13.26, 13.60, 14.67, 16.40, 17.66, 19.96, 20.37, 20.76, 21.09, 21.25, and 23.30 degrees 2θ;

Compound 1 •tosylate Form 22 is characterized by an XRPD pattern comprising one or more peaks selected from 13.75, 14.20, 14.77, 18.05, 19.28, 19.88, 20.51, 22.63, 25.41, 25.48, and 27.29 degrees 2θ;

Compound 1 •succinate Form 23 is characterized by an XRPD pattern comprising one or more peaks selected from 6.35, 11.82, 12.20, 12.47, 13.76, 17.86, 18.04, 20.96, 21.96, 22.96, 23.79, 24.10, 24.96, and 25.59 degrees 2θ;

Compound 1 •malonate Form 24 is characterized by an XRPD pattern comprising one or more peaks selected from 6.77, 12.36, 12.86, 21.02, 22.85, 23.61, 25.12, 26.31, 28.01, and 30.36 degrees 2θ; and Compound 1 •mesylate Form 25 is characterized by an XRPD pattern comprising one or more peaks selected from 9.42, 9.75, 10.72, 11.98, 15.52, 17.71, 19.51, 19.66, 21.65, 21.96, 22.54, 23.35, 24.55, and 25.92 degrees 2θ.

4. The crystalline solid salts of claim 1, wherein

Compound 1 •citrate monohydrate Form 1 is characterized by an XRPD pattern comprising one or more peaks selected from 9.61, 13.35, 13.50, 21.50, 23.85, 26.83, and 27.12 degrees 2θ;

Compound 1 •malonate Form 2 is characterized by an XRPD pattern comprising one or more peaks selected from 6.36, 7.97, 12.75, 19.58, 20.57, 23.43, 25.01, 26.93, 27.36, and 27.42 degrees 2θ;

Compound 1 •oxalate Form 3 is characterized by an XRPD pattern comprising one or more peaks selected from 9.78, 10.36, 12.97, 13.60, 23.07, and 25.69 degrees 2θ;

Compound 1 •sulfate Form 5 is characterized by an XRPD pattern comprising one or more peaks selected from 9.56, 10.08, 13.29, 13.86, 22.60, and 25.16 degrees 2θ;

Compound 1 •esylate Form 7 is characterized by an XRPD pattern comprising one or more peaks selected from 14.79 and 19.92 degrees 2θ;

Compound 1 •mesylate Form 9 is characterized by an XRPD pattern comprising one or more peaks selected from 5.75, 15.57, 16.19, 17.90, 20.87, 22.69, and 23.08 degrees 2θ;

Compound 1 •tosylate Form 10 is characterized by an XRPD pattern comprising one or more peaks selected from 15.55, 18.29, 19.30, 20.12, 26.13, and 26.20 degrees 2θ;

Compound 1 •sulfate Form 11 is characterized by an XRPD pattern comprising one or more peaks selected from 12.70, 13.92, 23.58, 24.46, 24.52, and 26.66 degrees 2θ;

Compound 1 •oxalate Form 13 is characterized by an XRPD pattern comprising one or more peaks selected from 12.67, 13.63, 20.83, 22.65, 23.59, and 26.55 degrees 2θ;

Compound 1 •besylate Form 15 is characterized by an XRPD pattern comprising one or more peaks selected from 5.75, 10.42, 15.59, 16.47, and 24.36 degrees 2θ;

Compound 1 •mesylate dihydrate Form 16 is characterized by an XRPD pattern comprising one or more peaks selected from 9.70, 13.47, 21.77, 21.87, 23.98, and 26.86 degrees 2θ;

Compound 1 •succinate Form 17 is characterized by an XRPD pattern comprising one or more peaks selected from 5.96, 6.74, 11.88, 13.74, 20.70, and 24.76 degrees 2θ;

Compound 1 •esylate Form 18 is characterized by an XRPD pattern comprising one or more peaks selected from 9.45, 9.86, 20.83, and 21.72 degrees 2θ;

Compound 1 •sulfate monohydrate Form 21 is characterized by an XRPD pattern comprising one or more peaks selected from 6.61, 13.60, 20.37, 20.76, 21.09, and 23.30 degrees 2θ;

Compound 1 •tosylate Form 22 is characterized by an XRPD pattern comprising one or more peaks selected from 13.75, 14.77, 18.05, 19.88, 22.63, and 25.41 degrees 2θ;

Compound 1 •succinate Form 23 is characterized by an XRPD pattern comprising one or more peaks selected from 11.82, 12.47, 22.96, and 24.96 degrees 2θ;

Compound 1 •malonate Form 24 is characterized by an XRPD pattern comprising one or more peaks selected from 12.36, 12.86, 21.02, 22.85, 23.61, and 25.12 degrees 2θ; and Compound 1 •mesylate Form 25 is characterized by an XRPD pattern comprising one or more peaks selected from 9.42, 9.75, 19.66, 21.65, 22.54, 23.35, and 24.55 degrees 2θ.

5. The crystalline solid salts of claim 1, wherein

Compound 1 •citrate monohydrate Form 1 is characterized by an XRPD pattern comprising peaks at 9.61, 13.35, 13.50, 21.50, 23.85, 26.83, and 27.12 degrees 2θ;

Compound 1 •malonate Form 2 is characterized by an XRPD pattern comprising peaks at 6.36, 7.97, 12.75, 19.58, 20.57, 23.43, 25.01, 26.93, 27.36, and 27.42 degrees 2θ;

Compound 1•oxalate Form 3 is characterized by an XRPD pattern comprising peaks at 9.78, 10.36, 12.97, 13.60, 23.07, and 25.69 degrees 2θ;

Compound 1 •sulfate Form 5 is characterized by an XRPD pattern comprising peaks at 9.56, 10.08, 13.29, 13.86, 22.60, and 25.16 degrees 2θ;

Compound 1 •esylate Form 7 is characterized by an XRPD pattern comprising peaks at 14.79 and 19.92 degrees 2θ;

Compound 1 •mesylate Form 9 is characterized by an XRPD pattern comprising peaks at 5.75, 15.57, 16.19, 17.90, 20.87, 22.69, and 23.08 degrees 2θ;

Compound 1 •tosylate Form 10 is characterized by an XRPD pattern comprising peaks at 15.55, 18.29, 19.30, 20.12, 26.13, and 26.20 degrees 2θ;

Compound 1 •sulfate Form 11 is characterized by an XRPD pattern comprising peaks at 12.70, 13.92, 23.58, 24.46, 24.52, and 26.66 degrees 2θ;

Compound 1 •oxalate Form 13 is characterized by an XRPD pattern comprising peaks at 12.67, 13.63, 22.65, 23.59, and 26.55 degrees 2θ;

Compound 1 •besylate Form 15 is characterized by an XRPD pattern comprising peaks at 5.75, 10.42, 15.59, 16.47, and 24.36 degrees 2θ;

Compound 1 •mesylate dihydrate Form 16 is characterized by an XRPD pattern comprising peaks at 9.70, 13.47, 21.77, 21.87, 23.98, and 26.86 degrees 2θ;

Compound 1 •succinate Form 17 is characterized by an XRPD pattern comprising peaks at 5.96, 6.74, 11.88, 13.74, 20.70, and 24.76 degrees 2θ;

Compound 1 •esylate Form 18 is characterized by an XRPD pattern comprising peaks at 9.45, 9.86, 20.83, and 21.72 degrees 2θ;

Compound 1 •sulfate monohydrate Form 21 is characterized by an XRPD pattern comprising peaks at 13.60, 20.37, 20.76, 21.09, and 23.30 degrees 2θ;

Compound 1 •tosylate Form 22 is characterized by an XRPD pattern comprising peaks at 13.75, 14.77, 18.05, 19.88, 22.63, and 25.41 degrees 2θ;

Compound 1 •succinate Form 23 is characterized by an XRPD pattern comprising peaks at 11.82, 12.47, 22.96, and 24.96 degrees 2θ;

Compound 1 •malonate Form 24 is characterized by an XRPD pattern comprising peaks at 12.36, 12.86, 21.02, 22.85, 23.61, and 25.12 degrees 2θ; and Compound 1 •mesylate Form 25 is characterized by an XRPD pattern comprising peaks at 9.42, 9.75, 19.66, 21.65, 22.54, 23.35, and 24.55 degrees 2θ.

6. The crystalline solid salts of claim 1, wherein

Figure 2:
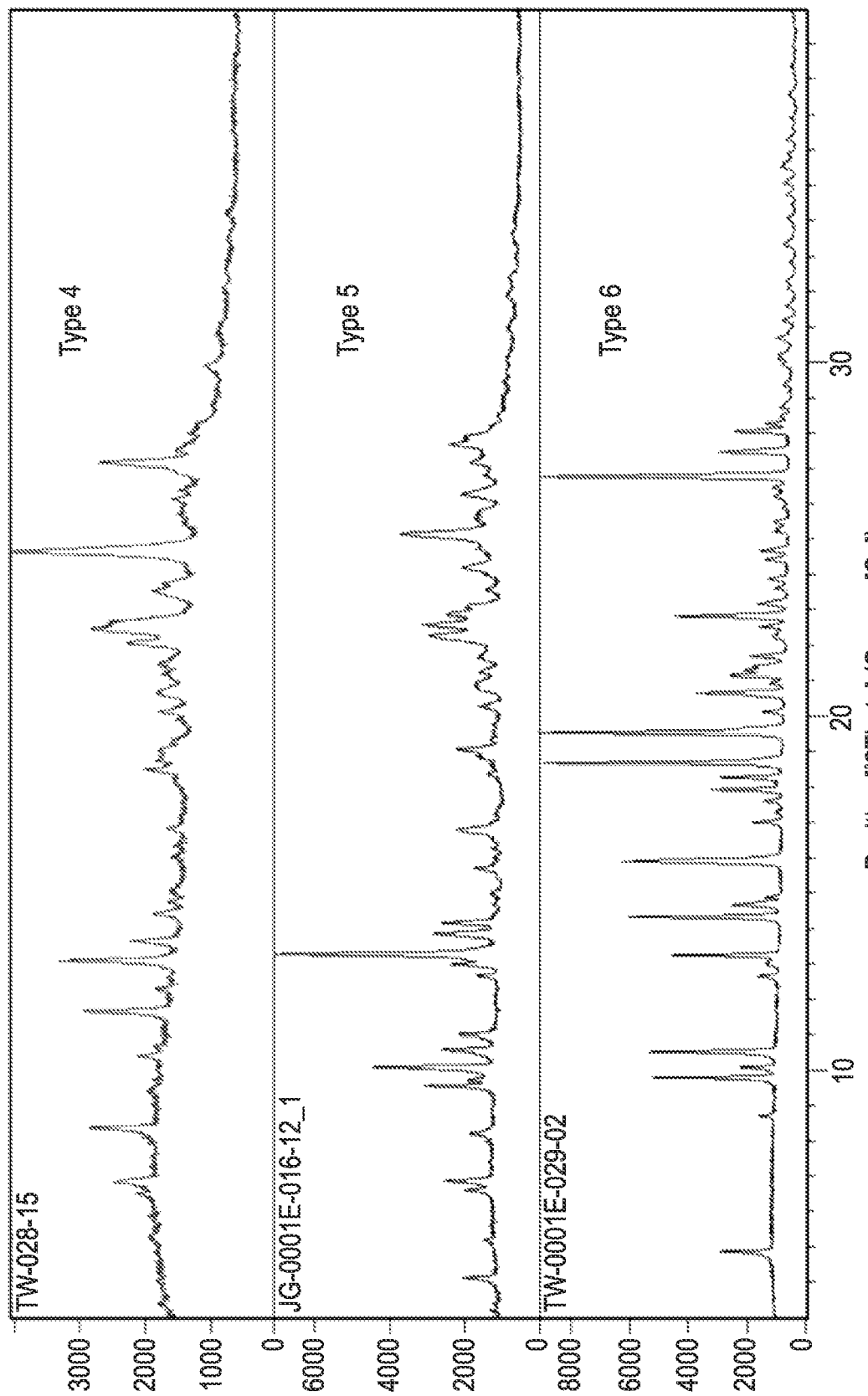
FIG. 2 is a chart showing the XRPD spectra of Forms 4, 5, and 6.
Figure 3:
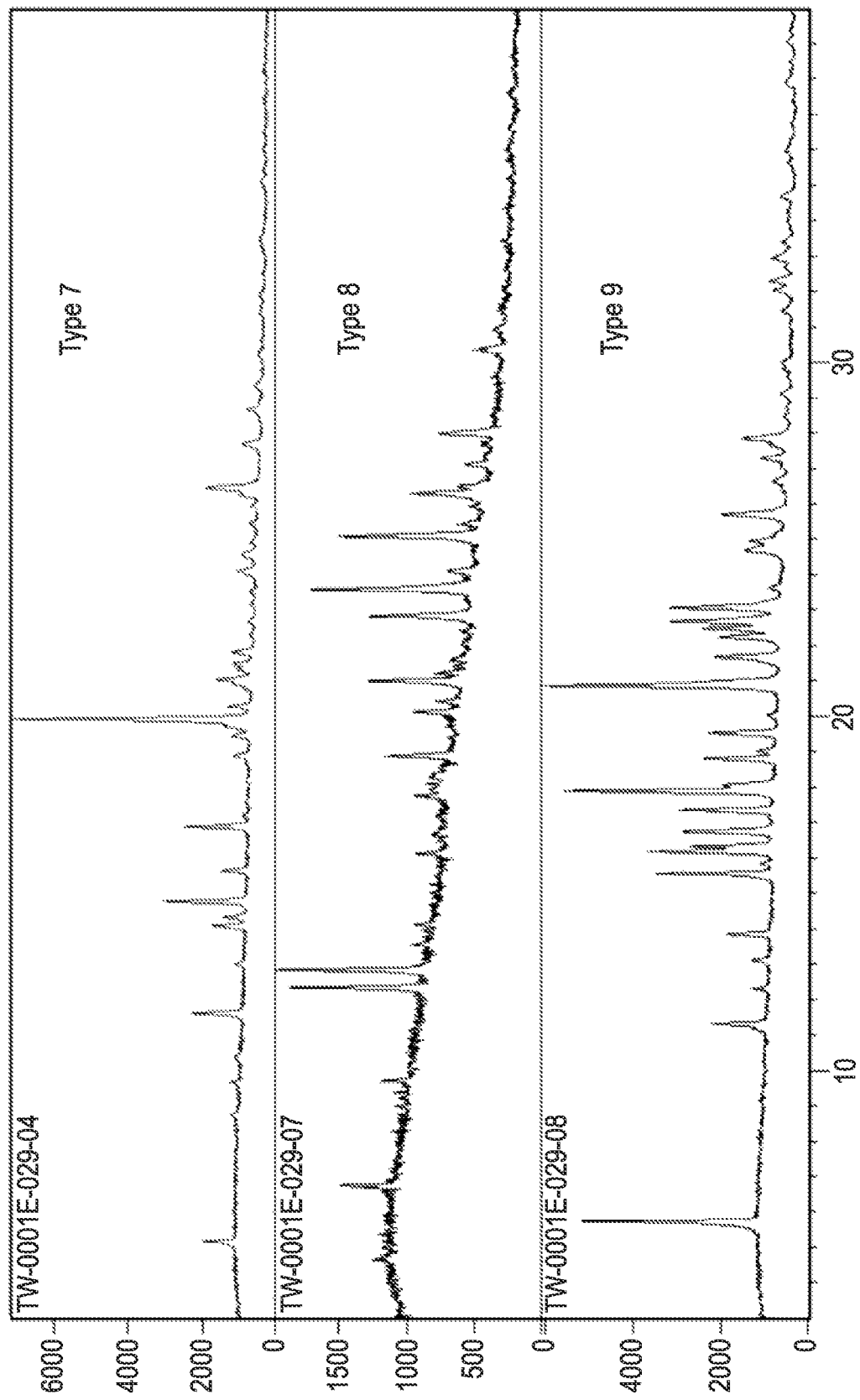
FIG. 3 is a chart showing the XRPD spectra of Forms 7, 8, and 9.
Figure 4:
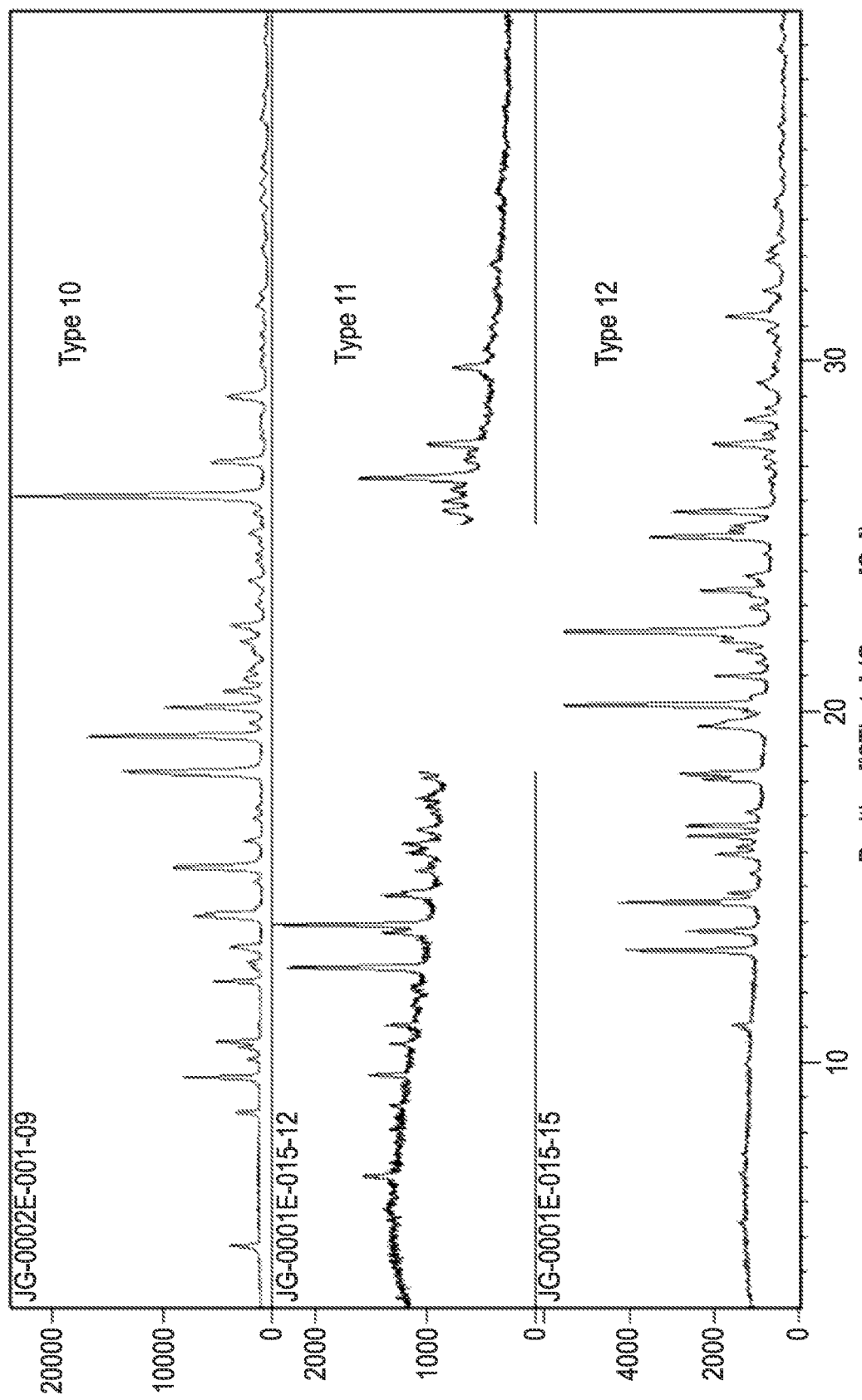
FIG. 4 is a chart showing the XRPD spectra of Forms 10, 11, and 12.
Figure 5:
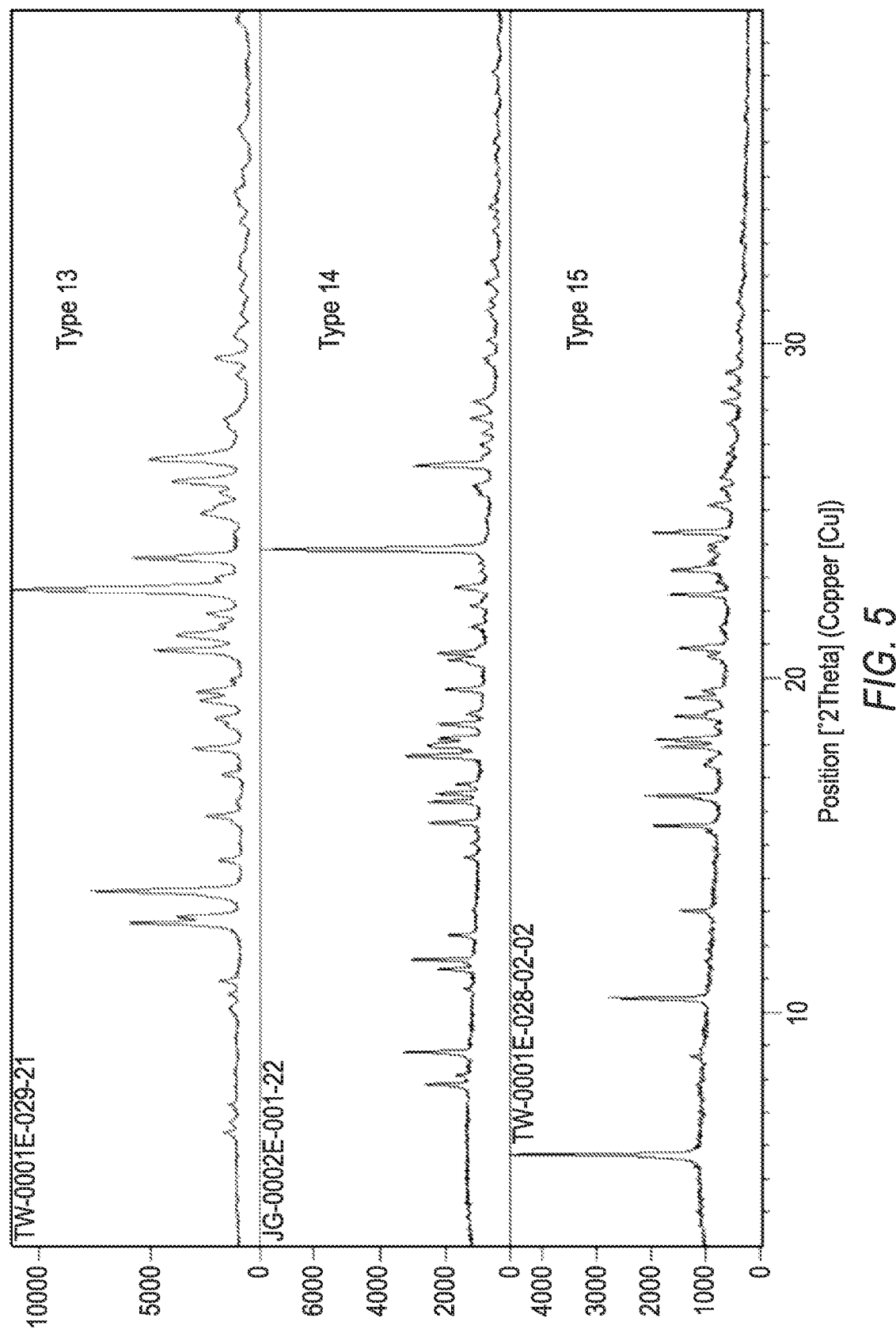
FIG. 5 is a chart showing the XRPD spectra of Forms 13, 14, and 15.
Figure 6:
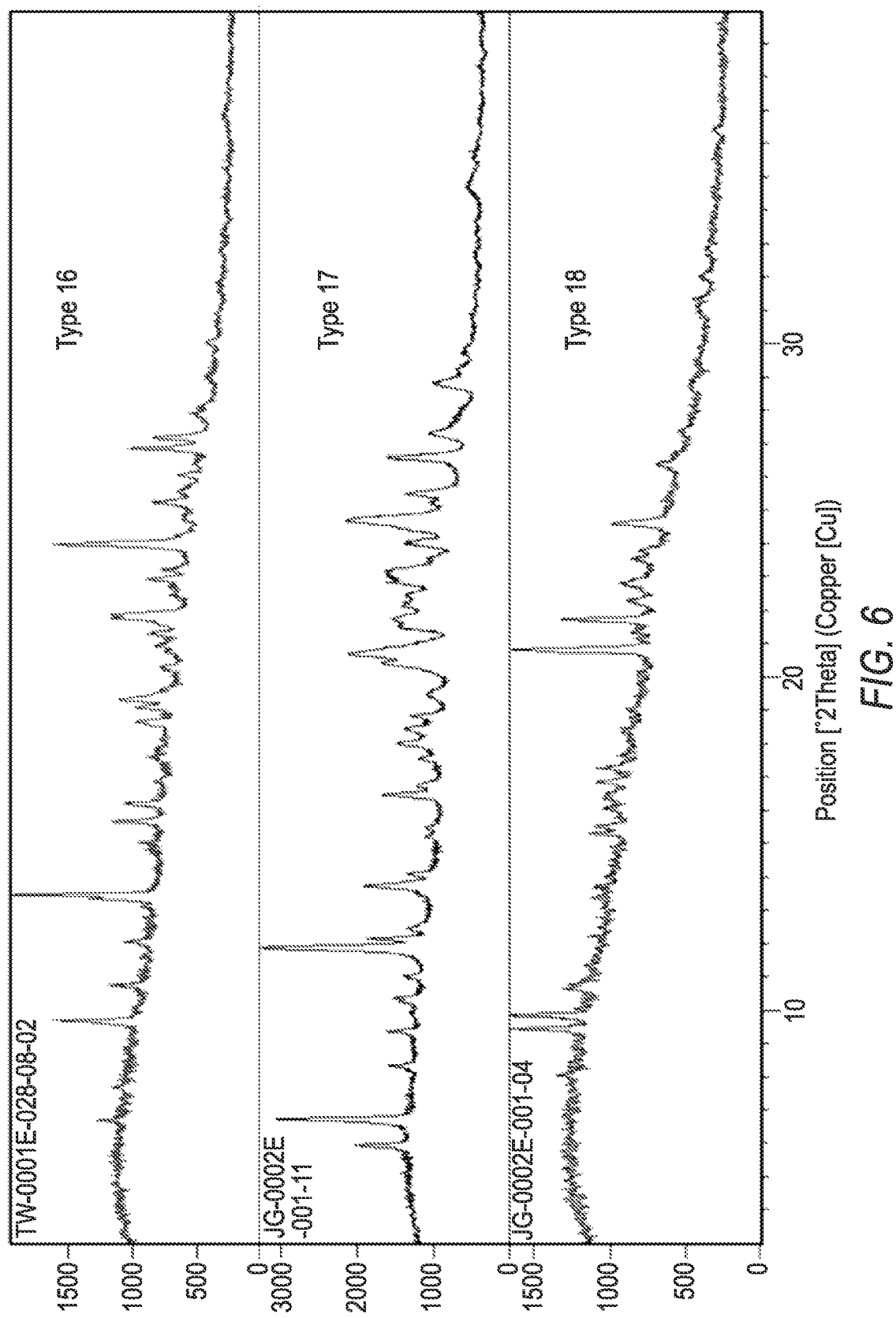
FIG. 6 is a chart showing the XRPD spectra of Forms 16, 17, and 18.
Figure 7:
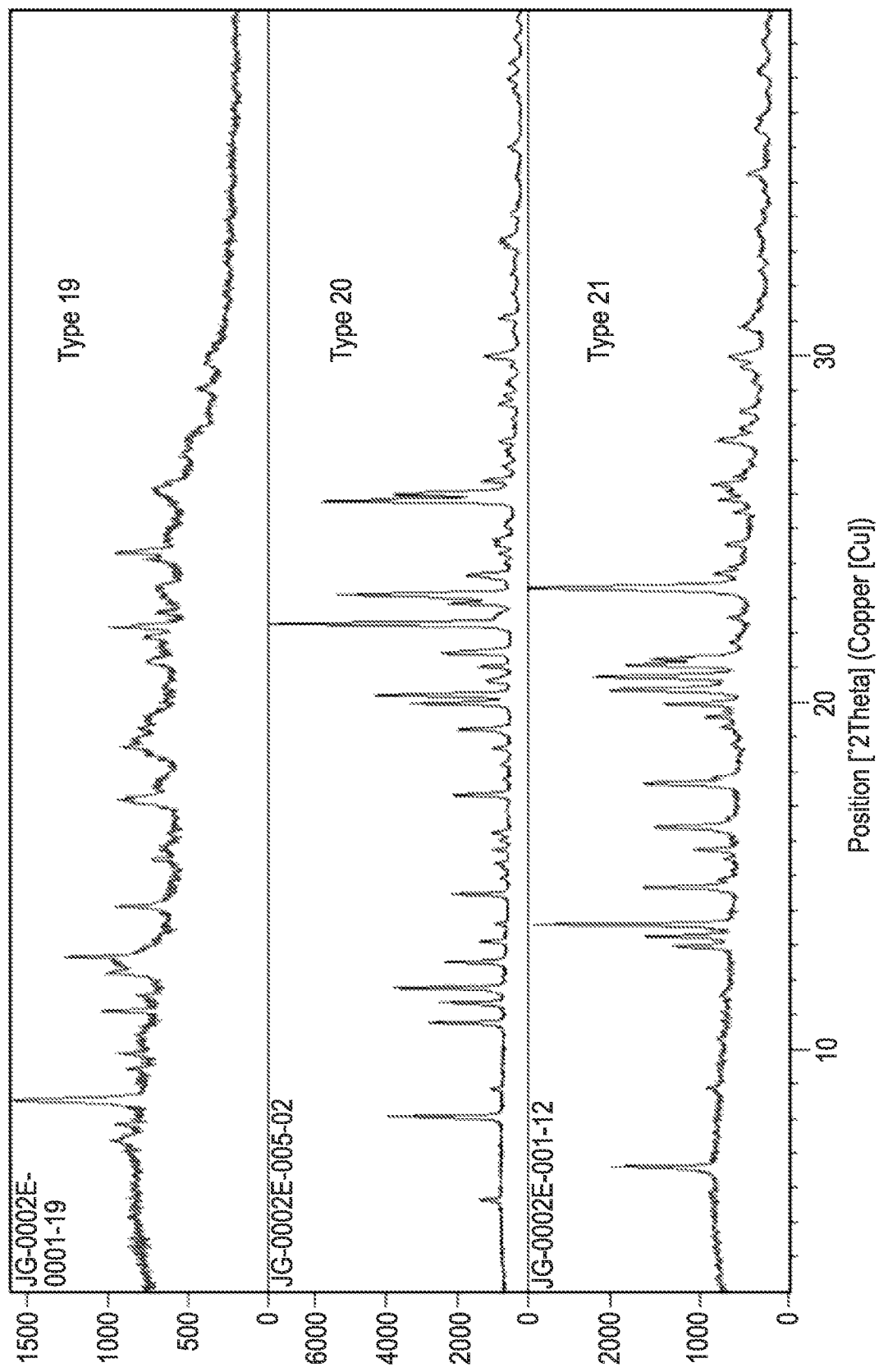
FIG. 7 is a chart showing the XRPD spectra of Forms 19, 20, and 21.
Figure 8:
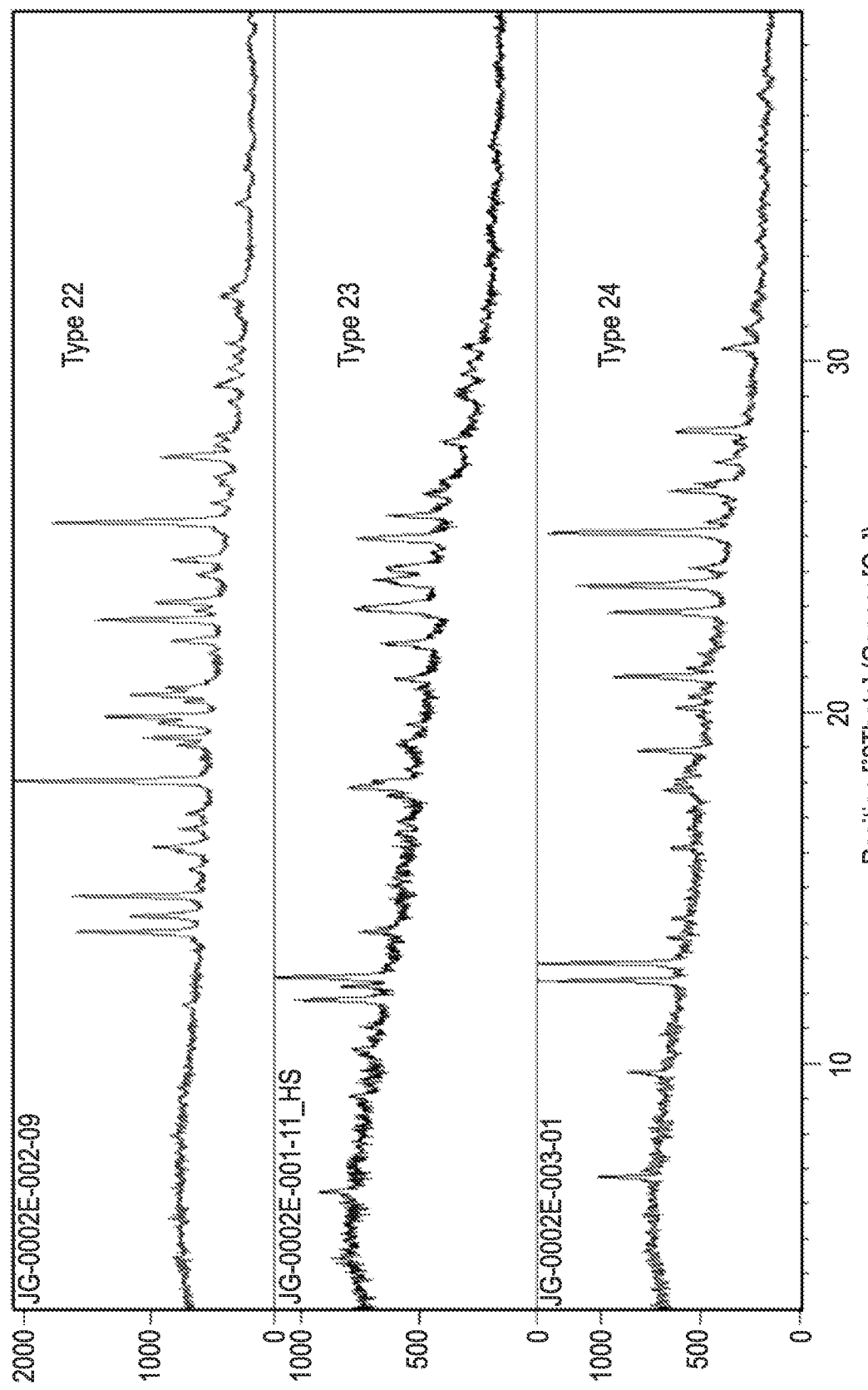
FIG. 8 is a chart showing the XRPD spectra of Forms 22, 23, and 24.
Figure 9:
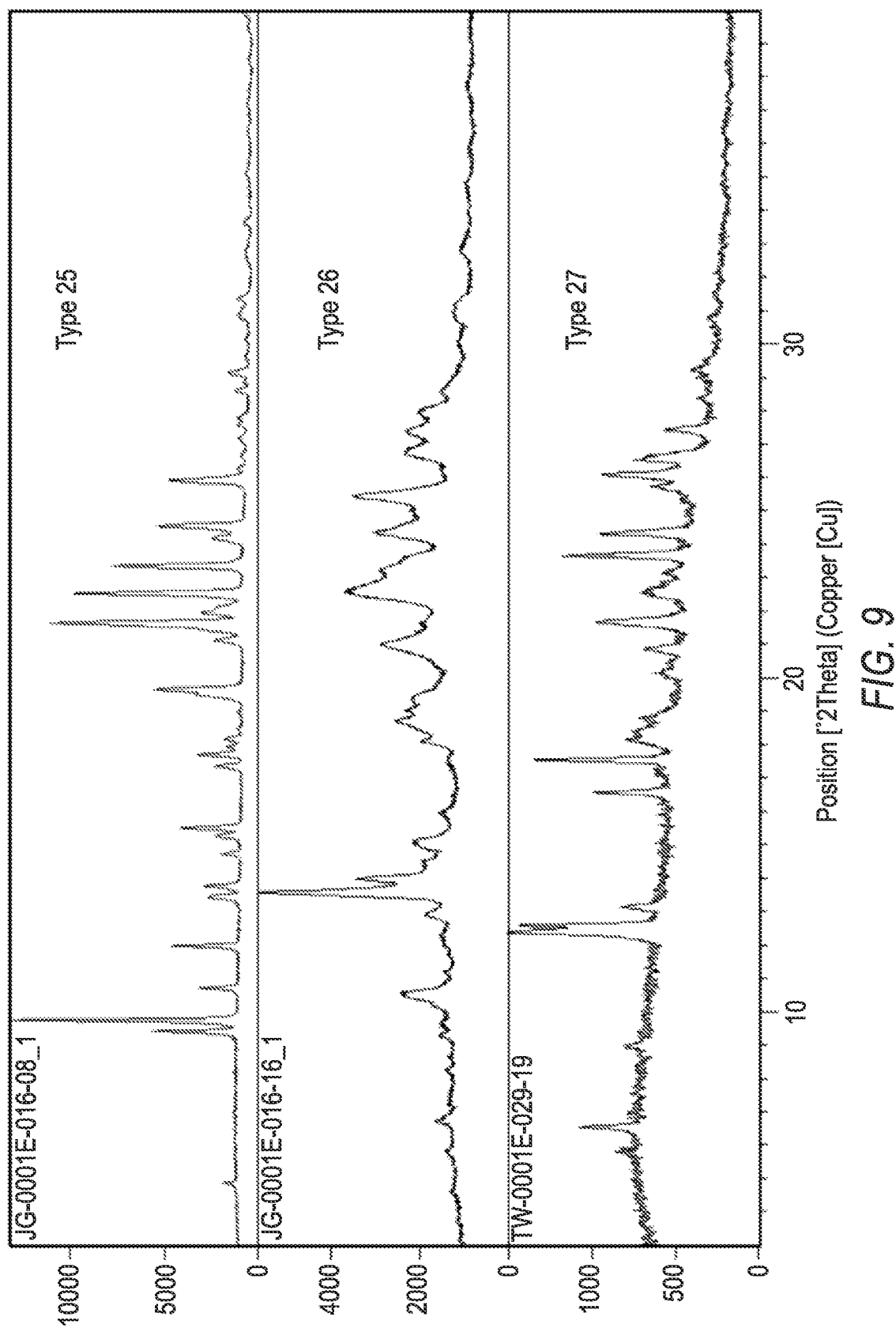
FIG. 9 is a chart showing the XRPD spectra of Forms 25, 26, and 27.
Figure 10:
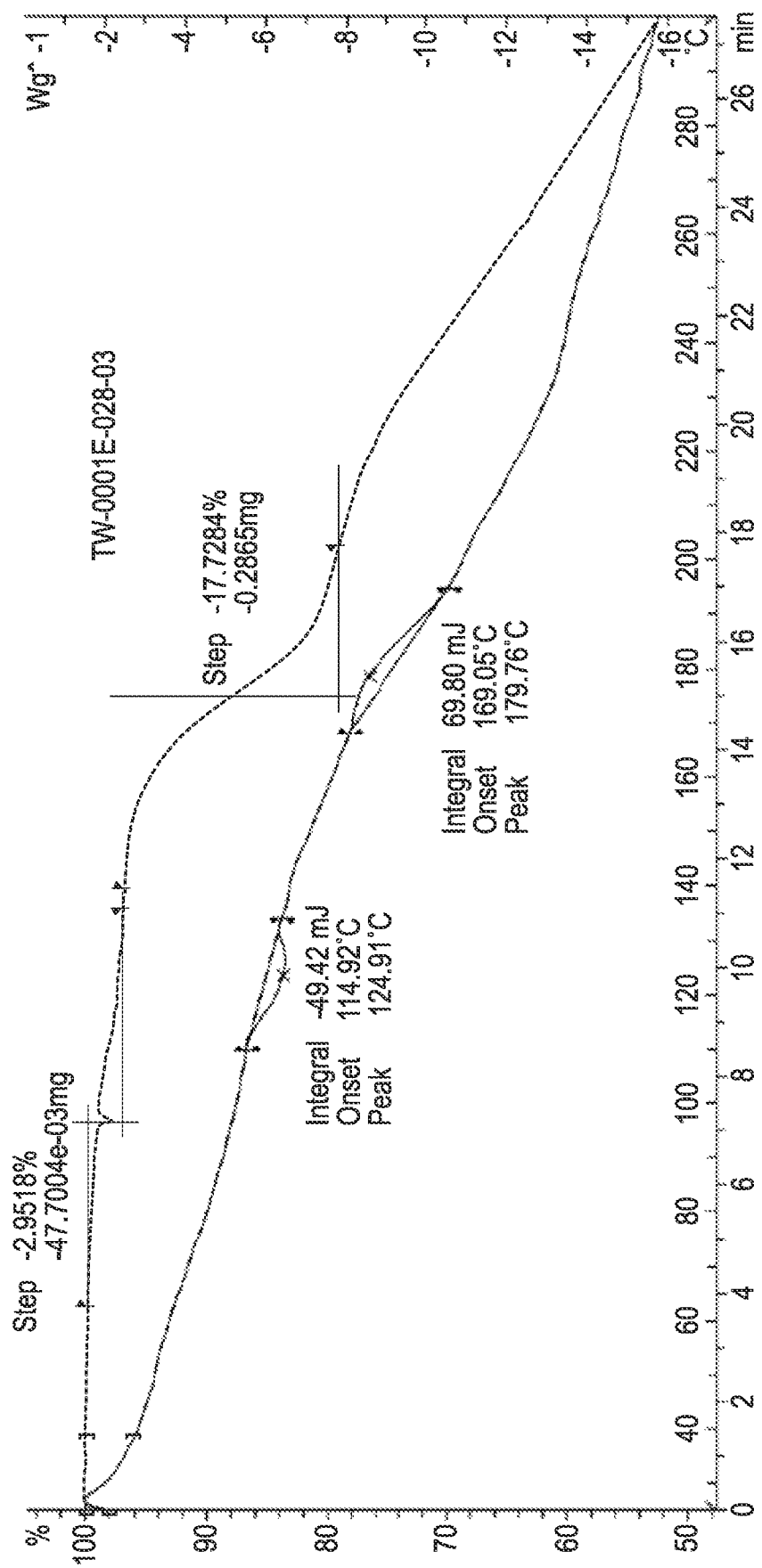
FIG. 10 is the TG/DTA trace of Form 1.
Figure 11:
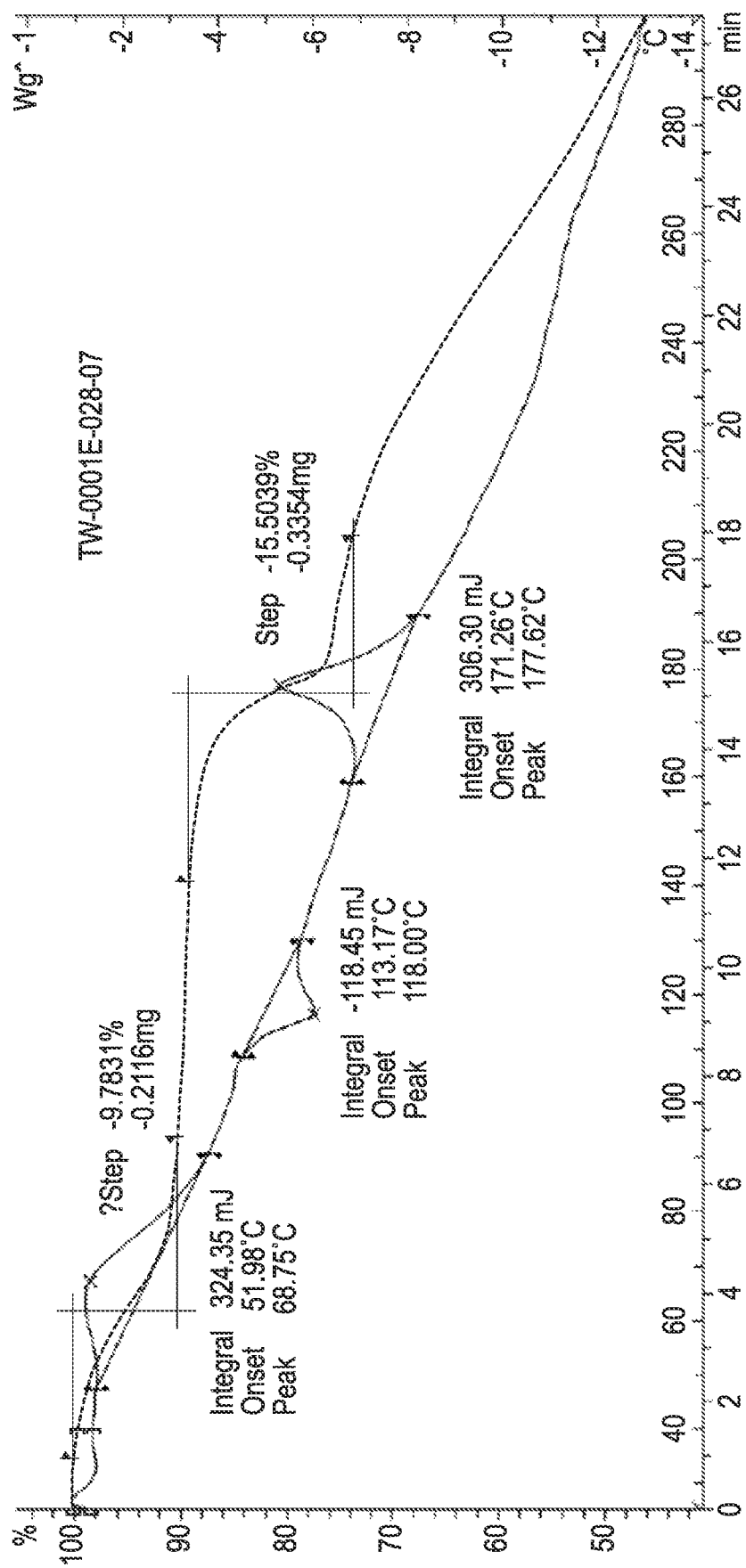
FIG. 11 is the TG/DTA trace of Form 2.
Figure 12:
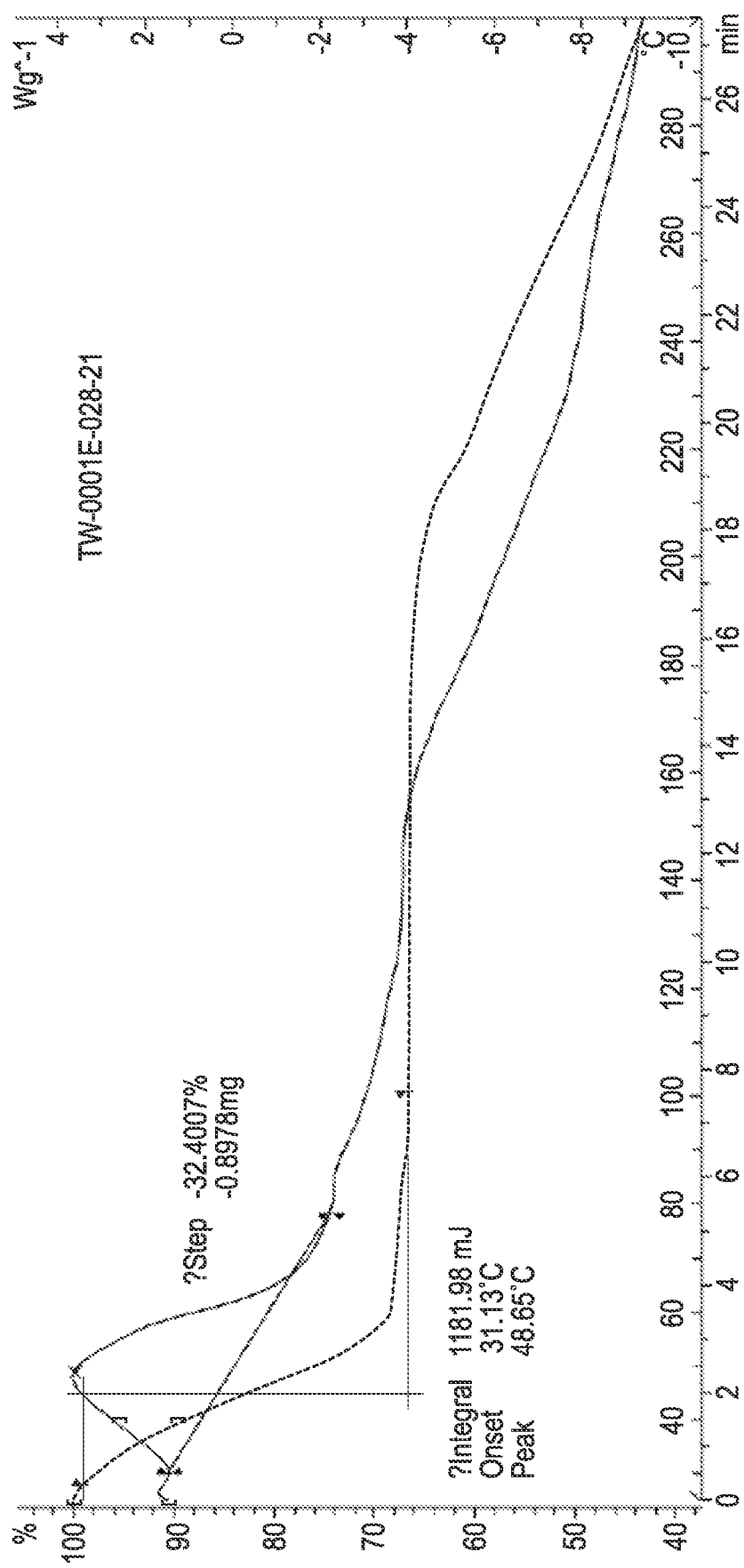
FIG. 12 is the TG/DTA trace of Form 3.
Figure 13:
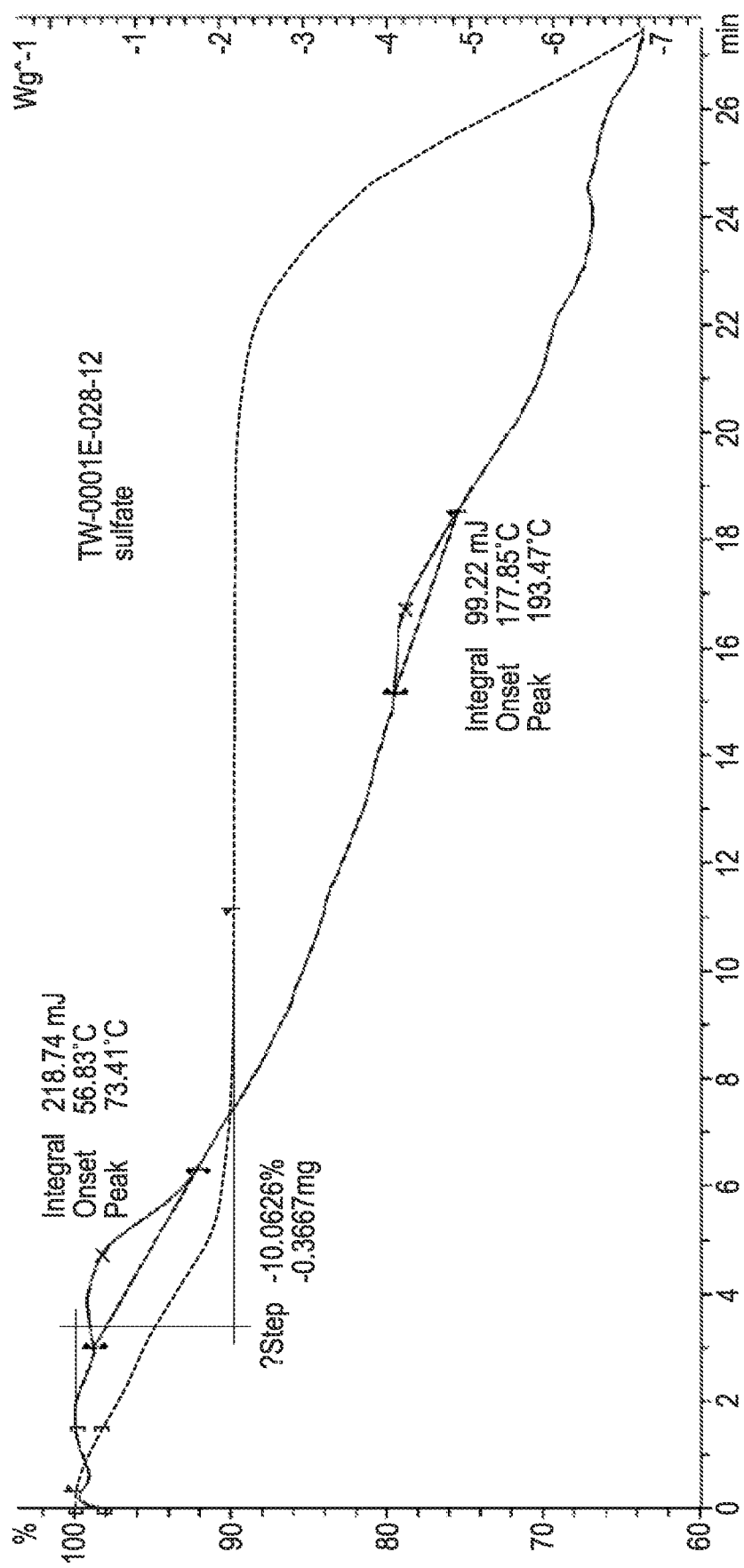
FIG. 13 is the TG/DTA trace of Form 5.
Figure 14:
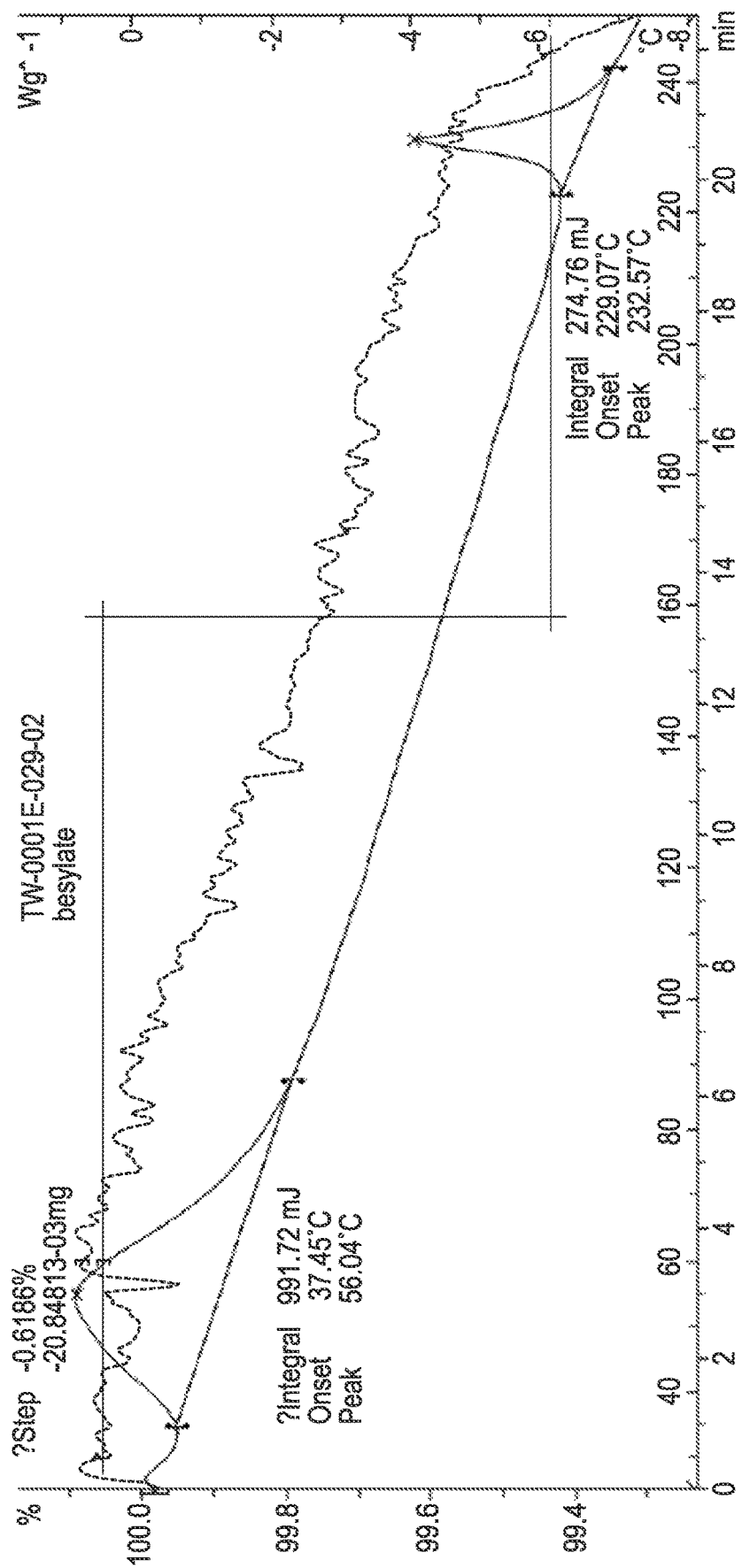
FIG. 14 is the TG/DTA trace of Form 6.
Figure 15:
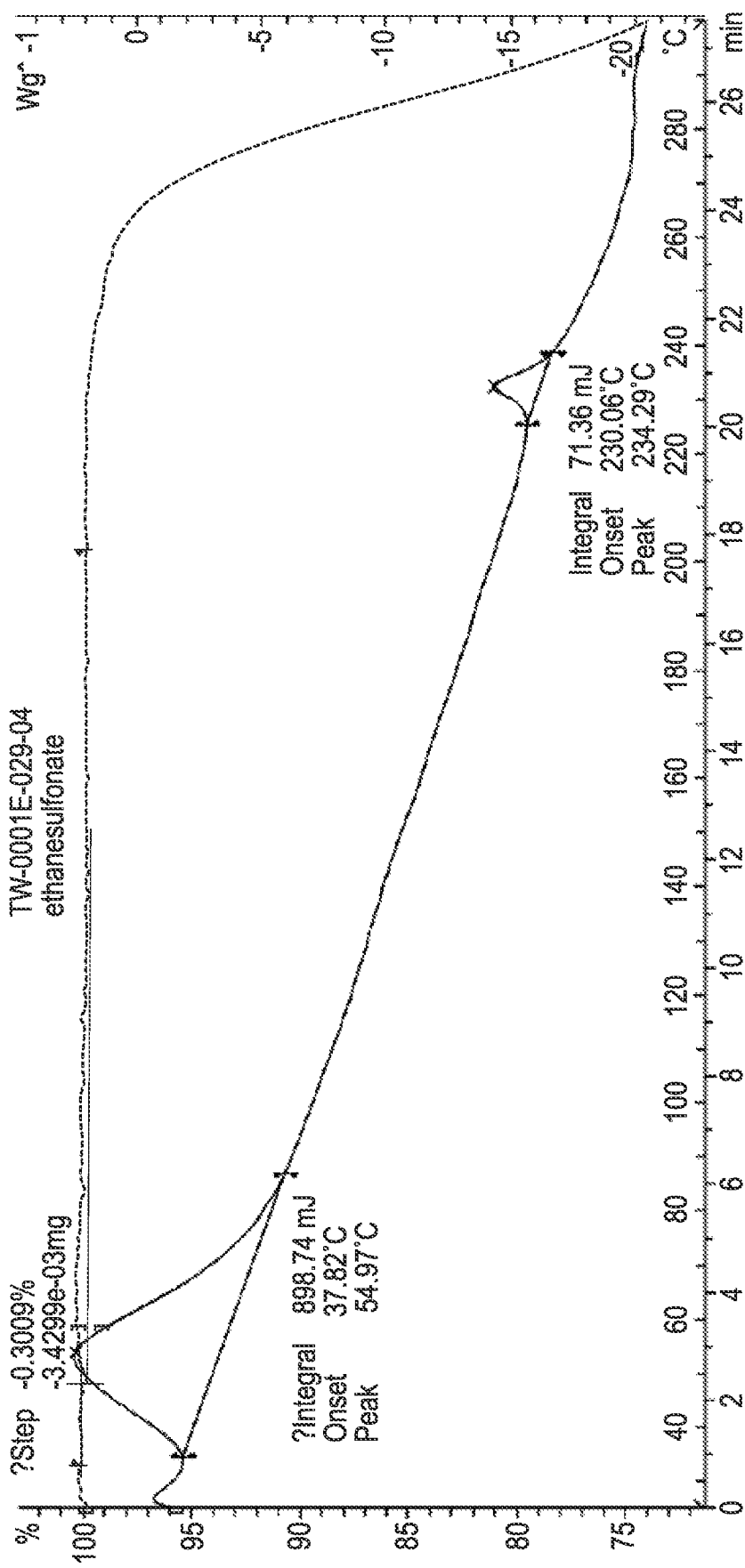
FIG. 15 is the TG/DTA trace of Form 7.
Figure 16:
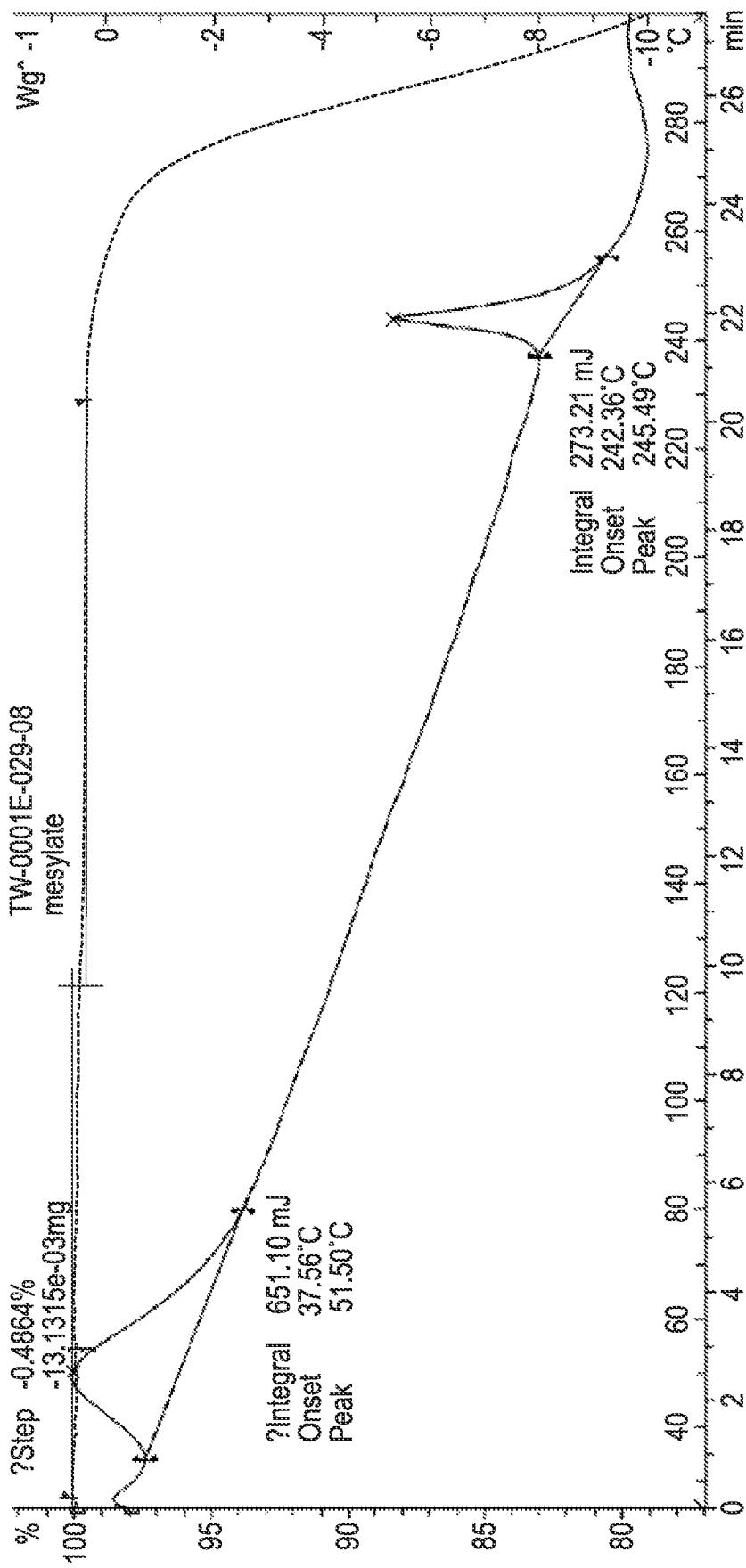
FIG. 16 is the TG/DTA trace of Form 9.
Figure 17:
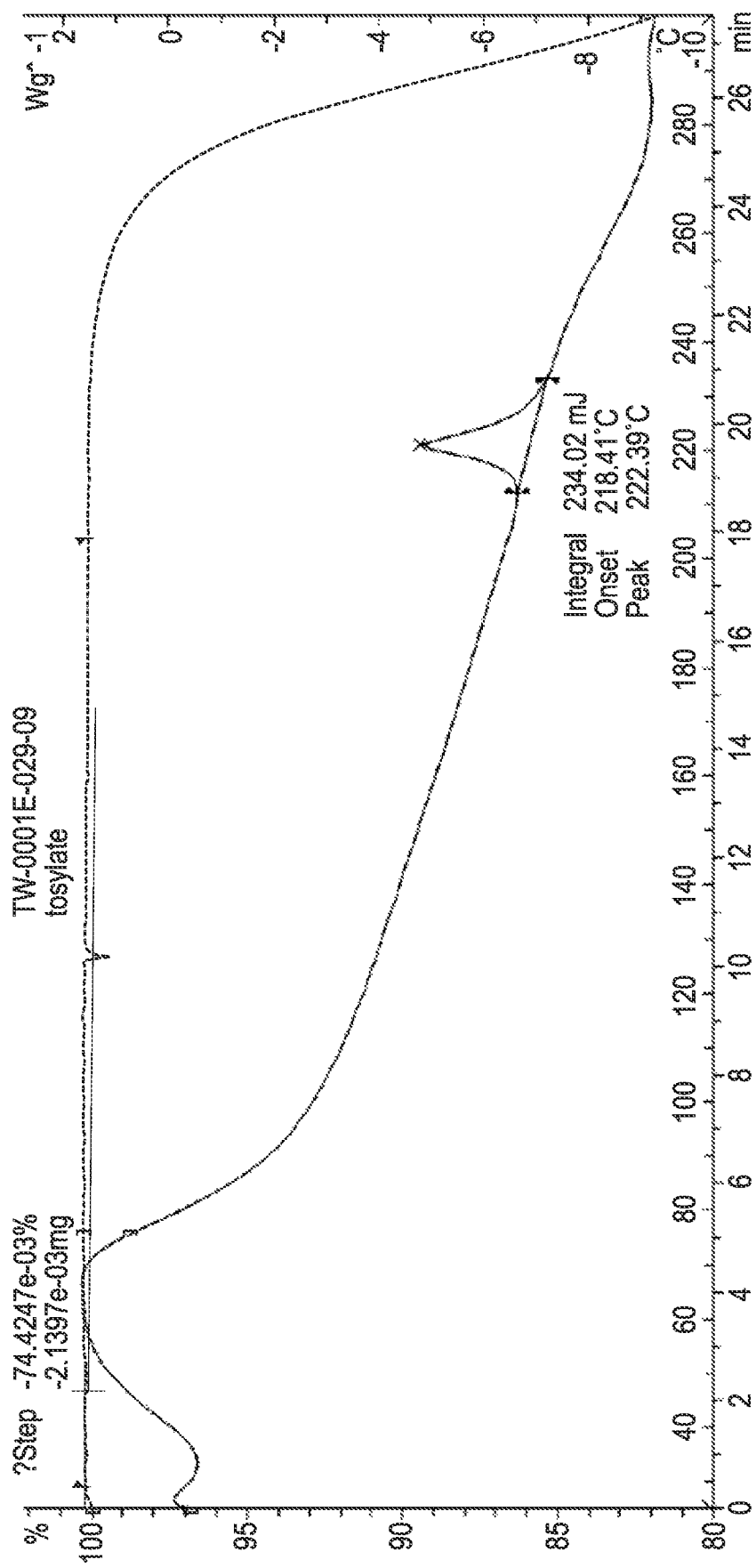
FIG. 17 is the TG/DTA trace of Form 10.
Figure 18:
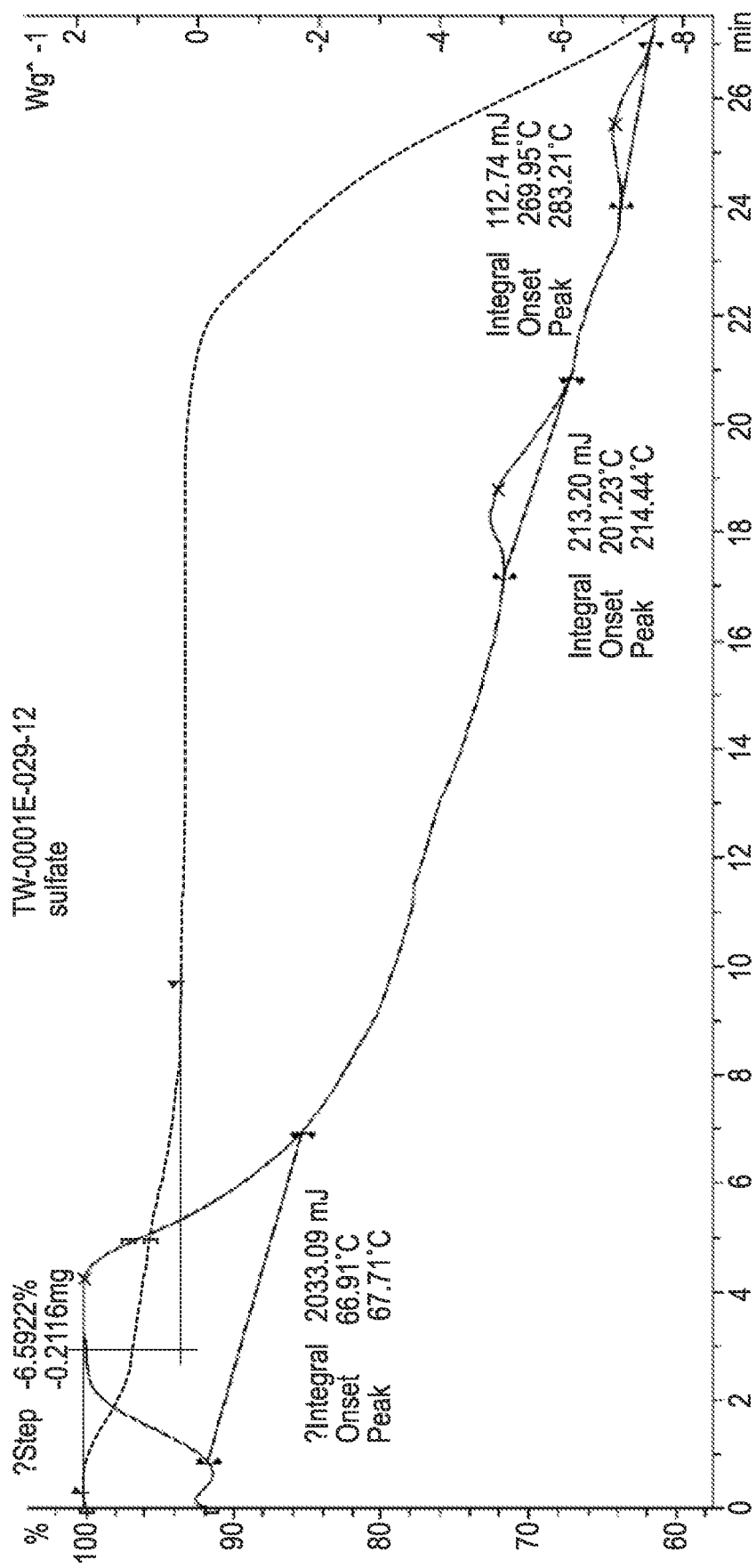
FIG. 18 is the TG/DTA trace of Form 11.
Figure 19:
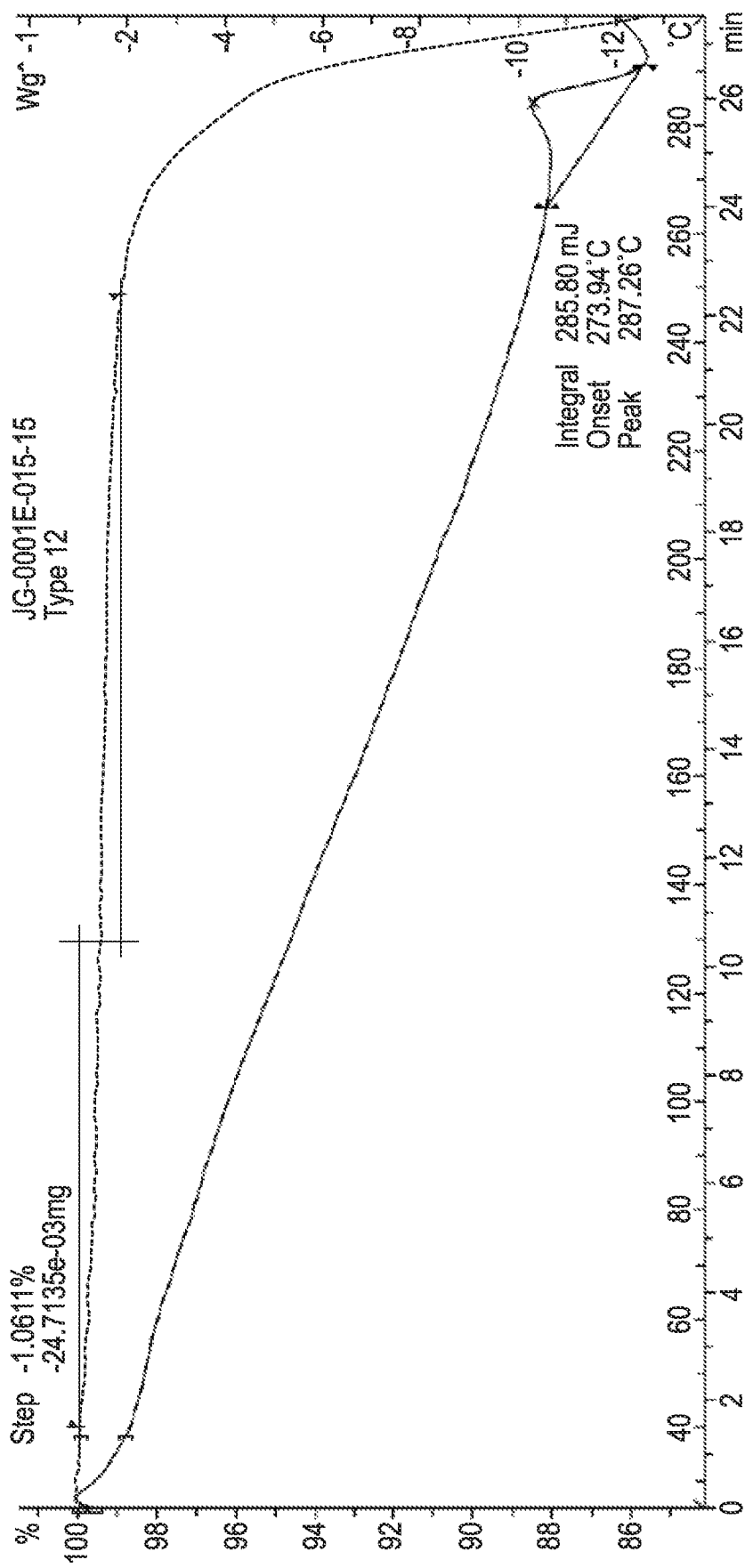
FIG. 19 is the TG/DTA trace of Form 12.
Figure 20:
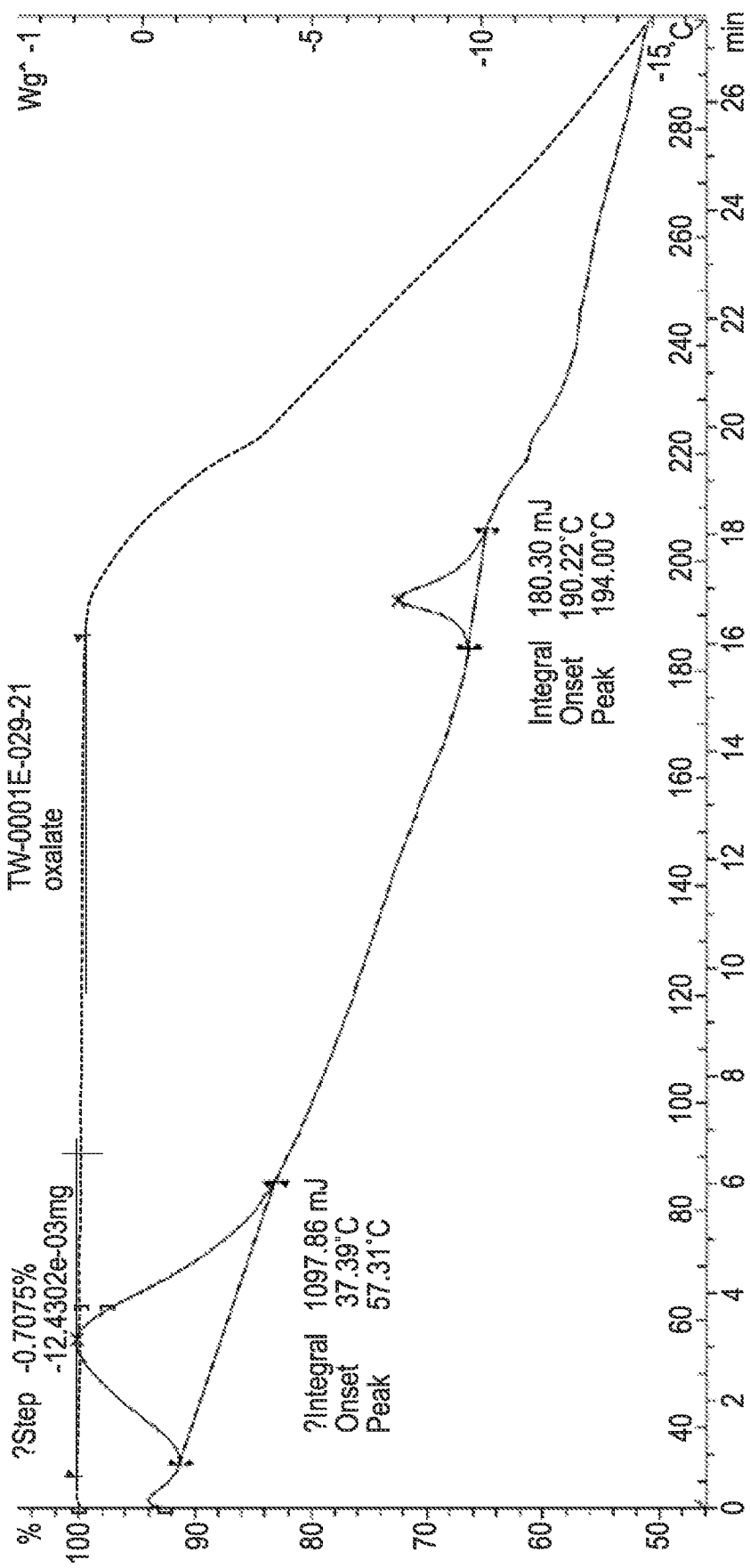
FIG. 20 is the TG/DTA trace of Form 13.
Figure 21:
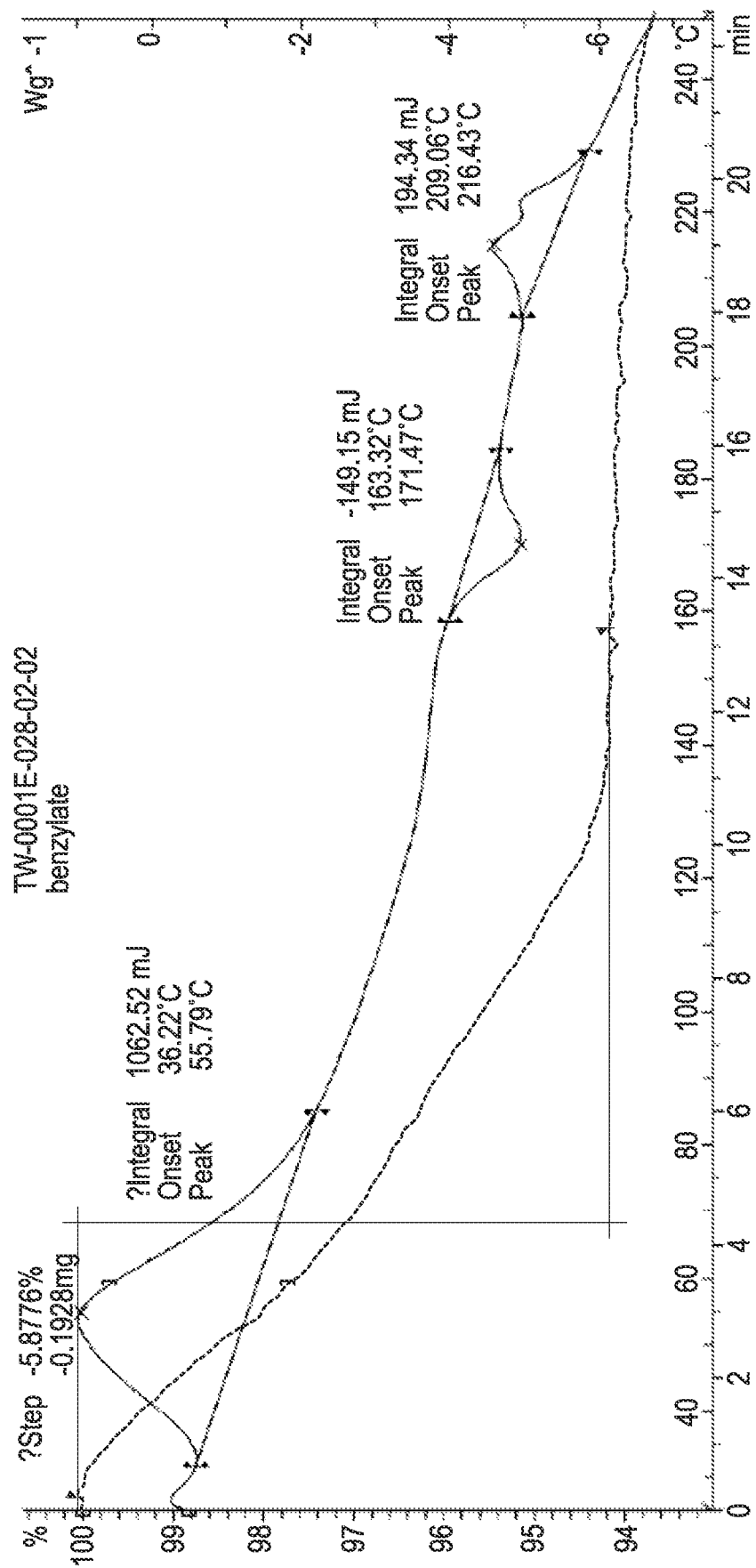
FIG. 21 is the TG/DTA trace of Form 15.
Figure 22:
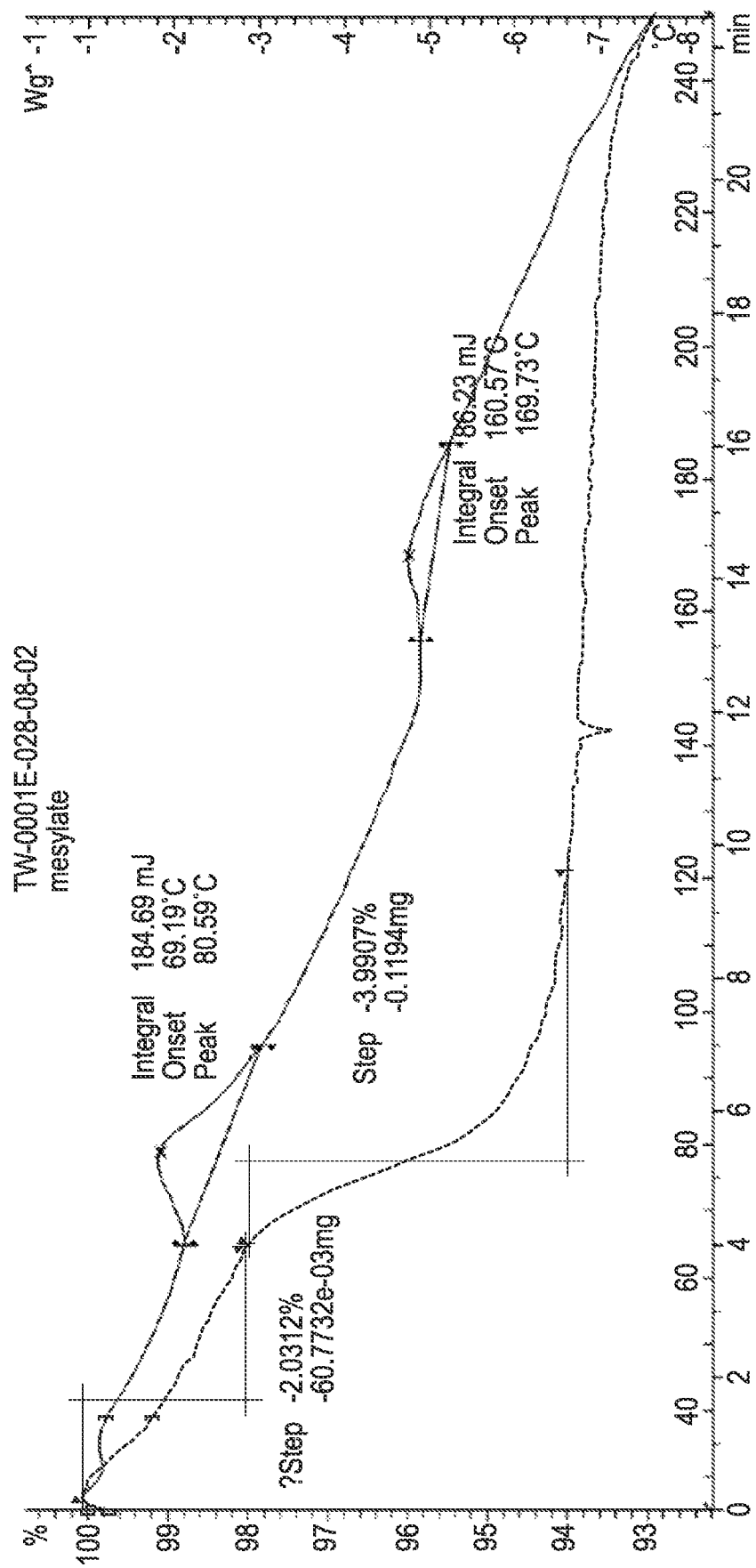
FIG. 22 is the TG/DTA trace of Form 16.
Figure 23:
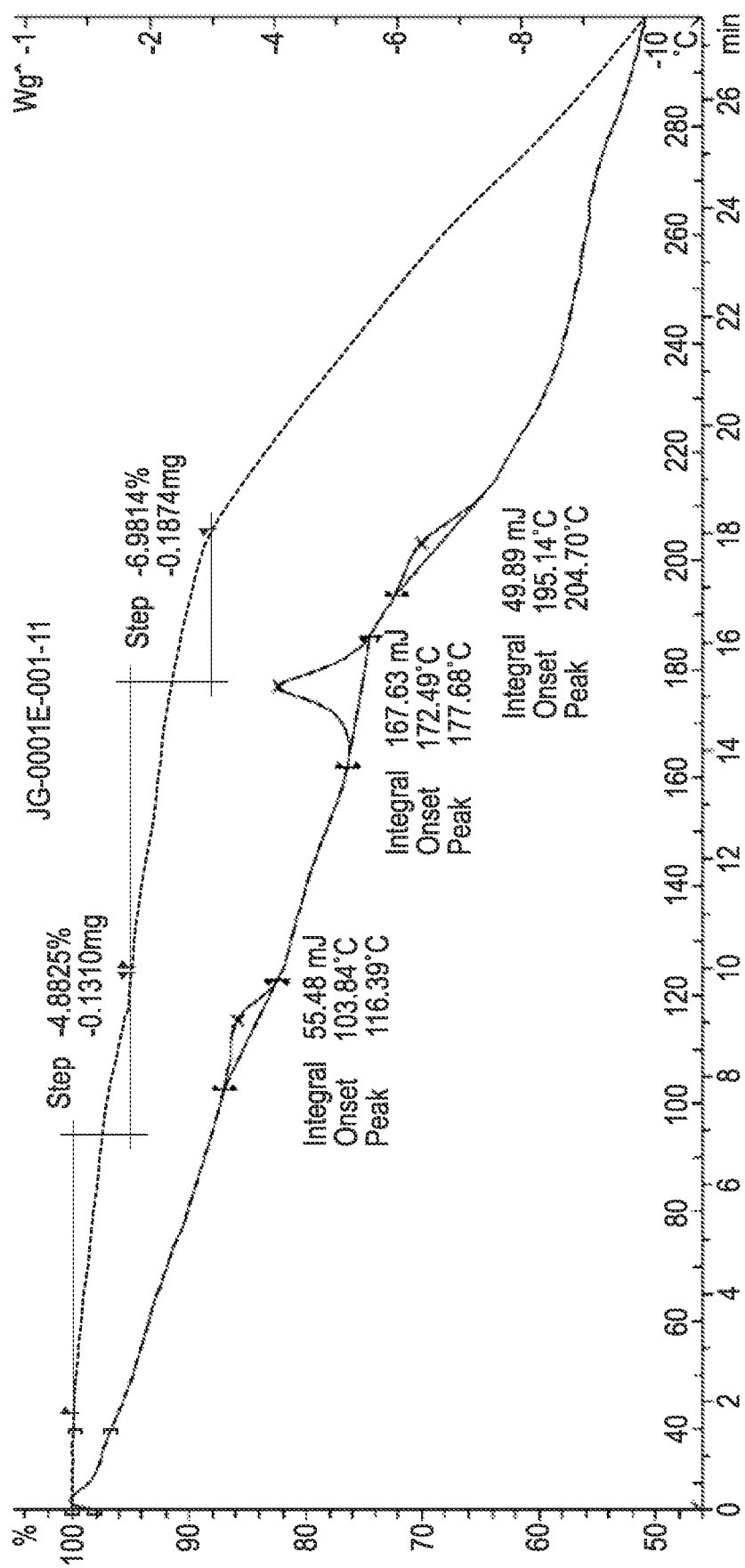
FIG. 23 is the TG/DTA trace of Form 17.
Figure 24:
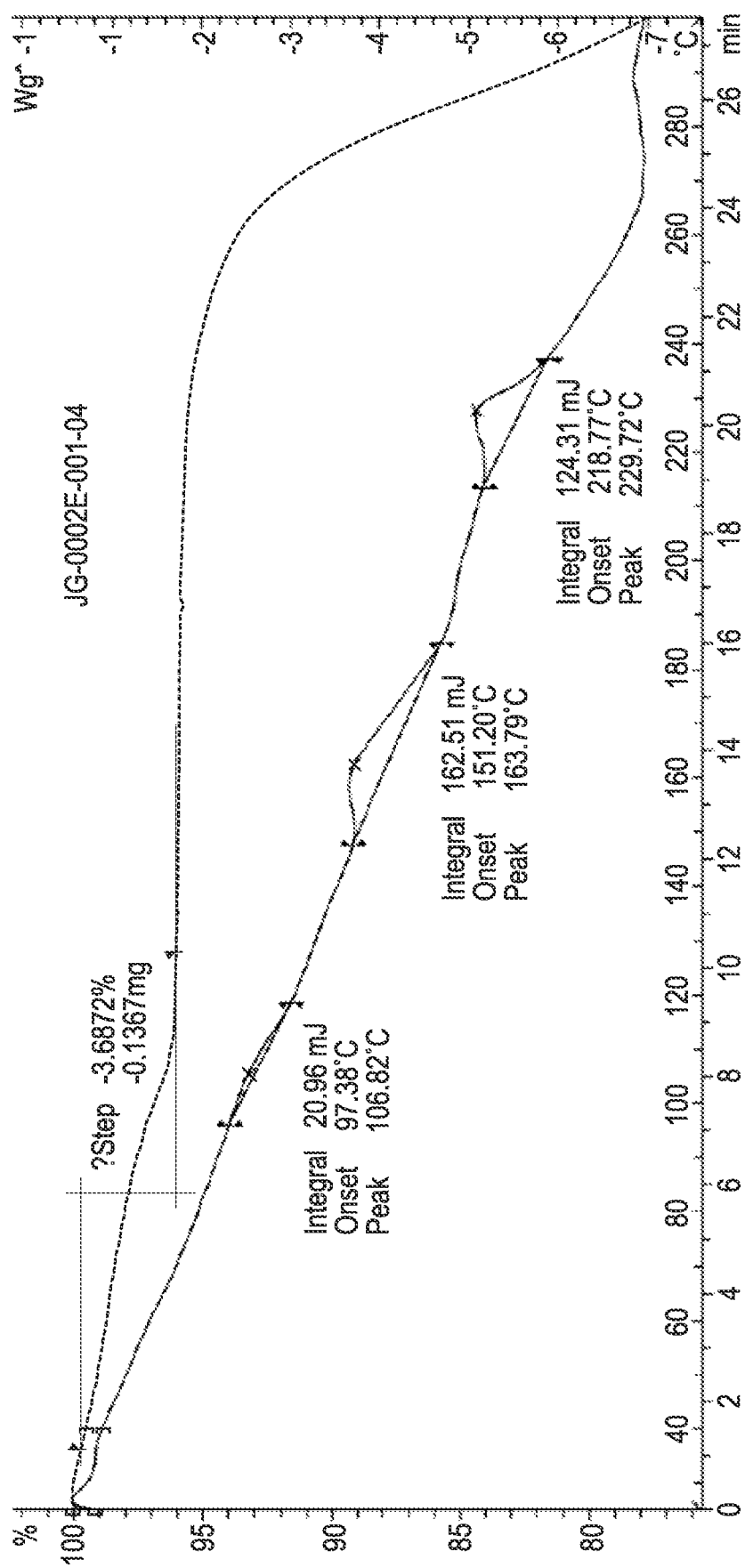
FIG. 24 is the TG/DTA trace of Form 18.
Figure 25:
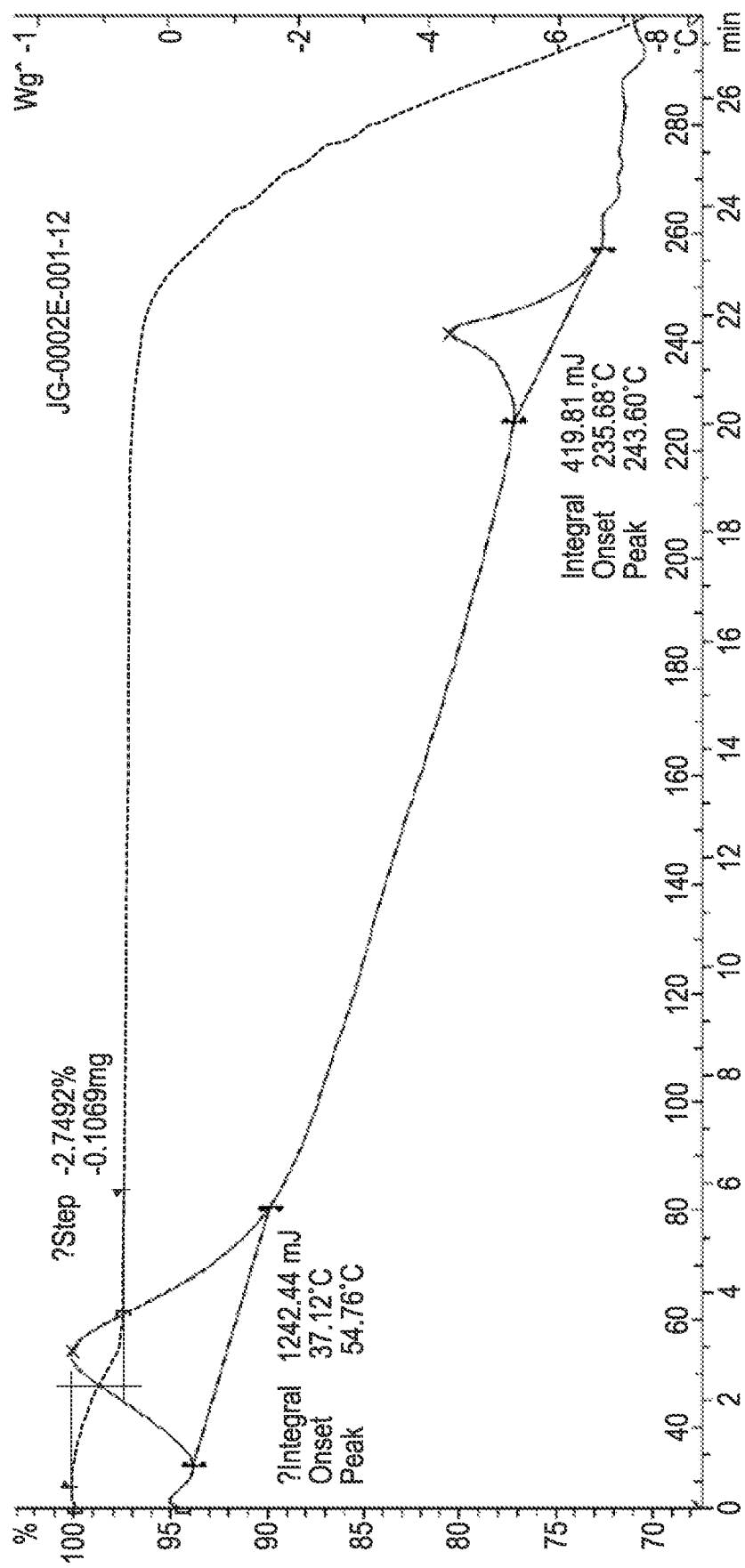
FIG. 25 is the TG/DTA trace of Form 21.
Figure 26:
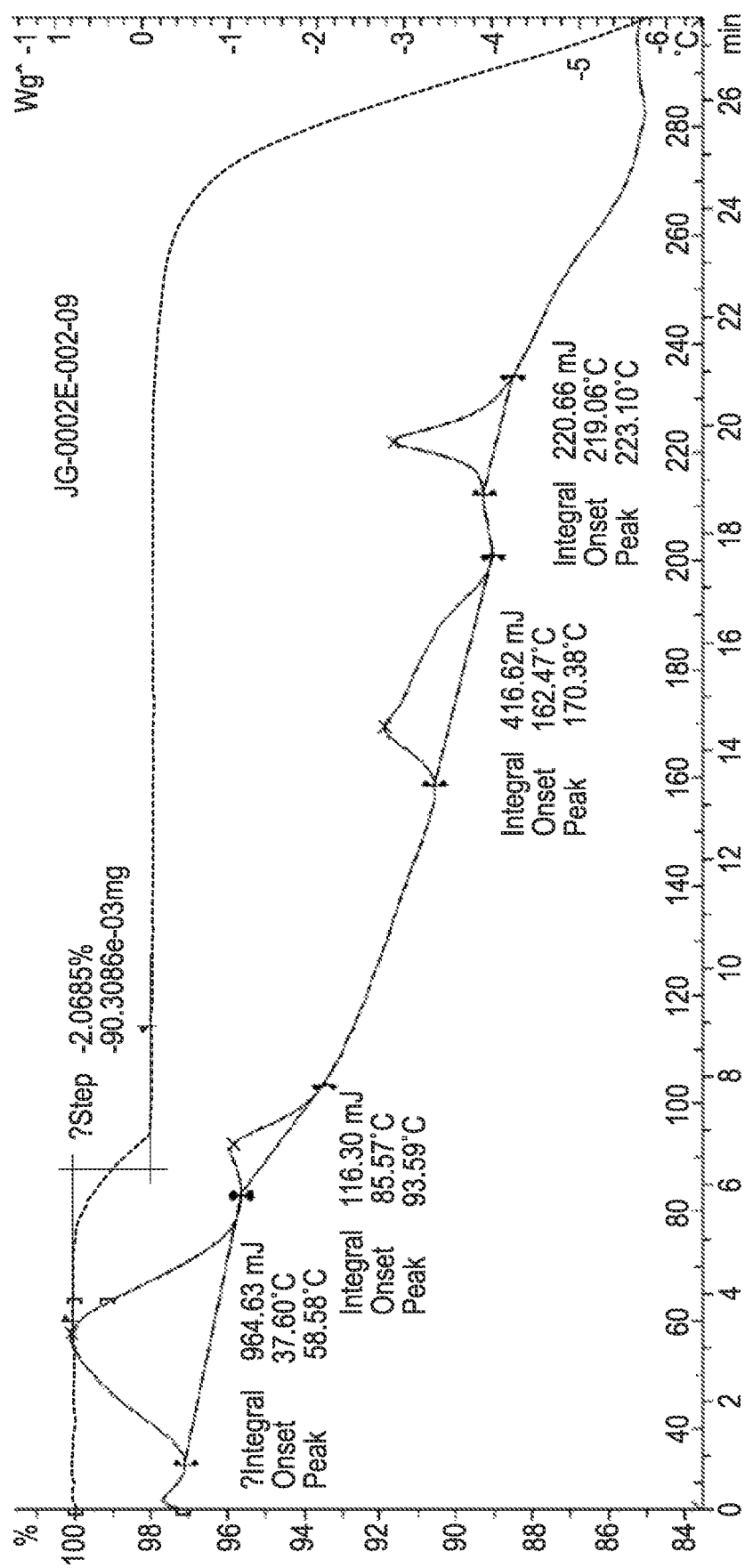
FIG. 26 is the TG/DTA trace of Form 22.
Figure 27:
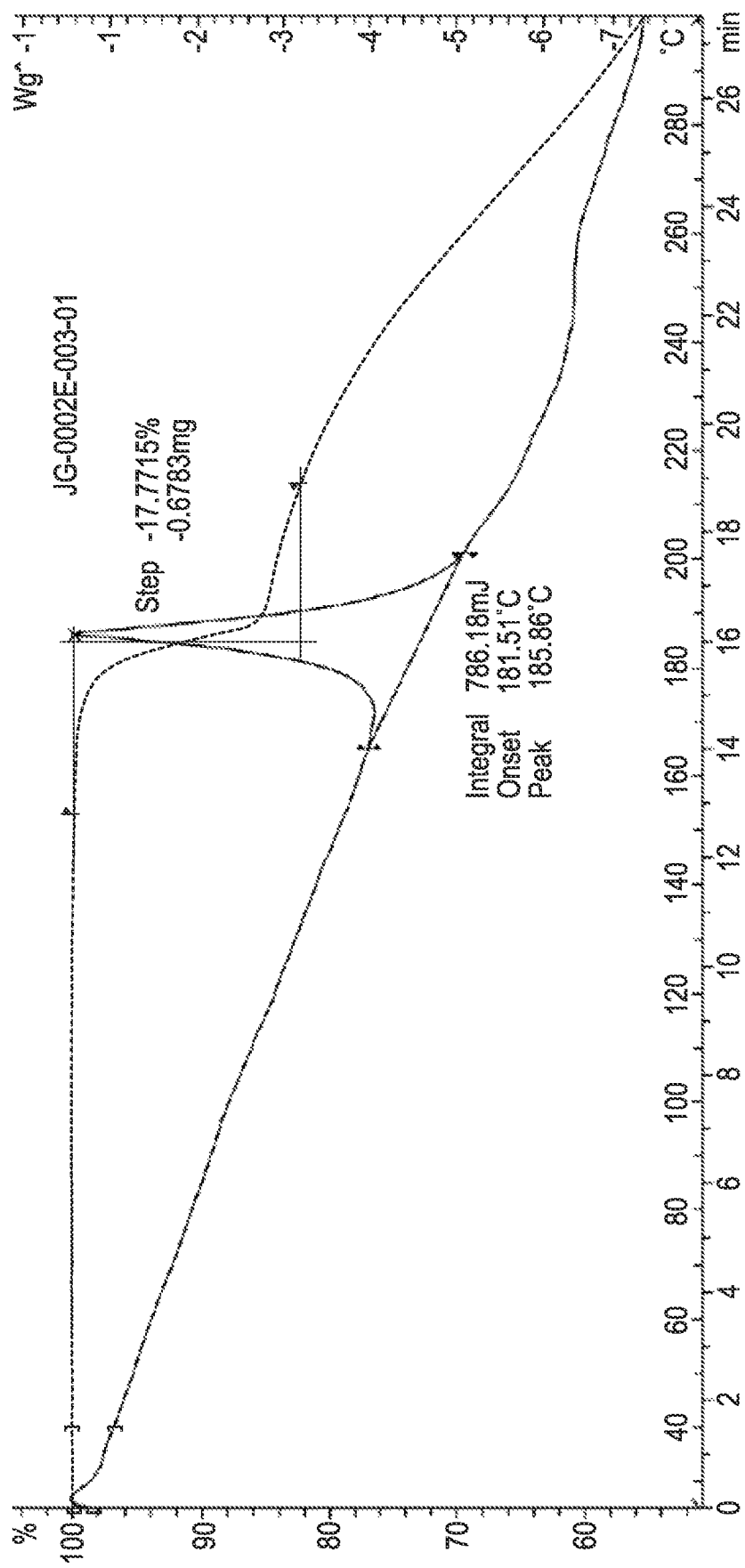
FIG. 27 is the TG/DTA trace of Form 24.
Figure 28:
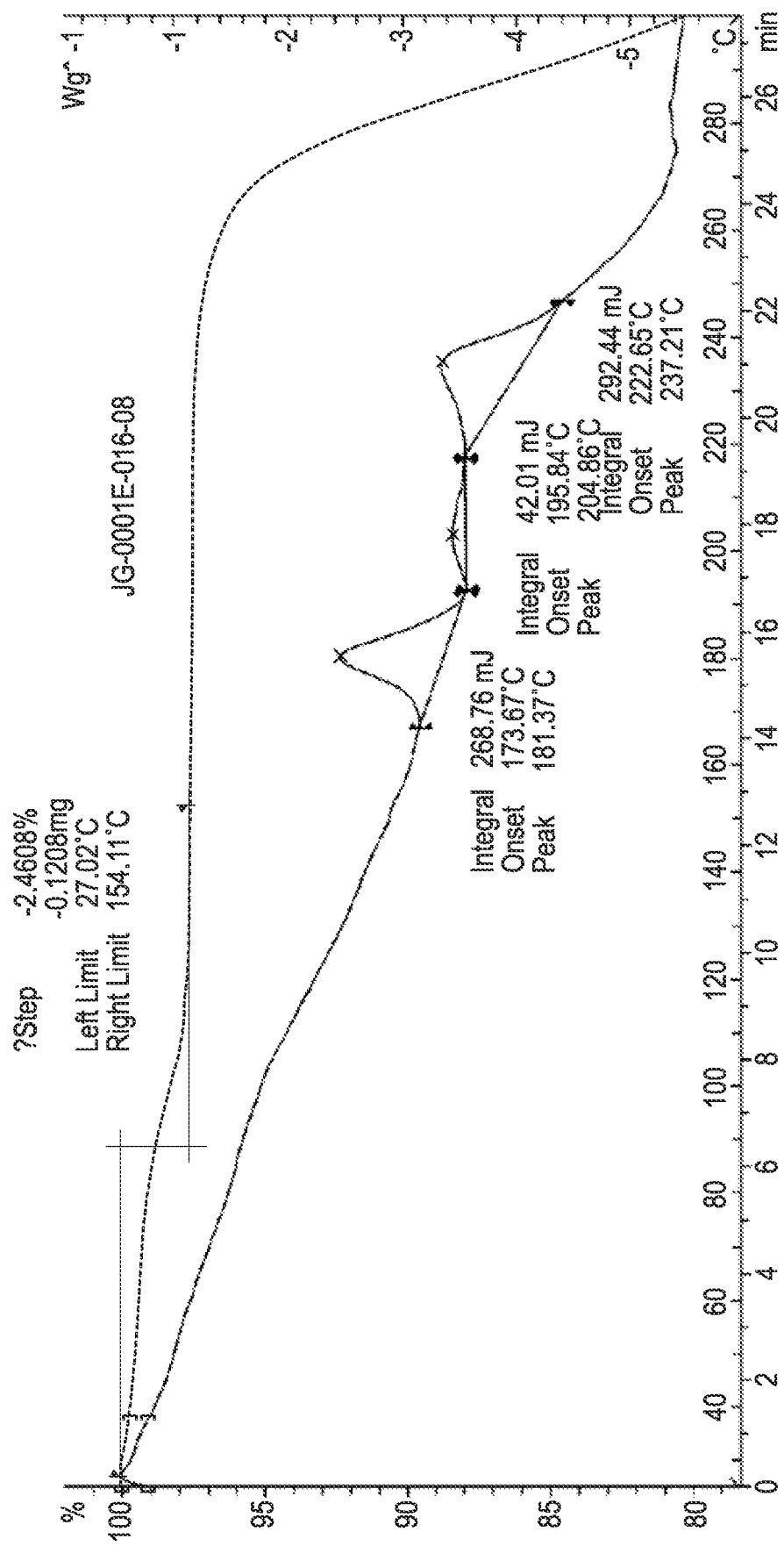
FIG. 28 is the TG/DTA trace of Form 25.
Figure 29:
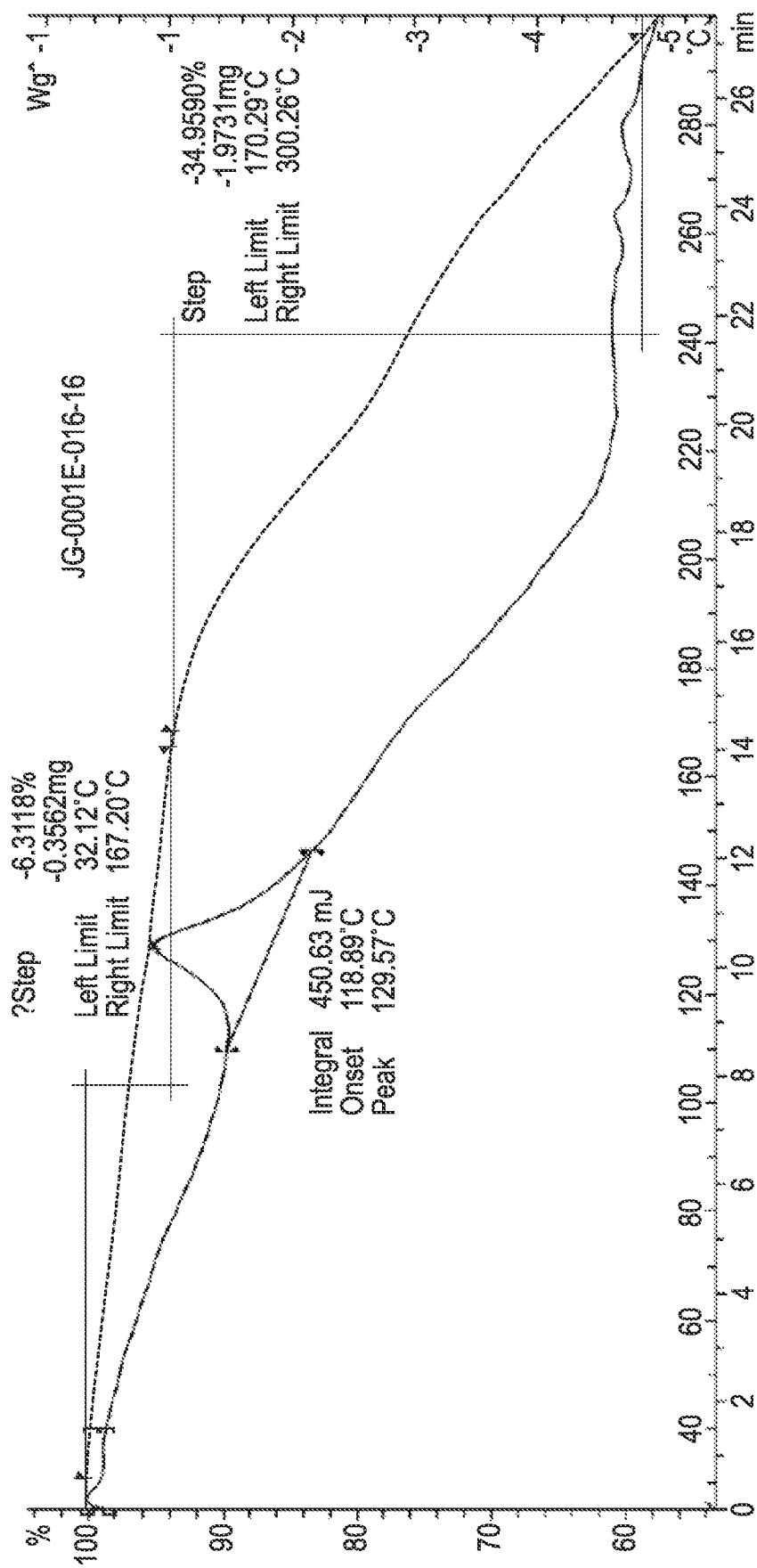
FIG. 29 is the TG/DTA trace of Form 26.
Figure 30:
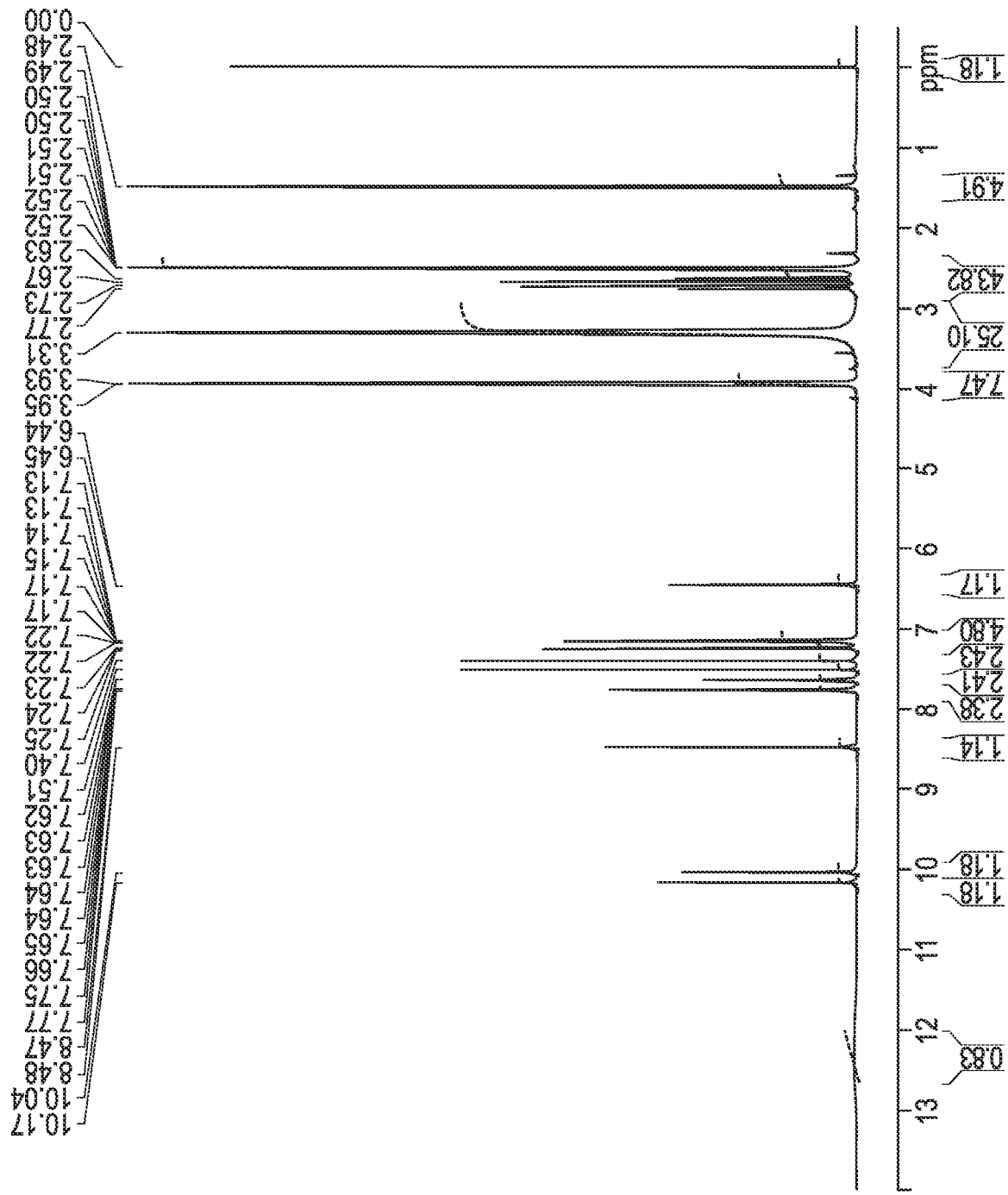
FIG. 30 is the NMR spectrum of Form 1 in DMSO-$d_6$.
Figure 31:
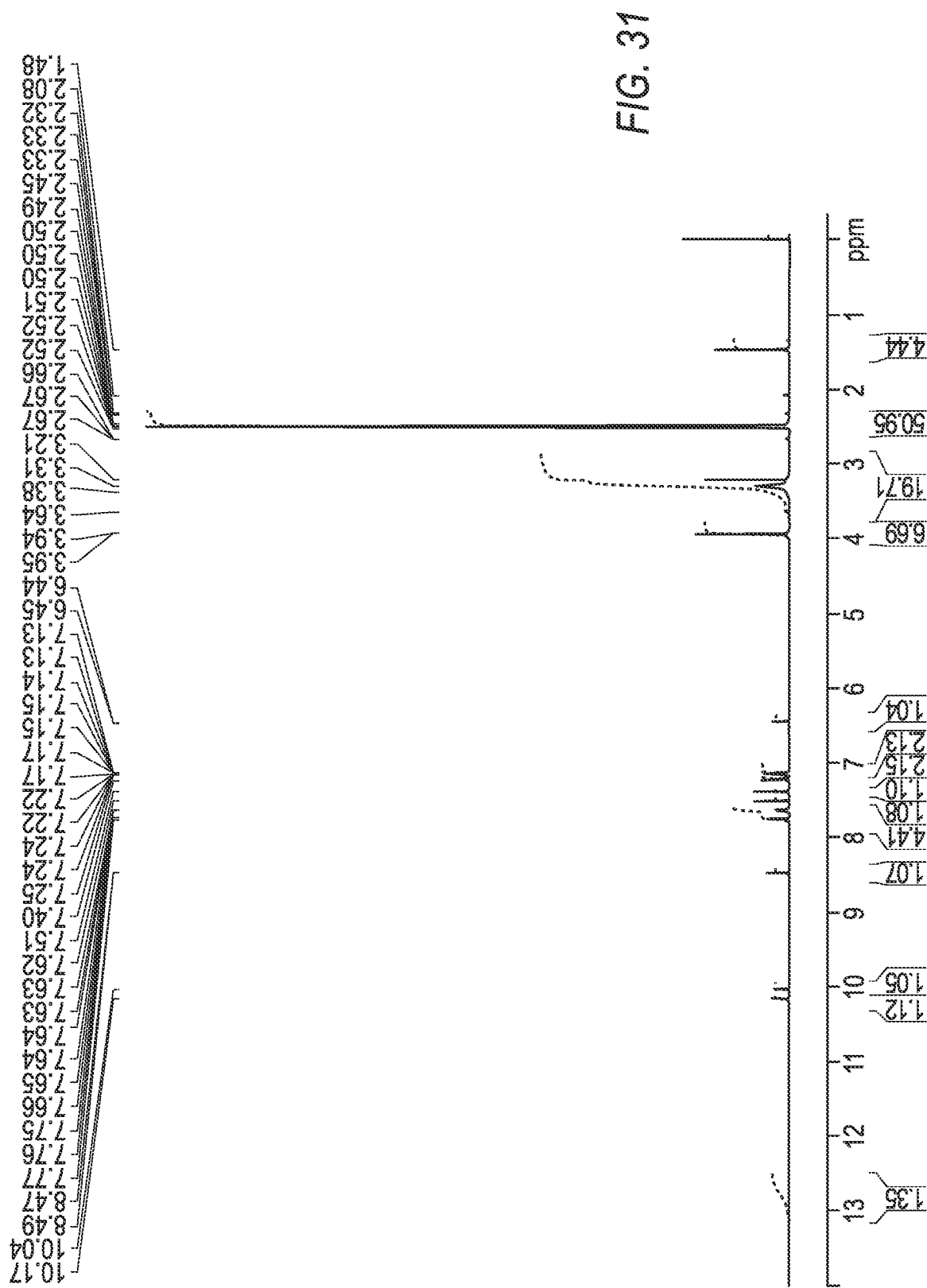
FIG. 31 is the NMR spectrum of Form 2 in DMSO-$d_6$.
Figure 32:
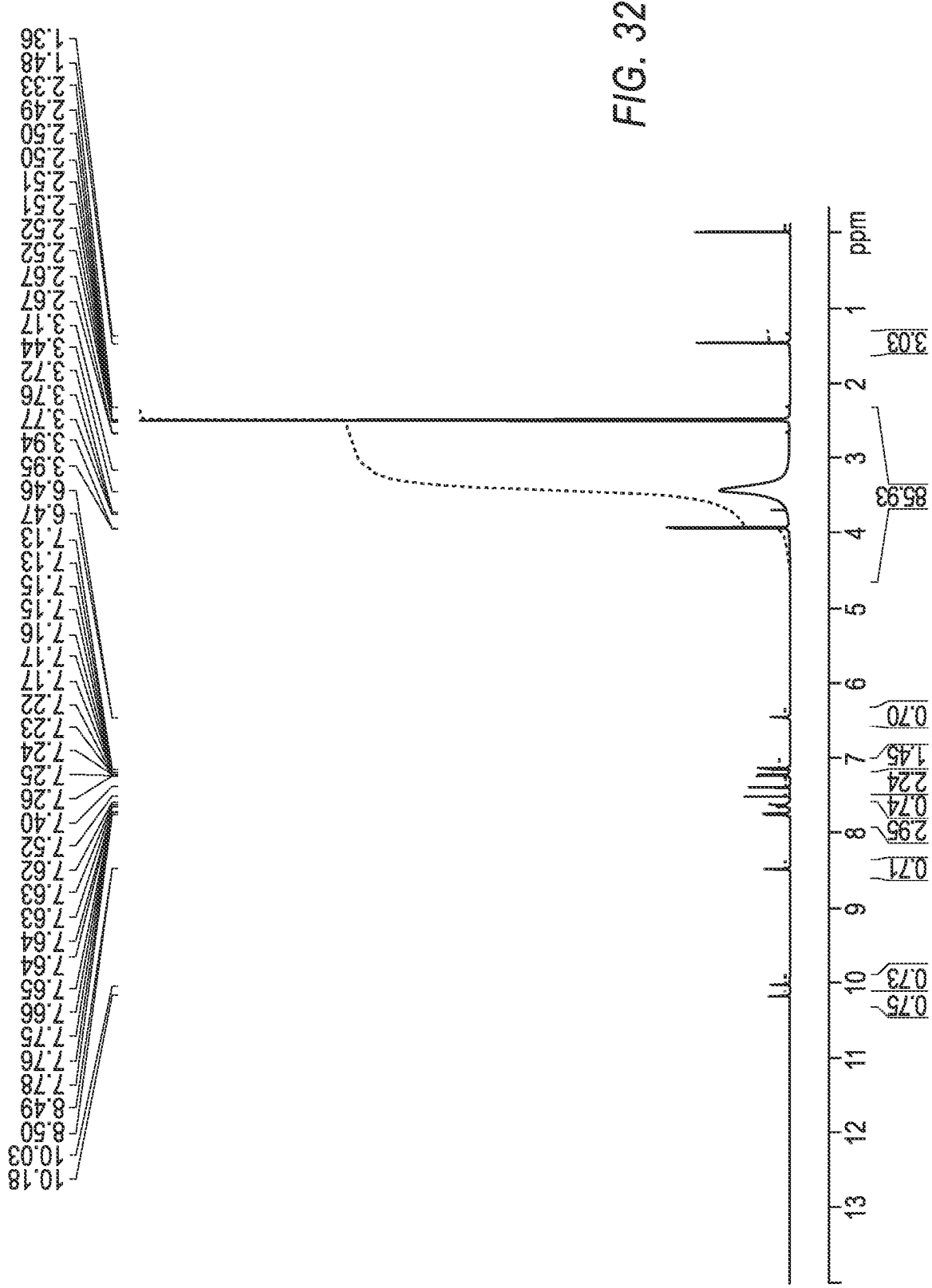
FIG. 32 is the NMR spectrum of Form 3 in DMSO-$d_6$.
Figure 33:
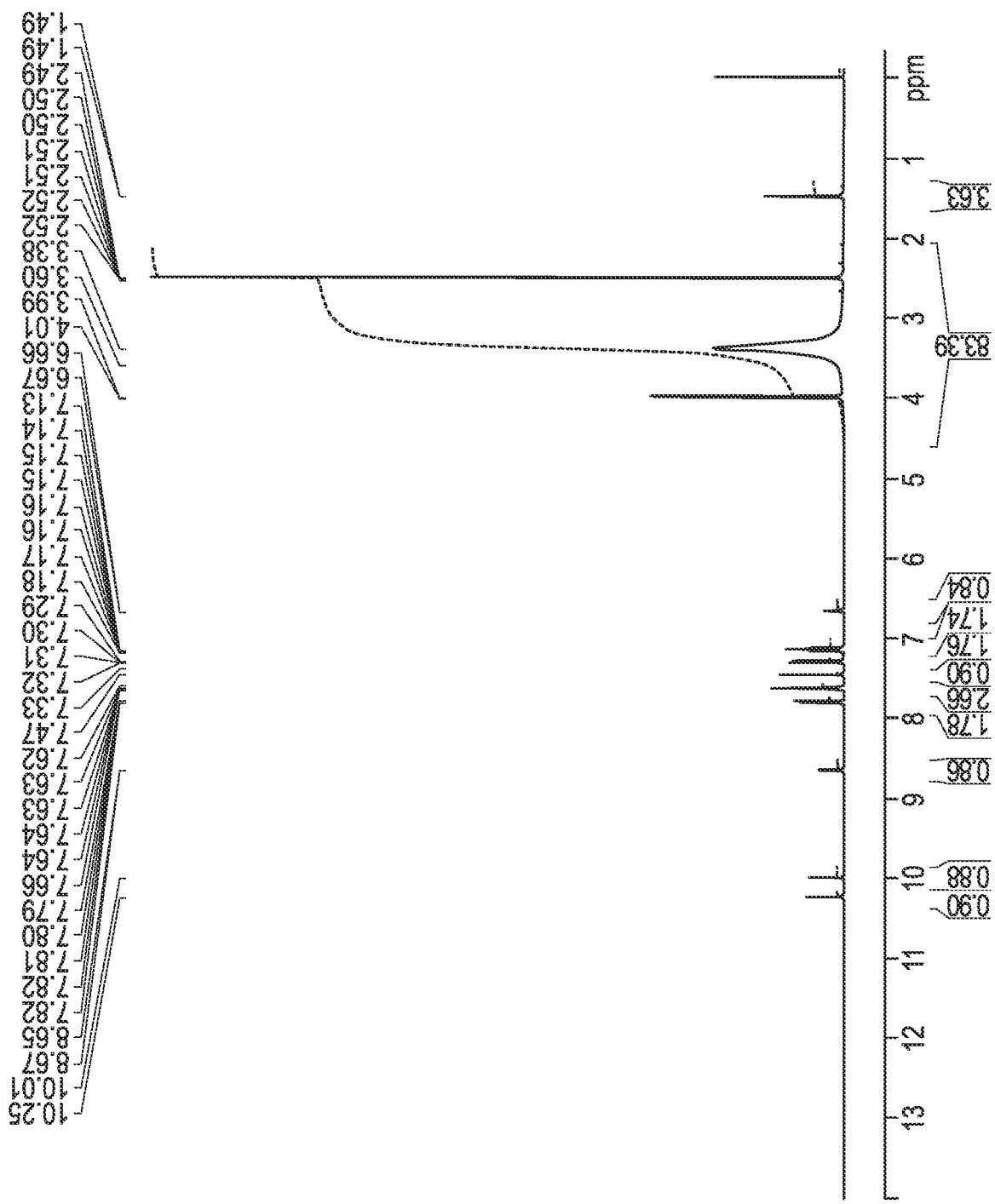
FIG. 33 is the NMR spectrum of Form 5 in DMSO-$d_6$.
Figure 34:
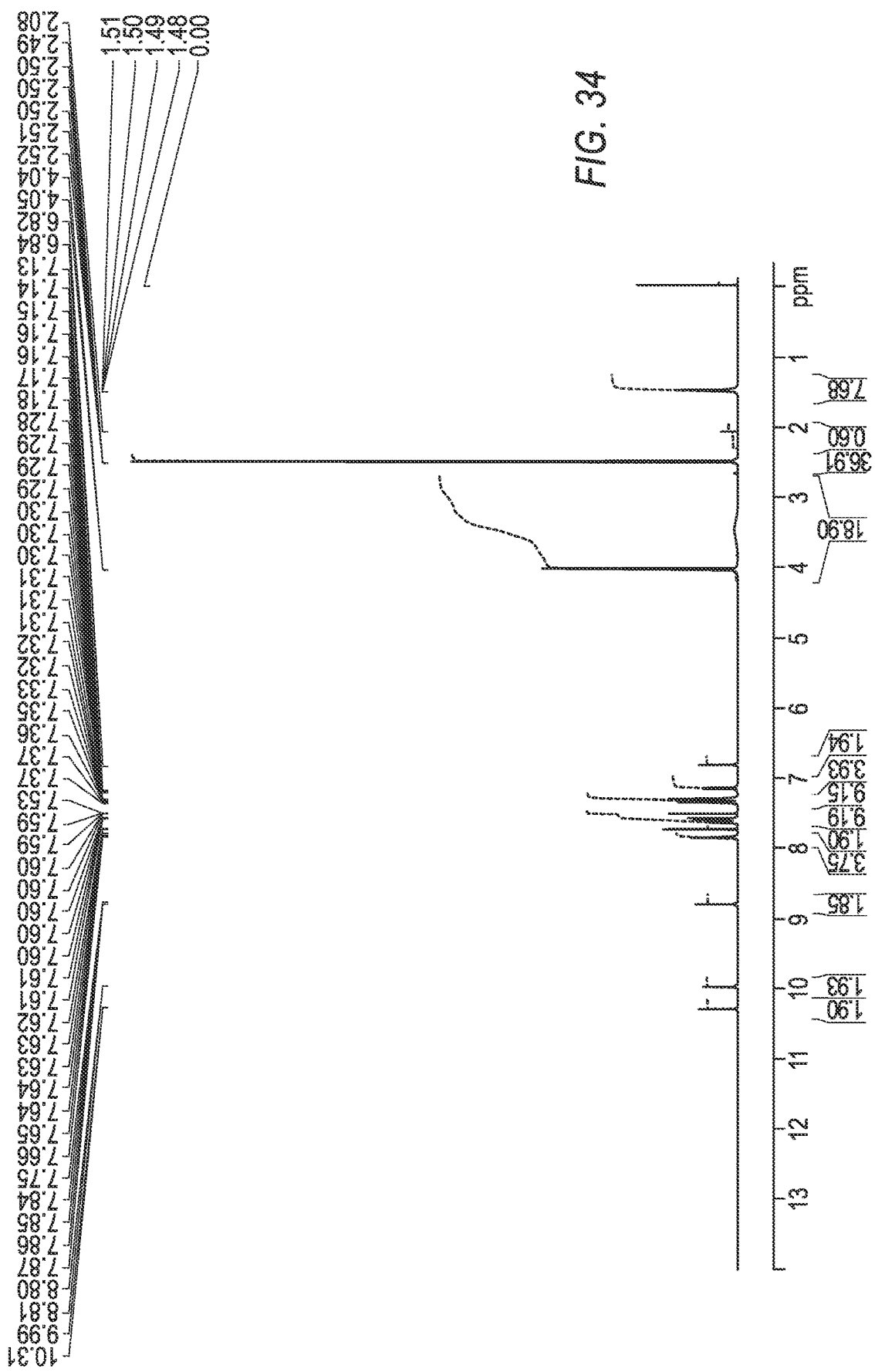
FIG. 34 is the NMR spectrum of Form 6 in DMSO-$d_6$.
Figure 35:
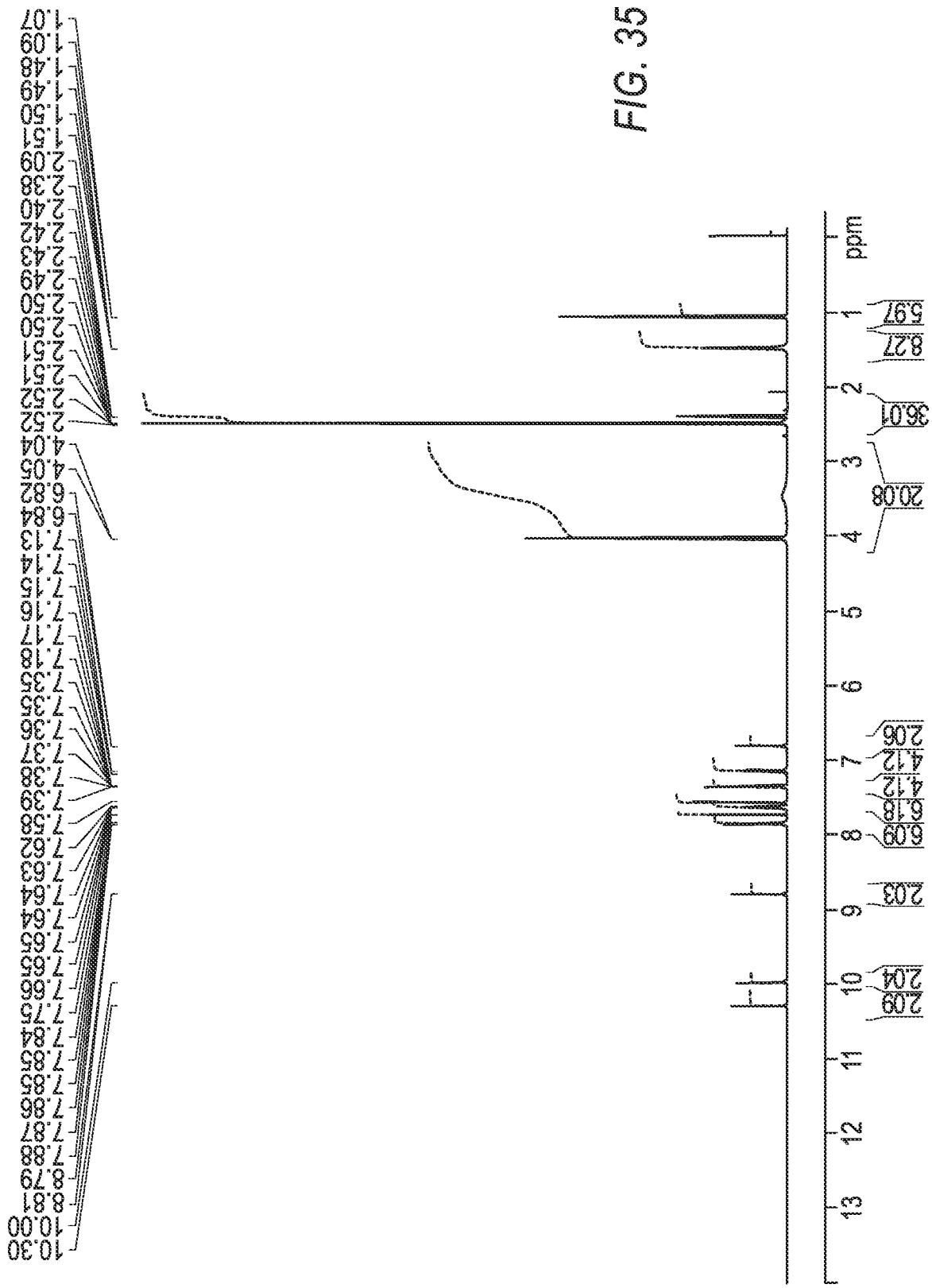
FIG. 35 is the NMR spectrum of Form 7 in DMSO-$d_6$.
Figure 36:
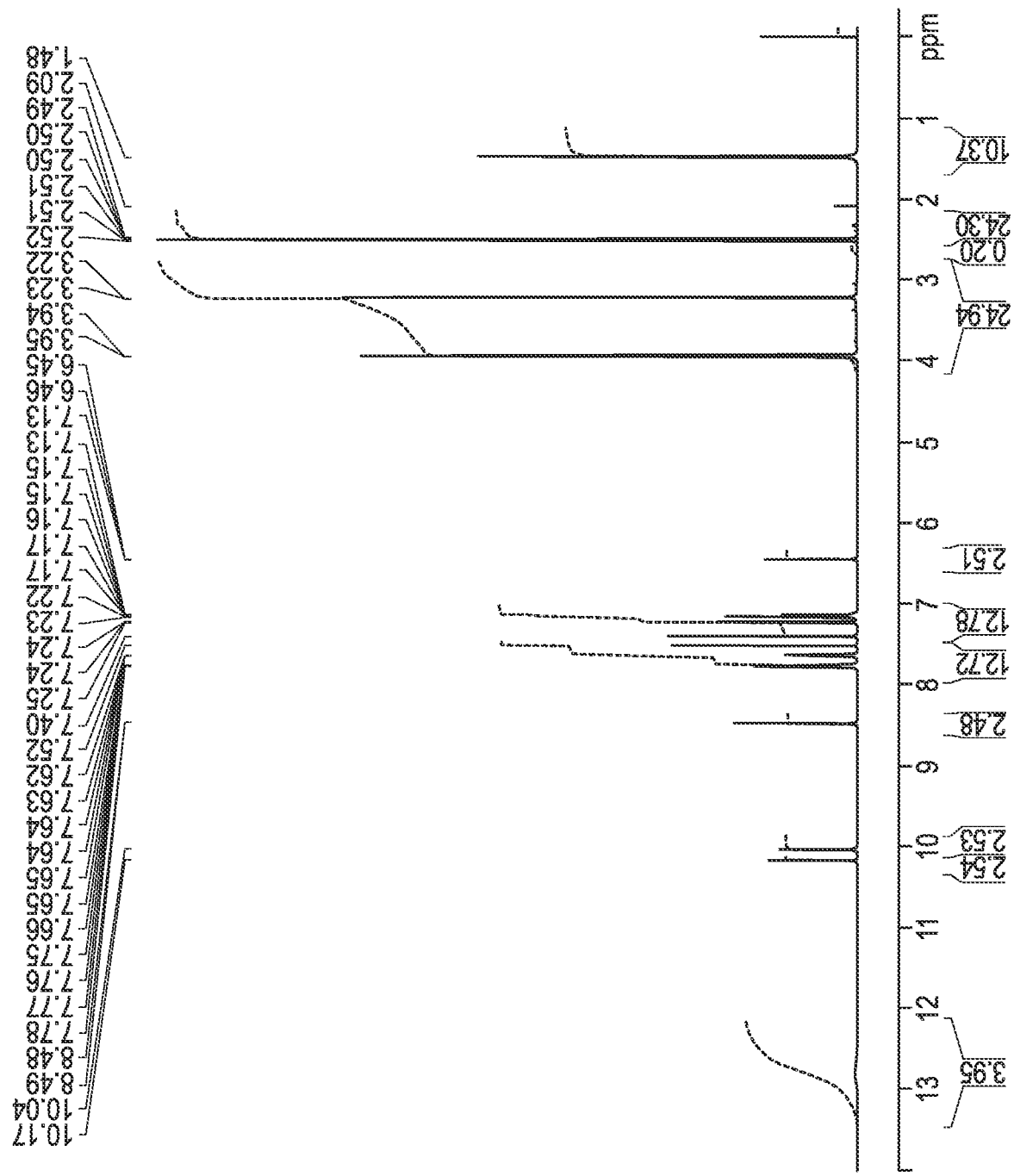
FIG. 36 is the NMR spectrum of Form 8 in DMSO-$d_6$.
Figure 37:
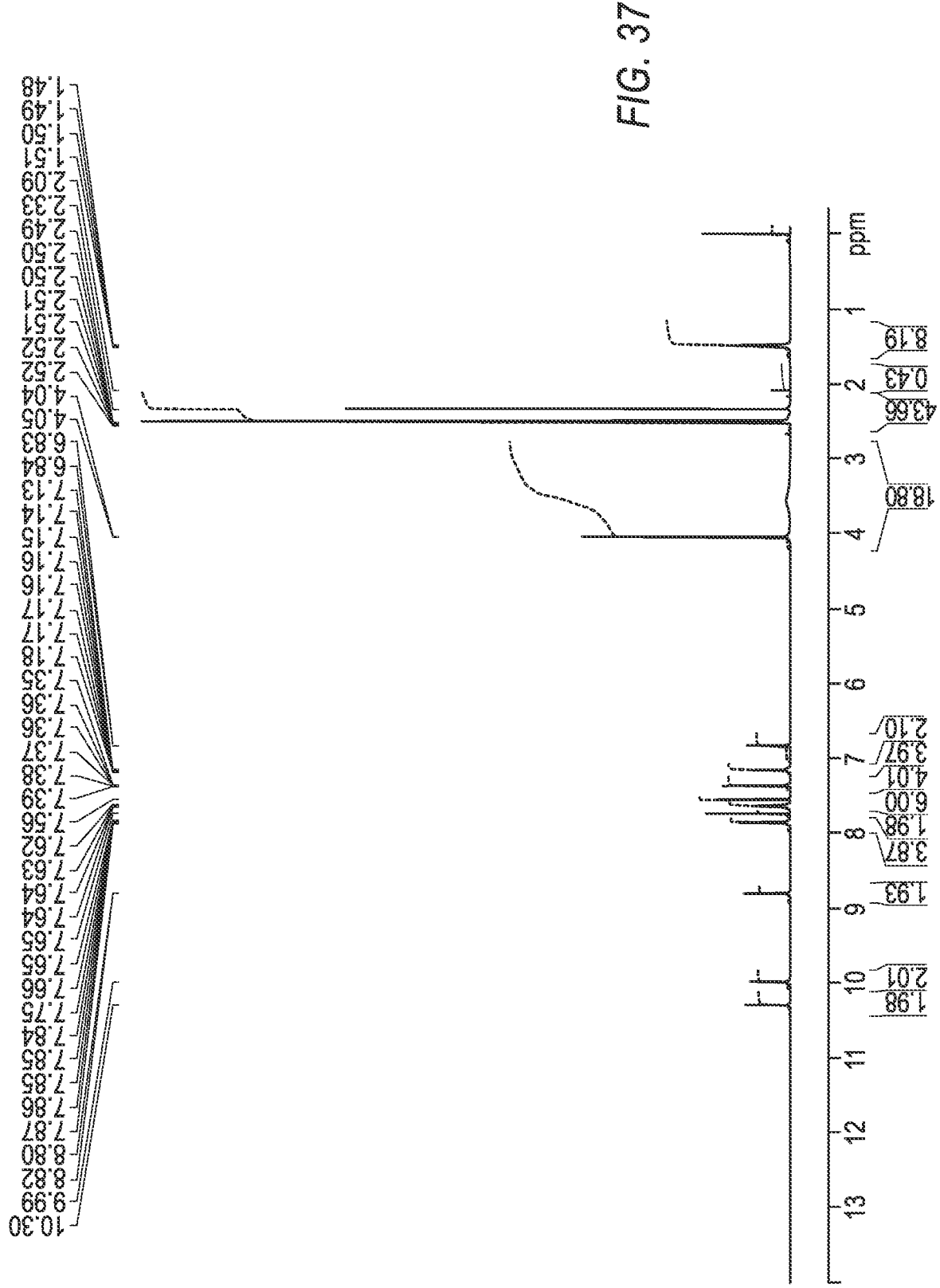
FIG. 37 is the NMR spectrum of Form 9 in DMSO-$d_6$.
Figure 38:
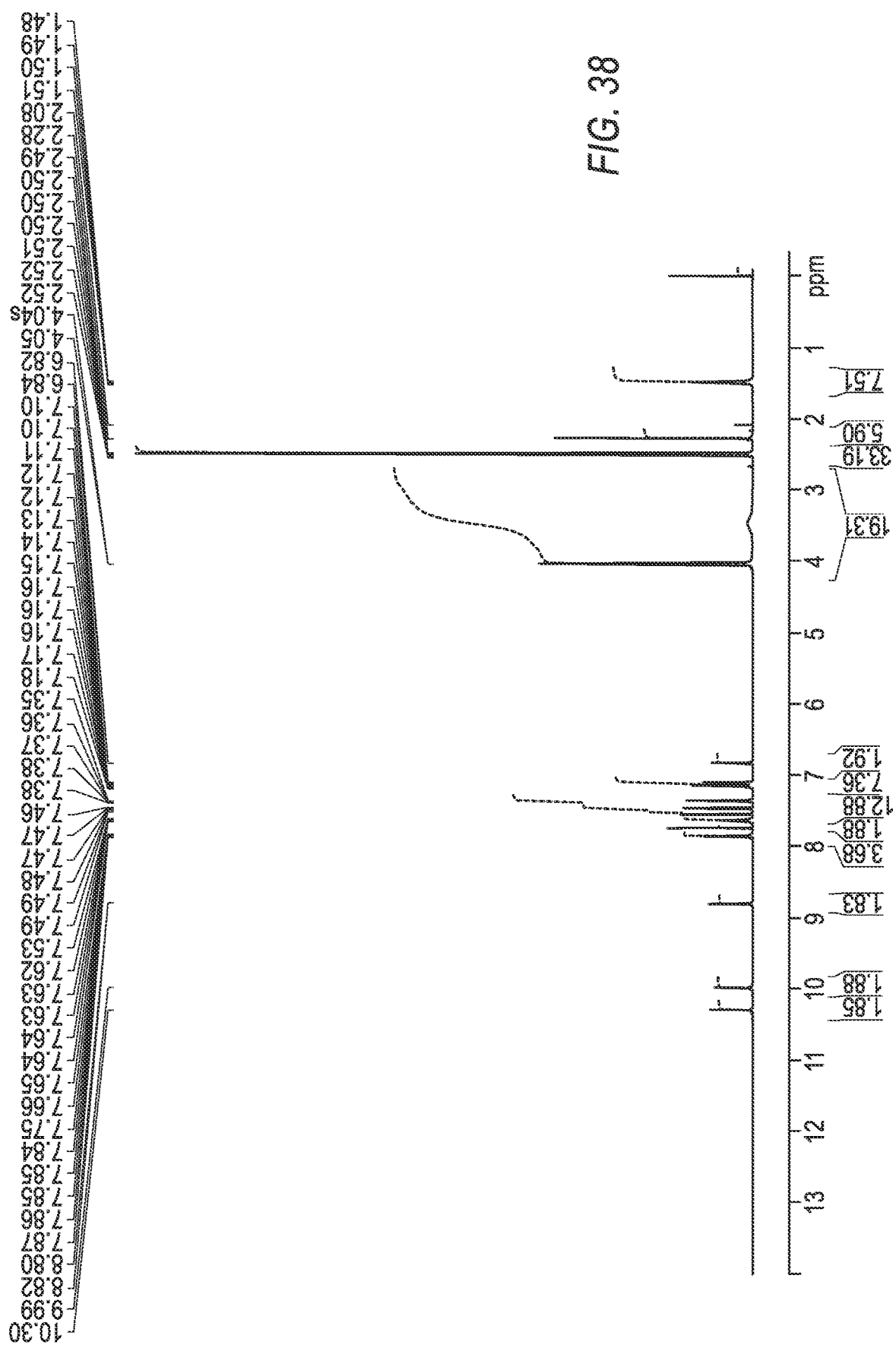
FIG. 38 is the NMR spectrum of Form 10 in DMSO-$d_6$.
Figure 39:
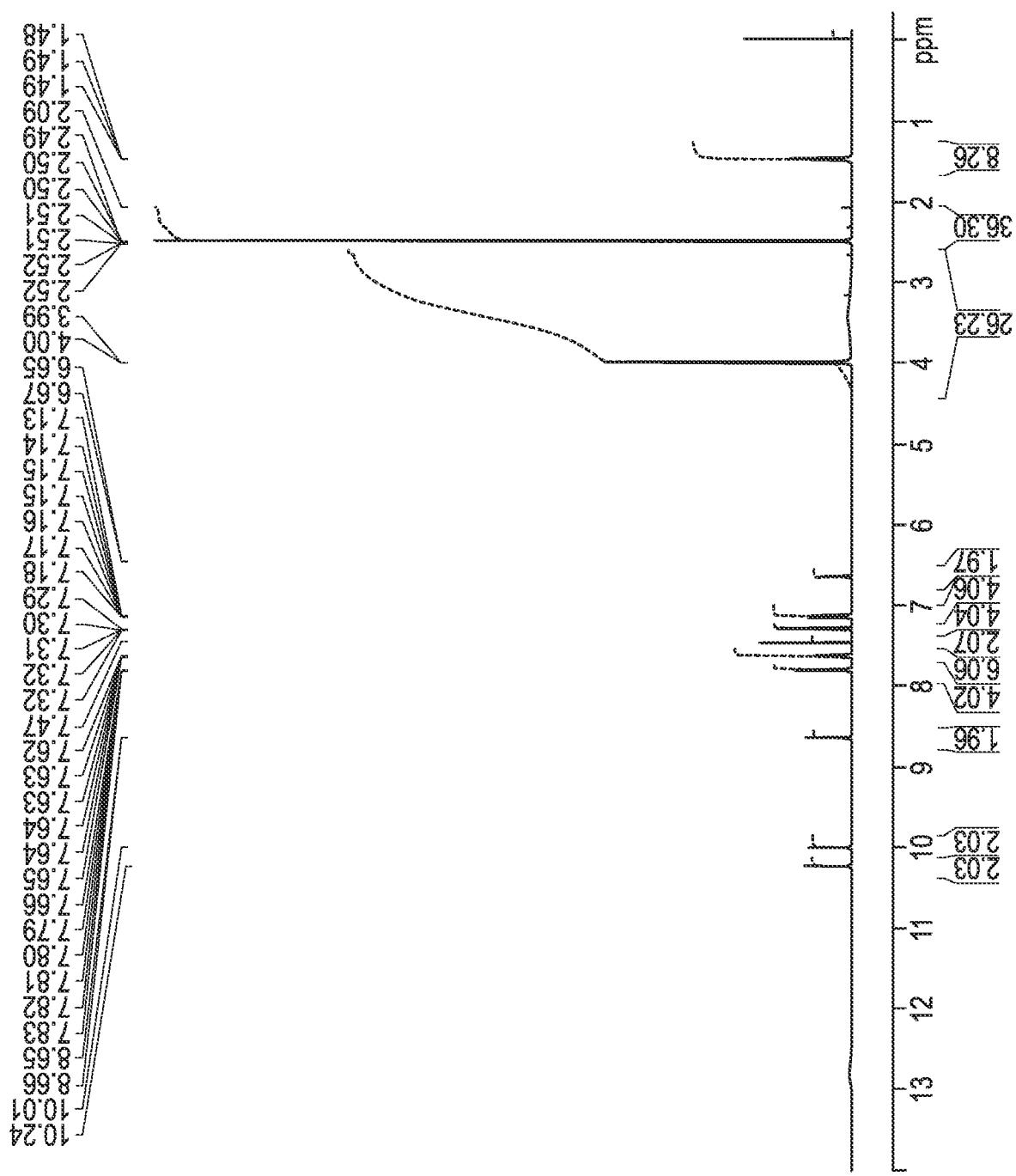
FIG. 39 is the NMR spectrum of Form 11 in DMSO-$d_6$.
Figure 40:
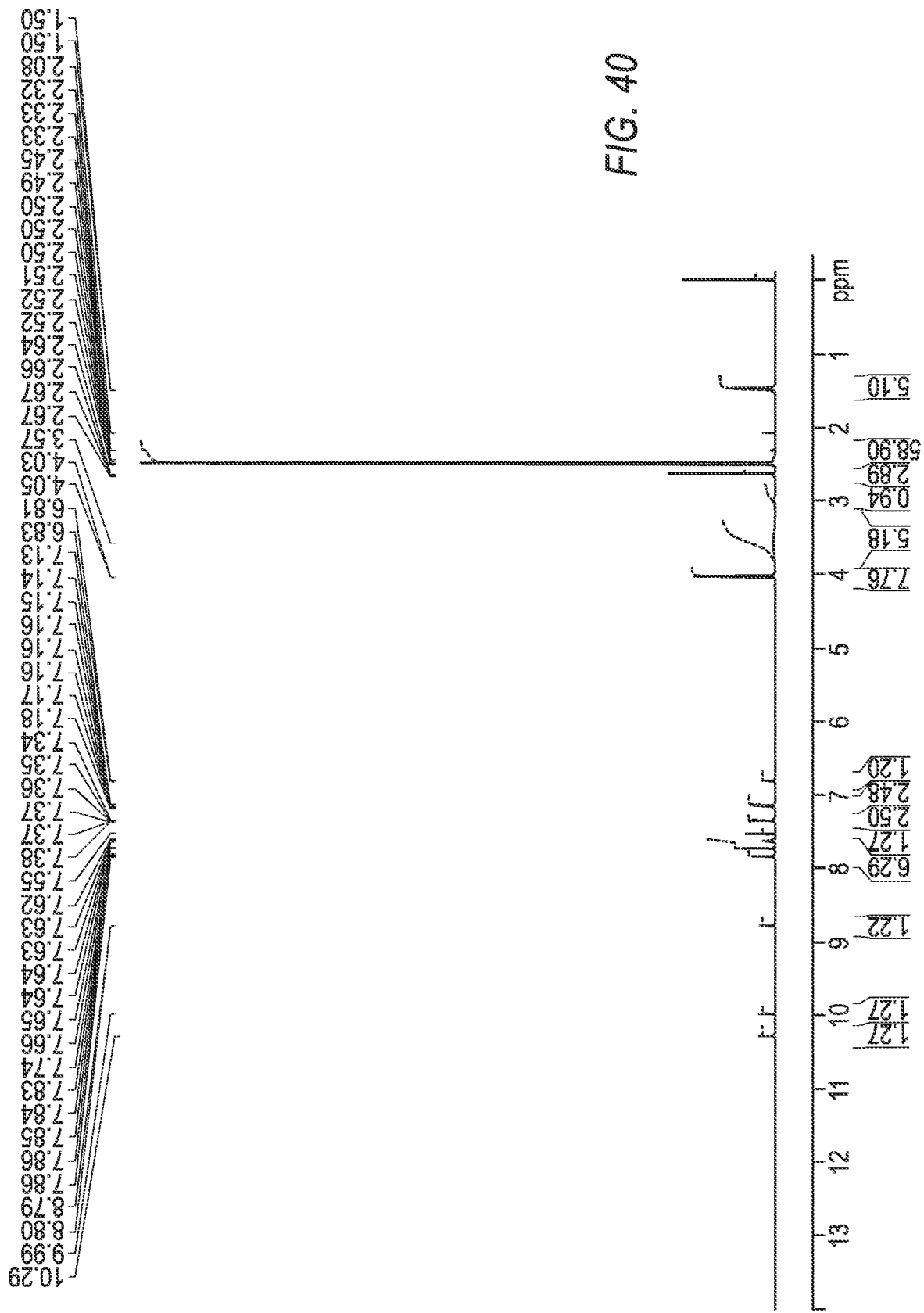
FIG. 40 is the NMR spectrum of Form 12 in DMSO-$d_6$.
Figure 41:
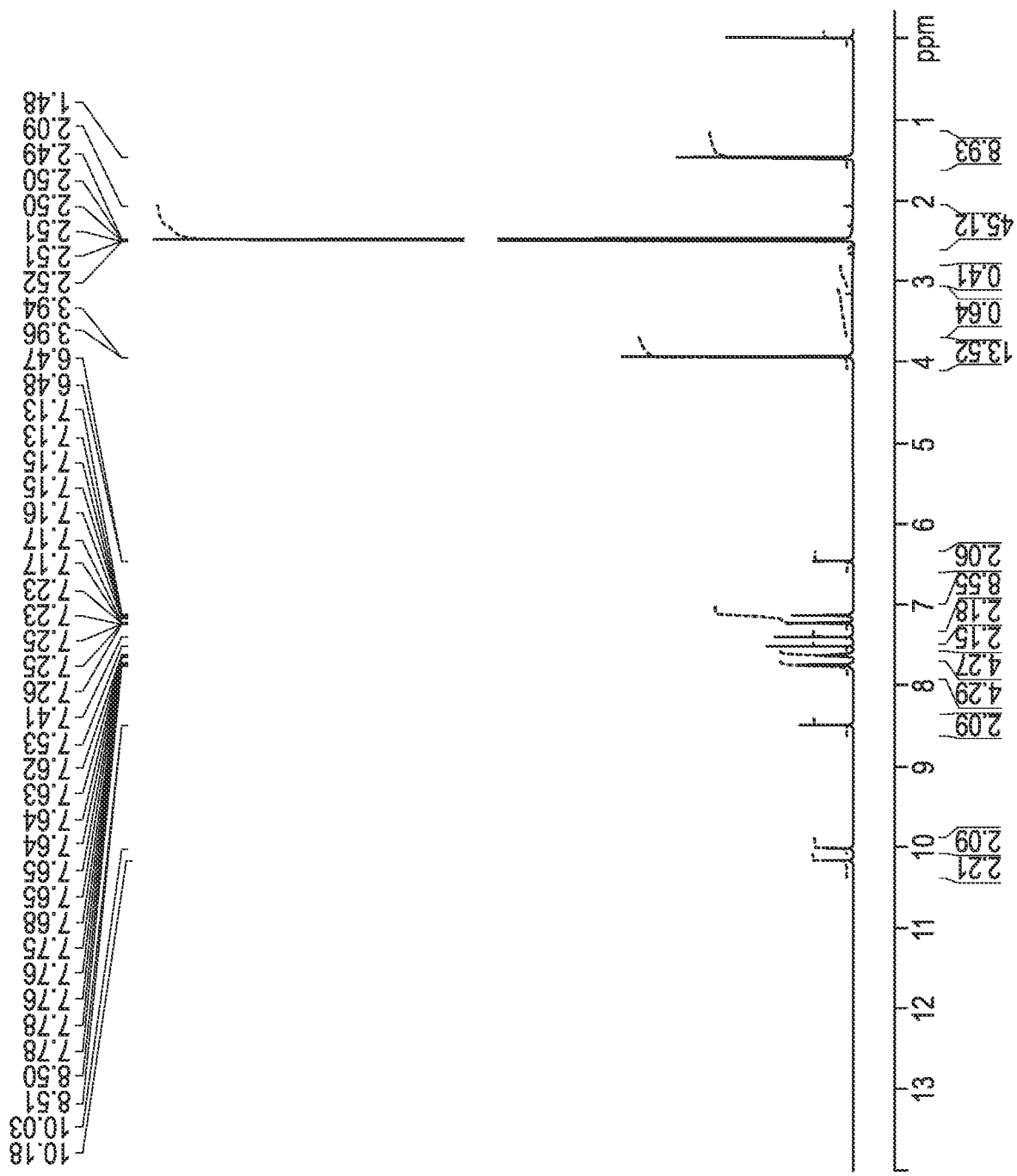
FIG. 41 is the NMR spectrum of Form 13 in DMSO-$d_6$.
Figure 42:
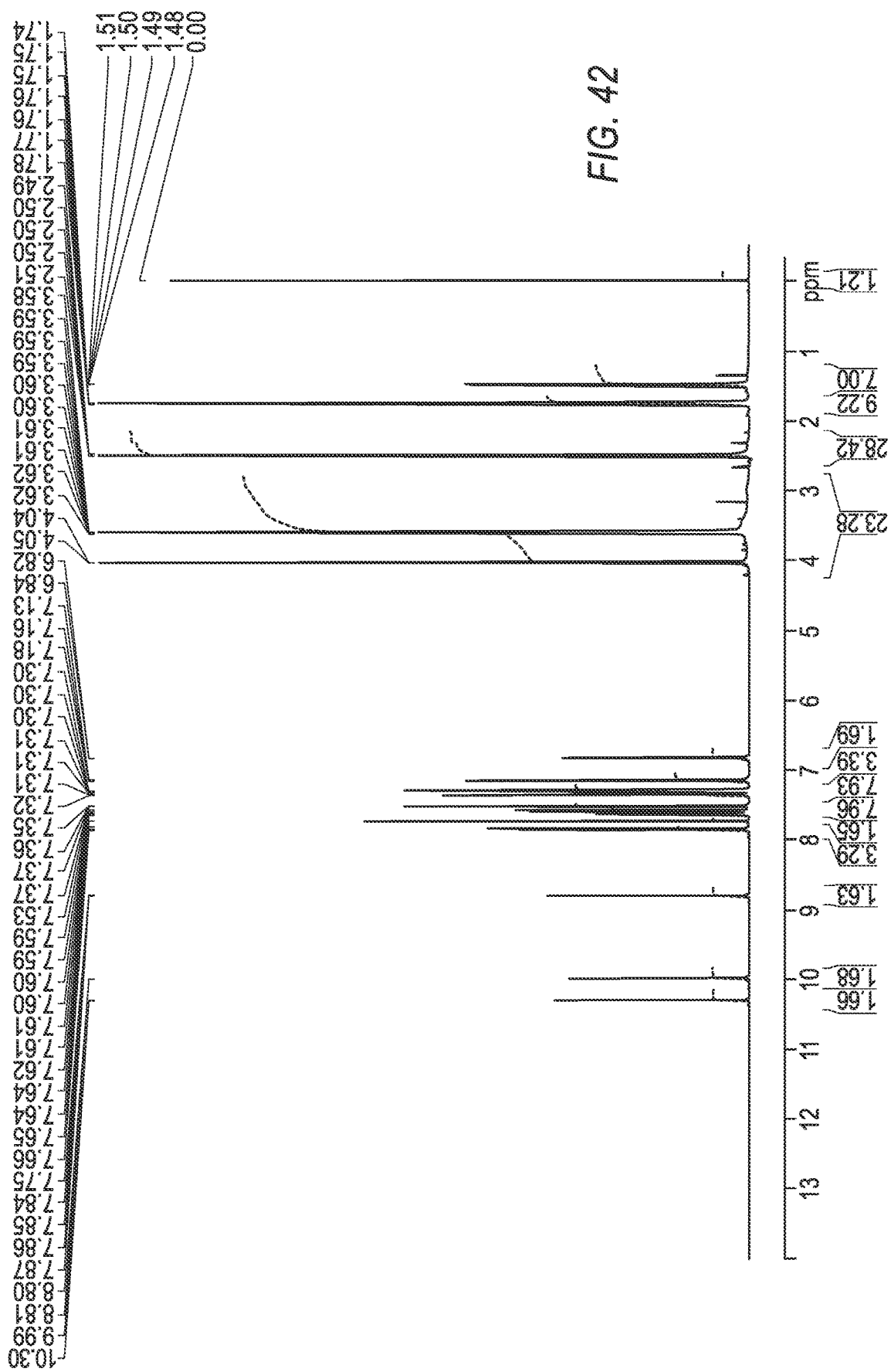
FIG. 42 is the NMR spectrum of Form 15 in DMSO-$d_6$.
Figure 43:
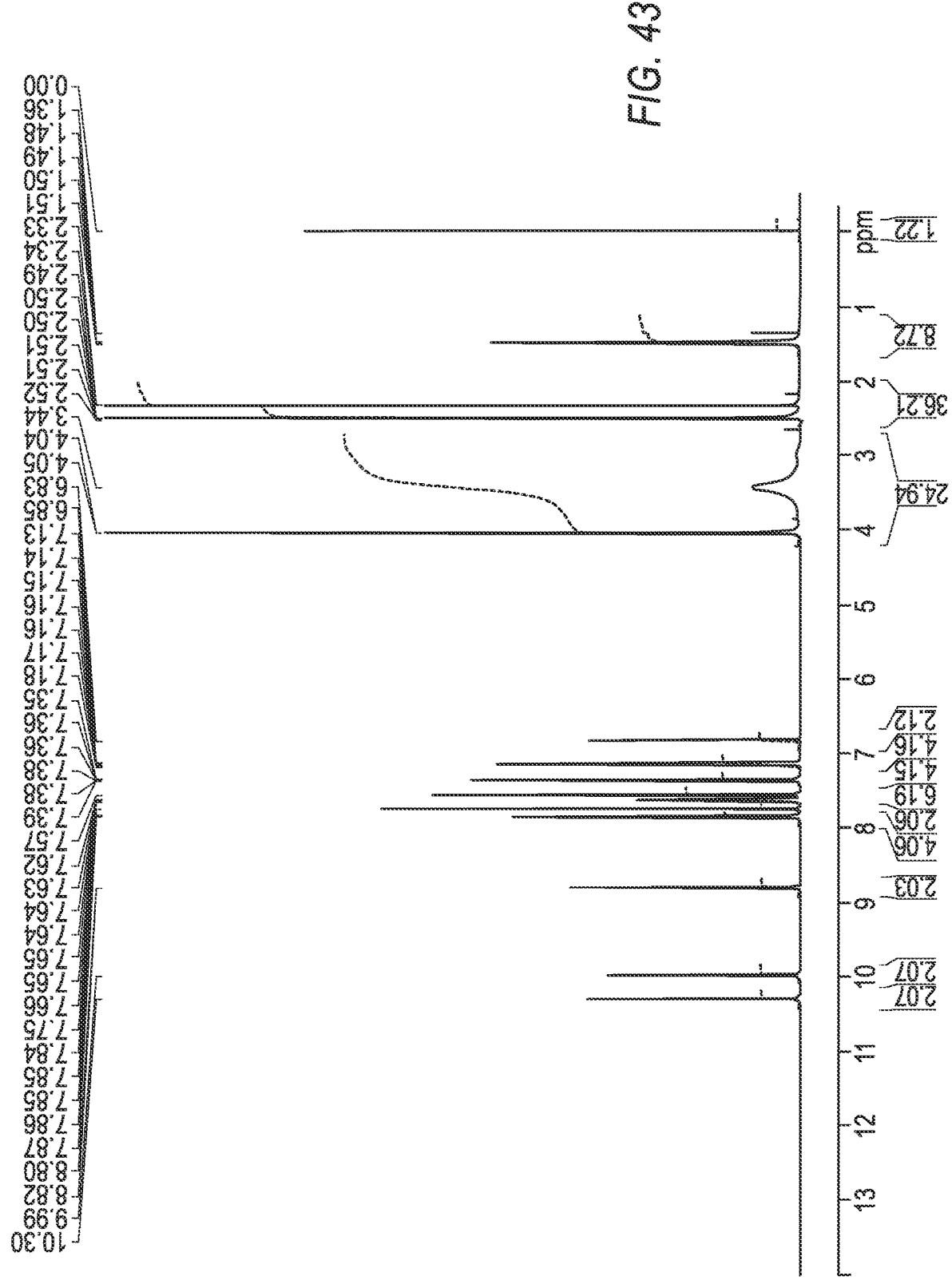
FIG. 43 is the NMR spectrum of Form 16 in DMSO-$d_6$.
Figure 44:
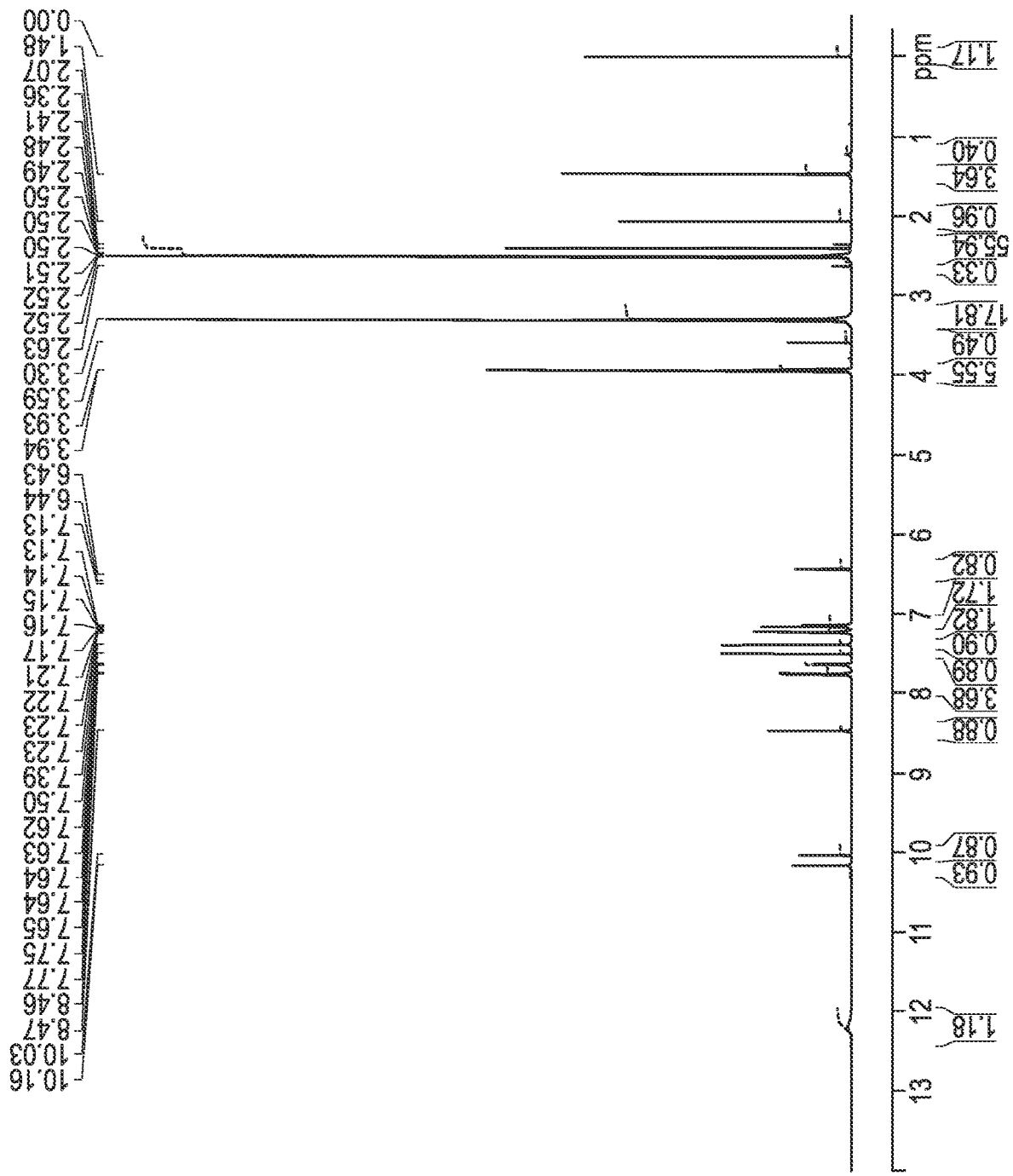
FIG. 44 is the NMR spectrum of Form 17 in DMSO-$d_6$.
Figure 45:
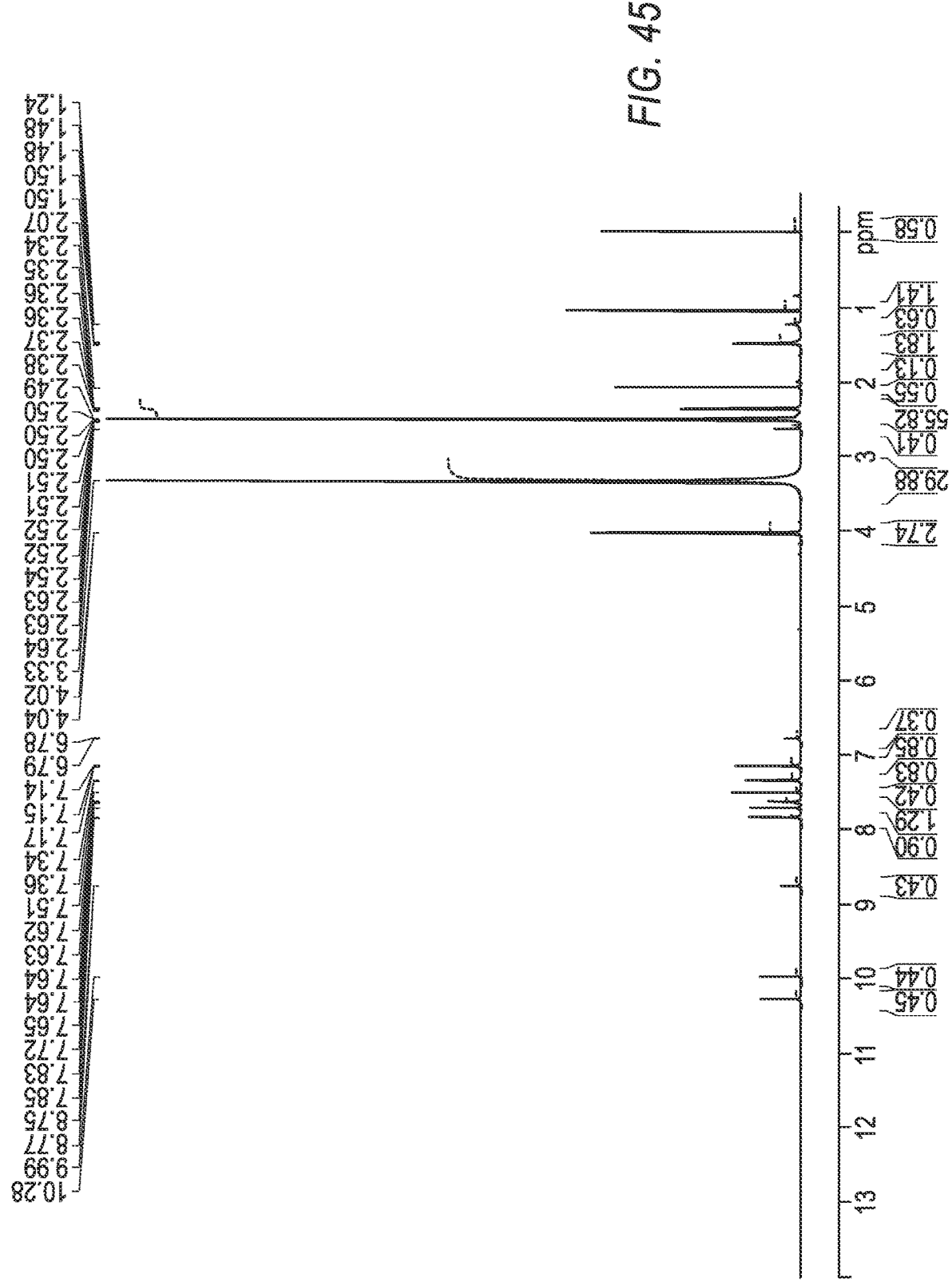
FIG. 45 is the NMR spectrum of Form 18 in DMSO-$d_6$.
Figure 46:
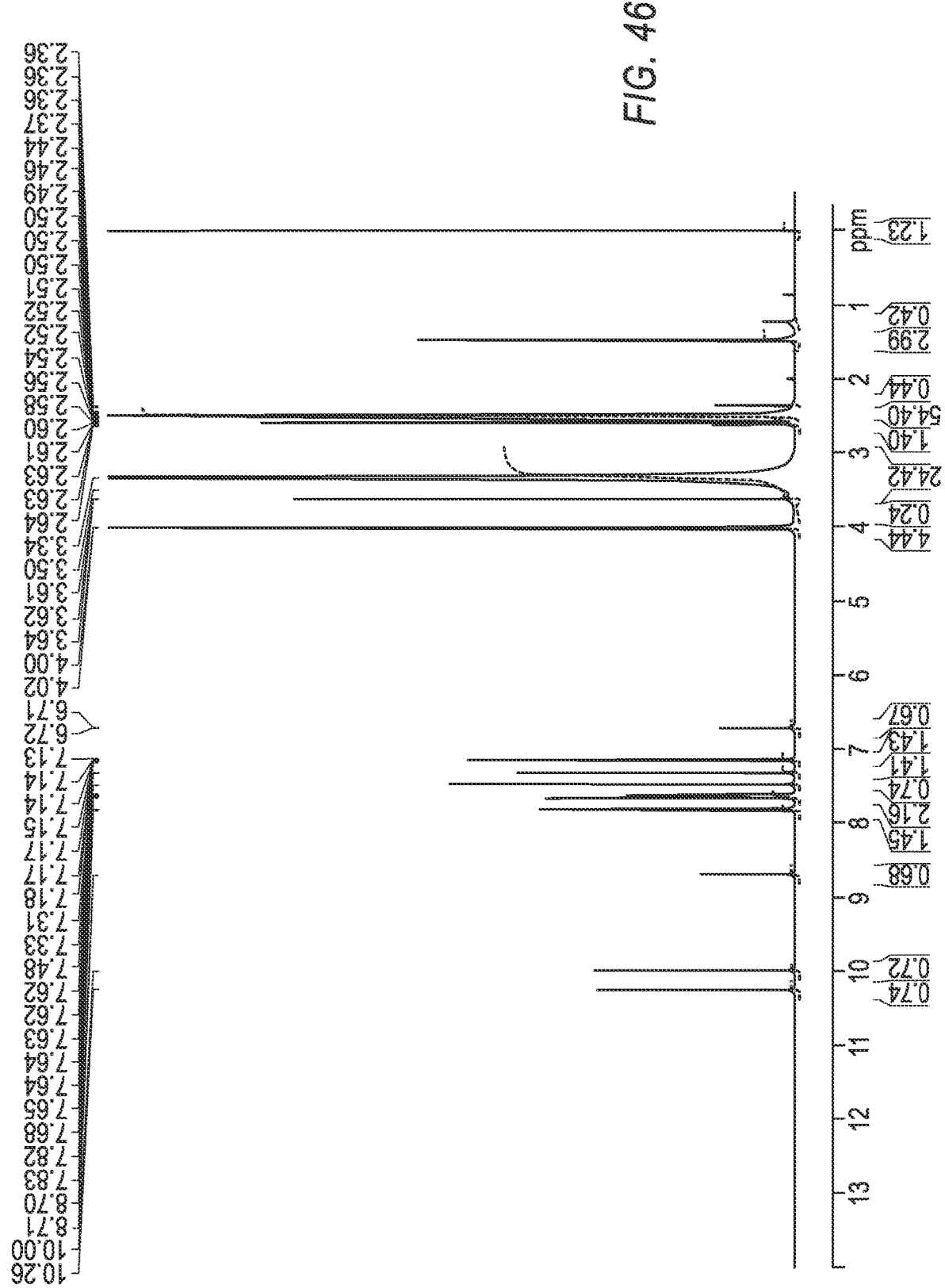
FIG. 46 is the NMR spectrum of Form 19 in DMSO-$d_6$.
Figure 47:
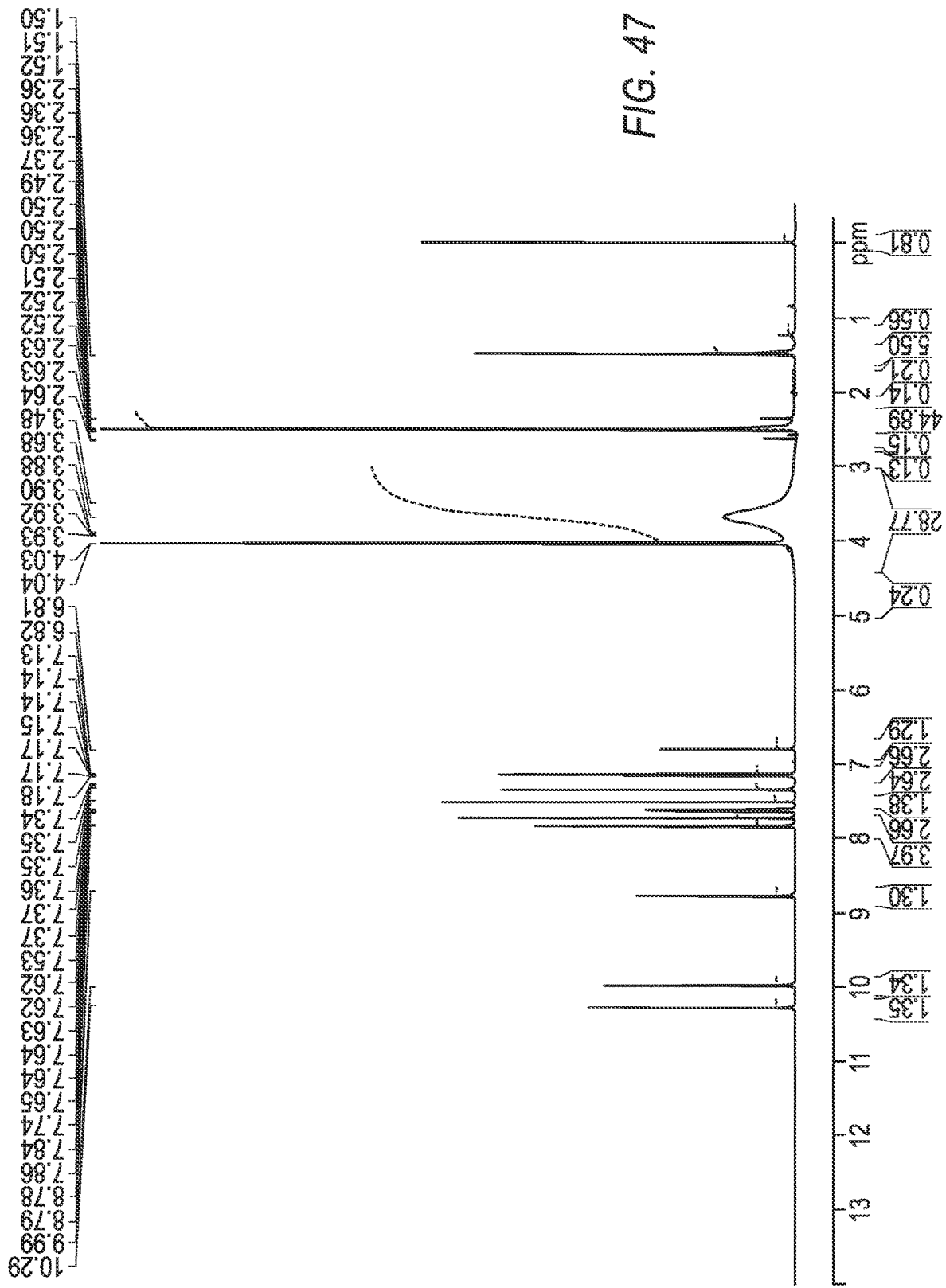
FIG. 47 is the NMR spectrum of Form 21 in DMSO-$d_6$.
Figure 48:
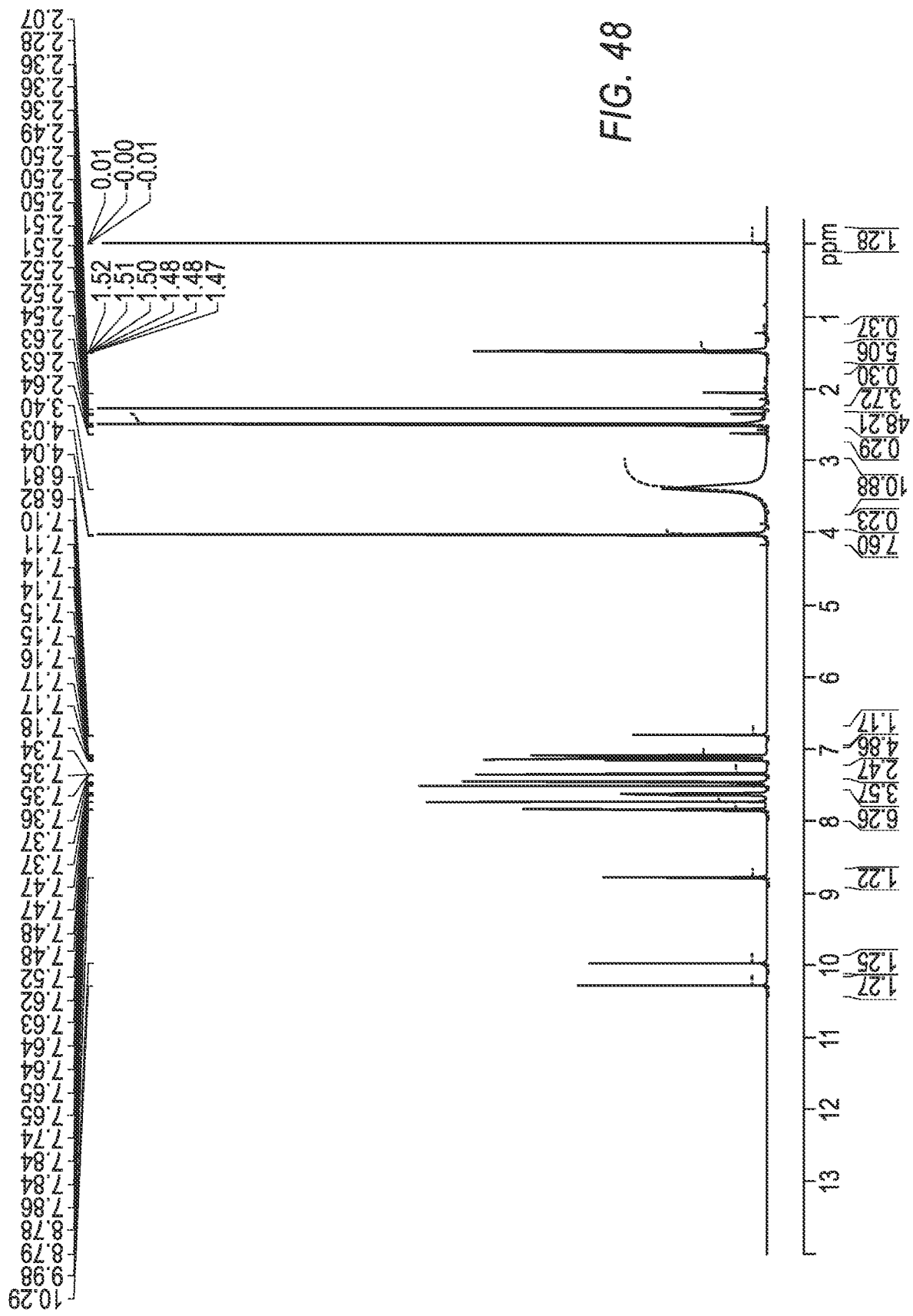
FIG. 48 is the NMR spectrum of Form 22 in DMSO-$d_6$.
Figure 49:
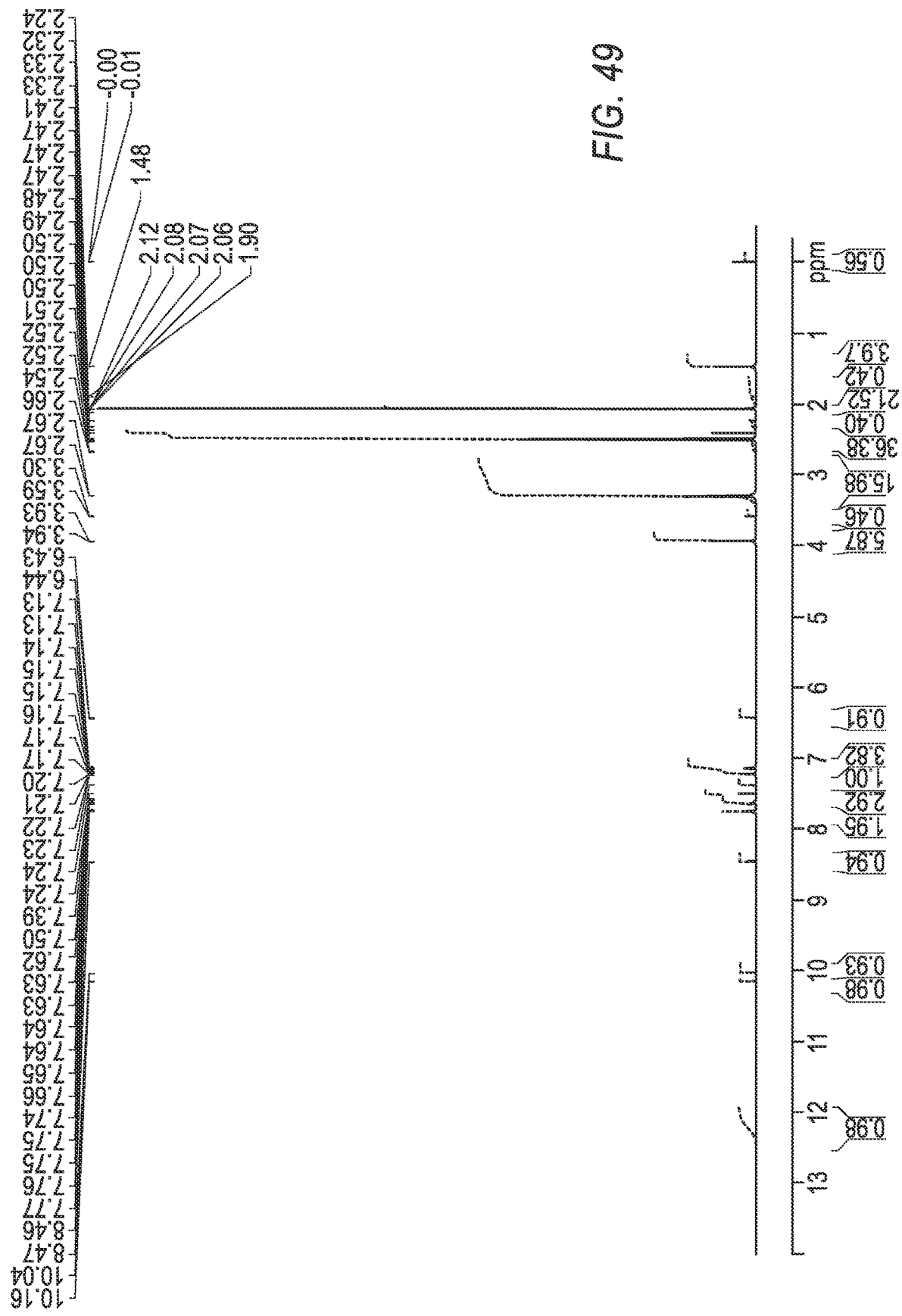
FIG. 49 is the NMR spectrum of Form 23 in DMSO-$d_6$.
Figure 50:
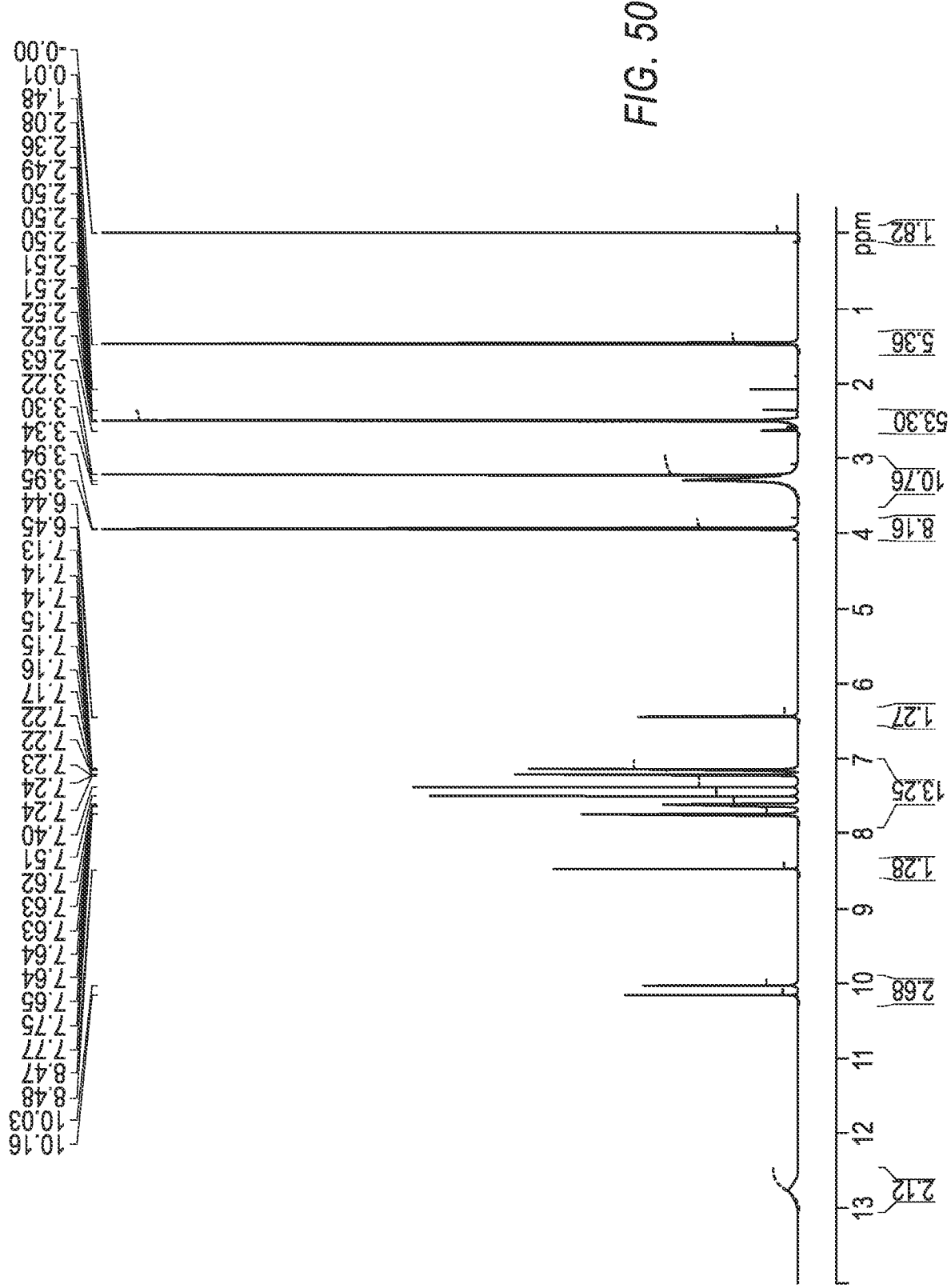
FIG. 50 is the NMR spectrum of Form 24 in DMSO-$d_6$.
Figure 51:
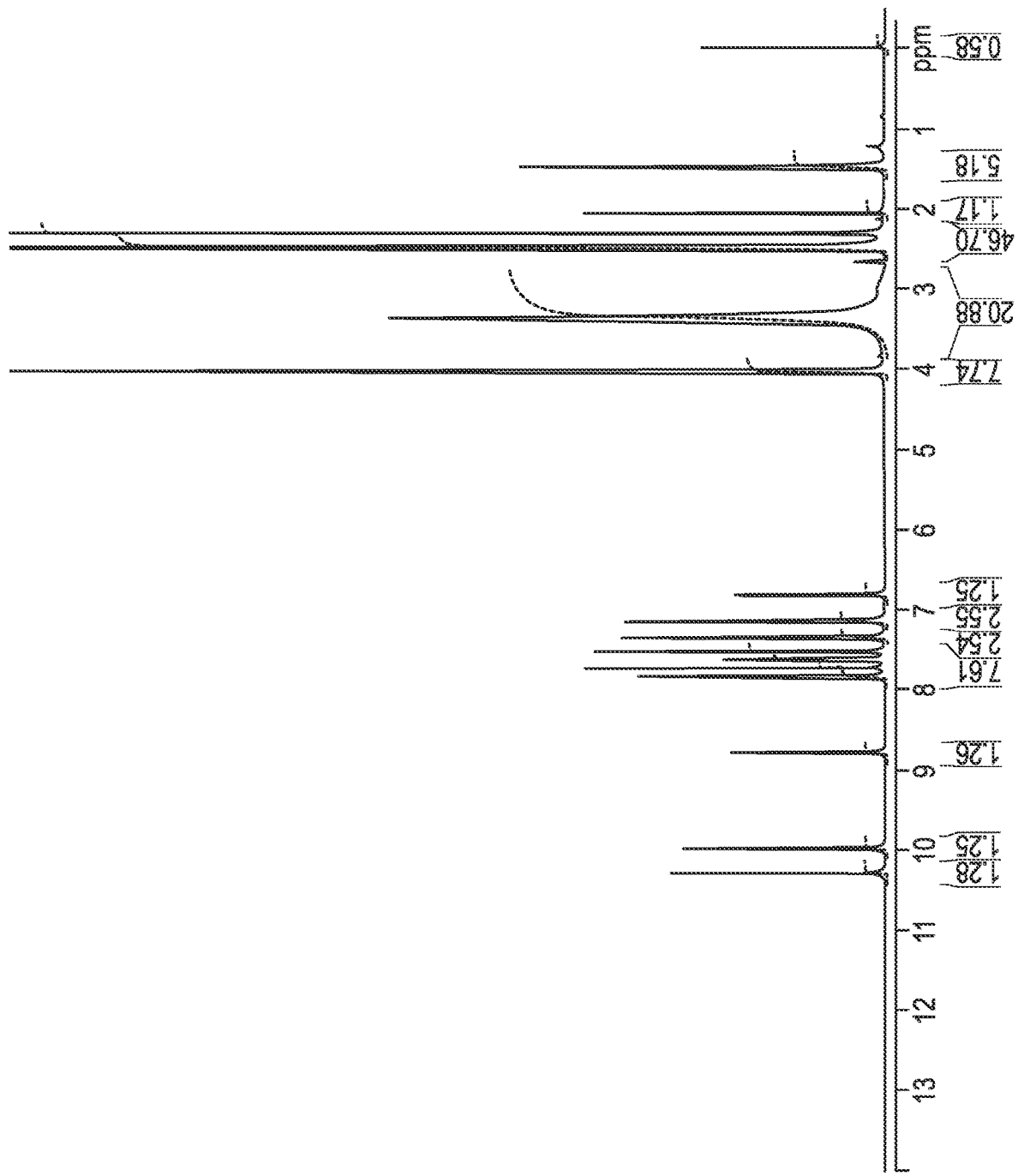
FIG. 51 is the NMR spectrum of Form 25 in DMSO-$d_6$.
Figure 52:
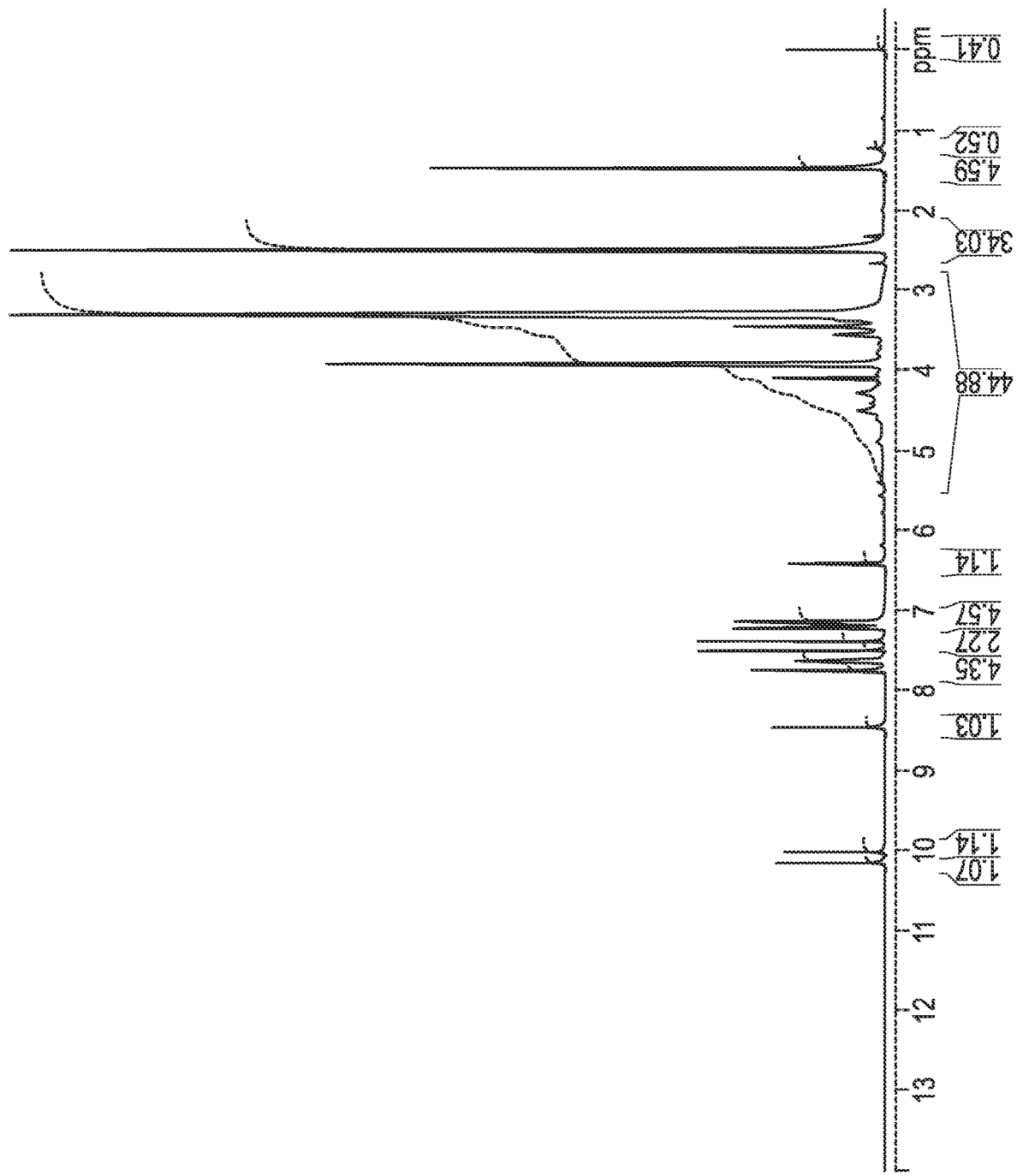
FIG. 52 is the NMR spectrum of Form 26 in DMSO-$d_6$.

Compound 1 •citrate monohydrate Form 1 is characterized by an XRPD pattern according to FIG. 1;

Compound 1 •malonate Form 2 is characterized by an XRPD pattern according to FIG. 1;

Compound 1 •oxalate Form 3 is characterized by an XRPD pattern according to FIG. 1;

Compound 1 •sulfate Form 5 is characterized by an XRPD pattern according to FIG. 2;

Compound 1 •esylate Form 7 is characterized by an XRPD pattern according to FIG. 3;

Compound 1 •mesylate Form 9 is characterized by an XRPD pattern according to FIG. 3;

Compound 1 •tosylate Form 10 is characterized by an XRPD pattern according to FIG. 4;

Compound 1 •sulfate Form 11 is characterized by an XRPD pattern according to FIG. 4;

Compound 1 •oxalate Form 13 is characterized by an XRPD pattern according to FIG. 5;

Compound 1 •besylate Form 15 is characterized by an XRPD pattern according to FIG. 5;

Compound 1 •mesylate dihydrate Form 16 is characterized by an XRPD pattern according to FIG. 6;

Compound 1 •succinate Form 17 is characterized by an XRPD pattern according to FIG. 6;

Compound 1 •esylate Form 18 is characterized by an XRPD pattern according to FIG. 6;

Compound 1 •sulfate monohydrate Form 21 is characterized by an XRPD pattern according to FIG. 7;

Compound 1 •tosylate Form 22 is characterized by an XRPD pattern according to FIG. 8;

Compound 1 •succinate Form 23 is characterized by an XRPD pattern according to FIG. 8;

Compound 1 •malonate Form 24 is characterized by an XRPD pattern according to FIG. 8; and Compound 1 •mesylate Form 25 is characterized by an XRPD pattern according to FIG. 9.

7. A pharmaceutical composition comprising a therapeutically effective amount of a substantially pure crystalline solid salt of Compound 1 as recited in claim 1 and a pharmaceutically acceptable carrier.

8. A method of treating cancer comprising administering to a subject a therapeutically effective amount of a substantially pure crystalline solid salt of Compound 1 as recited in claim 1.

9. The method of claim 8, wherein the cancer is selected from the group consisting of thyroid cancer, stomach cancer, esophageal carcinoma, kidney cancer, liver cancer, ovarian carcinoma, cervical carcinoma, bladder cancer, large bowel cancer, small bowel cancer, brain cancer, lung cancer, bone cancer, prostate carcinoma, pancreatic carcinoma, skin cancer, bone cancer, lymphoma, solid tumors, Hodgkin's disease, and non-Hodgkin's lymphoma.

* * * * *